(12) United States Patent
Cox et al.

(10) Patent No.: US 7,329,675 B2
(45) Date of Patent: Feb. 12, 2008

(54) SUBSTITUTED AZABICYCLIC COMPOUNDS

(75) Inventors: Paul Joseph Cox, Flemington, NJ (US); Shelley Bower, Bedminster, NJ (US); David John Aldous, Gillette, NJ (US); Peter Charles Astles, Kent (GB); Daniel Gerard McGarry, Branchburg, NJ (US); Christopher Hulme, Phoenixville, PA (US); John Robinson Regan, Larchmont, NY (US); Fu-Chih Huang, Belle Mead, NJ (US); Stevan Wakefield Djuric, Libertyville, PA (US); Kevin Joseph Moriarty, Norristown, PA (US); Rose Mappilakunnel Mathew, Collegeville, PA (US); Gregory Bernard Poli, Bethlehem, PA (US)

(73) Assignee: Aventis Pharma Limited, West Malling (GB)

( * ) Notice: Subject to any disclaimer, the term of this patent is extended or adjusted under 35 U.S.C. 154(b) by 157 days.

(21) Appl. No.: 10/933,077

(22) Filed: Sep. 1, 2004

(65) Prior Publication Data

US 2005/0038069 A1 Feb. 17, 2005

Related U.S. Application Data

(63) Continuation of application No. 09/612,530, filed on Jul. 7, 2000, now Pat. No. 6,800,645, which is a continuation of application No. 09/216,392, filed on Dec. 18, 1998, now Pat. No. 6,303,600, which is a continuation of application No. PCT/GB97/01639, filed on Jun. 19, 1997.

(60) Provisional application No. 60/023,047, filed on Aug. 2, 1996.

(30) Foreign Application Priority Data

Jun. 19, 1996 (GB) .................... 9612760.0

(51) Int. Cl.
*A61K 31/44* (2006.01)
*A61K 43/40* (2006.01)
*C07D 405/00* (2006.01)

(52) U.S. Cl. ................ 514/284.4; 514/339; 546/282.1

(58) Field of Classification Search ............. 546/282.1; 514/339, 284.4
See application file for complete search history.

(56) References Cited

U.S. PATENT DOCUMENTS

| 5,216,003 | A | | 6/1993 | Vazquez |
| 5,260,320 | A | * | 11/1993 | Haga et al. ................ 514/336 |
| 5,279,620 | A | | 1/1994 | Junino |
| 6,444,038 | B1 | | 8/1995 | James et al. |
| 5,958,953 | A | | 9/1999 | Marfat |

FOREIGN PATENT DOCUMENTS

| DE | 3930473 | 3/1990 |
| EP | 0266326 | 5/1988 |
| EP | 0774462 | 5/1997 |
| EP | 0882718 | 12/1998 |
| GB | 2065121 | 6/1981 |
| WO | WO 91/16313 | 10/1991 |
| WO | WO 93/03015 | 2/1993 |
| WO | WO 94/02465 | 2/1994 |
| WO | WO 94/12461 | 6/1994 |
| WO | WO 94/22852 | 10/1994 |

(Continued)

OTHER PUBLICATIONS

Wolff, Manfred E. "Burger's Medicinal Chemistry, 5ed, Part I", John Wiley & Sons, 1995, pp. 975-977.*

(Continued)

*Primary Examiner*—Janet L. Andres
*Assistant Examiner*—Binta Robinson
(74) *Attorney, Agent, or Firm*—Ronald G. Ort

(57) ABSTRACT

This invention is directed to physiologically active compounds of formula (I)

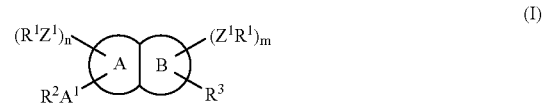

wherein

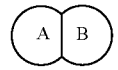

represents a bicyclic ring system, of about 10 to about 13 ring members, in which the ring

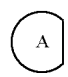

is an azaheterocycle, and the ring

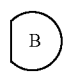

represents an azaheteroaryl ring, or an optionally halo substituted benzene ring; and N-oxides thereof, and pharmaceutically acceptable salts of the compounds of formula (I) and N-oxides thereof, Such compounds inhibit the production or physiological effects of TNF and inhibit cyclic AMP phosphodiesterase. The invention is also directed to pharmnaceutical compositions comprising compoundS of formula (I), their phatmaceUtical use and methods for their preparation.

15 Claims, No Drawings

FOREIGN PATENT DOCUMENTS

| | | |
|---|---|---|
| WO | WO 95/33748 | 12/1995 |
| WO | WO 95/35107 | 12/1995 |
| WO | WO 96/11917 | 4/1996 |
| WO | WO 96/12720 | 5/1996 |
| WO | WO 96/32979 | 10/1996 |
| WO | WO 97/12615 | 4/1997 |
| WO | WO 97/24334 | 7/1997 |
| WO | WO 97/42174 | 11/1997 |
| WO | WO 97/49702 | 12/1997 |
| WO | WO 98/09981 | 3/1998 |

OTHER PUBLICATIONS

Banker, G.S. et al, "Modern Pharmaceutics, 3ed.", Marcel Dekker, New York, 1996, pp. 451 and 596.*

West, Anthony R., Solid State Chemistry and its Applications, Wiley, New York, 1988, pp. 358 & 365.*

Alabaster et al., 2(1H)-Quinolinones with Cardiac Stimulant Activity. 1. Synthesis and Biological Activities of (Six-Membered Heteroaryl)-Substituted Derivatives, J.Med.Chem., 1988, 31, 2048-2056.

Buckle et al., Novel 1H-Benzimidazol-4-ole with Potent 5-Lipoxygenase Inhibitory Activity, J.Med.Chem., 1987, 30, 2216-2221.

Tietze et al., Synthesis of the Reduced A-Unit (C1) of the Antitumor Antibiotic CC-1065, Chem. Ber., 1993, 126, 2733-2797.

Abstract DE2137508.

Abstract GB1356245.

Abstract JP3258770.

Abstract JP4360874.

Abstract JP5222000.

Computer Search Report, Beilstein Reg. #19537.

Computer Search Report, Beilstein Reg. #218639.

Derwent Abstract, EP385850.

Derwent Abstract, BE770442.

Derwent Abstract, WO9636624-A1.

* cited by examiner

SUBSTITUTED AZABICYCLIC COMPOUNDS

This application is a continuation application of U.S. patent application Ser. No. 09/216,392, filed Dec. 18, 1998, which is a continuation application of International Patent Application No. PCT/GB97/01639, filed Jun. 19, 1999, which application, in turn, is a continuation-in-part application of U.S. provisional patent application No. 60/023,047, filed Aug. 2, 1996, now abandoned.

This invention is directed to substituted azabicyclic compounds, their preparation, pharmaceutical compositions containing these compounds, and their pharmaceutical use in the treatment of disease states associated with proteins that mediate cellular activity.

Tumour necrosis factor (TNF) is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and adult respiratory distress syndrome, and its role in many other immunologic processes, this factor is regarded as an important mediator of general inflammation.

TNF primes or activates neutrophils, eosinophils, fibroblasts and endothelial cells to release tissue damaging mediators. TNF also activates monocytes, macrophages and T-lymphocytes to cause the production of colony stimulating factors and other pro-inflammatory cytokines such $IL_1$, $IL_6$, $IL_8$ and GM-CSF, which in some case mediate the end effects of TNF. The ability of TNF to activate T-lymphocytes, monocytes, macrophages and related cells has been implicated in the progression of Human immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF on the hypothalamus and in reducing the anti-coagulant activity of vascular endothelial cells. The cachexia associated with certain disease states is mediated through indirect effects on protein catabolism. TNF also promotes bone resorption and acute phase protein synthesis.

The discussion herein relates to disease states associated with TNF including those disease states related to the production of TNF itself, and disease states associated with other cytokines, such as but not limited to IL-1, or IL-6, that are modulated by associated with TNF. For example, a IL-1 associated disease state, where IL-1 production or action is exacerbated or secreted in response to TNF, would therefore be considered a disease state associated with TNF. TNF-alpha and TNF-beta are also herein referred to collectively as "TNF" unless specifically delineated otherwise, since there is a close structural homology between TNF-alpha (cachectin) and TNF-beta (lymphotoxin) and each of them has a capacity to induce similar biological responses and bind to the same cellular receptor.

Cyclic AMP phosphodiesterases are important enzymes which regulate cyclic AMP levels and in turn thereby regulate other important biological reactions. The ability to regulate cyclic AMP phosphodiesterases therefore, has been implicated as being capable of treating assorted biological conditions. In particular, inhibitors of type IV cyclic AMP phosphodiesterase have been implicated as being bronchodilators agents, prophylactic agents useful against asthma and as agents for inhibiting eosinophil accumulation and of the function of eosinophils, and for treating other diseases and conditions characterised by, or having an etiology involving, morbid eosinophil accumulation. Inhibitors of cyclic AMP phosphodiesterase are also implicated in treating inflammatory diseases, proliferative skin diseases and conditions associated with cerebral metabolic inhibition.

It has already been reported that certain substituted monocyclic aromatic compounds have valuable pharmaceutical properties, in particular the ability to regulate proteins that mediate cellular activity, for example, type IV cyclic AMP phosphodiesterase and/or TNF, as described, for example, in the specification of International Patent Application Publication No. WO 95/04045.

Certain substituted bicyclic aromatic compounds, for example amino-substituted benzofurans and benzothiophenes, are reported in European Patent Application EP-A-0685475, to have the ability to regulate elevated cellular cyclic AMP levels probably due to inhibition of type IV cyclic AMP phosphodiesterase.

Further examples of substituted bicyclic aromatic compounds with type IV cyclic AMP phosphodiesterase and/or TNF inhibitory activity include dihydrobenzofurans reported in WO 96/36625 and WO 96/36626.

We have now found a novel group of azabicyclic compounds which have valuable pharmaceutical properties, in particular the ability to regulate proteins that mediate cellular activity, for example, cyclic AMP phosphodiesterases (in particular type IV) and/or TNF.

Thus, in one aspect, the present invention is directed to compounds of general formula (I):

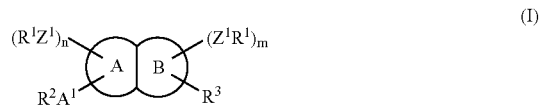

wherein

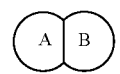

represents a bicyclic ring system, of about 10 to about 13 ring members, in which the ring

is an azaheterocycle, and the ring

represents an azaheteroaryl ring, or an optionally halo substituted benzene ring;

$R^1$ represents hydrogen or a straight- or branched-chain alkyl group of 1 to about 4 carbon atoms, optionally substituted by hydroxy or one or more halogen atoms, or when $Z^1$ represents a direct bond $R^1$ may also represent a lower alkenyl or lower alkynyl group, or a formyl group;

$R^2$ represents hydrogen, alkenyl, alkoxy, alkyl, alkylsulphinyl, alkylsulphonyl, alkylthio, aryl, arylalkyloxy, arylalkylsulphinyl, arylalkylsulphonyl, arylalkylthio, aryloxy, arylsulphinyl, arylsulphonyl, arylthio, cyano, cycloalkenyl, cycloalkenyloxy, cycloalkyl, cycloalkyloxy, heteroaryl, heteroarylalkyloxy, heteroaryloxy, hydroxy, —$SO_2NR^4R^5$, —$NR^4SO_2R^5$, —$NR^4R^5$, —$C(=O)R^5$, —$C(=O)C(=O)R^5$, —$C(=O)NR^4R^5$, —$C(=O)OR^5$, —$O(C=O)NR^4R^5$, or —$NR^4C(=O)R^5$ (where $R^4$ and $R^5$, which may be the same or different, each represent a hydrogen atom, or an alkyl, aryl, arylalkyl, cycloalkyl, heteroaryl, or heteroarylalkyl group);

$R^3$ represents a group selected from:
(i) —$C(=Z)$—$N(R^7)R^6$
(ii) —$C(=Z)$—$CHR^{12}R^6$
(iii) —$C(=Z)$—$R^6$
(iv) —$CR^8=C(R^9)(CH_2)_p$—$R^6$
(v) —$C(R^{10})=C(R^{11})R^{12}$
(vi) —$C(R^{13})(R^{10})C(R^{11})(R^{14})R^{12}$
(vii) —$C(R^8)(R^{15})CH(R^9)(CH_2)_p$—$R^6$
(viii) —$R^6$
(ix) —$N(R^{16})C(=Z)R^6$
(x) —$C(R^{17})=N$—$OC(=O)R^{18}$
(xi) —$C(=O)$—$N(R^{19})OR^{20}$
(xii) —$C\equiv C$—$R^6$
(xiii) —$CH_2$—$C(=Z)$—$R^6$
(xiv) —$C(=Z)$—$C(=Z)R^6$
(xv) —$CH_2$—$NHR^6$
(xvi) —$CH_2$—$ZR^6$
(xvii) —$CH_2$—$SOR^6$
(xviii) —$CH_2$—$SO_2R^6$
(xix) —$CF_2$—$OR^6$
(xx) —$NH$—$CH_2R^6$
(xxi) —$Z$—$CH_2R^6$
(xxii) —$SO$—$CH_2R^6$
(xxiv) —$SO_2$—$CH_2R^6$
(xxv) —$O$—$CF_2R^6$
(xxiii) —$O$—$C(=Z)R^6$
(xxvi) —$N=N$—$R^6$
(xxvii) —$NH$—$SO_2R^6$
(xxviii) —$SO_2$—$NR^{21}R^{22}$
(xxix) —$CZ$—$CZ$—$NHR^6$
(xxx) —$NH$—$CO$—$OR^6$
(xxxi) —$O$—$CO$—$NHR^6$
(xxxii) —$NH$—$CO$—$NHR^6$
(xxxiii) —$R^{23}$
(xxxiv) —$CX^1=CX^2R^6$
(xxxv) —$C(=NOR^{24})$—$(CH_2)_qR^6$
(xxxvi) —$CH_2$—$CO$—$NH(CH_2)_qR^6$
(xxxvii) —$CH_2$—$NH$—$CO(CH_2)_qR^6$
(xxxviii) —$CH_2$—$CO$—$CH_2R^6$
(xxxix) —$C(=NR^{25})$—$NH(CH_2)_qR^6$
(xxxx) —$C(X^3)=N$—$(CH_2)_qR^6$
(xxxxi) —$CH(X^4)$—$CH_2R^6$

[where:
$R^6$ is aryl or heteroaryl;
$R^7$ is a hydrogen atom or an alkyl or amino group;
$R^8$ and $R^9$, which may be the same or different, is each a hydrogen atom or alkyl, —$CO_2R^5$, —$C(=Z)NR^{26}R^{27}$ (where $R^{26}$ and $R^{27}$ may be the same or different and each is as described for $R^5$), —$CN$ or —$CH_2CN$;
$R^{10}$ and $R^{11}$, which may be the same or different, is each a group —$(CH_2)_pR^6$;
$R^{12}$ is a hydrogen atom or an alkyl group;
$R^{13}$ is a hydrogen or halogen atom or an —$OR^{28}$ group (where $R^{28}$ is a hydrogen atom or an alkyl, alkenyl, alkoxyalkyl, acyl, carboxamido or thiocarboxamido group);
$R^{14}$ is a hydrogen atom or an alkyl group;
$R^{15}$ is a hydrogen atom or a hydroxyl group;
$R^{16}$ is a hydrogen atom or an alkyl, amino, aryl, arylalkyl, or hydroxy group;
$R^{17}$ is a hydrogen atom or a $C_{1-4}$alkyl or aryl$C_{1-4}$alkyl group;
$R^{18}$ is an amino, alkylamino, arylamino, alkoxy or aryloxy group;
$R^{19}$ is an alkyl, aryl, heteroaryl, arylalkyl or heteroarylalkyl group;
$R^{20}$ is $R^5$, $(CH_2)_pCO_2R^5$ or $(CH_2)_pCOR^5$;
$R^{21}$ is a group -$L^1$-$R^{29}$ [where $L^1$ is a straight or branched $C_{1-6}$alkylene chain, a straight or branched $C_{2-6}$alkenylene chain, a straight or branched $C_{2-6}$alkynylene chain or a straight or branched $C_{1-6}$alkylene chain containing an oxygen or sulphur atom, a phenylene, imino (—NH—) or alkylimino linkage, or a sulphinyl or sulphonyl group, in which each of the alkylene, alkenylene and alkynylene chains may be optionally substituted, the substituents chosen from alkoxy, aryl, carboxy, cyano, cycloalkyl, halogen, heteroaryl, hydroxyl or oxo; and $R^{29}$ is hydrogen, or arylalkoxycarbonyl, carboxy or an acid bioisostere, cyano, —$NY^1Y^2$, {where $Y^1$ and $Y^2$ are independently hydrogen, alkyl, aryl, arylalkyl, heterocycloalkyl, heteroaryl or heteroarylalkyl, or the group —$NY^1Y^2$ may form a 4-6 membered cyclic amine (which may optionally contain a further heteroatom selected from O, S, or $NY^1$, or which may be fused to an additional aromatic or heteroaromatic ring)}], or $R^{21}$ is an optionally substituted cycloalkyl, cycloalkenyl or heterocycloalkyl group which may optionally be fused to an additional optionally substituted aromatic, heteroaromatic, carbocyclic or heterocycloalkyl ring (where the one or more optional substituents, for either or both rings, may be represented by -$L^1$-$R^{29}$);

$R^{22}$ is a hydrogen atom, a group -$L^1$-$R^{29}$, or an optionally substituted aryl, heteroaryl, cycloalkyl, cycloalkenyl or heterocycloalkyl group which may optionally be fused to an additional optionally substituted aromatic, heteroaromatic, carbocyclic or heterocycloalkyl ring (where the one or more optional substituents, for either or both rings, may be represented by -$L^1$-$R^{29}$); or both $R^{21}$ and $R^{22}$ represent aryl or heteroaryl each optionally substituted by -$L^1$-$R^{29}$; or the group —$NR^{21}R^{22}$ represents an optionally substituted saturated or unsaturated 3 to 8 membered cyclic amine ring, which may optionally contain one or more heteroatoms selected from O, S or N, and may also be fused to an additional optionally substituted aromatic, heteroaromatic, carbocyclic or heterocycloalkyl ring (where the one or more optional substituents, for any of the rings, may be represented by -L$^1$-R$^{29}$);

{where:
R$^{30}$ is a hydrogen atom or an alkyl, hydroxyalkyl or alkoxyalkyl group;
R$^{31}$ is a hydrogen atom or an alkyl, carboxy, CONHOR$^{14}$, N-alkylaminoalkyl, N,N-dialkylaminoalkyl or alkoxyalkyl group; or R$^{30}$ and R$^{31}$ together represent a —CH$_2$—O—CH$_2$—O—CH$_2$— group;
R$^{32}$ is a hydrogen atom, or amino, alkyl, aminoalkyl, hydroxyalkyl, hydroxy, acyl, alkoxycarbonyl, methoxycarbonylalkyl, —(CH$_2$)$_p$CONY$^3$Y$^4$ (where Y$^3$ and Y$^4$ are each independently hydrogen or alkyl), —(CH$_2$)$_p$SO$_2$NY$^3$Y$^4$, —(CH$_2$)$_p$PO$_3$H$_2$, —(CH$_2$)$_p$SO$_2$NHCOalkyl, or —(CH$_2$)$_p$SO$_2$NHCOR$^6$;
R$^{33}$ is C$_{1-4}$alkyl, CH$_2$NHCOCONH$_2$, CH═C(R$^{43}$)R$^{44}$ (where R$^{43}$ is R$^{44}$ or fluorine and R$^{44}$ is hydrogen or C$_{1-4}$alkyl optionally substituted by 1 to 3 fluorine atoms), cyclopropyl (optionally substituted by R$^{43}$), CN, CH$_2$OR$^{44}$ or CH$_2$NR$^{44}$R$^{45}$ (where R$^{45}$ is hydrogen, OR$^{44}$, or C$_{1-4}$alkyl optionally substituted by 1 to 3 fluorine atoms, or the group NR$^{44}$R$^{45}$ represents a 5 to 7 membered cyclic amine optionally containing one or more additional heteroatom selected from O, N, or S);
R$^{34}$ is methyl or ethyl optionally substituted by 1 or more halogen atoms;
R$^{35}$ is R$^{14}$, —OR$^{14}$, —CO$_2$R$^{14}$, —COR$^{14}$, —CN, —CONY$^3$Y$^4$ or —NY$^3$Y$^4$;
R$^{36}$ is —C(═Z)R$^{14}$, —CO$_2$R$^{14}$, —CONY$^3$Y$^4$ or —CN;
R$^{37}$ and R$^{39}$, which may be the same or different, is each a hydrogen atom, alkyl, acyl, arylalkyl, —(CH$_2$)$_p$CO$_2$R$^5$, —CONHR$^5$, heteroarylalkyl, aryl, or heteroaryl;
R$^{38}$ is acyl, aroyl, —C(═O)cycloalkyl, alkoxycarbonyl, cycloalkoxycarbonyl, carboxy, alkoxyalkyl, —NO$_2$, —CH$_2$OH, —CN, —NR$^{14}$COR$^5$, —NR$^{14}$CONY$^5$Y$^6$, —NR$^{14}$SO$_2$R$^{46}$ [where R$^{46}$ is alkyl, cycloalkyl, trifluoromethyl, aryl, arylalkyl or —NY$^5$Y$^6$ (where Y$^5$ and Y$^6$ are independently selected from hydrogen, alkyl, cycloalkyl, aryl or arylalkyl, or Y$^5$ and Y$^6$ together form a 4- to 7-membered heterocyclic or carbocyclic ring)], —SO$_2$R$^{46}$ or —CONY$^5$Y$^6$;
R$^{40}$ is hydrogen, alkyl, haloalkyl, cycloalkyl, aryl, acyl, aroyl, —C(═O)cycloalkyl, —CH$_2$OH, alkoxyalkyl, alkoxycarbonyl, cycloalkoxycarbonyl, aryloxycarbonyl, —CN, —NO$_2$, or —SO$_2$R$^{46}$;
R$^{41}$ is —CN, —C(Z)R$^{47}$ (where R$^{47}$ is hydrogen, alkyl, haloalkyl, cycloalkyl, aryl, arylalkyl, heteroaryl, C$_{1-6}$alkyloxy, arylalkyloxy, aryloxy or —NY$^5$Y$^6$) or SO$_2$R$^{46}$;
R$^{42}$ is hydrogen, alkyl, cycloalkyl, acyl, aroyl, —C(═O) cycloalkyl, alkoxycarbonyl, cycloalkoxycarbonyl, carboxy, —CN, —SO$_2$R$^{46}$ or —CONY$^5$Y$^6$;
W is (CH$_2$)$_r$ or NR$^{39}$;
Z$^3$ is an oxygen atom, NR$^{14}$ or NOR$^{14}$;
s is zero or an integer 1 to 4;
r is 1 to 4; and
Y is an oxygen atom, C(═O), CH(OH) or C(OR$^{14}$)(CH$_2$)$_p$R$^6$};
R$^{24}$ is R$^5$ or CONHR$^{25}$;
R$^{25}$ is hydrogen, C$_{1-3}$alkyl or (CH$_2$)$_q$R$^6$;
p is zero or an integer 1 to 5;
q is zero or 1;
X$^1$ and X$^2$, which may be the same or different, is each a hydrogen or fluorine atom;
X$^3$ is a chlorine or fluorine atom, alkoxy, aryloxy, heteroaryloxy, arylalkyloxy or heteroarylalkyl;
X$^4$ is a halogen atom or hydroxy;
Z represents an oxygen or sulphur atom];
A$^1$ represents a direct bond, or a straight or branched C$_{1-6}$alkylene chain optionally substituted by hydroxyl, alkoxy, oxo, cycloalkyl, aryl or heteroaryl, or A$^1$ represents a straight or branched C$_{2-6}$alkenylene or C$_{2-6}$alkynylene chain;
Z$^1$ represents a direct bond, an oxygen or sulphur atom or NH;
n and m each represent zero or 1, provided that n is 1 when m is zero and n is zero when m is 1;
and N-oxides thereof, and their prodrugs, and pharmaceutically acceptable salts and solvates (e.g. hydrates) of the compounds of formula (I) and N-oxides thereof, and their prodrugs.

In the present specification, the term "compounds of the invention", and equivalent expressions, are meant to embrace compounds of general formula (I) as hereinbefore described, which expression includes the N-oxides, the prodrugs, the pharmaceutically acceptable salts, and the solvates, e.g. hydrates, where the context so permits. Similarly, reference to intermediates, whether or not they themselves are claimed, is meant to embrace their N-oxides, salts, and solvates, where the context so permits. For the sake of clarity, particular instances when the context so permits are sometimes indicated in the text, but these instances are purely illustrative and it is not intended to exclude other instances when the context so permits.

It is to be understood that $R^2A^1$, $(R^1Z^1)_n$ and $(R^1Z^1)_m$ may be attached at either a ring carbon or nitrogen atom whereas $R^3$ is attached at a ring carbon.

As used above, and throughout the description of the invention, the following terms, unless otherwise indicated, shall be understood to have the following meanings:

"Patient" includes both human and other mammals.

"Acyl" means an H—CO— or alkyl-CO— group in which the alkyl group is as described herein. Preferred acyls contain a $C_{1-4}$alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain, optionally substituted by one or more halogen atoms. Particular alkyl groups have 1 to about 12 carbon atoms in the chain, more particularly from 1 to about 6 carbon atoms. Exemplary alkyl groups for $R^1$ include methyl, fluoromethyl, difluoromethyl, trifluoromethyl and ethyl. Exemplary alkyl groups for $R^2$ include methyl, ethyl, n-propyl, i-propyl, n-butyl, s-butyl, t-butyl, n-pentyl, 3-pentyl, heptyl, octyl, nonyl, decyl and dodecyl.

"Alkylsulphonyl" means an alkyl-$SO_2$— group in which the alkyl group is as previously described. Preferred groups are those in which the alkyl group is $C_{1-4}$alkyl.

"Alkylsulphinyl" means an alkyl-SO— group in which the alkyl group is as previously described. Preferred groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Aroyl" means an aryl-CO— group in which the aryl group is as described herein. Exemplary groups include benzoyl and 1- and 2-naphthoyl.

"Aroylamino" is an aroyl-NH— group wherein aroyl is as previously defined.

"Aryl" as a group or part of a group denotes an optionally substituted monocyclic or multicyclic aromatic carbocyclic moiety of about 6 to about 10 carbon atoms. When $R^3$ contains an optionally substituted aryl group this may particularly represent an aromatic carbocyclic moiety of about 6 to about 10 carbon atoms such as phenyl or naphthyl optionally substituted with one or more aryl group substituents which may be the same or different, where "aryl group substituent" includes, for example, acyl, acylamino, alkyl, alkoxy, alkoxycarbonyl, alkylthio, alkylsulphinyl, alkylsulphonyl, aroyl, aroylamino, aryl, arylalkyl, arylalkyloxy, arylalkyloxycarbonyl, arylalkylthio, aryloxy, aryloxycarbonyl, arylsulphinyl, arylsulphonyl, carboxy, cyano, halo, heteroaroyl, heteroaryl, heteroarylalkyl, heteroarylamino, heteroaryloxy, hydroxy, hydroxyalkyl, nitro, arylthio, $Y^7Y^8N$—, $Y^7Y^8NCO$— or $Y^7Y^8NSO_2$— (where $Y^7$ and $Y^8$ are independently hydrogen, alkyl, aryl, and arylalkyl).

Preferred aryl group substituents within $R^3$ include acyl, acylamino, alkoxycarbonyl, alkyl, alkylthio, aroyl, cyano, halo, hydroxy, nitro, $Y^7Y^8N$—, $Y^7Y^8NCO$— and $Y^7Y^8NSO_2$— (where $Y^7$ and $Y^8$ are independently hydrogen or alkyl). When $R^2$ contains an optionally substituted aryl group this may particularly represent a phenyl group optionally substituted by one or more substituents selected from the "aryl group substituents" listed above. Preferred aryl group substituents within $R^2$ include halogen, alkoxy, carboxamido, cyano and heteroaryl.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkylsulphinyl" means an aryl-alkyl-SO— group in which the aryl and alkyl moieties are as previously described.

"Arylalkylsulphonyl" means an aryl-alkyl-SO— group in which the aryl and alkyl moieties are as previously described.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include optionally substituted phenoxy and naphthoxy.

"Aryloxycarbonyl" means an aryl-O—CO— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylthio" means an aryl-S— group in which the aryl group is as previously described. Exemplary arylthio groups include phenylthio and naphthylthio.

"Azaheterocycle" means a heterocycle of about 5 to about 7 ring members in which one of the ring members is nitrogen and the other ring members are chosen from carbon, oxygen, sulphur, nitrogen and $NR^5$, but excluding compounds where two O or S atoms are in adjacent positions. Exemplary azaheterocycles include pyridyl, imidazolyl, pyrrolyl, pyrrolinyl, oxazolyl, thiazolyl, pyrazolyl, pyridazyl, pyrimidinyl, morpholinyl, piperidinyl.

"Azaheteroaryl" means an aromatic carbocyclic moiety of 5 or 6 ring members in which one of the ring members is nitrogen and the other ring members are chosen from carbon, oxygen, sulphur, or nitrogen. Exemplary azaheteroaryl rings include isoxazolyl, pyridyl and pyrimidinyl.

"Cycloalkenyl" means a non-aromatic monocyclic ring system containing a carbon-carbon double bond and having about 3 to about 10 carbon atoms. Exemplary monocyclic cycloalkenyl rings include cyclopentenyl, cyclohexenyl and cycloheptenyl.

"Cycloalkenyloxy" means a cycloalkenyl-O— group in which the cycloalkenyl moiety is as previously defined.

Exemplary cycloalkyloxy groups include cyclopentenyloxy, cyclohexenyloxy and cycloheptenyloxy.

"Cycloalkyl" means a saturated monocyclic or bicyclic ring system of about 3 to about 10 carbon atoms. Exemplary monocyclic cycloalkyl rings include cyclopropyl, cyclopentyl, cyclohexyl and cycloheptyl.

"Cycloalkyloxy" means a cycloalkyl-O— group in which the cycloalkyl moiety is as previously defined. Exemplary cycloalkyloxy groups include cyclopropyloxy, cyclopentyloxy, cyclohexyloxy and cycloheptyloxy.

"Heteroaroyl" means a heteroaryl-CO— group in which the heteroaryl group is as described herein. Exemplary groups include pyridylcarbonyl.

"Heteroaryl" as a group or part of a group denotes an optionally substituted aromatic monocyclic or multicyclic organic moiety of about 5 to about 10 ring members in which one or more of the ring members is/are element(s) other than carbon, for example nitrogen, oxygen or sulphur. Examples of suitable optionally substituted heteroaryl groups include furyl, isoxazolyl, isoquinolinyl, isothiazolyl, oxadiazole, pyrazinyl, pyridazinyl, pyridyl, pyrimidinyl, quinolinyl, 1,3,4-thiadiazolyl, thiazolyl, thienyl, and 1,2,4-triazinyl groups, optionally substituted by one or more aryl group substituents as defined above. When $R^2$ or $R^3$ contains an optionally substituted heteroaryl group this may particularly represent an optionally substituted "azaheteroaryl" group. Optional substituents for the heteroaryl group within $R^2$ or $R^3$ include, for example, halogen atoms and alkyl, aryl, arylalkyl, hydroxy, oxo, hydroxyalkyl, haloalkyl (for example trifluoromethyl), alkoxy, haloalkoxy (for example trifluoromethoxy), aryloxy and arylalkyloxy groups. Preferred heteroaryl groups within $R^2$ or $R^3$ include optionally substituted pyridyl. Preferred heteroaryl groups represented by $R^6$ within the groups —C(=Z)NHR$^6$ and —C(=Z)CH$^2$R$^6$ are optionally substituted pyridyl groups, especially wherein the optional substituents are alkyl groups or, more particularly, halogen atoms. Preferred heteroaryl groups represented by $R^6$ within the group —C(=Z)R$^6$ are optionally substituted pyridyl groups, especially wherein the optional substituent is an aryloxy group.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroaryloxy" means an heteroaryl-O— group in which the heteroaryl group is as previously described. Exemplary heteroaryloxy groups include optionally substituted pyridyloxy.

"Heteroarylalkoxy" means an heteroarylalkyl-O— group in which the heteroarylalkyl group is as previously described. Exemplary heteroaryloxy groups include optionally substituted pyridylmethoxy.

"Heterocycloalkyl" means a cycloalkyl group which contains one or more heteroatoms selected from O, S or NY$^1$.

"Hydroxyalkyl" means a HO-alkyl-group in which alkyl is as previously defined. Preferred hydroxyalkyl groups contain $C_{1-4}$alkyl. Exemplary hydroxyalkyl groups include hydroxymethyl and 2-hydroxyethyl.

"Y$^7$Y$^8$N—" means a substituted or unsubstituted amino group, wherein Y$^7$ and Y$^8$ are as previously described. Exemplary groups include amino ($H_2N$—), methylamino, ethylmethylamino, dimethylamino and diethylamino.

"Y$^7$Y$^8$NCO—" means a substituted or unsubstituted carbamoyl group, wherein Y$^7$ and Y$^8$ are as previously described. Exemplary groups are carbamoyl ($H_2NCO$—) and dimethylcarbamoyl ($Me_2NCO$—).

"Y$^7$Y$^8$NSO$_2$—" means a substituted or unsubstituted sulphamoyl group, wherein Y$^7$ and Y$^8$ are as previously described. Exemplary groups are sulphamoyl ($H_2NSO_2$—) and dimethylsulphamoyl ($Me_2NSO_2$—).

"Halo" or "halogen" means fluoro, chloro, bromo, or iodo. Preferred are fluoro or chloro.

"Prodrug" means a compound which is convertible in vivo by metabolic means (e.g. by hydrolysis) to a compound of formula (I), including N-oxides thereof, for example an ester of a compound of formula (I) containing a hydroxy group.

Suitable esters are of many different types, for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

An especially useful class of esters may be formed from acid moieties selected from those described by Bundgaard et. al., J. Med. Chem., 1989, 32, page 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallization techniques, or they are separately prepared from the appropriate isomers of their intermediates. Additionally, in situations where tautomers of the compounds of formula (I) are possible, the present invention is intended to include all tautomeric forms of the compounds.

With reference to formula (I) above, the following are particular and preferred groupings:

$R^1$ preferably represents a $C_{1-4}$alkyl group optionally substituted by one or more halogen (e.g. chlorine or fluorine) atoms. $R^1$ more preferably represents methyl or difluoromethyl.

$R^2$ may particularly represent $C_{1-7}$alkyl (for example methyl, ethyl, propyl, butyl, pentyl, hexyl, heptyl).

$R^2$ may also particularly represent $C_{1-4}$alkoxy (for example methoxy).

$R^2$ may also particularly represent $C_{3-7}$cycloalkyl (for example cyclopropyl, cyclopentyl, cyclohexyl, cycloheptyl).

$R^2$ may also particularly represent aryl (for example optionally substituted phenyl or naphthyl).

$R^2$ may also particularly represent aryloxy (for example optionally substituted phenoxy).

$R^2$ may also particularly represent heteroaryl (for example optionally substituted thienyl, pyridyl, furanyl).

$R^2$ may also particularly represent heterocycloalkyl (for example tetrahydrofuranyl, tetrahydropyranyl).

$R^2$ may also particularly represent arylalkylsulphonyl (for example 4-methylphenylsulphonyl and 4-methoxyphenylsulphonyl) when the group $R^2A^1-$ is attached to a ring nitrogen atom.

It is to be understood that the aforementioned heteroaryl and heterocycloalkyl moieties represented by $R^2$ when containing at least one nitrogen atom may be presented as the corresponding N-oxides.

$R^3$ may particularly represent $-OCH_2R^6$, $-C(=Z)-N(R^7)R^6$, preferably wherein $R^7$ represents a hydrogen atom, or $-C(=Z)-CHR^{12}R^6$ especially where $R^{12}$ is hydrogen.

Within such groups $R^6$ may preferably represent substituted phenyl, especially a phenyl group substituted on one or both, more preferably on both, of the positions adjacent to a position of attachment of $R^6$ to the rest of the molecule. It is also preferred that the phenyl substituent is alkyl, especially methyl, or halo, especially chloro or fluoro. Within such groups $R^6$ may also preferably represent substituted azaheteroaryl, where the azaheteroaryl group is preferably substituted on one or both, more preferably on both, of the positions adjacent to a position of attachment of $R^6$ to the rest of the molecule. It is also preferred that the heteroaryl substituent is alkyl, especially methyl, or halo, especially chloro or fluoro.

$R^3$ may also particularly represent $-C(=Z)-R^6$ wherein $R^6$ is preferably azaheteroaryl (e.g. pyridyl), particularly when substituted by aryloxy (e.g. 3-chlorophenoxy).

$R^3$ may also particularly represent $-CR^8=C(R^9)(CH_2)_p-R^6$ where $R^8$ is preferably $CH_3$ or more preferably hydrogen, $R^9$ is preferably hydrogen, CN or $CH_3$ and p is zero, 1 or 2, especially zero and $R^6$ is as defined above.

$R^3$ may also particularly represent $-C(R^{10})=C(R^{11})R^{12}$ where $R^{10}$ and $R^{11}$ are each preferably $CH_2R^6$ or especially $R^6$ (where $R^6$ is as defined above), and $R^{12}$ is hydrogen.

$R^3$ may also particularly represent $-C(R^{13})(R^{10})C(R^{11})(R^{14})R^{12}$ where $R^{10}$ and $R^{11}$ are each preferably $CH_2R^6$ or especially $R^6$ (where $R^6$ is as defined above), $R^{13}$ is preferably hydrogen or hydroxy, $R^{12}$ and $R^{14}$ are preferably methyl or more especially hydrogen.

$R^3$ may also particularly represent $-C(R^8)(R^{15})CH(R^9)(CH_2)_p-R^6$ where $R^8$ is preferably $CH_3$ or more preferably hydrogen, $R^9$ and is preferably hydrogen, CN or $CH_3$, more preferably hydrogen, p is zero, 1 or 2, especially zero, $R^{15}$ is preferably hydrogen and $R^6$ is as defined above.

$R^3$ may also particularly represent $-R^6$ where $R^6$ is as defined above.

$R^3$ may also particularly represent $-N(R^{16})C(=Z)R^6$ where $R^{16}$ is hydrogen and $R^6$ is as defined above.

$R^3$ may also particularly represent $-C(R^{17})=N-OC(=O)R^{18}$ where $R^{17}$ is $C_{1-4}$alkyl and $R^{18}$ is amino.

$R^3$ may also particularly represent $-C(=O)-N(R^{19})OR^{20}$ where $R^{19}$ is $C_{1-4}$alkyl or aryl and $R^{20}$ is $C_{1-4}$alkyl or arylalkyl.

$R^3$ may also particularly represent $-C\equiv C-R^6$, $-CH_2-NHR^6$, $-CH_2-SOR^6$, $-CH_2-SO_2R^6$, $-CF_2-OR^6$, $-NH-CH_2R^6$, $-SO-CH_2R^6$, $-SO_2-CH_2R^6$, $-O-CF_2R^6$, $-N=N-R^6$, $-NH-SO_2R^6$, $-NH-CO-OR^6$, $-O-CO-NHR^6$, $-NH-CO-NHR^6$ or $-CH_2-CO-CH_2R^6$ where $R^6$ is as defined above.

$R^3$ may also particularly represent $-SO_2-NR^{21}R^{22}$ where $R^{21}$ and $R^{22}$ are as defined above.

$R^3$ may also particularly represent $-CH_2-C(=Z)-R^6$, $-C(=Z)-C(=Z)R^6$, $-CH_2-ZR^6$, $-Z-CH_2R^6$, $CZ-CZ-NHR^6$ or $-O-C(=Z)R^6$ where Z and $R^6$ are as defined above.

$R^3$ may also particularly represent $-CX^1=CX^2R^6$ where $X^1$, $X^2$ and $R^6$ are as defined above.

$R^3$ may also particularly represent $-C(=NOR^{24})-(CH_2)_q R^6$ where $R^{24}$, q and $R^6$ are as defined above.

$R^3$ may also particularly represent —$CH_2$—CO—NH$(CH_2)_qR^6$ or —$CH_2$—NH—CO$(CH_2)_qR^6$ where q and $R^6$ are as defined above.

$R^3$ may also particularly represent —$C(=NR^{25})$—NH$(CH_2)_qR^6$ where $R^{25}$, q and $R^6$ are as defined above.

$R^3$ may also particularly represent —$C(X^3)=N$—$(CH_2)_q R^6$ or where $X^3$, q and $R^6$ are as defined above.

$R^3$ may also particularly represent —$CH(X^4)$—$CH_2R^6$ where $X^4$ and $R^6$ are as defined above.

$R^3$ may also particularly represent

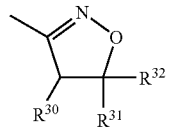

where $R^{30}$ and $R^{32}$ are hydrogen and $R^{31}$ is —$CO_2H$ or —CONHOH.

$R^3$ may also particularly represent

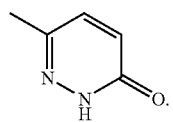

$R^3$ may also particularly represent

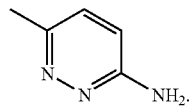

$R^3$ may also particularly represent

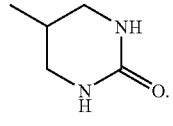

$R^3$ may also particularly represent

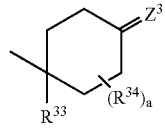

where $R^{33}$ is CN, s is zero and $Z^3$ is an oxygen atom.

$R^3$ may also particularly represent

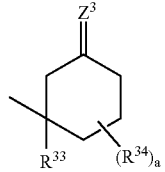

where $R^{33}$ is CN, s is zero and $Z^3$ is an oxygen atom.

$R^3$ may also particularly represent

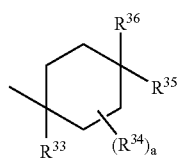

where $R^{33}$ is CN, s is zero, $R^{35}$ is hydrogen and $R^{36}$ is $CO_2H$.

$R^3$ may also particularly represent

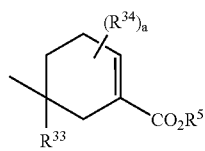

where $R^{33}$ is CN, s is zero and
$R^5$ is hydrogen or $C_{1-4}$alkyl, especially methyl.

$R^3$ may also particularly represent

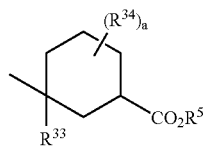

where $R^{33}$ is CN, s is zero and
$R^5$ is hydrogen or $C_{1-4}$alkyl, especially methyl.

$R^3$ may also particularly represent

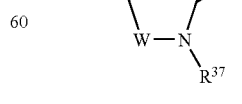

where W is $NR^{39}$ [where $R^{39}$ is $C_{1-4}$alkyl, especially methyl] and $R^{37}$ is $CONHR^5$ [where $R^5$ is heteroarylalkyl, especially pyridylmethyl].

R³ may also particularly represent

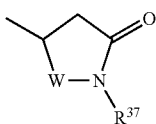

where W is CH₂ and R³⁷ is hydrogen.

R³ may also particularly represent

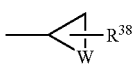

where W is CH₂ and R³⁸ is hydroxymethyl.

R³ may also particularly represent

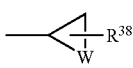

where W is CH₂ and R³⁸ is carboxy.

R³ may also particularly represent

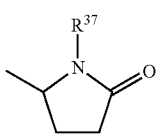

where R³⁷ is hydrogen.

R³ may also particularly represent

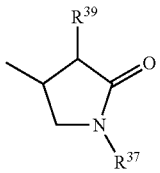

where R³⁷ and R³⁹ are alkoxycarbonyl.

R³ may also particularly represent

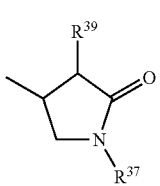

where R³⁷ is hydroxy and R³⁹ is hydrogen.

R³ may also particularly represent

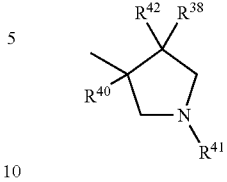

where $R^{40}$ is hydrogen, $R^{41}$ is $C_{1-4}$alkoxycarbonyl, especially methyl, $R^{42}$ is $C_{1-4}$alkyl, especially methyl, and $R^{38}$ is $C_{1-4}$acyl, especially acetyl.

R³ may also particularly represent

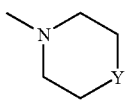

where Y is defined above.

The moiety $A^1$ may particularly represent a direct bond or a straight- or branched-chain alkylene linkage containing from 1 to 6 carbon atoms, optionally substituted by alkoxy.

$Z^1$ may particularly represents an oxygen atom.

$Z^1$ may also particularly represents a direct bond.

The moiety $R^3$ is preferably —C(=O)—NHR⁶, —C(=O)—CH₂R⁶ or —OCH₂R⁶ wherein R⁶ represents an optionally substituted azaheteroaryl group, especially a pyridyl or isoxazolyl, substituted (by one or two methyl groups or halogen, e.g. chlorine atoms) on one or both, more preferably both, of the positions adjacent to the position of attachment of R⁶ to the rest of the molecule. Particular examples of R⁶-include a 3,5-dimethyl- or 3,5-dihalopyrid-4-yl moiety (more especially a 3,5-dimethylpyrid-4-yl moiety) or 3,5-dimethyl-isoxazol-4-yl.

It is to be understood that the aforementioned heteroaryl moieties present within R³ when containing at least one nitrogen atom may be presented as the corresponding N-oxides, and such N-oxides are also preferred. Thus, R³ may preferably contain a 3,5-dialkyl- or 3,5-dihalo-1-oxido-4-pyridinio group, such as a 3,5-dimethyl- or 3,5-dichloro-1-oxido-4-pyridinio group.

In compounds of formula (I) ring

may particularly represent a 5-membered azaheterocycle containing at least one nitrogen atom, and ring

may particularly represent a 6-membered azaheteroaryl or preferably a benzene ring. Such compounds in which n is zero and m is 1 are preferred.

The bicycle

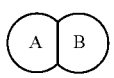

may particularly represent

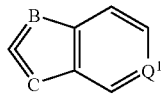

where $Q^1$ is a CH or $CX^5$ linkage (where $X^5$ is halogen), or a nitrogen atom, or $N^+$—$O^-$, especially a CH linkage, and the moiety

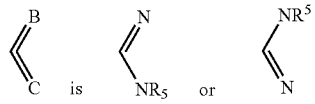

especially where $R^5$ represents a hydrogen atom or a methyl group, more especially where $R^5$ is hydrogen. Preferred compounds have $R^2A^1$ attached to position 2 of the benzimidazole ring.

It will be appreciated that compounds of formula (I) in which the bicycle

where the moiety

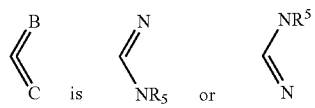

where $R^5$ represents a hydrogen atom, are tautomers.

The bicycle

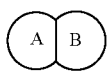

may also particularly represent

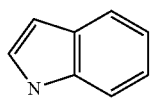

especially where $R^2A^1$ is attached to the ring nitrogen atom.

The bicycle

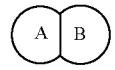

may also particularly represent

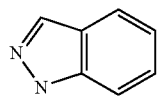

especially where $R^2A^1$ is attached to the ring nitrogen atom.

The bicycle

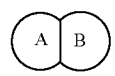

may also particularly represent

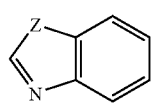

(wherein Z is as hereinbefore defined, especially an oxygen atom) especially where $R^2A^1$ is attached to position 2 of the benzoxazole ring.

The bicycle

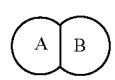

may also particularly represent

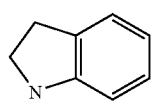

especially where $R^2A^1$ is attached to the ring nitrogen atom.

The bicycle

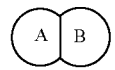

may also particularly represent

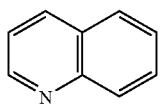

especially where $R^2A^1$ is attached to position 2 of the quinoline ring.

It is to be understood that this invention covers all appropriate combinations of the particular and preferred groupings referred to herein.

A further particular group of compounds of the present invention are compounds of formula (Ia):

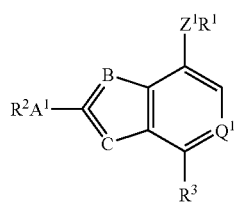

(Ia)

wherein $R^1$, $R^2$, $R^3$, $A^1$,

$Z^1$ and $Q^1$ are as defined previously, and N-oxides thereof, and their prodrugs, and pharmaceutically acceptable salts and solvates (e.g. hydrates) of the compounds of formula (Ia) and N-oxides thereof, and their prodrugs.

Compounds of formula (Ia) in which $R^1$ represents $C_{1-4}$alkyl optionally substituted by one or more halogen atoms (especially methyl or difluoromethyl) are preferred.

Compounds of formula (Ia) in which $R^2$ represents a straight- or branched-chain $C_{1-4}$alkyl group (e.g. isopropyl), or cycloalkyl (e.g. cyclopropyl), alkoxy (e.g. methoxy), aryl, aryloxy or heteroaryl (e.g. pyridyl) are preferred.

Compounds of formula (Ia) in which $R^3$ represents —C(=O)—NHR$^6$, —C(=O)—CH$_2$R$^6$ or —O—CH$_2$R$^6$ where $R^6$ represents a disubstituted azaheteroaryl group, or an N-oxide thereof, more particularly a dialkyl- or dihalo-azaheteroaryl group or an N-oxide thereof, are preferred. Azaheteroaryl groups substituted on both of the positions adjacent to the position of attachment of $R^6$ to the rest of the molecule, for example 3,5-dimethyl-isoxazol-4-yl, or 3,5-dimethyl- or 3,5-dichloro-pyrid-4-yl or an N-oxide thereof, are most preferred.

Compounds of formula (Ia) in which $A^1$ represents a direct bond are a preferred group of compounds.

Compounds of formula (Ia) in which $A^1$ represents a straight or branched chain alkylene linkage containing from 1 to 6 carbon atoms, for example a methylene, ethylene, propylene, methylmethylene, or butylmethylene linkage, (especially methylene) are also a preferred group of compounds.

Compounds of formula (Ia) in which $A^1$ represents a straight or branched chain alkylene linkage containing from 1 to 6 carbon atoms which is substituted by alkoxy, for example a methoxymethylene or methoxypropylmethylene, are a further preferred group of compounds.

Compounds of formula (Ia) in which the moiety

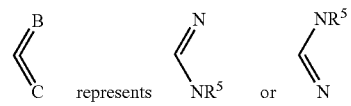

where $R^5$ represents a hydrogen atom or a methyl group (especially a hydrogen atom) are preferred.

Compounds of formula (Ia) in which $Q^1$ is a CH linkage are preferred.

Compounds of formula (Ia) in which $Z^1$ is an oxygen atom are preferred.

A preferred group of compounds of the invention are compounds of formula (Ia) in which: $R^1$ is methyl or difluoromethyl; $R^2$ is $C_{1-4}$alkyl (e.g. isopropyl), $C_{3-6}$cycloalkyl (e.g. cyclopropyl), $C_{1-4}$alkoxy (e.g. methoxy), aryl, aryloxy or azaheteroaryl; $R^3$ represents —C(=O)—NHR$^6$, —C(=O)—CH$_2$R$^6$ or —O—CH$_2$R$^6$ where $R^6$ is a dimethyl- or dihalo-azaheteroaryl (e.g. 3,5-dimethyl- isoxazol-4-yl, or 3,5-dimethyl- or 3,5-dichloro-pyrid-4-yl, or an N-oxide thereof); $A^1$ is a direct bond or a methylene linkage;

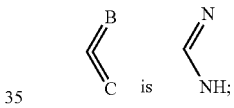

$Q^1$ is a CH linkage and $Z^1$ is an oxygen atom, and N-oxides thereof, and their prodrugs, and pharmaceutically acceptable salts and solvates (e.g. hydrates) of the compounds of formula (Ia) and N-oxides thereof, and their prodrugs.

A further particular group of compounds of the present invention are compounds of formula (Ib):

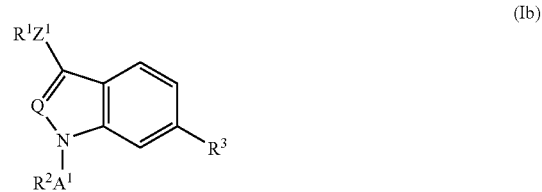

(Ib)

wherein $R^1$, $R^2$, $R^3$, $A^1$ and $Z^1$ are as defined previously, and Q represents a CH linkage or a nitrogen atom, and N-oxides thereof, and their prodrugs, and pharmaceutically acceptable salts and solvates (e.g. hydrates) of the compounds of formula (Ib) and N-oxides thereof, and their prodrugs.

Compounds of formula (Ib) in which $R^1$ represents methyl is preferred.

Compounds of formula (Ib) in which $R^2$ represents a straight- or branched-chain $C_{4-9}$alkyl group (e.g. heptyl), a cycloalkyl group (e.g. cyclopentyl, cyclohexyl), an aryl (e.g. optionally substituted phenyl), a heteroaryl (e.g. optionally substituted thienyl) or heterocycloalkyl (e.g. tetrahydofuranyl, tetrahydropyranylmethyl) are preferred. Compounds of formula (Ib) in which $R^3$ represents —C(=O)—NHR$^6$, —C(=O)—CH$_2$R$^6$ or —O—CH$_2$R$^6$ where R$^6$ represents a disubstituted azaheteroaryl group, or a N-oxide thereof, more particularly a dialkyl- or dihalo-azaheteroaryl group or an N-oxide thereof, are preferred. Azaheteroaryl groups substituted on both of the positions adjacent to the position of attachment of R$^6$ to the rest of the molecule, for example 3,5-dimethyl-isoxazolyl, or 3,5-dimethyl- or 3,5-chloro-pyridyl or an N-oxide thereof, are most preferred.

Compounds of formula (Ib) in which $A^1$ represents a direct bond are a preferred group of compounds.

Compounds of formula (Ib) in which $A^1$ represents a straight or branched chain alkylene linkage containing from 1 to 6 carbon atoms, for example a methylene, ethylene, propylene, methylmethylene, butylmethylene linkage, (especially methylene) are also a preferred group of compounds.

Compounds of formula (Ib) in which Q represents a CH linkage or a nitrogen atom are preferred.

Compounds of formula (Ib) in which $Z^1$ represents a direct bond are preferred.

A preferred group of compounds of the invention are compounds of formula (Ib) in which: $R^1$ is hydrogen or methyl; $R^2$ is $C_{4-9}$alkyl (e.g. heptyl), $C_{3-7}$cycloalkyl (e.g. cyclopentyl, cyclohexyl), aryl, heteroaryl (e.g. optionally substituted thienyl), heterocycloalkyl (e.g. tetrahydofuranyl, tetrahydropyranylmethyl); $R^3$ represents —C(=O)—NHR$^6$, —C(=O)—CH$_2$R$^6$ or —O—CH$_2$R$^6$ where R$^6$ is a dimethyl- or dihalo-azaheteroaryl (e.g. 3,5-dimethyl-isoxazol-4-yl, or 3,5-dimethyl- or 3,5-dichloro-pyrid-4-yl, or an N-oxide thereof); $A^1$ is a direct bond or a methylene linkage and $Z^1$ is a direct bond and Q is a CH linkage or a nitrogen atom, and N-oxides thereof, and their prodrugs, and pharmaceutically acceptable salts and solvates (e.g. hydrates) of the compounds of formula (Ib) and N-oxides thereof, and their prodrugs.

A further particular group of compounds of the present invention are compounds of formula (Ic):

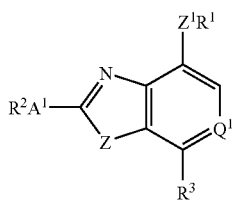

(Ic)

wherein $R^1$, $R^2$, $R^3$, $A^1$, $Q^1$, Z and $Z^1$ are as defined previously, and N-oxides thereof, and their prodrugs, and pharmaceutically acceptable salts and solvates (e.g. hydrates) of the compounds of formula (Ic) and N-oxides thereof, and their prodrugs.

Compounds of formula (Ic) in which $R^1$ represents methyl or difluoromethyl are preferred.

Compounds of formula (Ic) in which $R^2$ represents a straight- or branched-chain $C_{1-4}$alkyl group (e.g. isopropyl), a cycloalkyl group (e.g. cyclopropyl), alkoxy (e.g. methoxy), aryl, aryloxy, heteroaryl (e.g. pyridyl) are preferred.

Compounds of formula (Ic) in which $R^3$ represents —C(=O)—NHR$^6$, —C(=O)—CH$_2$R$^6$ or —O—CH$_2$R$^6$ where R$^6$ represents a disubstituted azaheteroaryl group, or a N-oxide thereof, more particularly a dialkyl- or dihalo-azaheteroaryl group or an N-oxide thereof, are preferred. Azaheteroaryl groups substituted on both of the positions adjacent to the position of attachment of R$^6$ to the rest of the molecule, for example 3,5-dimethyl-isoxazol-4-yl, or 3,5-dimethyl- or 3,5-dichloro-pyrid-4-yl or an N-oxide thereof, are most preferred.

Compounds of formula (Ic) in which $A^1$ represents a direct bond are a preferred group of compounds.

Compounds of formula (Ic) in which $A^1$ represents a straight or branched chain alkylene linkage containing from 1 to 6 carbon atoms, for example a methylene, ethylene, propylene, methylmethylene, or butylmethylene linkage, (especially methylene) are also a preferred group of compounds.

Compounds of formula (Ic) in which $A^1$ represents a straight or branched chain alkylene linkage containing from 1 to 6 carbon atoms which is substituted by alkoxy, for example a methoxymethylene or methoxypropylmethylene, are a further preferred group of compounds.

Compounds of formula (Ic) in which $Q^1$ is a CH linkage are preferred.

Compounds of formula (Ic) in which Z is an oxygen atom are preferred.

Compounds of formula (Ic) in which $Z^1$ is an oxygen atom are preferred.

A preferred group of compounds of the invention are compounds of formula (Ic) in which: $R^1$ is methyl or difluoromethyl; $R^2$ is $C_{1-4}$alkyl (e.g. isopropyl), $C_{3-6}$cycloalkyl (e.g. cyclopropyl), $C_{1-4}$alkoxy (e.g. methoxy), aryl, aryloxy or azaheteroaryl; $R^3$ represents —C(=O)—NHR$^6$, —C(=O)—CH$_2$R$^6$ or —O—CH$_2$R$^6$ where R$^6$ is a dimethyl- or dihalo-azaheteroaryl (e.g. 3,5-dimethyl-isoxazol-4-yl, or 3,5-dimethyl- or 3,5-dichloro-pyrid-4-yl, or an N-oxide thereof); $A^1$ is a direct bond or a methylene linkage; $Q^1$ is a CH linkage; and Z and $Z^1$ are both oxygen atoms, and N-oxides thereof, and their prodrugs, and pharmaceutically acceptable salts and solvates (e.g. hydrates) of the compounds of formula (Ic) and N-oxides thereof, and their prodrugs.

A further particular group of compounds of the present invention are compounds of formula (Id):

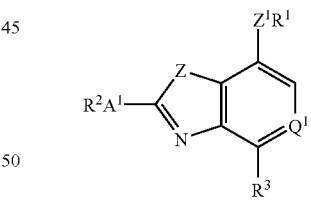

(Id)

wherein $R^1$, $R^2$, $R^3$, $A^1$, $Q^1$, Z and $Z^1$ are as defined previously, and N-oxides thereof, and their prodrugs, and pharmaceutically acceptable salts and solvates (e.g. hydrates) of the compounds of formula (Id) and N-oxides thereof, and their prodrugs.

Compounds of formula (Id) in which $R^1$ represents methyl or difluoromethyl are preferred.

Compounds of formula (Id) in which $R^2$ represents a straight- or branched-chain $C_{1-4}$alkyl group (e.g. isopropyl), a cycloalkyl group (e.g. cyclopropyl), alkoxy (e.g. methoxy), aryl, aryloxy, heteroaryl (e.g. pyridyl) are preferred.

Compounds of formula (Id) in which $R^3$ represents —C(=O)—NHR$^6$, —C(=O)—CH$_2$R$^6$ or —O—CH$_2$R$^6$ where R$^6$ represents a disubstituted azaheteroaryl group, or a N-oxide thereof, more particularly a dialkyl- or dihalo-azaheteroaryl group or an N-oxide thereof, are preferred. Azaheteroaryl groups substituted on both of the positions adjacent to the position of attachment of $R^6$ to the rest of the molecule, for example 3,5-dimethyl-isoxazol-4-yl, or 3,5-dimethyl- or 3,5-dichloro-pyrid-4-yl or an N-oxide thereof, are most preferred.

Compounds of formula (Id) in which $A^1$ represents a direct bond are a preferred group of compounds.

Compounds of formula (Id) in which $A^1$ represents a straight or branched chain alkylene linkage containing from 1 to 6 carbon atoms, for example a methylene, ethylene, propylene, methylmethylene, or butylmethylene linkage, (especially methylene) are also a preferred group of compounds.

Compounds of formula (Id) in which $A^1$ represents a straight or branched chain alkylene linkage containing from 1 to 6 carbon atoms which is substituted by alkoxy, for example a methoxymethylene or methoxypropylmethylene, are a further preferred group of compounds.

Compounds of formula (Id) in which $Q^1$ is a CH linkage are preferred.

Compounds of formula (Id) in which Z is an oxygen atom are preferred.

Compounds of formula (Id) in which $Z^1$ is an oxygen atom are preferred.

A preferred group of compounds of the invention are compounds of formula (Id) in which: $R^1$ is methyl or difluoromethyl; $R^2$ is $C_{1-4}$alkyl (e.g. isopropyl), $C_{3-6}$cycloalkyl (e.g. cyclopropyl), $C_{1-4}$alkoxy (e.g. methoxy), aryl, aryloxy or azaheteroaryl; $R^3$ represents —C(=O)—NHR$^6$, —C(=O)—CH$_2$R$^6$ or —O—CH$_2$R$^6$ where $R^6$ is a dimethyl- or dihalo-azaheteroaryl (e.g. 3,5-dimethyl-isoxazol-4-yl, or 3,5-dimethyl- or 3,5-dichloro-pyrid-4-yl, or an N-oxide thereof); $A^1$ is a direct bond or a methylene linkage; $Q^1$ is a CH linkage; and Z and $Z^1$ are both oxygen atoms, and N-oxides thereof, and their prodrugs, and pharmaceutically acceptable salts and solvates (e.g. hydrates) of the compounds of formula (Id) and N-oxides thereof, and their prodrugs.

A further particular group of compounds of the present invention are compounds of formula (Ie):

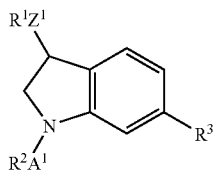

(Ie)

wherein $R^1$, $R^2$, $R^3$, $A^1$ and $Z^1$ are as defined previously, and N-oxides thereof, and their prodrugs, and pharmaceutically acceptable salts and solvates (e.g. hydrates) of the compounds of formula (Ie) and N-oxides thereof, and their prodrugs.

Compounds of formula (Ie) in which $R^1$ represents methyl are preferred.

Compounds of formula (Ie) in which $R^2$ represents a straight- or branched-chain $C_{4-9}$alkyl group (e.g. heptyl), a cycloalkyl group (e.g. cyclopentyl, cyclohexyl), an aryl (e.g. optionally substituted phenyl), a heteroaryl (e.g. optionally substituted thienyl) or heterocycloalkyl (e.g. tetrahydofuranyl, tetrahydropyranylmethyl) are preferred.

Compounds of formula (Ie) in which $R^3$ represents —C(=O)—NHR$^6$, —C(=O)—CH$_2$R$^6$ or —O—CH$_2$R$^6$ where $R^6$ represents a disubstituted azaheteroaryl group, or a N-oxide thereof, more particularly a dialkyl- or dihalo-azaheteroaryl group or an N-oxide thereof, are preferred. Azaheteroaryl groups substituted on both of the positions adjacent to the position of attachment of $R^6$ to the rest of the molecule, for example 3,5-dimethyl-isoxazolyl, or 3,5-dimethyl- or 3,5-chloro-pyridyl or an N-oxide thereof, are most preferred.

Compounds of formula (Ie) in which $A^1$ represents a direct bond are a preferred group of compounds.

Compounds of formula (Ie) in which $A^1$ represents a straight or branched chain alkylene linkage containing from 1 to 6 carbon atoms, for example a methylene, ethylene, propylene, methylmethylene, butylmethylene linkage, (especially methylene) are also a preferred group of compounds.

Compounds of formula (Ie) in which $Z^1$ represents a direct bond are preferred.

A preferred group of compounds of the invention are compounds of formula (Ie) in which: $R^1$ is hydrogen or methyl; $R^2$ is $C_{4-9}$alkyl (e.g. heptyl), $C_{3-7}$cycloalkyl (e.g. cyclopentyl, cyclohexyl), aryl, heteroaryl(e.g. optionally substituted thienyl) or heterocycloalkyl (e.g. tetrahydofuranyl, tetrahydropyranylmethyl); $R^3$ represents —C(=O)—NHR$^6$, —C(=O)—CH$_2$R$^6$ or —O—CH$_2$R$^6$ where $R^6$ is a dimethyl- or dihalo-azaheteroaryl (e.g. 3,5-dimethyl-isoxazol-4-yl, or 3,5-dimethyl- or 3,5-dichloro-pyrid-4-yl, or an N-oxide thereof); $A^1$ is a direct bond or a methylene linkage and $Z^1$ is a direct bond, and N-oxides thereof, and their prodrugs, and pharmaceutically acceptable salts and solvates (e.g. hydrates) of the compounds of formula (Ie) and N-oxides thereof, and their prodrugs.

A further particular group of compounds of the present invention are compounds of formula (If):

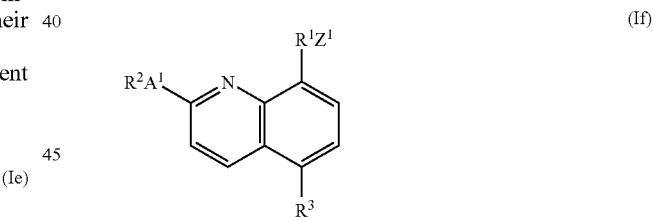

(If)

wherein $R^1$, $R^2$, $R^3$, $A^1$ and $Z^1$ are as defined previously, and N-oxides thereof, and their prodrugs, and pharmaceutically acceptable salts and solvates (e.g. hydrates) of the compounds of formula (If) and N-oxides thereof, and their prodrugs.

Compounds of formula (If) in which $R^1$ represents methyl or difluoromethyl are preferred.

Compounds of formula (If) in which $R^2$ represents a straight- or branched-chain $C_{1-4}$alkyl group (e.g. propyl), a cycloalkyl group (e.g. cyclopropyl), aryl, heteroaryl, or heterocycloalkyl are preferred.

Compounds of formula (If) in which $R^3$ represents —C(=O)—NHR$^6$, —C(=O)—CH$_2$R$^6$ or —O—CH$_2$R$^6$ where $R^6$ represents a disubstituted azaheteroaryl group, or a N-oxide thereof, more particularly a dialkyl- or dihalo-azaheteroaryl group or an N-oxide thereof, are preferred. Azaheteroaryl groups substituted on both of the positions adjacent to the position of attachment of $R^6$ to the rest of the molecule, for example 3,5-dimethyl-isoxazolyl, or 3,5-dimethyl- or 3,5-chloro-pyridyl or an N-oxide thereof, are most preferred.

Compounds of formula (If) in which $A^1$ represents a direct bond are a preferred group of compounds.

Compounds of formula (If) in which $A^1$ represents a straight or branched chain alkylene linkage containing from 1 to 6 carbon atoms, for example a methylene, ethylene, propylene, methylmethylene, butylmethylene linkage, (especially methylene) are also a preferred group of compounds.

Compounds of formula (If) in which $Z^1$ represents an oxygen atom are preferred.

A preferred group of compounds of the invention are compounds of formula (If) in which: $R^1$ is hydrogen or methyl; $R^2$ is $C_{1-4}$alkyl (e.g. propyl), $C_{3-7}$cycloalkyl (e.g. cyclopentyl, cyclohexyl), aryl, heteroaryl or heterocycloalkyl; $R^3$ represents —C(=O)—$NHR^6$, —C(=O)—$CH_2R^6$ or —O—$CH_2R^6$ where $R^6$ is dimethyl- or dihalo-azaheteroaryl (e.g. 3,5-dimethyl-isoxazol-4-yl, or 3,5-dimethyl- or 3,5-dichloro-pyrid-4-yl, or an N-oxide thereof); $A^1$ is a direct bond or a methylene linkage and $Z^1$ is an oxygen atom, and N-oxides thereof, and their prodrugs, and pharmaceutically acceptable salts and solvates (e.g. hydrates) of the compounds of formula (If) and N-oxides thereof, and their prodrugs.

A further preferred group of compounds of the invention are compounds of formula (Ig):

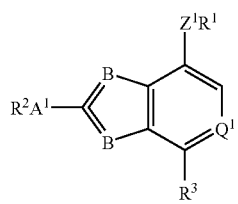

(Ig)

wherein $R^1$ represents hydrogen, or a straight- or branched-chain alkyl group of 1 to about 4 carbon atoms, optionally substituted by one or more halogen atoms;

$R^2$ represents hydrogen, alkoxy, alkyl, alkylsulphinyl, alkylsulphonyl, alkylthio, aryl, arylalkyloxy, arylalkylsulphinyl, arylalkylsulphonyl, arylalkylthio, aryloxy, arylsulphinyl, arylsulphonyl, arylthio, cycloalkenyl, cycloalkenyloxy, cycloalkyl, cycloalkyloxy, heteroaryl, heteroarylalkyloxy, heteroaryloxy, hydroxy, —$SO_2NR^4R^5$, —$NR^4SO_2R^5$, —$NR^4R^5$, —C(=O)$R^5$, —C(=O)C(=O)$R^5$, —C(=O)$NR^4R^5$, —C(=O)$OR^5$, —O(C=O)$NR^4R^5$, or —$NR^4$C(=O)$R^5$ where $R^4$ and $R^5$, which may be the same or different, each represent a hydrogen atom, or an alkyl, aryl, heteroaryl, arylalkyl or heteroarylalkyl group;

$R^3$ represents a group selected from:
(i) —C(=Z)—N($R^a$)$R^6$
(ii) —C(=Z)—$CH_2R^6$
(iii) —C(=Z)—$R^6$
(iv) —$CR^7$=$C(R^8)(CH_2)_n$—$R^6$
(v) —$C(R^9)$=$C(R^{10})R^{11}$
(vi) —$C(R^{12})(R^9)C(R^{10})(R^{13})R^{11}$
(vii) —$C(R^7)(R^{14})CH(R^8)(CH_2)_n$—$R^6$
(viii) —$R^6$
(ix) —$N(R^{15})C(=Z)R^6$
(x) —$C(CH_3)$=N—OC(=O)$NH_2$
(xi) —C(=O)—$N(CH_3)OCH_3$
(xii) —C≡C—$R^6$
(xiii) —$CH_2$—C(=Z)—$R^6$
(xiv) —C(=Z)—C(=Z)$R^6$
(xv) —$CH_2$—$NHR^6$
(xvi) —$CH_2$—$ZR^6$
(xvii) —$CF_2$—$OR^6$
(xviii) —NH—$CH_2R^6$
(xix) —Z—$CH_2R^6$
(xx) —SO—$CH_2R^6$
(xxi) —$SO_2$—$CH_2R^6$
(xxii) —O—$CF_2R^6$
(xxiii) —O—C(=Z)$R^6$
(xxiv) —N=N—$R^6$
(xxv) —NH—$SO_2R^6$
(xxvi) —$SO_2$—$NHR^6$
(xxvii) —CZ—CZ—$NHR^6$
(xxviii) —NH—CO—$OR^6$
(xxix) —O—CO—$NHR^6$
(xxx) —NH—CO—$NHR^6$
(xxxi) —$R^{16}$
(xxxii) —$CX^2$=$CX^3R^6$

[where $R^a$ is a hydrogen atom or alkyl, hydroxy or amino; $R^6$ is aryl or heteroaryl;

$R^7$ and $R^8$, which may be the same or different, is each a hydrogen atom or alkyl, —$CO_2R^{17}$ (where $R^{17}$ is hydrogen or an alkyl, arylalkyl or aryl group), —C(=Z)$NR^{18}R^{19}$ (where $R^{18}$ and $R^{19}$ may be the same or different and each is as described for $R^{17}$), —CN or —$CH_2CN$;

n is zero or an integer 1, 2 or 3;

$R^9$ and $R^{10}$, which may be the same or different, is each a group —$(CH_2)_nR^6$;

$R^{11}$ is a hydrogen atom or alkyl;

$R^{12}$ is a hydrogen or halogen atom or an —$OR^{20}$ group (where $R^{20}$ is a hydrogen atom or an alkyl, alkenyl, alkoxyalkyl or acyl group, or carboxamido or thiocarboxamido group);

$R^{13}$ represents hydrogen or alkyl;

$R^{14}$ is hydrogen or hydroxyl;

$R^{15}$ is hydrogen, alkyl, amino, aryl, arylalkyl, or hydroxy;

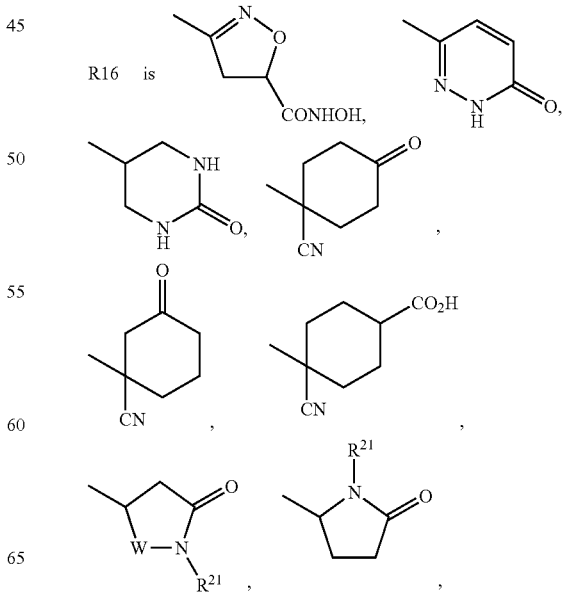

-continued

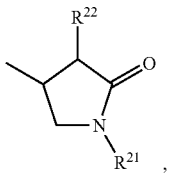

where W is $(CH_2)_m$ or $NR^{22}$;
$R^{21}$ and $R^{22}$ which may be the same or different is each a hydrogen atom, alkyl, acyl, arylalkyl, $-CO_2R^{17}$, heteroarylalkyl, aryl, or heteroaryl;
m is 1 to 4;
$X^2$ and $X^3$ which may be the same or different is each a hydrogen or fluorine atom;
Z represents an oxygen or sulphur atom];
$A^1$ represents a direct bond, or a straight or branched $C_{1-6}$alkylene chain optionally substituted by hydroxyl, alkoxy, oxo, cycloalkyl, aryl or heteroaryl.

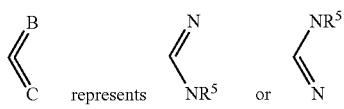

where $R^{23}$ represents a hydrogen atom or a $C_{1-4}$straight- or branched-chain alkyl, aryl, aryl$C_{1-4}$alkyl, heteroaryl or heteroaryl$C_{1-4}$alkyl group;
$Z^1$ represents a direct bond, or an oxygen or sulphur atom, or NH;
$Q^1$ represents a CH or $CX^1$ linkage or a nitrogen atom; and
$X^1$ represents a halogen atom;
and N-oxides thereof, and their prodrugs, pharmaceutically acceptable salts, and solvates (e.g. hydrates), thereof.

Particular compounds of the invention are selected from the following:
N-(3,5-dichloro-4-pyridyl)-7-methoxy-2-methoxymethyl-3H-benzimidazole-4-carboxamide;
N-(3,5-dichloro-4-pyridyl)-7-methoxy-2-phenyl-3H-benzimidazole-4-carboxamide;
N-(3,5-dichloro-4-pyridyl)-7-methoxy-2-phenethyl-3H-benzimidazole-4-carboxamide;
2-benzyl-N-(3,5-dichloro-4-pyridyl)-7-methoxy-3H-benzimidazole-4-carboxamide;
(RS)—N-(3,5-dichloro-4-pyridyl)-7-methoxy-2-(1-phenylethyl)-3H-benzimidazole-4-carboxamide;
(R)—N-(3,5-dichloro-4-pyridyl)-7-methoxy-2-(1-phenylethyl)-3H-benzimidazole-4-carboxamide;
(S)—N-(3,5-dichloro-4-pyridyl)-7-methoxy-2-(1-phenylethyl)-3H-benzimidazole-4-carboxamide;
N-(3,5-dichloro-4-pyridyl)-7-methoxy-2-(4-methoxybenzyl)-3H-benzimidazole-4-carboxamide;
(RS)-2-(cyclohexyl-phenyl-methyl)-N-(3,5-dichloro-4-pyridyl)-7-methoxy-3H-benzimidazole-4-carboxamide;
(R)-2-(cyclohexyl-phenyl-methyl)-N-(3,5-dichloro-4-pyridyl)-7-methoxy-3H-benzimidazole-4-carboxamide;
(S)-2-(cyclohexyl-phenyl-methyl)-N-(3,5-dichloro-4-pyridyl)-7-methoxy-3H-benzimidazole-4-carboxamide;
(RS)—N-(3,5-dichloro-4-pyridyl)-2-(1,2-diphenylethyl)-7-methoxy-3H-benzimidazole-4-carboxamide;
(R)—N-(3,5-dichloro-4-pyridyl)-2-(1,2-diphenylethyl)-7-methoxy-3H-benzimidazole-4-carboxamide;
(S)—N-(3,5-dichloro-4-pyridyl)-2-(1,2-diphenylethyl)-7-methoxy-3H-benzimidazole-4-carboxamide;
(RS)—N-(3,5-dichloro-4-pyridyl)-7-methoxy-2-(2-phenylpropyl)-3H-benzimidazole-4-carboxamide;
(R)—N-(3,5-dichloro-4-pyridyl)-7-methoxy-2-(2-phenylpropyl)-3H-benzimidazole-4-carboxamide;
(S)—N-(3,5-dichloro-4-pyridyl)-7-methoxy-2-(2-phenylpropyl)-3H-benzimidazole-4-carboxamide;
N-(3,5-dichloro-4-pyridyl)-7-methoxy-2-(4-methoxyphenoxymethyl)-3H-benzimidazole-4-carboxamide;
(RS)—N-(3,5-dichloro-4-pyridyl)-7-methoxy-2-(1-phenylbutyl)-3H-benzimidazole-4-carboxamide;
(R)—N-(3,5-dichloro-4-pyridyl)-7-methoxy-2-(1-phenylbutyl)-3H-benzimidazole-4-carboxamide;
(S)—N-(3,5-dichloro-4-pyridyl)-7-methoxy-2-(1-phenylbutyl)-3H-benzimidazole-4-carboxamide;
2-(4-bromobenzyl)-N-(3,5-dichloro-4-pyridyl)-7-methoxy-3H-benzimidazole-4-carboxamide;
(RS)—N-(3,5-dichloro-4-pyridyl)-7-methoxy-2-[3-methoxy-1-phenylpropyl]-3H-benzimidazole-4-carboxamide;
(R)—N-(3,5-dichloro-4-pyridyl)-7-methoxy-2-[3-methoxy-1-phenylpropyl]-3H-benzimidazole-4-carboxamide;
(S)—N-(3,5-dichloro-4-pyridyl)-7-methoxy-2-[3-methoxy-1-phenylpropyl]-3H-benzimidazole-4-carboxamide;
2-(4-cyanobenzyl)-N-(3,5-dichloro-4-pyridyl)-7-methoxy-3H-benzimidazole-4-carboxamide;
N-(3,5-dichloro-4-pyridyl)-7-methoxy-2-[4-(3-pyridyl)benzyl]-3H-benzimidazole-4-carboxamide;
N-(3,5-dichloro-4-pyridyl)-7-methoxy-2-(2-methoxybenzyl)-3H-benzimidazole-4-carboxamide;
(RS)—N-(3,5-dichloro-4-pyridyl)-7-methoxy-2-(methoxyphenyl)methyl-3H-benzimidazole-4-carboxamide;
(R)—N-(3,5-dichloro-4-pyridyl)-7-methoxy-2-(4-methoxyphenyl)methyl-3H-benzimidazole-4-carboxamide;
(S)—N-(3,5-dichloro-4-pyridyl)-7-methoxy-2-(4-methoxyphenyl)methyl-3H-benzimidazole-4-carboxamide;
N-(3,5-dichloro-4-pyridyl)-7-methoxy-2-(2-methoxyphenoxy)methyl-3H-benzimidazole-4-carboxamide;
N-(3,5-dichloro-4-pyridyl)-7-methoxy-2-(3-pyridyl)-3H-benzimidazole-4-carboxamide;
N-(3,5-dichloro-4-pyridyl)-2-isopropyl-7-methoxy-3H-benzimidazole-4-carboxamide;
N-(3,5-dichloro-4-pyridyl)-7-methoxy-2-methyl-3H-benzimidazole-4-carboxamide;
N-(3,5-dichloro-4-pyridyl)-7-methoxy-2-phenoxymethyl-3H-benzimidazole-4-carboxamide;
2-cyclopentyl-N-(3,5-dichloro-4-pyridyl)-7-methoxy-3H-benzimidazole-4-carboxamide;
2-benzyl-N-(3,5-dichloro-4-pyridyl)-3H-benzimidazole-4-carboxamide;
2-cyclopentyl-N-(3,5-dichloro-4-pyridyl)-7-methoxy-1-methyl-benzimidazole-4-carboxamide;
2-cyclopentyl-N-(3,5-dichloro-4-pyridyl)-7-methoxy-3-methyl-3H-benzimidazole-4-carboxamide;
N-(3,5-dichloro-4-pyridyl)-2,7-dimethoxy-3H-benzimidazole-4-carboxamide;
2-cyclopropyl-N-(3,5-dichloro-4-pyridyl)-7-methoxy-3H-benzimidazole-4-carboxamide;
2-cyclopropyl-N-(2,6-difluorophenyl)-7-methoxy-3H-benzimidazole-4-carboxamide;
2-cyclopropyl-N-(2,6-dibromophenyl)-7-methoxy-3H-benzimidazole-4-carboxamide;
2-cyclopropyl-N-(2,6-dimethylphenyl)-7-methoxy-3H-benzimidazole-4-carboxamide;
2-cyclopropyl-N-(2,4,6-trifluorophenyl)-7-methoxy-3H-benzimidazole-4-carboxamide;

2-cyclopropyl-N-(2,6-dichlorophenyl)-7-methoxy-3H-benzimidazole-4-carboxamide;
2-cyclopropyl-N-(3,5-dimethyl-4-pyridyl)-7-methoxy-3H-benzimidazole-4-carboxamide;
2-cyclopropyl-N-(3,5-dimethyl-4-isoxazolyl)-7-methoxy-3H-benzimidazole-4-carboxamide;
N-(3,5-dimethyl-4-isoxazolyl)-7-methoxy-2-methoxymethyl-3H-benzimidazole-4-carboxamide;
2-cyclopropyl-N-(4-carboxy-2,6-dimethylphenyl)-7-methoxy-3H-benzimidazole-4-carboxamide;
N-(4-carboxy-2,6-dimethylphenyl)-7-methoxy-2-methoxymethyl-3H-benzimidazole-4-carboxamide;
N-(3-chloro-4-pyridyl)-7-methoxy-2-propyl-3H-benzimidazole-4-carboxamide;
N-(3,5-dichloro-4-pyridyl)-8-methoxy-2-n-propyl quinoline-5-carboxamide;
N-(3,5-dichloro-4-pyridyl)-3-methyl-1H-indole-6-carboxamide;
1-butyloxycarbonyl-N-(3,5-dichloro-4-pyridyl)-3-methyl-indole-6-carboxamide;
N-(3,5-dichloro-4-pyridyl)-1H-indole-6-carboxamide;
1-(6,6-dimethyl-bicyclo[3.1.1]hept-2-ylmethyl)-3-methyl-N-(4-pyridyl)-1H-indole-6-carboxamide;
1-benzyl-N-(4-hydroxyphenyl)-3-methyl-1H-indole-6-carboxamide;
1-(2-cyclohexyl)ethyl-3-methyl-N-(4-pyrimidinyl)-1H-indole-6-carboxamide;
1-(6,6-dimethyl-bicyclo[3.1.1]hept-2-ylmethyl)-N-(3,5-dimethyl-[1,2,4]-triazol-4-yl)-3-methyl-1H-indole-6-carboxamide;
1-benzyl-N-(3,5-dichloro-4-pyridyl)-3-methyl-1H-indoline-6-carboxamide;
1-(2-cyclopentyl-7-methoxy-3H-benzimidazol-4-yl)-2-(4-pyridyl)ethanone;
2-(3,5-dichloro-4-pyridyl)-1-[1-(4-methoxybenzyl)-3-methyl-1H-indol-6-yl]-ethanone;
2-(3,5-dichloro-pyridin-4-yl)-1-[1-(1-toluene-4-sulphonyl)-3-methyl-1H-indol-6-yl]-ethanone;
1-[1-(4-methoxybenzyl)-3-methyl-1H-indol-6-yl]-2-(4-pyridyl)-ethanone;
1-(7-methoxy-2-methoxymethyl-3H-benzimidazol-4-yl)-2-(4-pyridyl)ethanone;
1,3-bis-(4-pyridyl)-2-(7-methoxy-2-methoxymethyl-3H-benzimidazol-4-yl)-propan-2-ol;
7-methoxy-2-methoxymethyl-4-[2-(4-pyridyl)ethyl]-3H-benzimidazole;
2-(4-carboxamidobenzyl)-N-(3,5-dichloro-4-pyridyl)-7-methoxy-3H-benzimidazole-4-carboxamide;
[2-(3-chlorophenoxy)-pyridin-3-yl]-(7-methoxy-2-methoxymethyl-3H-benzimidazol-4-yl)-methanone;
2-cyclopropyl-4-(3,5-dimethyl-4-pyridylmethoxy)-7-methoxy-3H-benzimidazole;
4-(3,5-dimethyl-4-pyridylmethoxy)-7-methoxy-2-methoxymethyl-3H-benzimidazole;
ethyl 5-(2-cyclopropyl-7-methoxy-benzimidazole-4-yl)pyridine-2-carboxylate;
2-cyclopropyl-7-methoxy-4-(4-morpholinosulphonyl)-3H-benzimidazole;
1-benzyl-7-methoxy-2-methoxymethyl-4-(2-(4-pyridyl)ethyl)-1H-benzimidazole;
1-cyclohexylmethyl-N-(3,5-dichloro-4-pyridyl)-3-methyl-1H-indole-6-carboxamide;
1-(2-cyclohexyl)ethyl-N-(3,5-dichloro-4-pyridyl)-3-methyl-1H-indole-6-carboxamide;
1-[3-(cyclohexyl)propyl]-N-(3,5-dichloro-4-pyridyl)-3-methyl-1H-indole-6-carboxamide;
N-(3,5-dichloro-4-pyridyl)-3-methyl-1-heptyl-1H-indole-6-carboxamide;
N-(3,5-dichloro-4-pyridyl)-3-methyl-1-(tetrahydro-2H-pyran-2-yl)methyl-1H-indole-6-carboxamide;
N-(3,5-dichloro-4-pyridyl)-3-methyl-1-(tetrahydrofuran-2-yl)methyl-1H-indole-6-carboxamide;
N-(3,5-dichloro-4-pyridyl)-3-methyl-1-(toluene-4-sulphonyl)-1H-indole-6-carboxamide;
N-(3,5-dichloro-4-pyridyl)-3-methyl-1-(tetrahydrofuran-3-yl)-1H-indole-6-carboxamide;
N-(3,5-dichloro-4-pyridyl)-3-methyl-1-(3-methoxy)cyclopentyl-1H-indole-6-carboxamide;
N-(3,5-dichloro-4-pyridyl)-3-methyl-1-(5-chlorothiophen-2-yl)methyl-1H-indole-6-carboxamide;
N-(3,5-dichloro-4-pyridyl)-3-methyl-1-(3,5-dimethylisoxazol-4-yl)methyl-1H-indole-6-carboxamide;
N-(3,5-dichloro-4-pyridyl)-3-methyl-1-(2-methyl-thiazol-4-yl)methyl-1H-indole-6-carboxamide;
methyl 5-[6-(3,5-dichloro-pyridin-4-ylcarbamoyl)-3-methyl-indol-1-ylmethyl]-furan-2-carboxylate;
N-(3,5-dichloro-4-pyridyl)-3-methyl-1-(5-phenyl-[1,2,4]oxadiazol-3-yl)methyl-1H-indole-6-carboxamide;
N-(3,5-dichloro-4-pyridyl)-3-methyl-1-(2-morpholin-4-yl)ethyl-1H-indole-6-carboxamide;
methyl 5-[6-(3,5-dichloro-pyridin-4-ylcarbamoyl)-3-methyl-indole-1-yl]-pentanoate;
N-(3,5-dichloro-4-pyridyl)-1-(4-trifluorobenzyl)-3-methyl-1H-indole-6-carboxamide;
N-(3,5-dichloro-4-pyridyl)-3-methyl-1-(4-methylsulphonylbenzyl)-1H-indole-6-carboxamide;
N-(3,5-dichloro-4-pyridyl)-1-(4-methoxycarbonylbenzyl)-3-methyl-1H-indole-6-carboxamide;
N-(3,5-dichloro-4-pyridyl)-3-methyl-1-(3-nitrobenzyl)-1H-indole-6-carboxamide;
N-(3,5-dichloro-4-pyridyl)-1-(naphthalen-2-yl)methyl-3-methyl-1H-indole-6-carboxamide;
N-(3,5-dichloro-4-pyridyl)-1-(biphenyl-4-yl)methyl-3-methyl-1H-indole-6-carboxamide;
N-(3,5-dichloro-4-pyridyl)-3-methyl-1-(1-benzyl-imidazol-2-yl)methyl-1H-indole-6-carboxamide;
N-(3,5-dichloro-pyridin-4-yl)-3-ethyl-1-(toluene-4-sulphonyl)-1H-indole-6-carboxamide;
N-(3,5-dichloro-pyridin-4-yl)-3-isopropyl-1-(toluene-4-sulphonyl)-1H-indole-6-carboxamide;
N-(3,5-dichloro-pyridin-4-yl)-3-(1-hydroxyethyl)-1-(toluene-4-sulphonyl)-1H-indole-6-carboxamide;
N-(3,5-dichloro-pyridin-4-yl)-3-(1-hydroxyisopropyl)-1-(toluene-4-sulphonyl)-1H-indole-6-carboxamide;
N-(3,5-dichloro-pyridin-4-yl)-3-formyl-1-(toluene-4-sulphonyl)-1H-indole-6-carboxamide;
N-(3,5-dichloro-pyridin-4-yl)-3-formyl-1H-indole-6-carboxamide;
1-benzyl-4-[3-methyl-1-(3-phenyl-propyl)-1H-indole-6-yl]-pyrrolidine-2-one;
4-[3-methyl-1-(3-phenyl-propyl)-1H-indole-6-yl]-pyrrolidine-2-one;
1-(4-methoxybenzyl)-3-methyl-6-(1-phenyl-2-pyridin-4-yl-ethyl)-1H-indole;
cis- and trans-[1-(4-methoxybenzyl)-3-methyl-6-(1-phenyl-2-pyridin-4-yl-vinyl)-1H-indole;
6-(1-hydroxy-1-phenyl-2-pyridin-4-yl)ethyl-1-(4-methoxybenzyl)-3-methyl-1H-indole;
[1-(4-methoxy-benzyl)-3-methyl-1H-indol-6-yl]-phenyl methanone;
N-methoxy-1-(4-methoxybenzyl)-3-methyl-N-methyl-1H-indole-6-carboxamide;

1-benzyl-N-(3,5-dichloro-4-pyridyl)-3-methyl-1H-indazole-6-carboxamide;

N-(3,5-dichloro-4-pyridyl)-1-(4-methoxybenzyl)-3-methyl-1H-indazole-6-carboxamide;

N-(3,5-dichloro-4-pyridyl)-4-methoxy-2-methoxymethyl-benzoxazole-7-carboxamide;

N-(3,5-dichloro-4-pyridyl)-3-isopropyl-1-methyl-1H-indole-5-carboxamide; and the corresponding pyridine N-oxides, and their prodrugs and pharmaceutically acceptable salts and solvates (e.g. hydrates) thereof.

Preferred compounds of the invention include:

N-(3,5-dichloro-4-pyridyl)-7-methoxy-2-methoxymethyl-3H-benzimidazole-4-carboxamide;

N-(3,5-dichloro-4-pyridyl)-2,7-dimethoxy-3H-benzimidazole-4-carboxamide;

2-cyclopropyl-N-(3,5-dichloro-4-pyridyl)-7-methoxy-3H-benzimidazole-4-carboxamide;

N-(3,5-dichloro-4-pyridyl)-2-isopropyl-7-methoxy-3H-benzimidazole-4-carboxamide;

2-cyclopropyl-N-(3,5-dimethyl-4-isoxazolyl)-7-methoxy-3H-benzimidazole-4-carboxamide;

N-(3,5-dimethyl-4-isoxazolyl)-7-methoxy-2-methoxymethyl-3H-benzimidazole-4-carboxamide;

2-cyclopropyl-4-(3,5-dimethyl-4-pyridylmethoxy)-7-methoxy-3H-benzimidazole;

4-(3,5-dimethyl-4-pyridylmethoxy)-7-methoxy-2-methoxymethyl-3H-benzimidazole; and the corresponding pyridine N-oxides, and their prodrugs, and pharmaceutically acceptable salts and solvates (e.g. hydrates) thereof.

A more preferred compound of the invention is:

2-cyclopropyl-4-(3,5-dimethyl-4-pyridylmethoxy)-7-methoxy-3H-benzimidazole; and its corresponding pyridine N-oxide, and its prodrugs, and pharmaceutically acceptable salts, and solvates (e.g. hydrates) thereof.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention exhibit marked pharmacological activities according to tests described in the literature which tests results are believed to correlate to pharmacological activity in humans and other mammals. Detailed in vitro and in vivo procedures are described hereinafter.

Compounds of the invention are inhibitors of tumor necrosis factor, especially TNF-alpha. Thus, in a further embodiment, the present invention provides compounds of the invention and compositions containing compounds of the invention for use in the treatment of a patient suffering from, or subject to, conditions which can be ameliorated by the administration of an inhibitor of TNF, especially TNF-alpha. For example, compounds of the present invention are useful in joint inflammation, including arthritis, rheumatoid arthritis and other arthritic conditions such as rheumatoid spondylitis and osteoarthritis. Additionally, the compounds are useful in the treatment of sepsis, septic shock, gram negative sepsis, toxic shock syndrome, adult respiratory distress syndrome, asthma and other chronic pulmonary diseases, bone resorption diseases, reperfusion injury, graft vs. host reaction, allograft rejection and leprosy. Furthermore, the compounds are useful in the treatment of infections such as viral infections and parasitic infections, for example malaria such as cerebral malaria, fever and myalgias due to infection, HIV, AIDS, cachexia such as cachexia secondary to AIDS or to cancer.

Compounds of the invention are also cyclic AMP phosphodiesterase inhibitors, in particular type IV cyclic AMP phosphodiesterase inhibitors. Thus, in another embodiment of the invention, we provide compounds of the invention and compositions containing compounds of the invention for use in the treatment of a patient suffering from, or subject to, conditions which can be ameliorated by the administration of an inhibitor of cyclic AMP phosphodiesterase, especially type IV cyclic AMP phosphodiesterase. For example, compounds within the present invention are useful as bronchodilators and asthma-prophylactic agents and agents for the inhibition of eosinophil accumulation and of the function of eosinophils, e.g. for the treatment of inflammatory airways disease, especially reversible airway obstruction or asthma, and for the treatment of other diseases and conditions characterised by, or having an etiology involving, morbid eosinophil accumulation. As further examples of conditions which can be ameliorated by the administration of inhibitors of cyclic AMP phosphodiesterase such as compounds of the invention there may be mentioned inflammatory diseases, such as atopic dermatitis, urticaria, allergic rhinitis, psoriasis, rheumatoid arthritis, inflammatory diseases (e.g. ulcerative colitis and Crohn's disease), adult respiratory distress syndrome and diabetes insipidus, other proliferative skin diseases such as keratosis and various types of dermatitis, conditions associated with cerebral metabolic inhibition, such as cerebral senility, multi-infarct dementia, senile dementia (Alzheimer's disease), and memory impairment associated with Parkinson's disease, and conditions ameliorated by neuroprotectant activity, such as cardiac arrest, stroke, and intermittent claudication.

Another group of conditions which may be treated with the compounds of the present invention includes diseases and disorders of the central nervous system such as brain trauma, ischaemia, Huntington's disease and tardive dyskinaesia.

Other disease states which may be treated with the compounds of the present invention include pyresis, autoimmune diseases (e.g. systemic lupus erythematosus, allergic erythematosus, multiple sclerosis), type I diabetes mellitus, psoriasis, Bechet's disease, anaphylactoid purpura nephritis, chronic glomerulonephritis and leukemia.

A special embodiment of the therapeutic methods of the present invention is the treating of asthma.

Another special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of cyclic AMP phosphodiesterase or of TNF, especially TNF-alpha, for example conditions as hereinbefore described, which comprises the administration to the patient of an effective amount of compound of the invention or a composition containing a compound of the invention. "Effective amount" is meant to describe an amount of compound of the present invention effective in inhibiting cyclic AMP phosphodiesterase and/or TNF and thus producing the desired therapeutic effect.

According to another aspect of the invention, there is provided the use of a compound of the invention in the manufacture of a medicament for the treatment of a patient suffering from, or subject to, conditions which can be ameliorated by the administration of an inhibitor of cyclic AMP phosphodiesterase, especially type IV cyclic AMP phosphodiesterase.

According to a further aspect of the invention, there is provided the use of a compound of the invention in the manufacture of a medicament for the treatment of a patient suffering from, or subject to, conditions which can be ameliorated by the administration of an inhibitor of TNF, especially of TNF-alpha.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention. The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

The compounds of the present invention may also be formulated for use in conjunction with other therapeutic agents such as agents which increase cyclic AMP production including β-agonists and $PGE_2$. It is to be understood that the present invention includes combinations of compounds of the present invention with one or more of the aforementioned therapeutic agents.

Compounds of the invention may be prepared by the application or adaptation of known methods, by which is meant methods used heretofore or described in the literature.

In particular, compounds of the invention in which the moiety $R^3$ is group (iv) may be prepared by methods similar to those described in WO 94/20455.

Compounds of the invention in which the moiety $R^3$ is group (v) may be prepared by methods similar to those described in WO 94/14800.

Compounds of the invention in which the moiety $R^3$ is group (vi) may be prepared by methods similar to those described in WO 94/14742.

Compounds of the invention in which the moiety $R^3$ is group (vii) may be prepared by methods similar to those described in WO 94/20446.

Compounds of the invention in which the moiety $R^3$ is group (viii) may be prepared by methods similar to those described in WO 94/10118 and WO 95/22520.

Compounds of the invention in which the moiety $R^3$ is group (ix) may be prepared by methods similar to those described in WO 93/25517.

Compounds of the invention in which the moiety $R^3$ is group (x) may be prepared by methods similar to those described in EP-A-0470805.

Compounds of the invention in which the moiety $R^3$ is group (xxviii) may be prepared by methods similar to those described in WO 96/36595, WO 96/36596 and WO 96/36611.

Compounds of the invention in which the moiety $R^3$ is group (xxxiii) wherein $R^{23}$ is

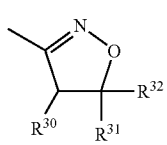

may be prepared by methods similar to those described in WO 95/14681.

Compounds of the invention in which moiety $R^3$ is group (xxxiii) wherein $R^{23}$ is

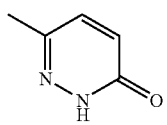

may be prepared by methods similar to those described in EP-A-0523513.

Compounds of the invention in which moiety $R^3$ is group (xxxiii) wherein $R^{23}$ is

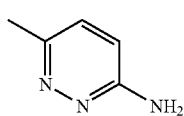

may be prepared by methods similar to those described in EP-A-0510562.

Compounds of the invention in which moiety $R^3$ is group (xxxiii) wherein $R^{23}$ is

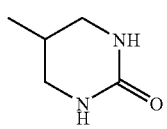

may be prepared by methods similar to those described in EP-A-0428313.

Compounds of the invention in which moiety $R^3$ is group (xxxiii) wherein $R^{23}$ is

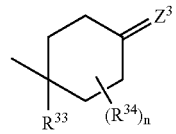

may be prepared by methods similar to those described in U.S. Pat. No. 5,449,686.

Compounds of the invention in which moiety $R^3$ is group (xxxiii) wherein $R^{23}$ is

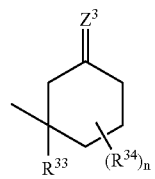

may be prepared by methods similar to those described in WO 95/09624.

Compounds of the invention in which moiety $R^3$ is group (xxxiii) wherein $R^{23}$ is

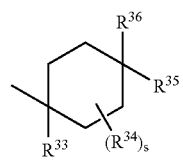

may be prepared by methods similar to those described in WO 93/19749.

Compounds of the invention in which moiety $R^3$ is group (xxxiii) wherein $R^{23}$ is

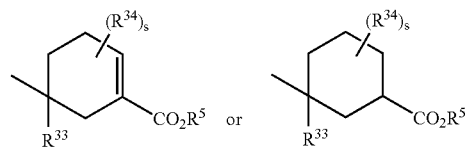

may be prepared by methods similar to those described in WO 95/03794.

Compounds of the invention in which moiety $R^3$ is group (xxxiii) wherein $R^{23}$ is

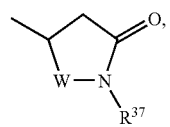

where W is $CH_2$ and $R^{37}$ is hydrogen, may be prepared by methods similar to those described in U.S. Pat. No. 5,420,154.

Compounds of the invention in which moiety $R^3$ is group (xxxiii) wherein $R^{23}$ is

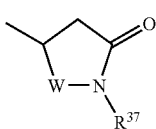

where W is $NR^{39}$ and $R^{37}$ and $R^{39}$ are as hereinbefore defined, may be prepared by methods similar to those described in EP-A-0511865.

Compounds of the invention in which moiety $R^3$ is group (xxxiii) wherein $R^{23}$ is

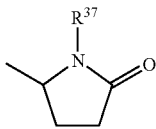

and $R^{37}$ is hydrogen or —$CO_2Me$, may be prepared by methods similar to those described by R. D. Miller and P. Goelitz, J. Org. Chem., 1981, 46, page 1616-1618.

Compounds of the invention in which moiety $R^3$ is group (xxxiii) wherein $R^{23}$ is

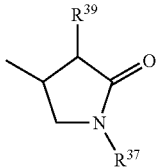

and $R^{37}$ and $R^{39}$ are as hereinbefore defined, may be prepared by methods similar to those described in WO 95/08534.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991.

Compounds of this invention may be represented by the formula (Iz):

$T^1$-$R^3$                (Iz)

wherein $R^3$ is as hereinbefore defined and $T^1$ represents a group of the formula:

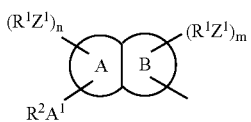

wherein

$R^1$, $R^2$, $A^1$, $Z^1$, n and m are as hereinbefore defined.

In a process (A), compounds of formula (I) wherein $R^3$ represents a —C(=O)—$NHR^6$ group in which $R^6$ is as hereinbefore defined may be prepared by the reaction of compounds of the general formula (II):

$T^1$-C(=O)$X^6$                (II)

wherein $T^1$ is as hereinbefore defined and $X^6$ represents an azido, O-benzotriazol-1-yl, or alkoxy group, such as methoxy, or a halogen atom, such as a bromine, or preferably, a chlorine atom, with compounds of the general formula (III):

$R^6NHR^{48}$                (III)

wherein $R^6$ is as hereinbefore described, including N-oxides of heteroaryl groups, and $R^{48}$ represents a hydrogen atom or an alkanoyl, e.g. acetyl group. The reaction may be carried out in the presence of a base such as an alkali metal dialkyldihydroaluminate, e.g. sodium diethyldihydroaluminate or an alkali metal hydride, e.g. sodium hydride, or in the presence of trimethylaluminium, optionally in an inert solvent, or mixture of inert solvents, chosen from for example a halogenated hydrocarbon (such as dichloromethane), toluene, dimethylformamide, or an ether (e.g. diethyl ether or tetrahydrofuran), preferably at a temperature from 0° C. to the reflux temperature or at the melting point of the reaction mixture. The use of sodium diethyldihydroaluminate is preferred when $R^6$ represents a heteroaryl group containing at least one nitrogen atom.

As another example, in a process (B), compounds of formula (I) wherein $R^3$ represents a —C(=O)—$CH_2R^6$ group in which $R^6$ is as hereinbefore defined, together with compounds of formula (I) wherein $R^3$ represents a —C($R^{13}$)($R^{10}$)C($R^{11}$)($R^{14}$)$R^{12}$ group in which $R^{10}$ and $R^{11}$ each represents a —$(CH_2)_pR^6$ group (where $R^6$ is as hereinbefore defined and p is 1), $R^{12}$ and $R^{14}$ represent hydrogen atoms and $R^{13}$ represents a hydroxy group, may be prepared by the reaction of compounds of the general formula (IV):

$T^1$-$CO_2R^{49}$                (IV)

wherein $T^1$ is as hereinbefore defined and $R^{49}$ represents a $C_{1-5}$alkyl group with compounds of the general formula (V):

$R^6$—$CH_3$                (V)

wherein $R^6$ is as hereinbefore defined, in the presence of a strong base such as lithium diisopropylamide (usually prepared in situ from butyl lithium and diisopropylamine), in an inert solvent, for example an ether, e.g. tetrahydrofuran, preferably at a temperature from −65° C. to 0° C.

Alternatively compounds of formula (I) wherein $R^3$ represents a —C(=O)—$CH_2R^6$ group and $R^6$ is as hereinbefore defined, may be prepared by the oxidation of compounds of the general formula (VI):

$T^1$-CH(OH)$CH_2R^6$                (VI)

wherein $T^1$ and $R^6$ are as hereinbefore defined, by the application or adaptation of known methods. The oxidation can be carried out, for example, by reaction with oxalyl chloride and dimethyl sulphoxide, in a solvent such as dichloromethane, and preferably at a temperature lower than −65° C. These conditions are especially convenient for the preparation of compounds wherein $Z^1$ represents a direct bond or an oxygen atom.

As another example, in a process (C), compounds of formula (I) wherein $R^3$ represents a —C(=O)—$R^6$ group and $R^6$ is as hereinbefore defined may be prepared by reaction of compounds of formula (I), wherein $R^3$ represents a group —C(=O)—N(CH$_3$)OCH$_3$, with compounds of the general formula (VII):

$R^6$—MgBr     (VII)

wherein $R^6$ is as hereinbefore defined, in an inert solvent, for example an ether, e.g. tetrahydrofuran, preferably at a temperature from about 0° C. to about reflux temperature.

Alternatively, in a process (D), compounds of formula (I) wherein $R^3$ represents a —C(=O)—$R^6$ group and $R^6$ is as hereinbefore defined may be prepared by reaction of compounds of formula (II), especially where $X^6$ represents O-benzotriazolyl, with the anion derived from reaction of compounds of formula $R^6$—Br (where $R^6$ is as hereinbefore defined) and butyllithium. The reaction is carried out in an inert solvent such as an ether, e.g. tetrahydrofuran, and at a temperature at about −70° C.

As another example, compounds of formula (I), wherein $R^3$ represents a —CR$^8$=C(R$^9$)(CH$_2$)$_p$—R$^6$ group and $R^6$, $R^8$, $R^9$ and p are as hereinbefore defined, may be prepared by the reaction of compounds of formula (VIII):

$T^1$-C(=O)R$^8$     (VIII)

wherein $T^1$ and $R^8$ are as hereinbefore defined, with the reaction product of a compound of the formula (IX):

[(R$^{50}$)$_3$PCH(R$^9$)(CH$_2$)$_p$R$^6$]$^+$X$^-$     (IX)

wherein $R^9$, $R^6$ and p are as hereinbefore defined, $R^{50}$ represents an aryl, such as phenyl group, and X represents halo, preferably bromo, with a base such as an alkali metal alkoxide (for example potassium t-butoxide), or an alkali metal hydride (for example sodium hydride), or butyl lithium. The reaction is preferably carried out in a solvent such as dimethylformamide or tetrahydrofuran.

Compounds of formula (I) wherein $R^3$ represents a —C(R$^{10}$)=C(R$^{11}$)R$^{12}$ group and $R^{10}$, $R^{11}$ and $R^{12}$ are as hereinbefore defined, may be similarly prepared by the reaction of compounds of formula (X):

$T^1$-C(=O)R$^{10}$     (X)

wherein $T^1$ and $R^{10}$ are as hereinbefore defined, with the phosphorane obtained by treating a compound of the formula (XI):

[(R$^{50}$)$_3$PCH(R$^{11}$)R$^{12}$]$^+$X$^-$     (XI)

wherein $R^{11}$ and $R^{12}$ and $R^{50}$ are as hereinbefore defined with a base as described above.

As another example, compounds of formula (I) wherein $R^3$ represents a —CR$^8$=C(R$^9$)(CH$_2$)$_p$—R$^6$ group, where $R^6$, $R^8$, $R^9$ and p are as hereinbefore defined, may be prepared by the reaction of compounds of formula (VIII), wherein $T^1$ is as hereinbefore defined, with the reaction product of a compound of the formula (XII):

(R$^{51}$O)$_2$P(=O)CH(R$^9$)(CH$_2$)$_p$R$^6$     (XII)

wherein $R^6$, $R^9$ and p are as hereinbefore defined and $R^{51}$ represents a C$_{1-4}$alkyl group, with a base such as an alkali metal alkoxide (for example potassium t-butoxide), or an alkali metal hydride (for example sodium hydride). The reaction is preferably carried out in a solvent such as dimethylformamide or tetrahydrofuran. Compounds of formula (I) wherein $R^3$ represents a —C(R$^{10}$)=C(R$^{11}$)R$^{12}$ group and $R^{10}$, $R^{11}$ and $R^{12}$ are as hereinbefore defined may be prepared in a similar manner to that described above from compounds of formula (X), wherein $T^1$ and $R^{10}$ are as hereinbefore defined, and compounds of formula (XIII):

(R$^{51}$O)$_2$P(=O)CH(R$^{11}$)R$^{12}$     (XIII)

wherein $R^{11}$, $R^{12}$ and $R^{51}$ are as hereinbefore defined.

As another example, compounds of formula (I) wherein $R^3$ represents a —C(R$^{10}$)=C(R$^{11}$)R$^{12}$ group where $R^{10}$, $R^{11}$ and $R^{12}$ are as hereinbefore defined may also conveniently be prepared from compounds of formula (XIV):

$T^1$-C(R$^{10}$)(OH)CH(R$^{11}$)R$^{12}$     (XIV)

wherein $T^1$, $R^{10}$, $R^{11}$ and $R^{12}$ are as hereinbefore defined, by dehydration using an acid such as a Lewis acid (e.g. thionyl bromide) at an elevated temperature, for example the reflux temperature, optionally in the presence of a suitable base such as 1,8-diazabicyclo-[5.4.0]undec-7-ene.

Compounds of formula (I) wherein $R^3$ represents —C(R$^8$)=C(R$^9$)(CH$_2$)$_p$R$^6$ where $R^6$, $R^8$, $R^9$ and p are as hereinbefore defined may be prepared by dehydration of compounds of formula (XV):

$T^1$-C(R$^8$)(OH)CH(R$^9$)(CH$_2$)$_p$R$^6$     (XV)

wherein $T^1$, $R^6$, $R^8$, $R^9$ and p are as hereinbefore defined, using an acid such as a Lewis acid (e.g. thionyl bromide) at an elevated temperature, for example the reflux temperature, optionally in the presence of a suitable base such as 1,8-diazabicyclo-[5.4.0]undec-7-ene. Alternatively the dehydration may be carried out using an acid catalyst, such as 4-toluenesulphonic acid, in an inert solvent, such as benzene, at a temperature from about 0° C. to about reflux temperature.

As another example, compounds of formula (I) wherein $R^3$ represents a —C(R$^{13}$)(R$^{10}$)C(R$^{11}$)(R$^{14}$)R$^{12}$ group where $R^{10}$, $R^{11}$ and $R^{12}$ are as hereinbefore defined, and $R^{13}$ and $R^{14}$ each represent a hydrogen atom, may be prepared by hydrogenation of compounds of the general formula (I) wherein $R^3$ represents a —C(R$^{10}$)=C(R$^{11}$)R$^{12}$ where $R^{10}$, $R^{11}$ and $R^{12}$ are as hereinbefore defined. The hydrogenation may be carried out using hydrogen in the presence of a suitable metal catalyst, e.g. platinum or palladium optionally supported on an inert carrier such as carbon, preferably in a solvent such as methanol or ethanol. Compounds of formula (I) wherein $R^3$ represents a —C(R$^8$)(R$^{15}$)CH(R$^9$)(CH$_2$)$_p$—R$^6$ group where $R^8$, $R^9$ and p are as hereinbefore defined and $R^{15}$ represents a hydrogen atom, may be prepared in a similar manner to that described above by hydrogenation of compounds of the general formula (I) wherein $R^3$ represents a —C(R$^8$)=C(R$^9$)(CH$_2$)$_p$R$^6$ where $R^8$, $R^9$ and p are as hereinbefore defined.

Compounds of formula (I), wherein $R^3$ represents a —C(R$^8$)(R$^{15}$)CH(R$^9$)(CH$_2$)$_p$—R$^6$ group where $R^6$ is as hereinbefore defined and $R^8$, $R^9$ and $R^{15}$ represent hydrogen atoms and p is zero, may be prepared by reduction of compounds of the general formula (I) wherein $R^3$ represents a —C(=O)—CH$_2$R$^6$, where $R^6$ is as hereinbefore defined. The reduction may be carried out with hydrazine hydrate, in the presence of an alkali metal hydroxide, such a potassium hydroxide, in an inert solvent, such as diethylene glycol, at a temperature up to about 100° C.

As another example, compounds of formula (I) wherein $R^3$ represents a $R^6$ group may be prepared by the reaction of compounds of the general formula (XVI):

$$T^1\text{-B(OH)}_2 \tag{XVI}$$

wherein $T^1$ is as hereinbefore defined, with a compound of the general formula (XVII):

$$R^6\text{—}X^7 \tag{XVII}$$

wherein $R^6$ is as hereinbefore described and $X^7$ represents a halogen atom for example a bromine or chlorine atom, or a triflate group, in the presence of a complex metal catalyst such as tetrakis(triphenylphosphine)palladium(0).

Alternatively compounds of formula (I) wherein $R^3$ represents a $R^6$ group may be similarly prepared by the reaction of compounds of the general formula (XVIII):

$$T^1\text{-}X^7 \tag{XVIII}$$

wherein $T^1$ and $X^7$ are as hereinbefore defined, with a compound of the general formula (XIX):

$$R^6\text{—B(OH)}_2 \tag{XIX}$$

wherein $R^6$ is as hereinbefore defined in the presence of a complex metal catalyst such as tetrakis(triphenylphosphine)palladium(0).

Compounds of formula (I) wherein $R^3$ represents a $R^6$ group may also be prepared by reaction of compounds of formula (XVIII) wherein $T^1$ is as hereinbefore defined and $X^7$ is a bromine atom, with a solution of butyllithium in hexane, in an inert solvent such as tetrahydrofuran, at a temperature at about –70° C., followed by reaction with tributyltin chloride and subsequent reaction of the tributyltin intermediate with compounds of formula (XVII) wherein $R^6$ is as hereinbefore defined and $X^7$ is a bromine atom, in the presence of bis(dibenzylidene)acetone palladium(0) and triphenylphosphine in dimethylformamide at a temperature up to about 120° C.

As another example, compounds of formula (I) wherein $R^3$ represents a —NHC(=O)$R^6$ group where $R^6$ is as hereinbefore defined, may be prepared by the reaction of compounds of the general formula (XX):

$$T^1\text{-NH}_2 \tag{XX}$$

wherein $T^1$ is as hereinbefore defined with compounds of formula (XXI):

$$R^6C(=O)X^8 \tag{XXI}$$

wherein $R^6$ is as hereinbefore defined and $X^8$ represents an azido group or a halogen atom, e.g. bromine or, preferably, chlorine atom, are as hereinbefore defined, preferably in the presence of a base such as a tertiary amine, e.g. triethylamine, preferably in a solvent such as dichloromethane.

As another example, compounds of formula (I) wherein $R^3$ represents a —C(CH$_3$)=N—OC(=O)NH$_2$ group may be prepared by the reaction of compounds of the general formula (XXII):

$$T^1\text{-C(=NOH)CH}_3 \tag{XXII}$$

wherein $T^1$ is as hereinbefore defined, with sodium cyanate in an inert solvent such as dichloromethane in the presence of an acid such as acetic acid or trifluoroacetic acid at a temperature at about ambient temperature.

As another example, compounds of formula (I) wherein $R^3$ represents a —C(=O)—N(Me)OCH$_3$ group may be prepared by the reaction of compounds of the general formula (II), wherein $T^1$ is as hereinbefore defined and $X^6$ is a halogen atom, such as a chlorine atom, with N-methyl-O-methylhydroxylamine in an inert solvent such as dimethylformamide.

As another example, compounds of formula (I) wherein $R^3$ represents a —C≡C—$R^6$ group where $R^6$ is as hereinbefore defined, may be prepared by the reaction of compounds of the general formula (XXIII):

$$T^1\text{-I} \tag{XXIII}$$

wherein $T^1$, is as hereinbefore defined, with acetylenes of the general formula (XXIV):

$$R^6C\equiv CH \tag{XXIV}$$

wherein $R^6$ is as hereinbefore defined. Preferably the reaction is carried out with the aid of a catalyst, e.g. palladium on carbon and cuprous iodide, preferably with the aid of a base such as a tertiary amine, e.g. triethylamine, preferably in a solvent such as dimethylformamide.

As another example, compounds of formula (I) wherein $R^3$ represents a —CH$_2$—C(=O)—$R^6$ group where $R^6$ is as hereinbefore defined may be prepared by oxidation of compounds of the general formula (XXV):

$$T^1\text{-CH}_2\text{CH(OH)}R^6 \tag{XXV}$$

wherein $T^1$ and $R^6$ are as hereinbefore defined. The oxidation may conveniently be carried out, for example, by reaction with oxalyl chloride and dimethyl sulphoxide, in a solvent such as dichloromethane, and preferably at a temperature lower than –65° C. Alternatively, the oxidation may be carried out by reaction with chromium trioxide in the presence of 3,5-dimethylpyrazole.

As another example, compounds of formula (I) wherein $R^3$ represents a —C(=O)—C(=O)$R^6$ group where $R^6$ is as hereinbefore defined may be prepared by the oxidation of compounds of formula (I) wherein $R^3$ represents a —C(=O)—CH$^2R^6$ group where $R^6$ is as hereinbefore defined. The oxidation may be carried out, for example, by reaction with pyridinium dichromate, preferably in a solvent such as dichloromethane. This reaction is particularly suitable for the preparation of compounds wherein $R^6$ represents a heteroaryl, for example an optionally substituted pyridyl, group.

As another example, compounds of formula (I) wherein $R^3$ represents —CH$_2$—NH$R^6$ group where $R^6$ is as hereinbefore defined may be prepared by the reaction of compounds of the general formula (XXVI):

$$T^1\text{-C(=O)H} \tag{XXVI}$$

wherein $T^1$ is as hereinbefore defined, with compounds of formula (III) wherein $R^6$ is as hereinbefore defined and $R^{48}$ is hydrogen, followed by reduction with sodium cyanoborohydride. This reaction is especially suitable for the preparation of compounds wherein $R^6$ represents an optionally substituted phenyl or naphthyl group.

Alternatively, compounds of formula (I) wherein $R^3$ represents —CH$_2$—NH$R^6$ group where $R^6$ is as hereinbefore defined may be prepared by the reaction of compounds of the general formula (XXVII):

$$T^1\text{-CH}_2X^9 \tag{XXVII}$$

wherein $T^1$ is as hereinbefore defined and $X^9$ represents halogen, preferably a bromine atom, with compounds of formula (III) wherein $R^6$ is as hereinbefore defined and $R^{48}$ is hydrogen. The reaction preferably takes place in the presence of a base such as sodium hydride. The reaction is especially suitable for the preparation of compounds wherein $R^6$ represents an optionally substituted heteroaryl group.

As another example, compounds of formula (I) wherein $R^3$ represents —$CH_2$—$OR^6$ group where $R^6$ is as hereinbefore defined may be prepared by the reaction of compounds of the general formula (XXVII) wherein $T^1$ and $X^9$ are as hereinbefore defined with compounds of formula (XXVIII):

$R^6$—OH (XXVIII)

wherein $R^6$ is as hereinbefore defined, preferably with the aid of a base such as an alkali metal alkoxide, e.g. potassium t-butoxide.

Alternatively compounds of formula (I) wherein $R^3$ represents a —$CH_2$—$OR^6$ group where $R^6$ is as hereinbefore defined may be prepared by the reaction of compounds of the general formula (XXIX):

$T^1$-$CH_2$OH (XXIX)

wherein $T^1$ is as hereinbefore defined, with compounds of formula (XVII) wherein $R^6$ and $X^7$ are as hereinbefore defined, preferably with the aid of a base such as an alkali metal alkoxide, e.g. potassium t-butoxide. The reaction is preferably carried out in a solvent such as tetrahydrofuran.

Alternatively compounds of formula (I) wherein $R^3$ represents a —$CH_2$—$OR^6$ group where $R^6$ is as hereinbefore defined may be prepared by reaction of compounds of the general formula (XXIX) with compounds of formula (XXVIII) wherein $R^6$ is as hereinbefore defined, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

As another example, compounds of formula (I) wherein $R^3$ represents a —$CH_2$—$SR^6$ group where $R^6$ is as hereinbefore defined may be prepared by the reaction of compounds of the general formula (XXVIII), wherein $T^1$ and $X^9$ are as hereinbefore defined with compounds of the general formula (XXX):

$R^6$—SH (XXX)

wherein $R^6$ is as hereinbefore defined, preferably with the aid of a base such as an alkali metal carbonate, e.g. potassium carbonate.

As another example, compounds of formula (I) wherein $R^3$ represents a —$CF_2$—$OR^6$ group where $R^6$ is as hereinbefore defined may be prepared by the reaction of compounds of the general formula (XXXI):

$T^1$-$CF_2$Br (XXXI)

with compounds of the general formula (XXVIII) wherein $R^6$ is as hereinbefore defined, preferably with the aid of a base such as sodium hydride, preferably in a solvent such as dimethylformamide.

As another example, compounds of formula (I) wherein $R^3$ represents a —NH—$CH_2R^6$ group where $R^6$ is as hereinbefore defined may be prepared by the reaction of compounds of the general formula (XX) wherein $T^1$ is as hereinbefore defined, with compounds of the general formula (XXXII):

$R^6$CHO (XXXII)

wherein $R^6$ is as hereinbefore defined, in the presence of a reducing agent such as sodium cyanoborohydride.

As another example, compounds of formula (I) wherein $R^3$ represents a —O—$CH_2R^6$ group where $R^6$ is as hereinbefore defined may be prepared by the reaction of compounds of the general formula (XXXIII):

$T^1$-OH (XXXIII)

wherein $T^1$ is as hereinbefore defined, with compounds of the general formula (XXXIV):

$R^6CH_2X^{10}$ (XXXIV)

wherein $R^6$ is as hereinbefore defined and $X^{10}$ represents hydroxy or a halogen atom. When $X^{10}$ represents hydroxy the reaction is conveniently carried out in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature. When $X^{10}$ represents a halogen atom, especially a chlorine atom, the reaction is preferably carried out in the presence of a base such as an alkali metal carbonate, e.g. potassium carbonate, preferably in an solvent such as dimethylformamide, and at a temperature from about room temperature to about 80° C.

As another example, compounds of formula (I) wherein $R^3$ represents a —S—$CH_2R^6$ group where $R^6$ is as hereinbefore defined may be prepared by the reaction of compounds of the general formula (XXXV):

$T^1$-SH (XXXV)

wherein $T^1$ is as hereinbefore defined, with compounds of formula (XXXIV) wherein $R^6$ is as hereinbefore defined and $X^{10}$ is a halogen atom, preferably a bromine atom. The reaction is preferably carried out in the presence of a base such as an alkali metal alkoxide, e.g. sodium methoxide.

As another example, compounds of formula (I) wherein $R^3$ represents a —O—$CF_2R^6$ group where $R^6$ is as hereinbefore defined may be prepared by the reaction of compounds of the general formula (XXXIII) wherein $T^1$ is as hereinbefore defined with compounds of the general formula (XXXVI):

$R^6CF_2Br$ (XXXVI)

wherein $R^6$ is as hereinbefore defined, preferably with the aid of a base such as sodium hydride, preferably in a solvent such as dimethylformamide.

As another example, compounds of formula (I) wherein $R^3$ represents a —O—C(=O)$R^6$ group where $R^6$ is as hereinbefore defined may be prepared by the reaction of compounds of the general formula (XXXIII), wherein $T^1$ is as hereinbefore defined, with compounds of the general formula (XXI) wherein $R^6$ is as hereinbefore defined, and $X^8$ represents a halogen atom, for example a bromine or, preferably, a chlorine atom, preferably in the presence of a base such as a tertiary amine, e.g. triethylamine, preferably in a solvent such as dichloromethane.

As another example, compounds of formula (I) wherein $R^3$ represents a trans —N=N—$R^6$ group where $R^6$ is as hereinbefore defined may be prepared by the reaction of compounds of the general formula (XXXVII):

$T^1$-$N_2^+BF_4^-$ (XXXVII)

wherein $T^1$ is as hereinbefore defined, with compounds of the general formula (XXXVIII):

$R^6H$ (XXXVIII)

wherein $R^6$ is as hereinbefore defined, preferably with the aid of a base such as lithium diisopropylamide.

As another example, compounds of formula (I) wherein $R^3$ represents a —NH—SO$_2$R$^6$ group where $R^6$ is as hereinbefore defined may be prepared by the reaction of compounds of the general formula (XX), wherein $T^1$ is as hereinbefore defined, with compounds of the general formula (XXXIX):

$$R^6SO_2X^{11} \quad (XXXIX)$$

wherein $R^6$ is as hereinbefore defined and $X^{11}$ represents a halogen, preferably chlorine, atom, preferably with the aid of a base such as a tertiary amine, e.g. triethylamine, preferably in a solvent such as tetrahydrofuran.

As another example, compounds of formula (I) wherein $R^3$ represents a —SO$_2$—NR$^{21}$R$^{22}$ group where $R^{21}$ and $R^{22}$ are as hereinbefore defined may be prepared by the reaction of compounds of the general formula (XXXX):

$$T^1SO_2Cl \quad (XXXX)$$

wherein $T^1$ is as hereinbefore defined with compounds of the general formula (XXXXI):

$$R^{21}-NH-R^{22} \quad (XXXXI)$$

wherein $R^{21}$ and $R^{22}$ are as hereinbefore defined, preferably with the aid of a base such as a tertiary amine, e.g. triethylamine, preferably in a solvent such as tetrahydrofuran.

As another example, compounds of formula (I) wherein $R^3$ represents a —C(=O)—C(=O)—NHR$^6$ group where $R^6$ is as hereinbefore defined may be prepared by the reaction of compounds of the general formula (XXXXII):

$$T^1\text{-COCOOH} \quad (XXXXII)$$

wherein $T^1$ is as hereinbefore defined, with thionyl chloride in an inert solvent such as dichloromethane, followed by reaction with compounds of formula (III) wherein $R^6$ is as hereinbefore defined and $R^{48}$ is hydrogen.

As another example, compounds of formula (I) wherein $R^3$ represents a —NH—CO—OR$^6$ group where $R^6$ is as hereinbefore defined may be prepared by the reaction of compounds of the general formula (XXXXIII):

$$T^1\text{-NCO} \quad (XXXXIII)$$

wherein $T^1$ is as hereinbefore defined, with compounds of formula (XXVIII) wherein $R^6$ is as hereinbefore defined, preferably with the aid of a base such as a tertiary amine, e.g. triethylamine, preferably in a solvent such as dichloromethane.

As another example, compounds of formula (I) wherein $R^3$ represents a —O—CO—NHR$^6$ group where $R^6$ is as hereinbefore defined may be prepared by the reaction of compounds of the general formula (XXXIII) wherein $T^1$ is as hereinbefore defined, with compounds of formula (III) wherein $R^6$ is as hereinbefore defined and $R^{48}$ is hydrogen, together with phosgene or a source thereof, preferably, bis(trichloromethyl)carbonate, preferably with the aid of a base such as a tertiary amine, e.g. triethylamine, preferably in a solvent such as dichloromethane.

As another example, compounds of formula (I) wherein $R^3$ represents a —NH—CO—NHR$^6$ group where $R^6$ is as hereinbefore defined may be prepared by the reaction of compounds of the general formula (XX), wherein $T^1$ is as hereinbefore defined with compounds of the general formula (XXXXIV):

$$R^6\text{NCO} \quad (XXXXIV)$$

wherein $R^6$ is as hereinbefore defined, preferably in the presence of a base such as a tertiary amine, e.g. triethylamine, preferably in a solvent such as dichloromethane.

According to a further feature of the present invention, compounds of formula (I) wherein $R^3$ represents a —NH—CO—NHR$^6$ group where $R^6$ is as hereinbefore defined may be prepared by the reaction of compounds of formula (XX) wherein $T^1$ is as hereinbefore defined with compounds of formula (III) wherein $R^6$ is as hereinbefore defined and $R^{48}$ is hydrogen, together with phosgene or a source thereof. The reaction is preferably carried out by reacting the compound of formula (XX) with phosgene or, preferably, bis(trichloromethyl) carbonate, and by then reacting the product of that reaction with the anion derived from the compound of formula (III), for example by reaction with a base such as sodium hydride. The reactions may be preferably carried out in suitable solvents such as dichloromethane and tetrahydrofuran.

According to a further feature of the present invention, compounds of formula (Ia) wherein

 represents  NH, $A^1$, $R^1$, $R^2$, $R^3$, $Q^1$ and $Z^1$ are as hereinbefore defined, (with the proviso that when $A^1$ is a direct bond then $R^2$ is alkyl, cycloalkyl, aryl, or heteroaryl), may be prepared by reaction of compounds of formula (XXXXV):

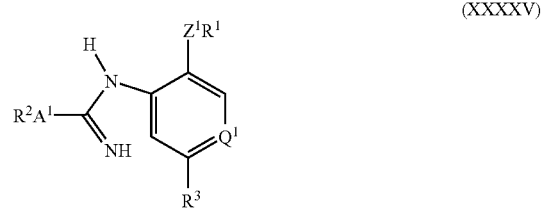

(XXXXV)

wherein $A^1$, $R^1$, $R^2$, $R^3$, $Q^1$ and $Z^1$ are as hereinbefore defined, (with the proviso that when $A^1$ is a direct bond then $R^2$ is alkyl, cycloalkyl, aryl, or heteroaryl), with sodium hypochlorite in the presence of an aqueous acid such as dilute hydrochloric acid, in an alcohol, such as methanol, and at a temperature at about ambient temperature, followed by treatment with an alkali metal carbonate, such as sodium carbonate, at a temperature of about reflux temperature.

According to a further feature of the present invention, compounds of formula (Ia), wherein

 represents NH, $A^1$, $R^1$, $R^2$, $R^3$, $Q^1$ and $Z^1$ are as hereinbefore defined, (with the proviso that when $A^1$ is a direct bond then $R^2$ is alkyl, cycloalkyl, aryl, or heteroaryl), may be prepared by reaction of compounds of formula (XXXXVI):

(XXXXVI)

wherein $R^1$, $R^3$, $Q^1$ and $Z^1$ are as hereinbefore described, with compounds of formula (XXXXVII):

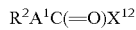
(XXXXVII)

wherein $R^2$ and $A^1$ are as hereinbefore defined, (with the proviso that when $A^1$ is a direct bond then $R^2$ is alkyl, cycloalkyl, aryl, or heteroaryl), and $X^{12}$ represents a hydroxy group or a halogen atom, preferably a chlorine atom. When $X^{12}$ represents a hydroxy group the reaction is preferably carried out in the hydrochloric acid at a temperature at about 125° C. When $X^{12}$ represents a halogen atom the reaction is preferably carried out in an inert solvent, such as dichloromethane, optionally in the presence of triethylamine and at a temperature from about 0° C. to about ambient temperature, followed by reaction of the product with acetic acid at a temperature at about reflux.

According to a further feature of the present invention, compounds of formula (Ia), wherein $R^1$, $R^3$, $Q^1$ and $Z^1$ are as hereinbefore defined, $R^2$ represents a $C_{1-5}$alkoxy group optionally substituted by one or more fluorine atoms, $A^1$ represents a direct bond and

 represents , may be prepared by reaction of compounds of formula (XXXXVI) wherein $R^1$, $R^3$, $Q^1$ and $Z^1$ are as hereinbefore described, with compounds of formula (XXXXVIII):

$(R^{49}O)_4C$ (XXXXVIII)

wherein $R^{49}$ is a $C_{1-5}$alkyl group optionally substituted by one or more fluorine atoms. The reaction may conveniently be carried out in acetic acid at a temperature up to about reflux temperature.

As another example, compounds of formula (Ia) wherein

$R^1$, $R^3$, $Q^1$ and $Z^1$ are as hereinbefore described, $R^2$ is alkylthio, arylthio or arylalkylthio and $A^1$ represents a direct bond, may be prepared by reaction of compounds of formula (XXXXIX):

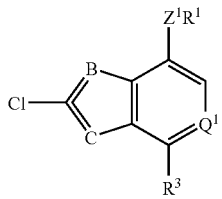
(XXXXIX)

wherein

$R^1$, $R^3$, $Q^1$ and $Z^1$ are as hereinbefore described, with the appropriate alkyl- or aryl- or arylalkylthiol. The reaction may conveniently be carried out in an inert solvent such as methanol or dimethylformamide, at a temperature from about room temperature to about 80° C., optionally in the presence of an alkali metal carbonate, such as potassium carbonate.

Alternatively compounds of formula (Ia) wherein

$R^1$, $R^3$, $Q^1$ and $Z^1$ are as hereinbefore described, $R^2$ represents alkylthio or arylalkylthio and $A^1$ represents a direct bond, may be prepared by reaction of compounds of formula (L):

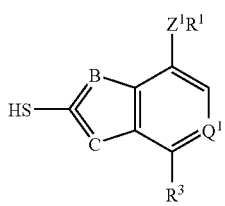
(L)

wherein $R^1$, $R^3$,

$Q^1$ and $Z^1$ are as hereinbefore described, with the appropriate alkyl- or arylalkylhalide. The reaction may conveniently be carried out in an inert solvent such as methanol or dimethylformamide, at a temperature from about room temperature to about 80° C., optionally in the presence of an alkali metal carbonate, such as potassium carbonate.

As another example, compounds of formula (Ia) wherein

$R^1$, $R^3$, $Q^1$ and $Z^1$ are as hereinbefore described, $R^2$ represents $NR^4R^5$ where $R^4$ and $R^5$ are as hereinbefore described and $A^1$ represents a direct bond, may be prepared by reaction of compounds of formula (XXXXIX) wherein

$R^1$, $R^3$, $Q^1$ and $Z^1$ are as hereinbefore described, with compounds of formula (LI):

$$HNR^4R^5 \qquad (LI)$$

wherein $R^4$ and $R^5$ are as hereinbefore described. The reaction may conveniently be carried out in an inert solvent for example an alcohol such as isopropanol, at a temperature from about room temperature to about 80° C., optionally in the presence of an alkali metal carbonate, such as potassium carbonate.

As another example, compounds of formula (Ia) wherein

$R^1$, $R^3$, $Q^1$ and $Z^1$ are as hereinbefore described, $R^2$ represents —C(=O)$R^5$, in which $R^5$ is aryl or heteroaryl, and $A^1$ represents a direct bond, may be prepared by reaction of compounds of formula (LII):

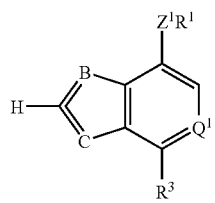

(LII)

wherein $R^1$, $R^3$,

$Q^1$ and $Z^1$ are as hereinbefore described, with compounds of formula (LIII):

$$R^5C(=O)X^{13} \qquad (LIII)$$

wherein $R^5$ is aryl or heteroaryl and $X^{13}$ is a chlorine atom. The reaction may conveniently be carried out in an inert solvent for example dimethylformamide, at a temperature up to about 150° C., under vacuo, optionally in the presence of triethylamine.

As another example, compounds of formula (I) wherein $R^3$ represents a

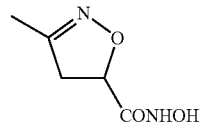

may be prepared by reaction of compounds of formula (I) wherein $R^3$ represents a

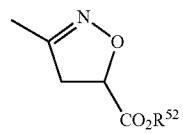

in which $R^{52}$ is a methyl or ethyl group, with hydroxylamine hydrochloride in the presence of sodium methoxide, in a solvent such as an alcohol, for example methanol, and at a temperature at about room temperature.

As another example, compounds of formula (I) wherein $T^1$ is as hereinbefore described and the moiety $R^3$ represents a

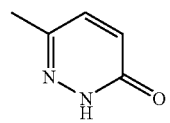

group may be prepared by reaction of compounds of formula (VIII) wherein $R^8$ is methyl, with glyoxylic acid monohydrate at about 100° C. to 150° C., followed by treatment with hydrazine hydrate at reflux.

As another example, compounds of formula (I) wherein $R^3$ represents a

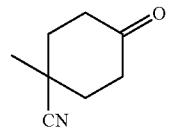

group may be prepared by reaction of compounds of formula (LIV):

$$T^1-C(CN)[(CH_2)_2CO_2R^{52}]_2 \qquad (LIV)$$

wherein $T^1$ is as hereinbefore described and $R^{52}$ is a methyl or an ethyl group, with an alkali metal hydride, for example sodium hydride, in an inert solvent, such as 1,2-dimethoxyethane, at a temperature about reflux temperature, followed by heating the product with a mixture of concentrated hydrochloric acid and 20% sulphuric acid in ethanol at reflux temperature.

As another example, compounds of formula (I) wherein $R^3$ represents a

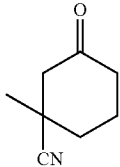

group may be prepared by reaction of compounds of formula (I), wherein $T^1$ is as hereinbefore described and the moiety $R^3$ represents a

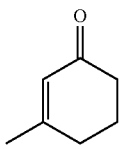

group, with diethyl aluminium cyanide in an inert solvent, such as toluene, and at a temperature at about room temperature.

Compounds of formula (I), wherein $R^3$ represents a

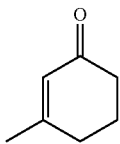

group may be prepared by reaction of compounds of formula (XVIII), wherein $T^1$ is as hereinbefore described and $X^7$ is a bromine atom, with an alkyl lithium, such as n-butyl lithium at −78° C., in an inert solvent, such as tetrahydrofuran, followed by reaction with 3-methoxycyclohex-2-enone (prepared according to the method of A. J. Pearson et al., J. Org. Chem., 1984, 49, pages 3887-3891) at a temperature at about 0° C.

As another example, compounds of formula (I) wherein $R^3$ represents a

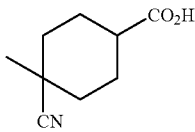

group may be prepared by hydrolysis of compounds of formula (I) wherein $R^3$ represents a

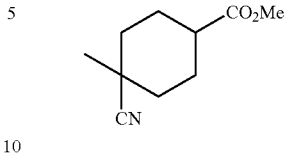

group, with an alkali metal hydroxide such as potassium hydroxide in an aqueous alcohol such as aqueous methanol and at a temperature from about room temperature to about reflux.

Compounds of formula (I), wherein $R^3$ represents a

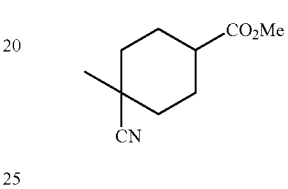

group, may be prepared by reaction of compounds of formula (I), wherein $R^3$ represents a

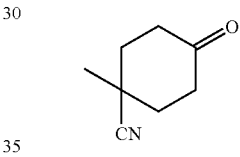

group, with triflic anhydride in the presence of an appropriate tertiary amine base, or with lithium diisopropylamide at −78° C., in an inert solvent such as tetrahydrofuran, followed by treatment with N-phenyl trifluorosulphonimide. The resulting enol triflate may be then be reacted with carbon monoxide in an alcohol such as methanol, optionally mixed with dimethylformamide, in the presence of an amine, such as triethylamine, and an appropriate palladium catalyst, such as tetrakis(triphenylphosphine)palladium, at a temperature at about room temperature.

As another example, compounds of formula (I) wherein $R^3$ represents a

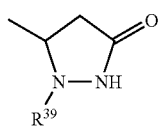

group, in which $R^{39}$ is hydrogen, alkyl, aryl, arylalkyl, heteroaryl, or heteroarylalkyl, may be prepared by reaction of compounds of formula (LV):

$$T^1\text{-CH}=\text{CH}-\text{CO}_2\text{H} \quad \text{(LV)}$$

wherein $T^1$ is as hereinbefore described, with a hydrazine of formula (LVI):

$$R^{39}\text{NH}-\text{NH}_2 \quad \text{(LVI)}$$

wherein $R^{39}$ is hydrogen, alkyl, aryl, arylalkyl, heteroaryl, or heteroarylalkyl. The reaction is preferably carried out in an inert solvent, such as toluene, at a temperature at about 100° C.

As another example, compounds of formula (I) wherein $R^3$ represents a

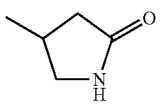

group may be prepared by reduction of compounds of the general formula (LVII):

 (LVII)

wherein $T^1$ and $R^{49}$ are as hereinbefore described, followed by hydrolysis with sodium hydroxide. The reduction may be carried out using hydrogen in the presence of Raney Nickel preferably in a solvent such as methanol or ethanol and at a temperature at about room temperature.

As another example, compounds of formula (I) wherein $R^3$ represents a group

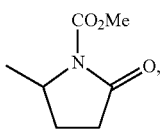

may be prepared by oxidation of compounds of formula (LVIII):

 (LVIII)

wherein $T^1$ is as hereinbefore described, with Jones reagent in acetone at room temperature.

According to a further feature of the present invention, in a process (E), compounds of the present invention of formula (Ia) wherein $R^1$, $R^2$, $R^3$, $A^1$, $Q^1$ and $Z^1$ are as hereinbefore defined, and

may be prepared by deprotection of compounds of formula (LIX):

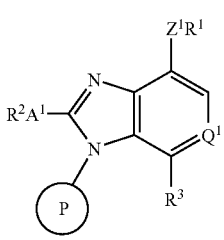 (LIX)

wherein $R^1$, $R^2$, $R^3$, $A^1$, $Q^1$ and $Z^1$ are as hereinbefore defined and ⓟ is a suitable protecting group, for example a 2-trimethylsilanyl-ethoxymethyl group. When ⓟ is a 2-trimethylsilanyl-ethoxymethyl group the deprotection reaction may conveniently be carried out by treatment with hydrochloric acid, in an alcohol, such as ethanol, and at a temperature at about reflux temperature. This process is particularly convenient for compounds of formula (Ia) wherein $R^3$ is a group —O—CH$_2$—R$^6$ in which $R^6$ is as hereinbefore defined.

According to a further feature of the present invention, in a process (F) compounds of the invention may be prepared by interconversion of other compounds of the invention.

For example compounds of the invention containing an imino group may be alkylated with an alkyl halide, arylalkyl halide or heteroarylalkyl halide. Thus compounds of formula (Ia) wherein

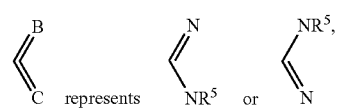

and $R^5$ represents $C_{1-4}$straight- or branched-chain alkyl, an aryl$C_{1-4}$alkyl or a heteroaryl$C_{1-4}$alkyl group may be prepared by reaction of compounds of formula (Ia) wherein

with a $C_{1-4}$straight- or branched-chain alkyl halide, an aryl$C_{1-4}$alkyl halide or a heteroaryl$C_{1-4}$alkyl halide. The alkylation may for example be carried out in the presence of a base, such as an alkali metal hydride, e.g. sodium hydride, in dimethylformamide, or dimethyl sulphoxide, at a temperature from about 0° C. to about 100° C.

As another example of the interconversion process, compounds of the invention containing an imino group may be acylated with an acyl halide, aroyl halide or heteroaroyl halide. The acylation may for example be carried out in the presence of a suitable base, such as triethylamine or pyridine, optionally in dimethylformamide, at a temperature from about 0° C. to about 100° C.

As another example of the interconversion process, compounds of the invention containing a heterocyclic group wherein the hetero atom is a nitrogen atom may be oxidised to their corresponding N-oxides. This interconversion is especially convenient for the preparation of compounds of the invention wherein $Z^1$ represents an oxygen atom and wherein neither $R^2$ or $R^3$ contain an oxidisable groups such as a thioether. The oxidation may conveniently be carried out by means of reaction with a mixture of hydrogen peroxide and an organic acid, e.g. acetic acid, preferably at or above room temperature, for example at a temperature of about 60-90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

As another example of the interconversion process, an N-oxide group within a compound of formula (I) may be reduced to a nitrogen atom. More particularly, one or more of the N-oxide groups in a compound of formula (I) wherein $Q^1$ represents a nitrogen atom in its oxidised form and $R^2$ and/or $R^3$ represents a heteroaryl group containing one or more nitrogen ring atoms in its oxidised form, may be reduced to a nitrogen atom. The reduction of an N-oxide group may be carried out by reaction with diphosphorus tetraiodide in an inert solvent, such as dichloromethane, preferably at or near room temperature, or by reaction with a chlorotrialkylsilane, preferably chlorotrimethylsilane, in the presence of zinc and an alkali metal iodide, e.g. potassium iodide, in an inert solvent, e.g. acetonitrile, at a temperature between about 0° C. and about room temperature, preferably below room temperature.

According to a further example of the interconversion process, compounds of the invention containing hydroxy moieties may be converted to esters by the application or adaptation of known methods of esterification, for example, by reaction with an acid chloride (prepared by treatment of the appropriate acid with thionyl chloride or oxalyl chloride), preferably in the presence of a base, for example a tertiary amine, e.g. triethylamine. Alternatively, compounds of the invention containing hydroxy moieties may be reacted with the appropriate acid in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

As another example of the interconversion process, compounds of the invention containing hydroxy moieties may be prepared by hydrolysis of corresponding esters of the invention. The hydrolysis may conveniently be carried out by alkaline hydrolysis using a base, such as an alkali metal hydroxide or carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example of the interconversion process, compounds of formula (I) wherein $R^3$ represents a group containing $R^6$ which is substituted by a formyl group may be prepared by oxidising the corresponding compounds of formula (I) wherein $R^3$ represents a group containing $R^6$ which is substituted by a hydroxymethyl group for example with oxalyl chloride and dimethyl sulphoxide, in a solvent such as dichloromethane, and preferably at a temperature lower than about −65° C., or, preferably, by reaction with a complex of sulphur trioxide with an amine such as pyridine, preferably in the presence of an amine such as triethylamine, preferably at about room temperature.

As another example of the interconversion process, compounds of formula (I) wherein $R^3$ represents a group containing $R^6$ which is substituted by an amino group may be prepared by reducing the corresponding compounds of formula (I) wherein $R^3$ represents a group containing $R^6$ which is substituted by a nitro group, preferably with iron in acidic conditions, such as in acetic acid, preferably at or above room temperature, more especially at the reflux temperature. Alternatively the reduction may be carried out by reaction with hydrazine hydrate in the presence of ferric chloride and activated carbon, conveniently in a solvent such as methanol, at temperatures from about 25° C. to about 80° C.

As another example of the interconversion process, compounds of formula (I) wherein $R^3$ represents a group containing $R^6$ which is substituted by an acylamino or aroylamino group may be prepared from compounds of formula (I) wherein $R^3$ represents a group containing $R^6$ which is substituted by an amino group, preferably by means of reaction with the appropriate acid halide or acid anhydride in the presence of a tertiary base, such as triethylamine, optionally in an inert solvent, and preferably at a temperature from about 0° C. to reflux.

As another example of the interconversion process, compounds of formula (I) wherein $R^3$ represents a group containing $R^6$ which is substituted by a carboxamido group may be prepared from compounds of formula (I) wherein $R^3$ represents a group containing $R^6$ which is substituted by a cyano group, by means of reaction with hydrogen peroxide and potassium carbonate in dimethyl sulphoxide.

As another example of the interconversion process, compounds of formula (I) wherein $R^3$ represents a group containing $R^6$ which is substituted by a cyano group may be prepared from compounds of formula (I) wherein $R^3$ represents a group containing $R^6$ which is substituted by a bromine atom, by means of reaction with zinc cyanide in the presence of tetrakis(triphenylphosphine) palladium(0) in an inert solvent, such as dimethylformamide, at a temperature at about 100° C.

As another example of the interconversion process, compounds of formula (I) wherein $R^1$ is substituted by fluorine on a carbon atom thereof alpha to the attachment of $R^1$ to $Z^1$ as sulphur, may be prepared by reacting xenon difluoride with corresponding compound of formula (I) wherein said alpha-carbon atoms carry hydrogen atoms instead of said fluorine atoms. The reaction is conveniently carried out in a solvent, such as dichloromethane, in the presence of a molecular sieve, and in an inert atmosphere, at a low temperature, such as at about 0° C.

As another example of the interconversion process, compounds of formula (I) wherein $R^1$ is a difluoromethyl group and $Z^1$ is an oxygen or sulphur atom, may be prepared by reacting a compound of formula (I) wherein $R^1$ is a hydrogen atom and $Z^1$ is an oxygen or sulphur atom, with $HCBrF_2$ in the presence of a strong base in an inert solvent.

As another example, compounds of formula (I) wherein $R^3$ represents a group containing $R^6$ which is a heteroaryl group containing one or more nitrogen ring atoms but carrying no halogen substituents may be prepared by the reduction of the corresponding compounds of formula (I) wherein $R^3$ represents a group containing $R^6$ which does carry one or more halo, such as chloro, substituents, for example by means of ammonium formate in the presence of a palladium catalyst.

As another example, compounds of formula (I) wherein the moiety $R^3$ contains a cis alkenyl group may be prepared by the action of ultraviolet radiation upon the trans-isomer.

As another example of the interconversion process, compounds of formula (I) wherein $R^3$ contains a cis —N═N— linkage may be prepared by the action of ultraviolet radiation upon their trans-isomers.

As another example of the interconversion process, compounds of formula (I) containing sulphoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (I) containing sulphone linkages may be prepared by the oxidation of corresponding compounds containing —S— or sulphoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I) wherein $R^3$ represents a group containing a —CSCH$_2$— linkage may be prepared from compounds of formula (I) wherein $R^3$ represents a group containing a —COCH$_2$— linkage by reaction with phosphorus pentasulphide or 2,4-bis(4-methoxyphenyl)-1,3-dithia-2,4-diphosphetane-2,4-disulphide, preferably in a solvent such as pyridine or toluene, and preferably at a temperature from 0° C. to the reflux temperature.

As another example of the interconversion process, compounds of formula (I) containing a hydroxymethyl group may be prepared by the reduction of the corresponding compounds of formula (I) containing an aryloxycarbonyl or, particularly, alkoxycarbonyl group, preferably by means of reaction with an alkali metal borohydride, preferably in an inert solvent, e.g. tetrahydrofuran, and preferably at or near room temperature.

As another example of the interconversion process, compounds of formula (Ib) in which $R^2$ is hydrogen and $A^1$ is a direct bond may be prepared by heating compounds of formula (Ib) in which the group $R^2$ is a butyloxycarbonyl group and $A^1$ is a direct bond.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from water.

The starting materials and intermediates may be prepared by the application or adaptation of known methods, for example methods as described in the Reference Examples or their obvious chemical equivalents.

Intermediates of formula (II, $T^1$-C(=O)$X^6$) wherein $T^1$ is as hereinbefore defined and $X^6$ represents an O-benzotriazol-1-yl group may be prepared by reaction of compounds of formula (1):

$$T^1\text{-CO}_2H \quad (1)$$

wherein $T^1$ is as hereinbefore defined, with O-benzotriazol-1-yl-N,N,N',N',-bis(tetramethylene)uronium tetrafluoroborate in an inert solvent, for example dichloromethane, at a temperature at about ambient temperature.

Intermediates of formula (II, $T^1$-C(=O)$X^6$) wherein $T^1$ is as hereinbefore defined and $X^6$ represents an azido group may be prepared from compounds of formula (1) wherein $T^1$ is as hereinbefore defined by the application or adaptation of known methods for the preparation of acid azides from carboxylic acids. For example, the reaction may be carried out by means of diphenylphosphoryl azide in the presence of triethylamine in dimethylformamide.

Intermediates of formula (II, $T^1$-C(=O)$X^6$) wherein $T^1$ is as hereinbefore defined and $X^6$ represents a halogen atom may be prepared from compounds of the general formula (1) wherein $T^1$ is as hereinbefore defined, by the application or adaptation of known methods for the preparation of acid halides from carboxylic acids. For example, when $X^6$ represents a chlorine atom, the reaction may be carried out by means of thionyl chloride or, preferably, oxalyl chloride, optionally in the presence of a small amount of dimethylformamide.

Compounds of formula (1, $T^1$-CO$_2$H), wherein $T^1$ is as hereinbefore defined may be prepared by hydrolysis of compounds of formula (IV, $T^1$-CO$_2R^{49}$) wherein $T^1$ and $R^{49}$ are as hereinbefore defined. The hydrolysis may for example be carried out by reaction with a base, such as an alkali metal hydroxide, e.g. sodium or lithium hydroxide, or an alkali metal carbonate, e.g. potassium carbonate, in the presence of water, in an alcohol such as methanol and at a temperature from about ambient to about reflux, followed by reaction with an aqueous acid such as dilute hydrochloric acid.

Intermediates of the general formula (III, $R^6NHR^{48}$)

wherein $R^6$ is as hereinbefore described, including N-oxides of heteroaryl groups, and $R^{48}$ represents an alkanoyl group, e.g. acetyl group may be prepared for example, by the application or adaptation of known methods for the acylation or aromatic amines.

Intermediates of formula (IV) represented by the formula (2):

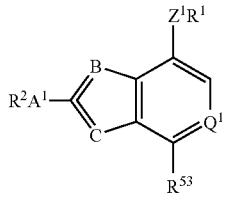
(2)

wherein

 represents $R^{53}$ represents $CO_2R^{49}$ (in which $R^{49}$ is as hereinbefore defined), and $R^1$, $A^1$, $Q^1$ and $Z^1$ are as hereinbefore defined (with the proviso that when $A^1$ is a direct bond then $R^2$ is alkyl, cycloalkyl, aryl, or heteroaryl), may be prepared by reaction of compounds of formula (3):

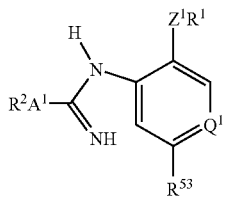
(3)

wherein $R^1$, $R^2$, $A^1$, $Q^1$ and $Z^1$ are as hereinbefore described (with the proviso that when $A^1$ is a direct bond then $R^2$ is alkyl, cycloalkyl, aryl, or heteroaryl), and $R^{53}$ represents —$CO_2R^{49}$ (in which $R^{49}$ is as hereinbefore defined), with sodium hypochlorite in the presence of an aqueous acid such as dilute hydrochloric acid, in an alcohol, such as methanol, and at a temperature at about ambient temperature, followed by treatment of the resultant chloroimine with an alkali metal carbonate, such as sodium carbonate, at a temperature of about reflux temperature.

Intermediates of formula (VIII) represented by the formula (2), wherein

 represents $R^{53}$ represents —C(=O)—$R^8$ (in which $R^8$ is optionally substituted alkyl), and $R^1$, $R^2$ and $A^1$ are as hereinbefore defined, $Q^1$ is CH and $Z^1$ is an oxygen atom (with the proviso that when $A^1$ is a direct bond then $R^2$ is alkyl, cycloalkyl, aryl, or heteroaryl), may be similarly prepared from compounds of formula (3) wherein $R^1$, $R^2$ and $A^1$ are as hereinbefore defined, $R^{53}$ is a group —C(=O)—$R^8$ (in which $R^8$ is optionally substituted alkyl), $Q^1$ is a CH linkage and $Z^1$ is an oxygen atom (with the proviso that when $A^1$ is a direct bond then $R^2$ is alkyl, cycloalkyl, aryl, or heteroaryl).

Intermediates of formula (X) represented by the formula (2), wherein

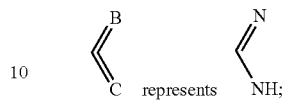 represents $R^{53}$ represents —C(=O)—$R^{10}$ (in which $R^{10}$ is a group —$(CH_2)_pR^6$ where $R^6$ and n are as hereinbefore defined); $R^1$, $R^2$ and $A^1$ are as hereinbefore defined; $Q^1$ is CH and $Z^1$ is an oxygen atom (with the proviso that when $A^1$ is a direct bond then $R^2$ is alkyl, cycloalkyl, aryl, or heteroaryl), may be similarly prepared from compounds of formula (3) wherein $R^1$, $R^2$ and $A^1$ are as hereinbefore defined, $R^{53}$ is a group —C(=O)—$R^{10}$ (in which $R^{10}$ is a group —$(CH_2)_pR^6$ in which $R^6$ and n are as hereinbefore defined), $Q^1$ is a CH linkage and $Z^1$ is an oxygen atom (with the proviso that when $A^1$ is a direct bond then $R^2$ is alkyl, cycloalkyl, aryl, or heteroaryl).

Intermediates of formula (XVIII) represented by the formula (2), wherein

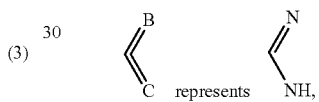 represents $R^{53}$ represents a halogen atom, $Q^1$ is a CH linkage, $Z^1$ is an oxygen atom and $R^1$, $R^2$ and $A^1$ are as hereinbefore defined, (with the proviso that when $A^1$ is a direct bond then $R^2$ is alkyl, cycloalkyl, aryl, or heteroaryl), may be similarly prepared from compounds of formula (3) wherein

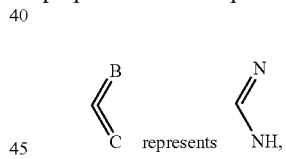 represents $R^{53}$ is a halogen atom, $Q^1$ is a CH linkage, $Z^1$ is an oxygen atom and $R^1$, $R^2$ and $A^1$ are as hereinbefore defined (with the proviso that when $A^1$ is a direct bond then $R^2$ is alkyl, cycloalkyl, aryl, or heteroaryl).

Compounds of formula (18) represented by the formula (2), wherein $R^{53}$ is a nitro group and

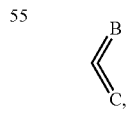

$R^1$, $R^2$, $A^1$, $Q^1$ and $Z^1$ are as hereinbefore defined (with the proviso that when $A^1$ is a direct bond then $R^2$ is alkyl, cycloalkyl, aryl, or heteroaryl), may be similarly prepared from compounds of formula (3) wherein $R^{53}$ is a nitro group and $R^1$, $R^2$, $A^1$, $Q^1$ and $Z^1$ are as hereinbefore defined (with the proviso that when $A^1$ is a direct bond then $R^2$ is alkyl, cycloalkyl, aryl, or heteroaryl).

Compounds of formula (19), represented by the formula (2), wherein $R^{53}$ is a methyl group and

$R^1$, $R^2$, $A^1$, $Q^1$ and $Z^1$ are as hereinbefore defined (with the proviso that when $A^1$ is a direct bond then $R^2$ is alkyl, cycloalkyl, aryl, or heteroaryl), may be similarly prepared from compounds of formula (3) wherein $R^{53}$ is a methyl group and $R^1$, $R^2$, $A^1$, $Q^1$ and $Z^1$ are as hereinbefore defined (with the proviso that when $A^1$ is a direct bond then $R^2$ is alkyl, cycloalkyl, aryl, or heteroaryl).

Compounds of formula (3), wherein $R^1$, $R^2$, $R^{53}$, $A^1$, $Q^1$ and $Z^1$ are as hereinbefore defined (with the proviso that when $A^1$ is a direct bond then $R^2$ is alkyl, cycloalkyl, aryl, or heteroaryl), may be prepared by reaction of compounds of formula (4):

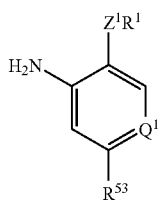

wherein $R^1$, $R^{53}$, $Q^1$ and $Z^1$ are as hereinbefore defined, with compounds of formula $R^2A^1C\equiv N$, wherein $R^2$ and $A^1$ are as hereinbefore defined (with the proviso that when $A^1$ is a direct bond then $R^2$ is alkyl, cycloalkyl, aryl, or heteroaryl), in the presence of an acid catalyst, such as 4-toluenesulphonic acid, at a temperature up to about 180° C.

Intermediates of formula (XXXXV) wherein $R^1$, $R^2$, $R^3$, $A^1$, $Q^1$ and $Z^1$ are as hereinbefore defined (with the proviso that when $A^1$ is a direct bond then $R^2$ is alkyl, cycloalkyl, aryl, or heteroaryl), may be similarly prepared by reaction of compounds of formula (4) wherein $R^1$, $Q^1$ and $Z^1$ are as hereinbefore defined and $R^{53}$ is a group —$R^3$, with compounds of formula $R^2A^1C\equiv N$, wherein $R^2$ and $A^1$ are as hereinbefore defined (with the proviso that when $A^1$ is a direct bond then $R^2$ is alkyl, cycloalkyl, aryl, or heteroaryl), in the presence of an acid catalyst, such as 4-toluenesulphonic acid, at a temperature up to about 180° C.

Compounds of formula (4) wherein $R^1$ is as hereinbefore defined, $R^{53}$ represents a group —$CO_2R^{49}$ in which $R^{49}$ is as hereinbefore defined, $Z^1$ represents an oxygen atom and $Q^1$ represents a nitrogen atom, may be prepared by reaction of compounds of formula (5):

wherein $R^1$ and $R^{49}$ are as hereinbefore defined, with ammonium hydroxide in the presence of sulphur dioxide according to the procedure of H. King, J. Chem. Soc, 1946, page 523.

Compounds of formula (4) wherein $R^1$ and $R^{53}$ are as hereinbefore defined, $Z^1$ represents an oxygen atom or a direct bond and $Q^1$ represents a CH or a CF linkage, may be prepared by reduction of compounds of formula (6):

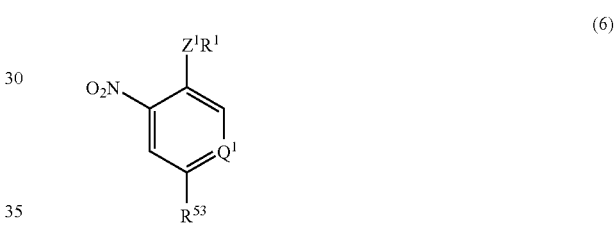

wherein $R^1$ and $R^{53}$ are as hereinbefore defined, $Z^1$ represents an oxygen atom or a direct bond and $Q^1$ represents a CH or a CF linkage. The reduction may conveniently be carried out using hydrogen in the presence of a suitable metal catalyst, e.g. platinum or palladium optionally supported on an inert carrier such as carbon, preferably in a solvent such as methanol or ethanol. Alternatively the reduction may be carried out ammonium chloride and iron, in an aqueous/organic solvent mixture, for example aqueous methanol, at a temperature at about reflux.

Compounds of formula (6), wherein $R^1$ and $R^{53}$ are as hereinbefore defined, $Z^1$ represents an oxygen atom or a direct bond and $Q^1$ represents a CH or a CF linkage, may be prepared by nitration of compounds of formula (7):

wherein $R^1$ and $R^{53}$ are as hereinbefore defined, $Z^1$ represents an oxygen atom or a direct bond and $Q^1$ represents a CH or a CF linkage, with fuming nitric acid at a temperature from about ambient temperature to about 60° C., and separation of the required nitro-isomer (6).

Compounds of formula (6), wherein $R^1$ is $C_{1-4}$alkyl, $R^{53}$ is a bromine atom, $Q^1$ represents a CH linkage and $Z^1$ represents an oxygen atom, may be prepared by bromination of the appropriate 2-($C_{1-4}$alkoxy)-nitrobenzene according to the procedure of S. Kajigaeshi et. al. J. C. S. Perkin Trans. I, 1990, page 897.

Compounds of formula (6), wherein $R^1$ is $C_{1-4}$alkyl, $R^{53}$ is an iodine atom, $Q^1$ represents a CH linkage and $Z^1$ represents an oxygen atom, may be prepared by thallation of the appropriate 2-($C_{1-4}$alkoxy)-nitrobenzene with thallium trifluoroacetate in trifluoroacetic acid followed by iodination with aqueous potassium iodide according to the procedure of A. Mckillop et. al. Tetrahedron. Letters, 1969, page 2427.

Compounds of formula (4), wherein $R^1$ is as hereinbefore defined and $R^{53}$ is a group —$SO_2NR^{21}R^{22}$ in which $R^{21}$ and $R^{22}$ are as hereinbefore described, $Q^1$ is a CH linkage and $Z^1$ is an oxygen atom, may be prepared from reaction of 3-acetamido-4-methoxybenzene sulphonyl chloride (prepared according to the procedure of B. M. Culbertson, J. Chem. Soc., 1968, page 992) with amines of formula $R^{21}R^{22}NH$ wherein $R^{21}$ and $R^{22}$ are as hereinbefore described and subsequent treatment with sodium hydroxide.

Compounds of formula (7), wherein $R^1$ is as hereinbefore defined, $R^{53}$ represents —$CO_2R^{49}$ (in which $R^{49}$ is as hereinbefore defined), $Z^1$ represents an oxygen atom and $Q^1$ represents a CF linkage may be prepared by reaction of compounds of formula (8):

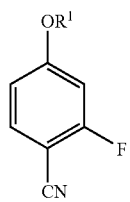

(8)

wherein $R^1$ is as hereinbefore defined, with the appropriate $C_{1-5}$alkyl alcohol, in the presence of hydrogen chloride at a temperature up to about reflux.

Compounds of formula (8), wherein $R^1$ is as hereinbefore defined, may be prepared by reaction of 4-hydroxy-2-fluorobenzonitrile with compounds of the formula (9):

$R^1X^{12}$ (9)

wherein $R^1$ is as hereinbefore described and $X^{12}$ is a bromine or chlorine atom, or a triflate group. The reaction may be carried out in the presence of an alkali metal carbonate, such as potassium carbonate, in an inert solvent such as dimethylformamide, and at a temperature from about room temperature to about 80° C.

Intermediates of formula (2), wherein

$R^{53}$ represents —$CO_2R^{49}$ (in which $R^{49}$ is as hereinbefore defined), $A^1$ is a direct bond, $R^2$ is an alkoxy group, and $R^1$, $Q^1$ and $Z^1$ are as hereinbefore defined, may be prepared by reaction of compounds of formula (10):

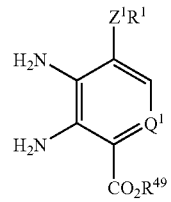

(10)

wherein $R^1$, $R^{49}$, $Q^1$ and $Z^1$ are as hereinbefore described, with compounds of formula (XXXXVIII), wherein $R^{49}$ is as hereinbefore defined. The reaction is carried out in acetic acid at a temperature up to about reflux temperature.

Intermediates of formula (2), wherein

$R^{53}$ represents —$CO_2R^{49}$ (in which $R^{49}$ is as hereinbefore defined), and $R^1$, $A^1$, $Q^1$ and $Z^1$ are as hereinbefore defined (with the proviso that when $A^1$ is a direct bond then $R^2$ is alkyl, cycloalkyl, aryl, or heteroaryl), may be prepared by reaction of compounds of formula (10), wherein $R^1$, $R^{49}$, $Q^1$ and $Z^1$ are as hereinbefore described, with compounds of formula (XXXXVII, $R^2A^1C(=O)X^{10}$), wherein $R^2$ and $A^1$ are as hereinbefore defined (with the proviso that when $A^1$ is a direct bond then $R^2$ is alkyl, cycloalkyl, aryl, or heteroaryl), and $X^{10}$ represents a hydroxy group or a halogen atom, preferably a chlorine atom. When $X^{10}$ represents a hydroxy group the reaction is preferably carried out in the hydrochloric acid at a temperature at about 125° C. When $X^{10}$ represents a chlorine atom the reaction is preferably carried out in an inert solvent, such as dichloromethane, optionally in the presence of triethylamine and at a temperature from about 0° C. to about ambient temperature, followed by reaction of the product with acetic acid at a temperature at about reflux.

Compounds of formula (10), wherein $R^1$, $R^{49}$ and $Z^1$ are as hereinbefore defined and $Q^1$ represents a CH linkage, may be prepared by reduction of compounds of formula (11):

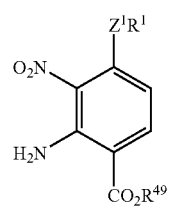

(11)

wherein $R^1$, $R^{49}$ and $Z^1$ are as hereinbefore described. The reduction may be carried out using hydrogen in the presence of a suitable metal catalyst, e.g. platinum or palladium optionally supported on an inert carrier such as carbon, preferably in a solvent such as methanol or ethanol.

Compounds of formula (11) wherein $R^1$, $R^{49}$ and $Z^1$ are as hereinbefore described may be prepared by conversion of the carboxy group in compounds of formula (12):

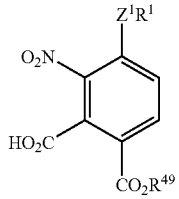
(12)

wherein $R^1$, $R^{49}$ and $Z^1$ are as hereinbefore described, into an amino group. The process involves initial reaction with thionyl chloride, in an inert solvent such as toluene, in the presence of dimethylformamide and at a temperature at about reflux, to form the corresponding acid chloride. The acid chloride is then reacted with a sodium azide in aqueous acetone at a temperature from about 0° C. to about ambient temperature to form the corresponding acid azide, which is heated in an aqueous alcohol, such as t-butanol, at a temperature at about reflux.

Compounds of formula (12) wherein $R^1$, $R^{49}$ and $Z^1$ are as hereinbefore described may be prepared by esterification of the corresponding phthalic acid of formula (13):

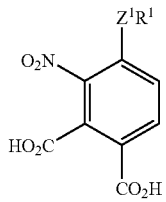
(13)

wherein $R^1$ and $Z^1$ are as hereinbefore described with the appropriate $C_{1-5}$alkyl alcohol.

Compounds of formula (13) wherein $R^1$ and $Z^1$ are as hereinbefore described may be prepared by nitration of the corresponding phthalic acid of formula (14):

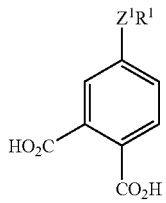
(14)

wherein $R^1$ and $Z^1$ are as hereinbefore described, with fuming nitric acid at a temperature from about ambient temperature to about 60° C.

Intermediates of formula (2), wherein

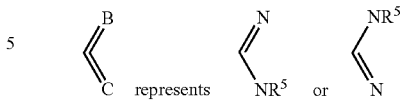

(in which $R^5$ represents a $C_{1-4}$straight- or branched-chain alkyl, an aryl$C_{1-4}$alkyl or a heteroaryl$C_{1-4}$alkyl group), $R^{53}$ represents —$CO_2R^{49}$ (in which $R^{49}$ is as hereinbefore defined), and $R^1$, $R^2$, $A^1$, $Q^1$ and $Z^1$ are as hereinbefore defined, may be prepared by reaction of compounds of formula (2), wherein

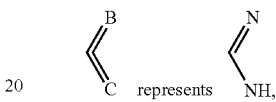

$R^{53}$ represents —$CO_2R^{49}$ (in which $R^{49}$ is as hereinbefore defined), and $R^1$, $R^2$, $A^1$, $Q^1$ and $Z^1$ are as hereinbefore defined, with a $C_{1-4}$straight- or branched-chain alkyl halide or a aryl$C_{1-4}$alkyl halide or a heteroaryl$C_{1-4}$alkyl halide respectively. The alkylation may for example be carried out in the presence of a base, such as an alkali metal hydride, e.g. sodium hydride, in dimethylformamide at a temperature from about 0° C. to about ambient temperature.

Intermediates of formula (IV) or (XXXIII) represented by formula (15):

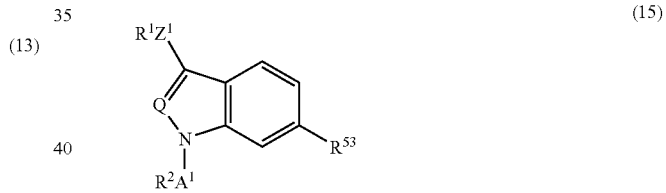
(15)

wherein $R^1$, $R^2$, $A^1$, and $Z^1$ are as hereinbefore defined, $R^{53}$ represents —$CO_2R^{49}$ (in which $R^{49}$ is as hereinbefore defined) or OH, and Q is CH or N, may be prepared for example by the application or adaptation of known methods for the substitution of the imino (NH) group in indoles or indazines of general formula (16):

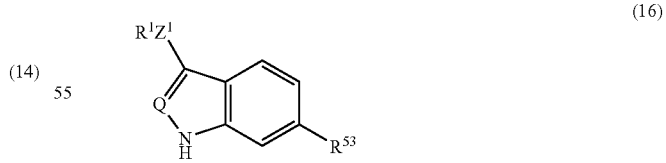
(16)

wherein $R^1$ and $Z^1$ are as defined previously, $R^{53}$ represents —$CO_2R^{49}$ (in which $R^{49}$ is as hereinbefore defined), and Q is CH or N.

Intermediates of formula (16) wherein $R^1$ and $Z^1$ are as defined previously, $R^{53}$ represents $CO_2R^{49}$ (in which $R^{49}$ is as hereinbefore defined) and Q is N may be prepared from compounds of general formula (17), wherein $R^1$ and $Z^1$ are as hereinbefore defined, as shown in Scheme (I):

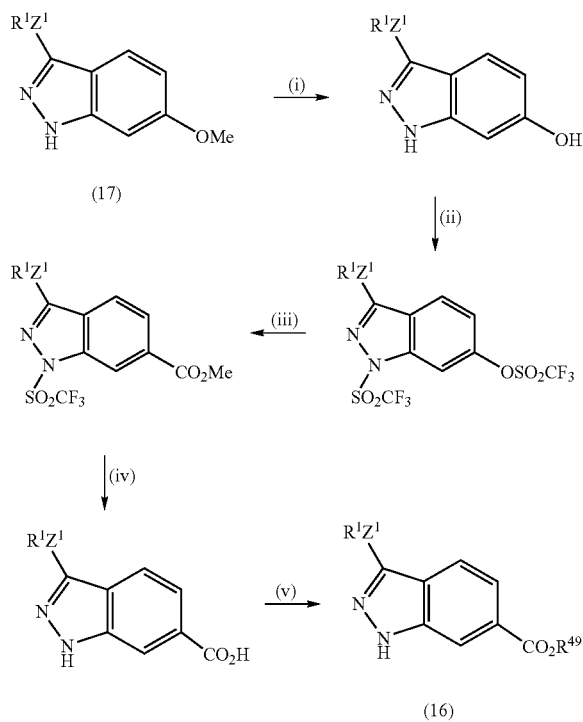

(17)

(16)

Scheme (I)
Reaction Conditions:
(i) treatment with boron tribromide in an inert solvent, such as dichloromethane, at a temperature from about 0° C. to about reflux temperature.
(ii) treatment with N-phenyltrifluoromethane sulphonimide in the presence of a suitable base such as sodium hydride in an inert solvent, such as tetrahydrofuran, at a temperature at about 50° C.
(iii) treatment with carbon monoxide in the presence of palladium acetate, diphenylphosphine ferrocene, triethylamine and methanol.
(iv) treatment with a suitable base, e.g. an alkali metal carbonate, such as potassium carbonate, in a mixture of an alcohol, such as methanol, and water at a temperature up to about reflux temperature.
(v) treatment with the appropriate alcohol $R^{49}$—OH in the presence of hydrogen chloride at room temperature.

Compounds of general formula (17), wherein $R^1$ is methyl and $Z^1$ is a direct bond may be prepared by treatment of 2-fluoro-4-methoxyacetophenone with hydrazine at a temperature up to about reflux temperature.

Compounds of formula (16) wherein $R^1$ and $Z^1$ are as defined previously, $R^{53}$ represents OH and Q is N may be prepared from compounds of general formula (17), wherein $R^1$ and $Z^1$ are as hereinbefore defined, as shown in the first step of Scheme (I).

Intermediates of formula (VI), wherein $T^1$ and $R^6$ are as hereinbefore defined, may be prepared by reaction of compounds of formula (XXVI) wherein $T^1$ is as hereinbefore defined with compounds of general formula (V), wherein $R^6$ is as hereinbefore described, in the presence of a strong base such as lithium diisopropylamine, in an inert solvent, for example an ether such as tetrahydrofuran, preferably at a temperature from −65° C. to 0° C.

Intermediates of formula (VIII), wherein $T^1$ is as hereinbefore defined, and $R_8$ is hydrogen [i.e. $T^1$-C(=O)H, compounds of formula (XXVI)] may be prepared by oxidation of compounds of formula (XXIX) with manganese dioxide in an inert solvent, such as dichloromethane or toluene (or a mixture of both), and at a temperature from about room temperature to about 85° C.

Intermediates of formula (XIV), wherein $T^1$, $R^{10}$, $R^{11}$ and $R^{12}$ are as hereinbefore defined, may be prepared by reaction of compounds of formula (X) wherein $T^1$ and $R^{10}$ are as hereinbefore defined, with an organometallic reagent $R^{11}(R^{12})$CHM [where M is a metal atom, for example a lithium atom] in a solvent such as an ether (e.g. tetrahydrofuran) at a low temperature, e.g. about −78° C. to ambient temperature. Reagents $R^{11}(R^{12})$CHM are either known compounds or may be prepared, preferably in situ during the above process, by reaction of a compound AlkCH$_2$M or [Alk]$_2$NM [where Alk is an alkyl group such as n-propyl or i-propyl] with a compound $R^{11}$CH$_2R^{12}$ using the just mentioned conditions. Intermediates of formula (XV, $T^1$-C($R^8$)(OH)CH($R^9$)(CH$_2$)$_p$R$^6$), wherein $T^1$, $R^6$, $R^8$ and $R^9$ are as hereinbefore defined, may be similarly prepared by reaction of compounds of formula (VIII) wherein $T^1$ and $R^8$ are as hereinbefore defined, with an organometallic reagent $R^6$(CH$_2$)$_p$($R^9$)CHM [where M is a metal atom, for example a lithium atom].

Intermediates of formula (XVI, $T^1$-B(OH)$_2$), wherein $T^1$ is as hereinbefore defined, may be prepared by reaction of compounds of formula (XVIII), wherein $T^1$ is as hereinbefore defined, with n-butyl lithium, in an inert solvent such as tetrahydrofuran, at a temperature about −78° C., followed by reaction with a trialkylborate, such as triethyl borate, and subsequent hydrolysis with a dilute mineral acid such as hydrochloric acid.

Intermediates of formula (XX, $T^1$-NH$_2$), wherein $T^1$ is as hereinbefore defined, may be prepared by hydrogenation of compounds of formula (18):

$T^1$-NO$_2$ (18)

wherein $T^1$ is as hereinbefore defined. The hydrogenation may be carried out using hydrogen in the presence of a suitable metal catalyst, e.g. palladium optionally supported on an inert carrier such as carbon, preferably in a solvent such as methanol or ethanol.

Intermediates of formula (XXII, $T^1$-C(=NOH)CH$_3$), wherein $T^1$ is as hereinbefore defined, may be prepared by reaction of compounds of formula (VIII) wherein $T^1$ is as hereinbefore described and $R^8$ is methyl, with hydroxylamine hydrochloride in the presence of pyridine, in an inert solvent, such as dichloromethane, at a temperature at about room temperature.

Intermediates of formula (XXV, $T^1$-CH$_2$CH(OH)$R^6$), wherein $T^1$ and $R^6$ are as hereinbefore defined, may be prepared by reaction of compounds of formula (19):

$T^1$-CH$_3$ (19)

wherein $T^1$ is as hereinbefore described, with a strong base such as lithium diisopropylamide, in an inert solvent, such as tetrahydrofuran at a temperature at about −78° C. followed by reaction of with compounds of formula (XXXII, $R^6$CHO) wherein $R^6$ is as hereinbefore described.

Intermediates of formula (XXVII, $T^1$-CH$_2X^7$), wherein $T^1$ is as hereinbefore described and $X^7$ is a bromine atom, may be prepared by bromination of compounds of formula (19), wherein $T^1$ is as hereinbefore described, with N-bromosuccinimide, optionally in the presence of a catalyst, such as benzoyl peroxide, in an inert solvent such as dichloromethane and at a temperature at about room temperature.

Alternatively intermediates of formula (XXVII, $T^1$-$CH_2X^7$), wherein $T^1$ is as hereinbefore described and $X^7$ is a bromine atom, may be prepared by reaction of compounds of formula (XXIX, $T^1$-$CH_2OH$), wherein $T^1$ is as hereinbefore described, with N-bromosuccinimide, optionally in the presence of a catalyst, such as benzoyl peroxide, in an inert solvent such as dichloromethane and at a temperature at about room temperature.

Intermediates of formula (XXIX, $T^1$-$CH_2OH$), wherein $T^1$ is as hereinbefore described may be prepared by reduction of compounds of formula (IV, $T^1$-$CO_2R^{49}$) wherein $T^1$ and $R^{49}$ are as hereinbefore described. The reduction may conveniently be carried out with diisobutylaluminium hydride in an inert solvent, such as tetrahydrofuran, at a temperature from about −78° C. to about room temperature. The reduction may also be carried out with lithium aluminium hydride in an inert solvent, such as an ether, for example diethyl ether, at a temperature from about room temperature to about reflux.

Intermediates of formula (XXXI) wherein $T^1$ is as hereinbefore defined may be prepared from compounds of the general formula (20):

$$T^1\text{-}CHF_2 \tag{20}$$

wherein $T^1$ is as hereinbefore defined, by reaction with bromine in carbon tetrachloride and ultraviolet radiation, at a temperature from about ambient to about reflux.

Compounds of formula (20) wherein $T^1$ is as hereinbefore defined may be prepared by the action of sulphur tetrafluoride and hydrofluoric acid on compounds of formula (XXVI) wherein $T^1$ is as hereinbefore defined, optionally in the presence of pyridine, at a temperature from about room temperature to about 125° C., or alternatively by the action of diethylaminosulphur trifluoride, preferably in an inert solvent, such as dichloromethane, preferably at a temperature from about 0° C. to about room temperature.

Intermediates of formula (XXXVII, $T^1$-$N_2^+BF_4^-$), wherein $T^1$ is as hereinbefore defined may be prepared by diazotisation of compounds of formula (XX) with sodium nitrite in the presence of hydrochloric acid, followed by treatment with sodium tetrafluoroborate.

Intermediates of formula (XXXX, $T^1$-$SO_2Cl$), wherein $T^1$ is as hereinbefore defined may be prepared by reaction of compounds of formula (XVIII, $T^1$-$X^7$), wherein $T^1$ is as hereinbefore defined and $X^7$ is a bromine atom with butyl-lithium in tetrahydrofuran at a temperature at about −70° C. followed by treatment with sulphur dioxide at about the same temperature and subsequent reaction of the resulting lithium sulphinate salt with sulphuryl chloride in an inert solvent such as dichloromethane at a temperature at about 0° C.

Intermediates of formula (XXXXII, $T^1$-C(=O)$CO_2H$), wherein $T^1$ is as hereinbefore defined may be prepared by the oxidation of compounds of formula (VIII, $T^1$-C(=O)$R_8$) wherein $T^1$ is as hereinbefore described and $R_8$ is methyl, by reaction with selenium dioxide in the presence of pyridine, using mild conditions, e.g. in a solvent such as ethanol, at or below room temperature.

Intermediates of the general formula (XXXXIII) wherein $T^1$ is as hereinbefore defined may be prepared by treatment of compounds of formula (XX) wherein $T^1$ is as hereinbefore defined with the phosgene equivalent (ClC(=O)$OCCl_3$) in an inert solvent such as dioxan at a temperature at about 60° C.

Intermediates of formulae (XXXXIX), (L) and (LII) wherein $R^1$, $R^3$,

$Q^1$ and $Z^1$ are as hereinbefore described, may be prepared by the application or adaptation of methods for the reactions of o-arylenediamines described in Comprehensive Heterocyclic Chemistry, page 470.

Intermediates of formula (LIV, $T^1$-C(CN)[$(CH_2)_2CO_2R^{52}]_2$), wherein $T^1$ is as hereinbefore described, may be prepared by reaction of compounds of formula (21):

$$T^1\text{-}CH_2CN \tag{21}$$

wherein $T^1$ is as hereinbefore described, with methyl (or ethyl) acrylate in methanol, in the presence of a suitable catalyst, such as Triton-B, and at reflux temperature.

Compounds of formula (21), wherein $T^1$ is as hereinbefore described, may be prepared by reaction of compounds of formula (XXVII), wherein $T^1$ is as hereinbefore described and $X^7$ represents a chlorine atom, with sodium cyanide in dimethylformamide.

Intermediates of the general formula (LV, $T^1$-CH=CH—$CO_2H$) wherein $T^1$ is as hereinbefore described may be prepared by reaction of compounds of formula (XXVI, $T^1$-CHO) with malonic acid in the presence of piperidine in a solvent such as pyridine at a temperature up to about reflux.

Intermediates of the general formula (LVII), wherein $T^1$ is as hereinbefore described may be prepared by reaction of compounds of formula (22):

$$T^1\text{-}CH\text{=}CHCO_2R^{49} \tag{22}$$

wherein $T^1$ and $R^{49}$ are as hereinbefore described, with an nitromethane in the presence of tetramethylguanidine at a temperature at about 65° C.

Compounds of formula (22), wherein $T^1$ and $R^{49}$ are as hereinbefore described may be prepared by reaction of compounds of formula (XXVI) with a carboalkoxymethylene triphenylphosphorane, e.g. carbomethoxymethylene triphenylphosphorane, in an inert solvent, such as toluene, and at a temperature from about room temperature to about 80° C.

Intermediates of formula (LVIII), wherein $T^1$ is as hereinbefore described, may be prepared from compounds of formula (23):

$$T^1\text{-}CH(NHCO_2Me)CH_2CH\text{=}CH_2 \tag{23}$$

wherein $T^1$ is as hereinbefore described, following hydroboration of the double bond with for example diisoamylborane in tetrahydrofuran at 0° C. and subsequent treatment with sodium hydroxide and hydrogen peroxide at 0° C.

Compounds of formula (23), wherein $T^1$ is as hereinbefore described, may be prepared by reaction of compounds of formula (24):

$$T^1\text{-}CH(CO_2H)CH_2CH\text{=}CH_2 \tag{24}$$

wherein $T^1$ is as hereinbefore described, with thionyl chloride, at room temperature, followed by reaction of the resulting acid chloride with sodium azide in acetone at 0° C. to room temperature then thermolysis by refluxing in an inert solvent such as benzene to furnish the isocyanate which may be converted to the required urethane by refluxing in methanol.

Compounds of formula (24, $T^1$-CH(CO$_2$H) CH$_2$CH=CH$_2$), wherein $T^1$ is as hereinbefore described, may be prepared by alkylation of the acid dianion (obtained following treatment with two equivalents of lithium diisopropylamine in tetrahydrofuran) derived from compounds of formula (25):

  (25)

wherein $T^1$ is as hereinbefore described, with allyl bromide.

Intermediates of formula (Iz) wherein $T^1$ is as hereinbefore described and the moiety $R^3$ represents a

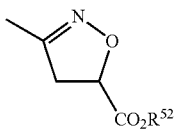

group in which $R^{52}$ is a methyl or ethyl group, may be prepared from compounds of formula (XXVI) by reaction with hydroxylamine hydrochloride in the presence of pyridine, followed by treatment of the so formed oxime with N-chlorosuccinimide and pyridine in an inert solvent, such as dichloromethane, and subsequent reaction of the chloroamidoxime with methyl or ethyl acrylate in the presence of triethylamine.

Intermediates of formula (LIX), wherein $R^1$, $R^2$, $A^1$, $Q^1$ and $Z^1$ are as hereinbefore defined, $R^3$ represents a —O—CH$^2$—$R^6$ group where $R^6$ is as hereinbefore defined, and Ⓟ is a suitable protecting group, for example a 2-trimethylsilanyl-ethoxymethyl group, may be prepared by reaction of compounds of formula (26):

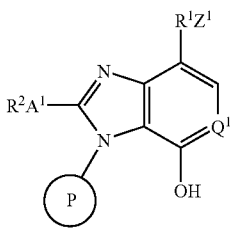  (26)

wherein $R^1$, $R^2$, $A^1$, $Q^1$ and $Z^1$ are as hereinbefore defined, and Ⓟ is a suitable protecting group, for example a 2-trimethylsilanyl-ethoxymethyl group, with compounds of formula (27):

  (27)

wherein $R^6$ is as hereinbefore defined, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Compounds of formula (26) wherein $R^1$, $R^2$, $A^1$, $Q^1$ and $Z^1$ are as hereinbefore defined, and Ⓟ is a suitable protecting group, for example a 2-trimethylsilanyl-ethoxymethyl group, may be prepared by reaction of compounds of formula (28):

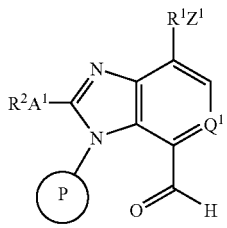  (28)

wherein $R^1$, $R^2$, $A^1$, $Q^1$ and $Z^1$ are as hereinbefore defined, and Ⓟ is a suitable protecting group, for example a 2-trimethylsilanyl-ethoxymethyl group, with m-chloroperbenzoic acid in an inert solvent such dichloromethane and at a temperature from about 0° C. to about room temperature followed by treatment with sodium hydrogen carbonate.

Intermediates of formula (XXXIII), wherein $T^1$ is as hereinbefore defined, may be similarly prepared by reaction of compounds of formula (XXVI), wherein $T^1$ is as hereinbefore defined, with m-chloroperbenzoic acid.

Compounds of formula (28) wherein $R^1$, $R^2$, $A^1$, $Q^1$ and $Z^1$ are as hereinbefore defined, and Ⓟ is a 2-trimethylsilanyl-ethoxymethyl group, may be prepared by reaction of compounds of formula (2), wherein

$R^{53}$ represents a formyl group, and $R^1$, $R^2$, $A^1$, $Q^1$ and $Z^1$ are as hereinbefore defined, with 2-(trimethylsilyl)ethoxymethyl chloride in the presence of sodium hydride, in an inert solvent such as dimethylformamide, and at a temperature at about room temperature.

Compounds of formula (XXXIV) wherein $R^6$ is as hereinbefore defined and $X^8$ is hydroxy may be prepared by reduction of compounds of formula (XXXII) wherein $R^6$ is as hereinbefore defined. The reduction may conveniently be carried out with sodium borohydride in an alcohol such as ethanol at a temperature at about room temperature.

Compounds of formula (XXXII) wherein $R^6$ is heteroaryl, such as a substituted pyridyl, for example 3,5-dimethylpyridyl, may be prepared by reaction of compounds of formula (29):

  (29)

wherein $R^6$ is heteroaryl, such as a substituted pyridyl, for example 3,5-dimethylpyridyl, with butyl lithium in an inert solvent, such as diethyl ether, at −78° C., and subsequent treatment of the resulting anion with dimethylformamide.

Compounds of formula (29) wherein $R^6$ is 3,5-dimethylpyridyl, may be prepared by reaction of 4-nitro-3,5-dimethylpyridine-N-oxide with phosphorous tribromide in a similar manner to the procedures described in J. Chem. Soc., 1956, page 771.

Intermediates of formula (IV) represented by formula (30):

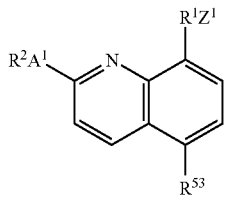

(30)

wherein $R^1$, $R^2$, $A^1$, and $Z^1$ are as hereinbefore defined, $R^{53}$ is $CO_2R^{49}$ (in which $R^{49}$ is as hereinbefore defined), may be prepared for example by reaction of compounds of formula (4), wherein $R^1$ and $Z^1$ are as hereinbefore defined, $R^{53}$ is $CO_2R^{49}$ (in which $R^{49}$ is as hereinbefore defined) and Q is CH, with compounds of formula (31):

$R^2A^1$-CH=CH—CHO  (31)

wherein $R^2$ and $A^1$ are as hereinbefore defined, in the presence of p-chloranil in a alcohol, such as butanol, and at a temperature at about reflux temperature.

Intermediates of formula (IV) represented by formula (32):

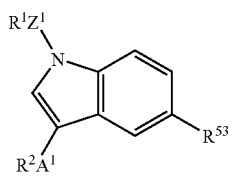

(32)

wherein $R^1$ is hydrogen, $R^2$ is alkyl, aryl or heteroaryl, $R^{53}$ is $CO_2R^{49}$ (in which $R^{49}$ is as hereinbefore defined), $Z^1$ is a direct bond, and $A^1$ is —$CH_2$— or —$CH(CH_3)$—, may be prepared for example by reaction of compounds of formula (33):

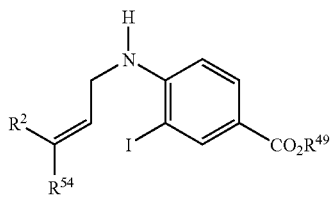

(33)

wherein $R^{49}$ is as hereinbefore defined, $R^2$ is alkyl, aryl or heteroaryl, and $R^{54}$ is hydrogen or methyl, with palladium acetate in the presence of triethylamine in an inert solvent such as acetonitrile, sealed in a bomb, and at a temperature up to about 110° C.

Compounds of formula (33), wherein $R^2$, $R^{53}$ and $A^1$ are as hereinbefore defined, may be prepared by reaction of compounds of formula (34):

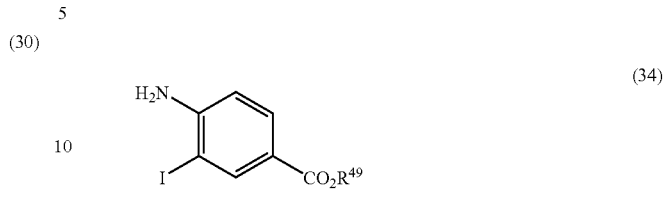

(34)

wherein $R^{53}$ is as hereinbefore defined with an allyl bromide of formula (35):

$R^2(R^{54})C$=CH—CHBr  (35)

wherein $R^2$ and $R^{54}$ are as defined above, in the presence of lithium diisopropylamide in an inert solvent such as an ether, e.g. tetrahydrofuran, at a temperature from about −78° C. to about room temperature.

Compounds of formula (34) may be prepared according to the method of Hill, Tetrahedron, 1990, 46, page 4587.

Intermediates of formula (IV) represented by formula (36):

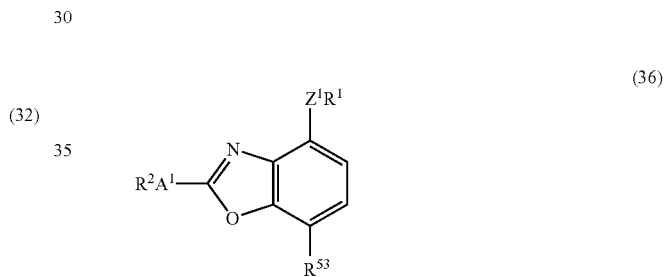

(36)

wherein $R^1$, $R^2$, $A^1$, and $Z^1$ are as hereinbefore defined, and $R^{53}$ is $CO_2R^{49}$, may be prepared for example by reaction of compounds of formula (37):

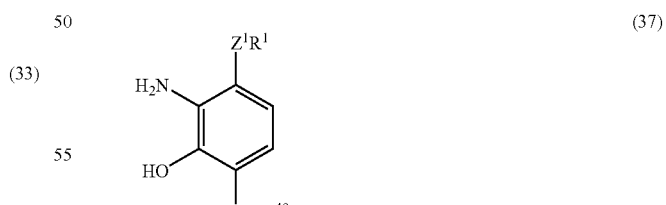

(37)

wherein $R^1$, $R^{49}$ and $Z^1$ are as hereinbefore defined, with compounds of formula $R^2A^1C\equiv N$, wherein $R^2$ and $A^1$ are as hereinbefore defined (with the proviso that when $A^1$ is a direct bond then $R^2$ is alkyl, cycloalkyl, aryl, or heteroaryl), in the presence of an acid catalyst, such as 4-toluenesulphonic acid, at a temperature up to about 180° C.

Compounds of formula (37), wherein $R^1$ and $Z^1$ are as hereinbefore defined, may be prepared by reduction of compounds of formula (38):

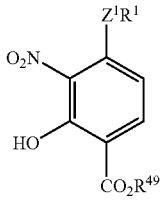
(38)

wherein $R^1$, $R^{49}$ and $Z^1$ are as hereinbefore defined. The reduction may be carried out using hydrogen in the presence of a suitable metal catalyst, e.g. platinum or palladium optionally supported on an inert carrier such as carbon, preferably in a solvent such as ethyl acetate.

Compounds of formula (38), wherein $R^{49}$ is as hereinbefore defined, $R^1$ is methyl and $Z^1$ is an oxygen atom, may be prepared by nitration of methyl 4-methoxysalicylate followed by separation of the required nitro-isomer. The nitration may be conveniently carried out using concentrated nitric acid in acetic acid at a temperature at about room temperature.

Intermediates of formula (IV) represented by formula (39):

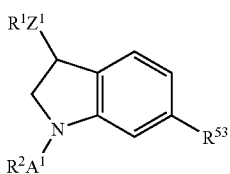
(39)

wherein $R^1$ is alkyl, $R^2$ is alkyl, aryl or heteroaryl, $R^{53}$ is $CO_2R^{49}$ (in which $R^{49}$ is as hereinbefore defined), $Z^1$ is a direct bond, and $A^1$ is as hereinbefore defined, may be prepared for example by reduction of compounds of formula (15), wherein $R^1$ is alkyl, $R^2$ is alkyl, aryl or heteroaryl, $R^{53}$ is $CO_2R^{49}$ (in which $R^{49}$ is as hereinbefore defined), Q is CH, $Z^1$ is a direct bond, and $A^1$ is as hereinbefore defined, using a solution of borane-tetrahydrofuran complex in tetrahydrofuran. The reaction may conveniently be carried out in trifluoroacetic acid at a temperature at about 0° C.

Intermediates of formula (IV) represented by formula (40):

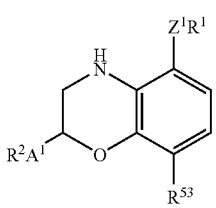
(40)

wherein $R^1$, $R^2$, $A^1$ and $Z^1$ are as hereinbefore defined, and $R^{53}$ is $CO_2R^{49}$ (in which $R^{49}$ is as hereinbefore defined), may be prepared for example by reaction of compounds of formula (37), wherein $R^1$, $R^{49}$ and $Z^1$ are as hereinbefore defined, with compounds of formula (41):

wherein $R^1$ and $A^1$ are as hereinbefore defined, in an inert solvent such as dichloromethane, in the presence of a base, such as sodium hydrogen carbonate, and at a temperature from about 0° C. to about room temperature, followed by heating the intermediate with potassium carbonate in dimethylformamide at 100° C. and then reduction with borane-dimethylsulphide complex in tetrahydrofuran at room temperature.

Intermediates of formula (IV) represented by formula (41):

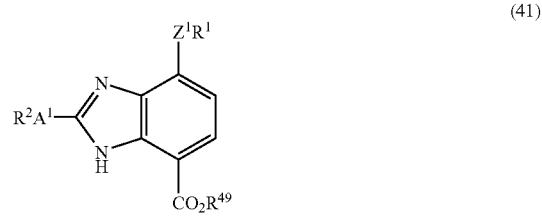
(41)

wherein $R^1$, $R^{49}$ and $Z^1$ are as hereinbefore defined, $R^2$ is alkoxy, arylalkyloxy, heteroarylalkyloxy or hydroxy and $A^1$ is methylene may be prepared for example by reaction of compounds of formula (42):

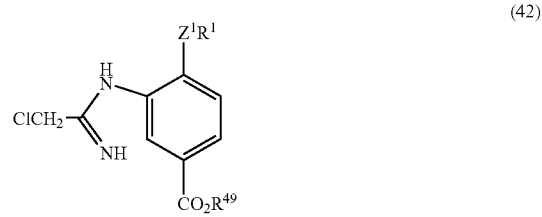
(42)

wherein $R^1$, $R^{49}$ and $Z^1$ are as hereinbefore defined, with with sodium hypochlorite in the presence of an aqueous acid such as dilute hydrochloric acid, in an alcohol, such as methanol, and at a temperature at about reflux temperature, followed by treatment of the resultant chloroimine with water or an alcohol of formula $R^2$—OH where $R^2$ is as defined immediately above, in the presence of an alkali metal carbonate, such as potassium carbonate, at a temperature at about reflux temperature Compounds of formula (42) wherein $R^1$, $R^{49}$ and $Z^1$ are as hereinbefore defined, may be prepared by reaction of compounds of formula (4) wherein $R^1$ and $Z^1$ are as hereinbefore defined, $R^{53}$ is $CO_2R^{49}$ (in which $R^{49}$ is as hereinbefore defined) and $Q^1$ is CH, with chlorocetonitrile in the presence of an acid catalyst, such as 4-toluenesulphonic acid, and at a temperature at about 180° C.

Intermediates of formulae (II), (IV), (VI), (VIII), (X), (XIV), (XV), (XVI), (XVIII), (XX), (XXII), (XXIII), (XXV), (XXVI), (XXVII), (XXIX), (XXXI), (XXXIII), (XXXV), (XXXVII), (XXXX), (XXXXII), (XXXXIII), (XXXXV), (XXXXIX), (L), (LII), (LIV), (LV), (LVIII) and (LIX) are novel compounds and, as such, they and their processes described herein for their preparation constitute further features of the present invention.

The present invention is further Exemplified but not limited by the following illustrative Examples and Reference Examples.

In the nuclear magnetic resonance spectra (NMR) the chemical shifts are expressed in ppm relative to tetramethylsilane. Abbreviations have the following significances: s=singlet; d=doublet; t=triplet; m=multiplet; dd=doublet of doublets; b=broad.

EXAMPLE 1

(a) N-(3,5-Dichloro-4-pyridyl)-7-methoxy-2-methoxymethyl-3H-benzimidazole-4-carboxamide A solution of 4-amino-3,5-dichloropyridine (24.3 g) in tetrahydrofuran (100 ml) was diluted with toluene (150 ml) and the mixture treated dropwise with a solution of sodium diethylaluminate in toluene (36 ml; 2 M, caution pyrophoric reagent). The mixture was stirred at ambient temperature for 30 minutes, then heated at reflux with stirring for a further 30 minutes. The resulting solution was cooled to room temperature and then treated with a solution of 1'-benzotriazolyl 7-methoxy-2-methoxymethyl-3H-benzimidazole-4-carboxylate [Reference Example 1(a)] in tetrahydrofuran (40 ml). The resulting mixture was refluxed for 2 hours, then cooled to ambient temperature, then diluted with chloroform and then washed with a dilute solution of sodium tartrate followed by brine. The organic phase was dried over magnesium sulphate and then evaporated. The solid residue was triturated overnight with ethyl acetate and the insoluble material was recrystallised from a mixture of methanol and toluene to give the title compound (6.06 g) as a white solid, m.p. 230-231° C. [Elemental analysis:—C, 50.0; H, 3.60; N, 14.4%. Calculated:—C, 50.4; H, 3.70; N, 14.7%].

(b) By proceeding in a similar manner to Example 1(a) but using Reference Example 1(b), there was prepared N-(3,5-dichloro-4-pyridyl)-7-methoxy-2-phenyl-3H-benzimidazole-4-carboxamide as a white solid, m.p. 344-345° C. [Elemental analysis:—C, 57.9; H, 3.40; N, 13.2%. Calculated:—C, 58.1; H, 3.41; N, 13.6%].

(c) By proceeding in a similar manner to Example 1(a) but using Reference Example 1(c), there was prepared N-(3,5-dichloro-4-pyridyl)-7-methoxy-2-phenethyl-3H-benzimidazole-4-carboxamide as a white solid, m.p. 211° C. [Elemental analysis:—C, 60.0; H, 4.20; N, 12.5%. Calculated:—C, 59.9; H, 4.11; N, 12.7%].

(d) By proceeding in a similar manner to Example 1(a) but using Reference Example 1(d), there was prepared 2-benzyl-N-(3,5-dichloro-4-pyridyl)-7-methoxy-3H-benzimidazole-4-carboxamide as a white solid, m.p. 200-201° C. [Elemental analysis:—C, 59.4; H, 3.80; N, 12.8%. Calculated:—C, 59.0; H, 3.77; N, 13.1%].

(e) By proceeding in a similar manner to Example 1(a) but using Reference Example 1(e), there was prepared (RS)—N-(3,5-dichloro-4-pyridyl)-7-methoxy-2-(1-phenylethyl)-3H-benzimidazole-4-carboxamide as a white solid, m.p. 220-222° C. [Elemental analysis:—C, 60.3; H, 4.10; N, 12.4%. Calculated:—C, 59.9; H, 4.11; N, 12.7%]. NMR (CDCl$_3$): δ 1.90(d, J=7.5 Hz, 3H), 3.97(s, 3H), 4.41(q, J=7.5 Hz, 1H), 6.80(d, J=8 Hz, 1H), 7.4(m, 5H), 8.19(d, J=8 Hz, 1H), 8.8(s, 2H), 9.05(bs, 1H).

(f) By proceeding in a similar manner to Example 1(a) but using Reference Example 1(f), there was prepared N-(3,5-dichloro-4-pyridyl)-7-methoxy-2-(4-methoxybenzyl)-3H-benzimidazole-4-carboxamide as a white solid, m.p. 225-226° C. [Elemental analysis:—C, 57.6; H, 3.90; N, 12.2%. Calculated:—C, 57.8; H, 3.97; N, 12.3%]. NMR (CDCl$_3$): δ 3.8(s, 3H), 3.95(s, 3H), 4.28(s, 2H), 6.79(d, J=8 Hz, 1H), 6.92(d, J=8 Hz, 2H), 7.26(d, J=8 Hz, 2H), 8.17(d, J=8 Hz, 1H), 8.55(s, 2H), 9.4(bs, 1H).

(g) By proceeding in a similar manner to Example 1(a) but using Reference Example 1(g), there was prepared (RS)-2-(cyclohexyl-phenyl-methyl)-N-(3,5-dichloro-4-pyridyl)-7-methoxy-3H-benzimidazole-4-carboxamide as a white solid; m.p. 281° C. with decomposition. [Elemental analysis:—C, 63.5; H, 5.30; N, 10.9%. Calculated:—C, 63.7; H, 5.14; N, 11.0%].

(h) By proceeding in a similar manner to Example 1(a) but using Reference Example 1(h), there was prepared (RS)—N-(3,5-dichloro-4-pyridyl)-2-(1,2-diphenylethyl)-7-methoxy-3H-benzimidazole-4-carboxamide as a white solid, m.p. 225-226° C. [Elemental analysis:—C, 64.2; H, 4.40; N, 10.5; H$_2$O, 2.0%. Calculated for C$_{28}$H$_{22}$Cl$_2$N$_4$O$_2$.0.5H$_2$O:—C, 63.8; H, 4.37; N, 10.6; H$_2$O, 1.7%].

(i) By proceeding in a similar manner to Example 1(a) but using Reference Example 1(i), there was prepared (RS)—N-(3,5-dichloro-4-pyridyl)-7-methoxy-2-(2-phenylpropyl)-3H-benzimidazole-4-carboxamide as a white solid, m.p. 103-105° C. [Elemental analysis:—C, 60.3; H, 4.50; N, 12.0%. Calculated:—C, 60.1; H, 4.43; N, 12.3%].

(j) By proceeding in a similar manner to Example 1(a) but using Reference Example 1(j), there was prepared N-(3,5-dichloro-4-pyridyl)-7-methoxy-2-(4-methoxyphenoxymethyl)-3H-benzimidazole-4-carboxamide as a white solid, m.p. 185-186° C. [Elemental analysis:—C, 55.2; H, 3.90; N, 11.4%. Calculated:—C, 55.8; H, 3.83; N, 11.8%].

(k) By proceeding in a similar manner to Example 1(a) but using Reference Example 1(k), there was prepared (RS)—N-(3,5-dichloro-4-pyridyl)-7-methoxy-2-(1-phenylbutyl)-3H-benzimidazole-4-carboxamide as a white solid, m.p. 223-224° C. [Elemental analysis:—C, 61.0; H, 4.70; N, 11.7%. Calculated:—C, 61.4; H, 4.72; N, 11.9%].

(l) By proceeding in a similar manner to Example 1(a) but using Reference Example 1(l), there was prepared 2-(4-bromobenzyl)-N-(3,5-dichloro-4-pyridyl)-7-methoxy-3H-benzimidazole-4-carboxamide as a yellow solid, m.p. 273-275° C. [Elemental analysis:—C, 49.8; H, 2.90; N, 10.6%. Calculated:—C, 49.8; H, 2.99; N, 11.1%]. NMR {(CD$_3$)$_2$SO}: δ 4.00(s, 3H), 4.25(s, 2H), 7.00(d, 1H), 7.35(d, 2H), 7.50(d, 2H), 7.90(d, 1H), 8.74(s, 1H), 12.95(s, 1H), 13.40(s, 1H).

(m) By proceeding in a similar manner to Example 1(a) but using Reference Example 1(m), there was prepared (RS)—N-(3,5-dichloro-4-pyridyl)-7-methoxy-2-[3-methoxy-1-phenylpropyl]-3H-benzimidazole-4-carboxamide as a white solid, m.p. 167-169° C. [Elemental analysis:—C, 59.1; H, 4.60; N, 11.3%. Calculated:—C, 59.3; H, 4.57; N, 11.5%]. NMR (CDCl$_3$): δ 2.33(m, 1H), 2.75(m, 1H), 3.31 (m, 1H), 3.33(s, 3H), 3.45(m, 1H), 4.0(s, 3H), 4.50(t, J=8 Hz, 1H), 6.82(d, J=8 Hz, 1H), 7.35(m, 5H), 8.18(d, J=8 Hz, 1H), 8.60(s, 2H), 9.63(bs, 1H).

(n) By proceeding in a similar manner to Example 1(a) but using Reference Example 1(n), there was prepared 2-(4-cyanobenzyl)-N-(3,5-dichloro-4-pyridyl)-7-methoxy-3H-benzimidazole-4-carboxamide as a white solid, m.p. 225-227° C. [Elemental analysis:—C, 58.4; H, 3.60; N, 14.8%. Calculated:—C, 58.4; H, 3.34; N, 15.5%]. NMR {(CD$_3$)$_2$SO}: δ 4.05(s, 3H), 4.35(s, 2H), 7.00(d, 1H), 7.60(d, 2H), 7.75(d, 2H), 7.90(d, 1H), 8.70(s, 2H), 11.90(s, 1H), 13.45(s, 1H).

(o) By proceeding in a similar manner to Example 1(a) but using Reference Example 1(o), there was prepared N-(3,5-dichloro-4-pyridyl)-7-methoxy-2-[4-(3-pyridyl)benzyl]-3H-benzimidazole-4-carboxamide as a tan coloured solid, m.p.

255° C. with decomposition. [Elemental analysis:—C, 61.3; H, 4.10; N, 13.2; H$_2$O, 0.90%. Calculated for C$_{26}$H$_{19}$Cl$_2$N$_5$O$_2$.0.25H$_2$O:—C, 60.8; H, 3.70; N, 13.6, H$_2$O, 0.88%]. NMR {(CD$_3$)$_2$SO}: δ 4.10(s, 3H), 4.35(s, 2H), 7.00(d, 1H), 7.50(m, 3H), 7.70(d, 2H), 7.90(d, 1H), 8.10(d, 1H), 8.55(d, 1H), 8.70(s, 1H), 8.85(d, 1H), 12.00(s, 1H), 13.40(s, 1H).

(p) By proceeding in a similar manner to Example 1(a) but using Reference Example 1(p), there was prepared N-(3,5-dichloro-4-pyridyl)-7-methoxy-2-(2-methoxybenzyl)-3H-benzimidazole-4-carboxamide as a white solid, m.p. 211-212° C. [Elemental analysis:—C, 57.7; H, 3.70; N, 12.0%. Calculated:—C, 57.8; H, 3.97; N, 12.3%].

(q) By proceeding in a similar manner to Example 1(a) but using Reference Example 1(q), there was prepared (RS)—N-(3,5-dichloro-4-pyridyl)-7-methoxy-2-(methoxy-phenyl-methyl)-3H-benzimidazole-4-carboxamide as a white solid, m.p. 227-229° C. [Elemental analysis:—C, 57.8; H, 3.50; N, 12.0%. Calculated:—C, 57.8; H, 3.97; N, 12.3%].

(r) By proceeding in a similar manner to Example 1(a) but using Reference Example 1(r), there was prepared N-(3,5-dichloro-4-pyridyl)-7-methoxy-2-(2-methoxyphenoxy)methyl-3H-benzimidazole-4-carboxamide as a white solid, m.p. 222-223° C. NMR (CDCl$_3$): δ 4.0(s, 3H), 4.07(s, 3H), 5.5(s, 2H), 6.86(d, J=8 Hz, 1H), 6.97(m, 2H), 7.09(m, 2H), 8.2(d, J=8 Hz, 1H), 8.59(s, 2H).

(s) By proceeding in a similar manner to Example 1(a) but using Reference Example 1(s), there was prepared N-(3,5-dichloro-4-pyridyl)-7-methoxy-2-(3-2pyridyl)-3H-benzimidazole-4-carboxamide as an off-white solid, m.p. 315° C. [Elemental analysis:—C, 54.4; H, 3.30; N, 16.3; H$_2$O, 1.10%. Calculated for C$_{19}$H$_{13}$Cl$_2$N$_5$O$_2$.0.25H$_2$O:—C, 54.5; H, 3.25; N, 16.7, H$_2$O, 1.07%].

(t) By proceeding in a similar manner to Example 1(a) but using Reference Example 1(t), there was prepared N-(3,5-dichloro-4-pyridyl)-7-methoxy-2-isopropyl-3H-benzimidazole-4-carboxamide as a white solid, m.p. 266° C. [Elemental analysis:—C, 53.7; H, 4.40; N, 14.5%. Calculated:—C, 53.8; H, 4.25; N, 14.8%].

(u) By proceeding in a similar manner to Example 1(a) but using Reference Example 1(u), there was prepared N-(3,5-dichloro-4-pyridyl)-7-methoxy-2-methyl-3H-benzimidazole-4-carboxamide as a white solid, m.p. 235° C. [Elemental analysis:—C, 51.3; H, 3.40; N, 15.8%. Calculated:—C, 51.3; H, 3.44; N, 16.0%].

(v) By proceeding in a similar manner to Example 1(a) but using Reference Example 1(v), there was prepared N-(3,5-dichloro-4-pyridyl)-7-methoxy-2-phenoxymethyl-3H-benzimidazole-4-carboxamide as a white solid, m.p. 215-219° C. with decomposition. [Elemental analysis:—C, 56.4; H, 3.90; N, 12.4%. Calculated:—C, 56.9; H, 3.64; N, 12.6%]. NMR [(CD$_3$)$_2$SO]: δ (Major tautomer/rotomer) 4.06(s, 3H), 5.40 (s, 2H), 6.95(m, 1H), 7.1(m, 3H), 7.32(m, 2H), 7.98(d, J=8 Hz, 1H), 8.75(s, 2H), 11.75(bs, 1H).

(w) By proceeding in a similar manner to Example 1(a) but using Reference Example 1(w), there was prepared 2-cyclopentyl-N-(3,5-dichloro-4-pyridyl)-7-methoxy-3H-benzimidazole-4-carboxamide as a white solid, m.p. >250° C. [Elemental analysis:—C, 56.4; H, 4.40; N, 13.5%. Calculated:—C, 56.3; H, 4.48; N, 13.8%].

(x) By proceeding in a similar manner to Example 1(a) but using Reference Example 1(x), there was prepared 2-benzyl-N-(3,5-dichloro-4-pyridyl)-3H-benzimidazole-4-carboxamide as a white solid, m.p. 162° C. [Elemental analysis:—C, 60.5; H, 3.80; N, 13.9%. Calculated:—C, 60.5; H, 3.55; N, 14.1%].

(y) By proceeding in a similar manner to Example 1(a) but using Reference Example 1(y), there was prepared 2-cyclopentyl-N-(3,5-dichloro-4-pyridyl)-7-methoxy-1-methyl-1H-benzimidazole-4-carboxamide as a white solid, m.p. 212° C. [Elemental analysis:—C, 57.2; H, 4.80; N, 13.2%. Calculated:—C, 57.3; H, 4.81; N, 13.4%].

(z) By proceeding in a similar manner to Example 1(a) but using Reference Example 1(z), there was prepared 2-cyclopentyl-N-(3,5-dichloro-4-pyridyl)-7-methoxy-3-methyl-3H-benzimidazole-4-carboxamide as a white solid, m.p. 180° C. [Elemental analysis:—C, 57.2; H, 4.80; N, 13.3%. Calculated:—C, 57.3; H, 4.81; N, 13.4%].

(aa) By proceeding in a similar manner to Example 1(a) but using Reference Example 1(aa), there was prepared N-(3,5-dichloro-4-pyridyl)-2,7-dimethoxy-3H-benzimidazole-4-carboxamide as a white solid, m.p. 238-239° C. [Elemental analysis:—C, 48.8; H, 3.20; N, 15.1%. Calculated:—C, 49.1; H, 3.29; N, 15.3%].

(ab) By proceeding in a similar manner to Example 1(a) but using Reference Example 1(ab), there was prepared 2-cyclopropyl-N-(3,5-dichloro-4-pyridyl)-7-methoxy-3H-benzimidazole-4-carboxamide as a white solid, m.p. 253-254° C. [Elemental analysis:—C, 54.13; H, 3.74; N, 14.85%. Calculated:—C, 54.07; H, 3.71; N, 14.85%].

(ac) By proceeding in a similar manner to Example 1(a) but using 2,6-difluoroaniline and Reference Example 1(ab), there was prepared 2-cyclopropyl-N-2,6-difluorophenyl)-7-methoxy-3H-benzimidazole-4-carboxamide as a white solid, m.p. 133-135° C. [Elemental analysis:—C, 62.81; H, 4.71; N, 10.42%; F, 11.55%. Calculated for C$_{18}$H$_{15}$F$_2$N$_3$O$_2$.0.25CH$_3$OH:—C, 62.39; H, 4.59; N, 10.82%; F, 11.96%].

(ad) By proceeding in a similar manner to Example 1(a) but using 2,6-dibromoaniline and Reference Example 1(ab), there was prepared 2-cyclopropyl-N-(2,6-dibromophenyl)-7-methoxy-3H-benzimidazole-4-carboxamide as a white solid, m.p. 258-260° C. [Elemental analysis:—C, 45.71; H, 3.75; N, 9.33%. Calculated for C$_{18}$H$_{15}$Br$_2$N$_3$O$_2$.CH$_3$OH:—C, 45.90; H, 3.85; N, 8.45%].

(ae) By proceeding in a similar manner to Example 1(a) but using 2,6-dimethylaniline and Reference Example 1(ab), there was prepared 2-cyclopropyl-N-(2,6-dimethylphenyl)-7-methoxy-3H-benzimidazole-4-carboxamide as a white solid, m.p. 247-249° C. [Elemental analysis:—C, 71.51; H, 6.54; N, 12.33%. Calculated:—C, 71.62; H, 6.31; N, 12.53%].

(af) By proceeding in a similar manner to Example 1(a) but using 2,4,6-trifluoraniline and Reference Example 1(ab), there was prepared 2-cyclopropyl-N-(2,4,6-trifluorophenyl)-7-methoxy-3H-benzimidazole-4-carboxamide as a white solid, m.p. 161-163° C. [Elemental analysis:—C, 59.79; H, 3.65; N, 11.52%; F, 11.52%. Calculated:—C, 59.83; H, 3.91; N, 11.63%; F, 11.63%].

(ag) By proceeding in a similar manner to Example 1(a) but using 2,6-dichloroaniline and Reference Example 1(ab), there was prepared 2-cyclopropyl-N-(2,6-dichlorophenyl)-7-methoxy-3H-benzimidazole-4-carboxamide as a white solid, m.p. 225-227° C. [Elemental analysis:—C, 57.35; H, 4.04; N, 11.10%; Cl, 18.78%. Calculated:—C, 57.46; H, 4.02; N, 11.17%; Cl, 18.85%].

(ah) By proceeding in a similar manner to Example 1(a) but using 4-amino-3,5-dimethylpyridine and Reference Example 1(ab), there was prepared 2-cyclopropyl-N-(3,5-dimethyl-4-pyridyl)-7-methoxy-3H-benzimidazole-4-carboxamide as a white solid, m.p. 268-270° C. [Elemental analysis:—C, 65.31; H, 5.80; N, 15.88%. Calculated for C$_{19}$H$_{20}$N$_4$O$_2$.0.2CH$_2$Cl$_2$:—C, 65.26; H, 5.82; N, 15.86%].

(ai) By proceeding in a similar manner to Example 1(a) but using 4-amino-3,5-dimethylisoxazole and Reference Example 1(ab), there was prepared 2-cyclopropyl-N-(3,5-dimethyl-4-isoxazolyl)-7-methoxy-3H-benzimidazole-4-carboxamide as a white solid, m.p. 232-234° C. [Elemental analysis:—C, 62.32; H, 5.85; N, 17.08%. Calculated:—C, 62.56; H, 5.56; N, 17.17%].

(aj) By proceeding in a similar manner to Example 1(a) but using 4-amino-3,5-dimethylisoxazole, there was prepared N-(3,5-dimethyl-4-isoxazolyl)-7-methoxy-2-methoxymethyl-3H-benzimidazole-4-carboxamide as a white solid, m.p. 232-234° C. [Elemental analysis:—C, 58.69; H, 5.50; N, 16.81%. Calculated:—C, 58.17; H, 5.49; N, 16.96%].

(ak) By proceeding in a similar manner to Example 1(a) but using 4-amino-3,5-dimethylpyridine and Reference Example 1(ab), there was prepared 2-cyclopropyl-N-(4-carboxy-2,6-dimethylphenyl)-7-methoxy-3H-benzimidazole-4-carboxamide as a white solid, m.p. 190-192° C. [Elemental analysis:—C, 62.26; H, 5.74; N, 10.21%. Calculated for $C_{21}H_{21}N_3O_4.1.5H_2O$:—C, 62.06; H, 5.95; N, 10.33%].

(al) By proceeding in a similar manner to Example 1(a) but using 4-carboxy-2,6-dimethylaniline, there was prepared N-(4-carboxy-2,6-dimethylphenyl)-7-methoxy-2-methoxymethyl-3H-benzimidazole-4-carboxamide as a white solid, m.p. 251-253° C. [Elemental analysis:—C, 61.73; H, 5.57; N, 10.59%. Calculated for $C_{20}H_{21}N_3O_5.0.25H_2O$:—C, 61.92; H, 5.59; N, 10.83%].

(am) By proceeding in a similar manner to Example 1(a) but using 4-amino-3-chloropyridine and Reference Example 1(ax), there was prepared N-(3-chloro-4-pyridyl)-7-methoxy-2-n-propyl-3H-benzimidazole-4-carboxamide as a green solid, m.p. 272-274° C. [Elemental analysis:—C, 59.04; H, 4.99; N, 15.99%. Calculated:—C, 59.22; H, 4.97; N, 16.24%].

(an) By proceeding in a similar manner to Example 1(a) but using Reference Example 1(as), there was prepared N-(3,5-dichloro-4-pyridyl)-8-methoxy-2-n-propylquinoline-5-carboxamide as a white solid, m.p. 227-230° C. [Elemental analysis:—C, 58.43; H, 4.12%. Calculated for $C_{19}H_{17}Cl_2N_3O_2$:—C, 58.47; H, 4.39%].

(ao) By proceeding in a similar manner to Example 1(a) but using 4-amino-3,5-dichloro-pyridine N-oxide and Reference Example 1(ac), there was prepared 1-cyclohexylmethyl-3-methyl-N-(3,5-dichloro-1-oxido-4-pyridinio)-1H-indole-6-carboxamide as a white solid, m.p. 226-228° C. [Elemental analysis:—C, 61.06; H, 5.23; N, 9.59%. Calculated for $C_{22}H_{23}Cl_2N_3O_2$:—C, 61.12; H, 5.36; N, 9.72%].

(ap) By proceeding in a similar manner to Example 1(a) but using 4-amino-3,5-dichloro-pyridine N-oxide and Reference Example 1(ad), there was prepared 1-cyclohexyl-3-methyl-N-(3,5-dichloro-1-oxido-4-pyridinio)-1H-indole-6-carboxamide as a white solid, m.p. 165-170° C. [Elemental analysis:—C, 60.95; H, 5.85; N, 9.20%. Calculated for $C_{21}H_{21}Cl_2N_3O_2$:—C, 60.30; H, 5.06; N, 10.04%].

(aq) By proceeding in a similar manner to Example 1(a) but using 4-amino-3,5-dichloro-pyridine N-oxide and Reference Example 1(ae), there was prepared 1-(2-cyclohexyl)ethyl-3-methyl-N-(3,5-dichloro-1-oxido-4-pyridinio)-1H-indole-6-carboxamide as an off-white solid, m.p 125-140° C. [Elemental analysis:—C, 60.95; H, 5.85; N, 9.20%. Calculated for $C_{23}H_{25}Cl_2N_3O_2$:—C, 61.87; H, 5.65; N, 9.41%].

(ar) By proceeding in a similar manner to Example 1(a) but using 4-amino-3,5-dichloro-pyridine N-oxide and Reference Example 1(af), there was prepared 1-(3-cyclohexyl) propyl-3-methyl-N-(3,5-dichloro-1-oxido-4-pyridinio)-1H-indole-6-carboxamide as a white solid, m.p 178° C. [Elemental analysis:—C, 62.63; H, 5.99; N, 8.87%. Calculated for $C_{24}H_{27}Cl_2N_3O_2$:—C, 62.61; H, 5.91; N, 9.13%].

(as) By proceeding in a similar manner to Example 1(a) but using 4-amino-3,5-dichloro-pyridine N-oxide and Reference Example 1(ag), there was prepared 1-heptyl-3-methyl-N-(3,5-dichloro-1-oxido-4-pyridinio)-1H-indole-6-carboxamide as a white solid, m.p 170° C. [Elemental analysis:—C, 60.72; H, 5.83; N, 9.51%. Calculated for $C_{22}H_{25}Cl_2N_3O_2$:—C, 60.83; H, 5.80; N, 9.67%].

(at) By proceeding in a similar manner to Example 1(a) but using 4-amino-3,5-dichloro-pyridine N-oxide and Reference Example 1(ah), there was prepared 1-cycloheptylmethyl-3-methyl-N-(3,5-dichloro-1-oxido-4-pyridinio)-1H-indole-6-carboxamide as a yellow solid, m.p 185° C. [Elemental analysis:—C, 61.89; H, 5.65; N, 9.41%. Calculated for $C_{23}H_{25}Cl_2N_3O_2$:—C, 61.6; H, 5.40; N, 9.70%].

(au) By proceeding in a similar manner to Example 1(a) but using 4-amino-3,5-dichloro-pyridine N-oxide and Reference Example 1(ai), there was prepared 1-(6,6-dimethylbicyclo[3.1.1.]hept-3-ylmethyl)-3-methyl-N-(3,5-dichloro-1-oxido-4-pyridinio)-1H-indole-6-carboxamide as an off-white solid, m.p 125-140° C. [Elemental analysis:—C, 62.37; H, 5.78; N, 8.51%. Calculated for $C_{23}H_{25}Cl_2N_3O_2$:—C, 63.50; H, 5.76; N, 8.89%]. NMR (CDCl$_3$): δ 0.65(s, 3H), 1.20(s, 3H), 1.30-1.40(m, 1H), 1.40-1.50(m, 1H), 1.65-1.70(m, 1H), 1.75-1.85(m, 2H), 1.90-1.95(m, 1H), 2.10-2.20(m, 1H), 2.50-2.60(m, 1H), 3.90-4.00(m, 2H), 7.00(s, 1H), 7.50-7.70(m, 2H), 7.80(s, 1H), 8.00(s, 1H), 8.30(s, 2H).

(av) By proceeding in a similar manner to Example 1(a) but using 4-amino-3,5-dichloro-pyridine N-oxide and Reference Example 1(aj), there was prepared 1-(3-phenyl)butyl-3-methyl-N-(3,5-dichloro-1-oxido-4-pyridinio)-1H-indole-6-carboxamide as a white solid, m.p 179° C. [Elemental analysis:—C, 64.24; H, 5.12; N, 8.99%. Calculated for $C_{25}H_{23}Cl_2N_3O_2$:—C, 64.11; H, 4.95; N, 8.97%].

(aw) By proceeding in a similar manner to Example 1(a) but using 4-amino-3,5-dichloro-pyridine N-oxide and Reference Example 1(ak), there was prepared N-(3,5-dichloro-1-oxido-4-pyridinio)-3-methyl-1-(4-trifluoromethylbenzyl)-1H-indole-6-carboxamide as a white solid, m.p 135° C. [Elemental analysis:—C, 55.08; H, 3.37; N, 8.32%. Calculated for $C_{23}H_{16}Cl_2F_3N_3O_2.0.5H_2O$:—C, 54.86; H, 3.41; N, 8.35%]. NMR {(CD$_3$)$_2$SO}: δ 2.30(s, 3H), 5.52(s, 1H), 7.20-7.30(m, 1H), 7.52(s, 1H), 7.70-7.80(m, 4H), 8.12(s, 1H), 8.72(s, 2H), 10.30(s, 1H).

(ax) By proceeding in a similar manner to Example 1(a) but using 4-amino-3,5-dichloro-pyridine N-oxide and Reference Example 1(al), there was prepared N-(3,5-dichloro-1-oxido-4-pyridinio)-3-methyl-1-(4-methylsulphonylbenzyl)-1H-indole-6-carboxamide as a yellow solid, m.p 157-160° C. [Elemental analysis:—C, 54.72; H, 4.27; N, 8.65%. Calculated for $C_{23}H_{19}Cl_2N_3O_4S$:—C, 54.77; H, 3.80; N, 8.33%].

(ay) By proceeding in a similar manner to Example 1(a) but using 4-amino-3,5-dichloro-pyridine N-oxide and Reference Example 1(am), there was prepared 1-(1,3-benzodioxol-5-yl)methyl-N-(3,5-dichloro-1-oxido-4-pyridinio)-3-methyl-1H-indole-6-carboxamide as a white solid, m.p. >245° C. [Elemental analysis:—C, 58.53; H, 3.77; N, 8.69%. Calculated for $C_{23}H_{17}Cl_2N_3O_4$:—C, 58.74; H, 3.64; N, 8.93%].

(az) By proceeding in a similar manner to Example 1(a) but using 4-amino-3,5-dichloro-pyridine N-oxide and Reference Example 1(an), there was prepared N-(3,5-dichloro-1-oxido-4-pyridinio)-3-methyl-1-(naphthalen-2-yl)methyl- 1H-indole-6-carboxamide as a white solid, m.p >230° C. NMR {(CD$_3$)$_2$SO)}: δ 2.30(s, 3H); 5.60(s, 2H); 7.35-7.40, 7.45-7.55, 7.60-7.80 and 7.80-7.90(m, 10H); 8.20(s, 1H); 8.70(s, 2H); 10.30(s, 1H).

(ba) By proceeding in a similar manner to Example 1(a) but using 4-amino-3,5-dichloro-pyridine N-oxide and Reference Example 1(ao), there was prepared N-(3,5-dichloro-1-oxido-4-pyridinio)-3-methyl-1-(tetrahydro-2H-pyran-2-yl)methyl-1H-indole-6-carboxamide as a beige coloured solid, m.p >150° C. with decomposition. [Elemental analysis:—C, 57.60; H, 5.30; N, 10.00%. Calculated for C$_{21}$H$_{21}$Cl$_2$N$_3$O$_3$:—C, 58.08; H, 4.87; N, 9.67%].

(bb) By proceeding in a similar manner to Example 1(a) but using 4-amino-3,5-dichloro-pyridine N-oxide and Reference Example 1(ap), there was prepared N-(3,5-dichloro-1-oxido-4-pyridinio)-3-methyl-1-(tetrahydrofurfuryl)methyl-1H-indole-6-carboxamide as a yellow solid, m.p 136° C. with decomposition. [Elemental analysis:—C, 55.08; H, 3.37; N, 8.32%. Calculated for C$_{23}$H$_{16}$Cl$_2$F$_3$N$_3$O$_2$.0.425H$_2$O:—C, 55.89; H, 3.26; N, 8.50%]. M$^+$419.

(bc) By proceeding in a similar manner to Example 1(a) but using 4-amino-3,5-dichloro-pyridine N-oxide and Reference Example 1(aq), there was prepared N-(3,5-dichloro-1-oxido-4-pyridinio)-3-methyl-1-(4-toluenesulphonyl)-1H-indole-6-carboxamide as a light brown solid, m.p. >127° C. with decomposition. [Elemental analysis:—C, 53.90; H, 3.60; N, 8.40%. Calculated for C$_{22}$H$_{17}$Cl$_2$N$_3$O$_4$:—C, 53.89; H, 3.49; N, 8.57%].

(bd) By proceeding in a similar manner to Example 1(a) but using 4-amino-3,5-dichloro-pyridine N-oxide and Reference Example 1(ar), there was prepared N-(3,5-dichloro-1-oxido-4-pyridinio)-3-methyl-1-(tetrahydrofuran-3-yl)-1H-indole-6-carboxamide as a beige coloured solid, m.p. >135° C. with decomposition. [Elemental analysis:—C, 56.00; H, 4.60; N, 9.80%. Calculated for C$_{19}$H$_{17}$Cl$_2$N$_3$O$_3$:—C, 56.17; H, 4.22; N, 10.34%].

(be) By proceeding in a similar manner to Example 1(a) but using Reference Example 1(at), there was prepared N-(3,5-dichloro-4-pyridyl)-3-methyl-1H-indole-6-carboxamide as a white solid, m.p. 223-225° C. [Elemental analysis:—C, 56.00; H, 3.50; N, 12.90%. Calculated for C$_{15}$H$_{11}$Cl$_2$N$_3$O:—C, 56.27; H, 3.46; N, 13.12%].

(bf) By proceeding in a similar manner to Example 1(a) but using 4-amino-3,5-dichloro-pyridine N-oxide and Reference Example 1(au), there was prepared 1-butyloxycarbonyl-N-(3,5-dichloro-1-oxido-4-pyridinio)-3-methyl-indole-6-carboxamide as a white solid. NMR {(CD$_3$)$_2$SO}: δ 1.60(s), 2.30(s), 7.60-7.70(m), 7.80-7.90(s), 8.70(s), 10.50(s).

(bg) By proceeding in a similar manner to Example 1(a) but using Reference Example 1(aw), there was prepared N-(3,5-dichloro-4-pyridyl)-1H-indole-6-carboxamide as a white solid.

(bh) By proceeding in a similar manner to Example 1(a) but using Reference Example 1(av), there was prepared 1-benzyl-N-(3,5-dichloro-4-pyridyl)-3-methyl-1H-indoline-6-carboxamide as a yellow solid, m.p. 223-225° C. [Elemental analysis:—C, 63.56; H, 4.94; N, 9.53%. Calculated for C$_{22}$H$_{19}$Cl$_2$N$_3$O:—C, 64.09; H, 4.69; N, 10.19%]. NMR (CD$_3$Cl): δ 1.20-1.30(m, 1H); 1.30(m, 1H); 2.90-3.00(m, 1H); 3.30-3.40(m, 1H); 3.50-3.60(m, 1H); 4.20-4.30 and 4.40-4.50(m, 2H); 7.00(m, 1H); 7.10-7.40(m, 7H); 7.70(s, 1H); 8.60(s, 2H).

(bi) By proceeding in a similar manner to Example 1(a) but using 4-aminopyridine and Reference Example 1(ai), there was prepared 1-(6,6-dimethyl-bicyclo[3.1.1]hept-2-yl-methyl)-3-methyl-N-(4-pyridyl)-1H-indole-6-carboxamide as a white solid. [Elemental analysis:—C, 76.08; H, 7.47; N, 10.50%. Calculated for C$_{25}$H$_{29}$N$_3$O.0.5H$_2$O:—C, 75.66; H, 7.63; N, 10.60%]. NMR (CDCl$_3$): δ 0.75(s, 3H), 1.1(s, 3H), 1.3-1.4(m, 1H), 1.4-1.5(m, 1H), 1.6-1.8(m, 4H), 1.8-1.9(m, 1H), 2.05-2.15(m, 1H), 2.3(s, 3H), 2.45-2.55(m, 1H), 3.8-3.9(m, 2H), 7.0(s, 1H), 7.4-7.5(m, 1H), 7.55-7.60, 7.6-7.65 (m, 3H), 8.0(s, 1H), 8.2(s, 1H), 8.5(m, 2H).

(bj) By proceeding in a similar manner to Example 1(a) but using 4-hydroxyaniline and Reference Example 1(av), there was prepared 1-benzyl-N-(4-hydroxyphenyl)-3-methyl-1H-indole-6-carboxamide as a white solid, m.p. 230-231° C. [Elemental analysis:—C, 75.46; H, 6.17; N, 7.05%. Calculated for C$_{23}$H$_{20}$ON$_2$O$_2$.0.6H$_2$O:—C, 75.16; H, 5.82; N, 7.63%]. NMR [(CD$_3$)$_2$CO]: δ 2.2(s, 3H), 5.5(s, 2H), 6.8-6.85(m, 2H), 7.2-7.3(m, 5H), 7.55-7.6(m, 3H), 7.7-7.75 (m, 1H), 8.1(s, 1H), 8.2(s, 1H), 9.4(s, 1H).

(bk) By proceeding in a similar manner to Example 1(a) but using 4-aminopyrimidine and Reference Example 1(ae), there was prepared 1-(2-cyclohexyl)ethyl-3-methyl-N-(4-pyrimidinyl)-1H-indole-6-carboxamide as a white solid, m.p. 192-194° C. [Elemental analysis:—C, 73.22; H, 7.24; N, 15.18%. Calculated for C$_{22}$H$_{26}$N$_4$O:—C, 72.90; H, 7.23; N, 15.46%]. NMR [(CD$_3$)$_2$CO]: δ 0.9-1.1, 1.1-1.3 (m, 6H), 1.6-1.9(m, 7H), 2.3(s, 3H), 4.3-4.4(m, 2H), 7.3(s, 1H), 7.6-7.65, 7.8-7.85(m, 2H), 8.3-8.4(m, 2H), 8.6-8.7(m, 1H), 8.9(s, 1H), 9.8(m, 1H).

(bl) By proceeding in a similar manner to Example 1(a) but using 4-amino-3,5-dimethyl-[1,2,4]-triazole and Reference Example 1(ai), there was prepared 1-(6,6-dimethyl-bicyclo[3.1.1hept-2-ylmethyl)-N-(3,5-dimethyl-[1,2,4-triazol-4-yl)-3-methyl-1H-indole-6-carboxamide as a white solid, m.p. 135-140° C. [Elemental analysis:—C, 69.61; H, 7.64; N, 17.71%. Calculated for C$_{24}$H$_{31}$N$_5$O:—C, 71.13; H, 7.71; N, 17.28%]. NMR (CDCl$_3$): δ 0.7(s, 3H), 1.19(s, 3H), 1.25-1.4, 1.4-1.45, 1.45-1.6, 1.6-1.7, 1.7-1.8, 1.8-1.9 (m, 7H), 2.0-2.1 (s, 1H), 2.3(s, 3H), 2.35(s, 3H), 2.4-2.55(m, 1H), 3.-4.1(m, 2H), 7.0(s, 1H), 7.65-7.7, 7.9-7.95(m, 2H), 8.35(s, 1H).

EXAMPLE 2

(a) (RS)-2-(Cyclohexyl-phenyl)methyl-N-(3,5-dichloro-1-oxido-4-pyridinio)-7-methoxy-3H-benzimidazole-4-carboxamide A solution of (RS)-2-(cyclohexyl-phenyl-methyl)-N-(3,5-dichloro-4-pyridyl)-7-methoxy-3H-benzimidazole-4-carboxamide [0.545 g, Example 1(g)] in chloroform (15 ml) was treated with meta-chloroperbenzoic acid (1.6 g, 70%). The reaction mixture was stirred at ambient temperature for 15 hours, then diluted with chloroform. The mixture was washed with saturated sodium bicarbonate solution, then with water and then with brine. The organic phase was dried over magnesium sulphate and then evaporated. The residue was subjected to flash chromatography on silica eluting with a mixture of ethyl acetate and hexanes (2:1, v/v) to give the title compound (0.12 g) as a tan coloured solid, m.p. 310-312° C. [Elemental analysis:—C, 61.0; H, 5.00; N, 10.2; H$_2$O, 1.70%. Calculated for C$_{27}$H$_{26}$Cl$_2$N$_4$O$_3$.0.5H$_2$O:—C, 60.6; H, 5.09; N, 10.5, H$_2$O, 1.07%].

(b) By proceeding in a similar manner to Example 2(a) but using Example 1(i), there was prepared (RS)—N-(3,5-dichloro-1-oxido-4-pyridinio)-7-methoxy-2-(2-phenyl)propyl-3H-benzimidazole-4-carboxamide as a yellow solid, m.p. 256-258° C. [Elemental analysis:—C, 57.4; H, 4.40; N, 11.4%. Calculated for $C_{23}H_{20}Cl_2N_4O_3.0.5H_2O$:—C, 57.1; H, 4.41; N, 11.7%].

(c) By proceeding in a similar manner to Example 2(a) but using Example 1(l), there was prepared 2-(4-bromobenzyl)-N-(3,5-dichloro-1-oxido-4-pyridinio)-7-methoxy-3H-benzimidazole-4-carboxamide as a pale yellow solid, m.p. 248° C. [Elemental analysis:—C, 48.1; H, 3.10; N, 10.0%. Calculated for $C_{21}H_{15}BrCl_2N_4O_3.0.5H_2O$:—C, 57.1; H, 4.41; N, 11.7%].

(d) By proceeding in a similar manner to Example 2(a) but using Example 1(n), there was prepared 2-(4-cyanobenzyl)-N-(3,5-dichloro-1-oxido-4-pyridinio)-7-methoxy-3H-benzimidazole-4-carboxamide as a white solid, m.p. 253° C. with decomposition. [Elemental analysis:—C, 53.9; H, 3.50; N, 13.8; $H_2O$, 4.60%. Calculated for $C_{22}H_{15}Cl_2N_4O_3.1.25H_2O$:—C, 53.8; H, 3.59; N, 14.3; $H_2O$, 4.59%].

(e) By proceeding in a similar manner to Example 2(a) but using Example 1(a), there was prepared N-(3,5-dichloro-1-oxido-4-pyridinio)-7-methoxy-2-methoxymethyl-3H-benzimidazole-4-carboxamide as a white solid, m.p. 244-247° C. [Elemental analysis:—C, 48.5; H, 3.60; N, 13.9%. Calculated:—C, 48.4; H, 3.55; N, 14.1%].

(f) By proceeding in a similar manner to Example 2(a) but using Example 1(e), there was prepared (RS)—N-(3,5-dichloro-1-oxido-4-pyridinio)-7-methoxy-2-(1-phenylethyl)-3H-benzimidazole-4-carboxamide as an off-white solid. [Elemental analysis:—C, 57.1; H, 3.90; N, 12.0%. Calculated for $C_{22}H_{18}Cl_2N_4O_3.0.25H_2O$:—C, 57.2; H, 4.04; N, 12.1%]. NMR $\{(CD_3)_2SO\}$: δ 1.75(d, J=7.5 Hz, 3H), 4.03(s, 3H), 4.46(q, J=7.5 Hz, 1H), 6.98(d, J=8 Hz, 1H), 7.3(m, 5H), 7.88(d, J=8 Hz, 1H), 8.77(s, 2H).

EXAMPLE 3

(a) 1-(2-Cyclopentyl-7-methoxy-3H-benzimidazol-4-yl)-2-(4-pyridyl)ethanone

A solution of diisopropylamine (0.47 ml) in tetrahydrofuran (6 ml), cooled to −10° C., was treated dropwise, with a solution of butyl lithium in hexanes (1.2 ml, 2.5 M). The resulting solution was stirred for 10 minutes, then cooled to −78° C. and then treated dropwise with a solution of 4-picoline (0.29 ml) in tetrahydrofuran (1 ml). This solution was stirred for 30 minutes then treated with a solution of methyl 2-cyclopentyl-7-methoxy-3H-benzimidazole-4-carboxylate [0.274 g, Reference Example 3(t)] in tetrahydrofuran (2 ml). The cold bath was removed and the reaction mixture stirred for 15 minutes at ambient temperature. The mixture was quenched with water, then diluted with ethyl acetate. The organic phase was separated then washed with brine, then dried over magnesium sulphate and then evaporated. The residue was subjected to flash chromatography on silica, eluting with a mixture of methanol and dichloromethane (8:92, v/v), to give the title compound (0.126 g) as a white solid. [Elemental analysis:—C, 71.7; H, 6.40; N, 12.5%. Calculated:—C, 71.6; H, 6.31; N, 12.5%]. NMR (CDCl$_3$): δ 1.63-2.05(m, 6H), 2.2(m, 2H), 3.33(m, 1H), 4.11(s, 3H), 4.35(s, 2H), 6.72(d, J=8 Hz, 1H), 7.23(m, 2H), 7.82(d, J=8 Hz, 1H), 8.6(m, 2H).

(b) By proceeding in a similar manner to Reference Example 3(a), but using 3,5-dichloro-4-methylpyridine and Reference Example 3(1), there was prepared 2-(3,5-dichloro-4-pyridyl)-1-[1-(4-methoxybenzyl)-3-methyl-1H-indol-6-yl]-ethanone as a white solid, m.p. 165-167° C. [Elemental analysis: C, 65.60; H, 4.80; N, 6.20%. Calculated for $C_{24}H_{20}Cl_2N_2O_2$: C, 65.61; H, 4.59; N, 6.38%].

(c) By proceeding in a similar manner to Reference Example 3(a), but using 3,5-dichloro-4-methylpyridine and Reference Example 3(s), there was prepared 2-(3,5-dichloro-pyridin-4-yl)-1-[1-(1-toluene-4-sulphonyl)-3-methyl-1H-indol-6-yl]-ethanone as a yellow solid, m.p. 193-198° C. [Elemental analysis: C, 57.90; H, 3.90; N, 5.80%. Calculated for $C_{23}H_{18}Cl_2N_2O_3S$: C, 58.36; H, 3.83; N, 5.92%].

(d) By proceeding in a similar manner to Reference Example 3(a), but using Reference Example 3(1), there was prepared 1-[1-(4-methoxybenzyl)-3-methyl-1H-indol-6-yl]-2-(4-pyridyl)-ethanone as a yellow solid, m.p. 109-110° C. [Elemental analysis: C, 77.20; H, 6.30; N, 7.40%. Calculated for $C_{24}H_{22}N_2O_2.0.25H_2O$: C, 76.86; H, 6.05; N, 7.48%]. NMR (CDCl$_3$): δ 2.30(s, 3H); 3.80(s, 3H); 4.30(s, 2H); 5.20(s, 2H); 6.80(s, 2H); 7.00-7.05(m, 3H); 7.15-7.20(m, 2H); 7.55-7.60(m, 1H); 7.70-7.75(m, 1H); 8.00(s, 1H); 8.45-8.50(m, 2H).

EXAMPLES 4 AND 5

1-(7-Methoxy-2-methoxymethyl-3H-benzimidazol-4-yl)-2-(4-pyridyl)ethanone and 1,3-bis-(4-pyridyl)-2-(7-methoxy-2-methoxymethyl-3H-benzimidazol-4-yl)-propan-2-ol A solution of diisopropylamine (1.51 g) in tetrahydrofuran (15 ml), under nitrogen, cooled to −10° C. was treated with butyl lithium in hexane (6 ml, 2.5 M). The solution was cooled to −78° C. then treated dropwise with a solution of 4-picoline (1.40 g) in tetrahydrofuran (10 ml) followed by a solution of methyl 7-methoxy-2-methoxymethyl-3H-benzimidazole-4-carboxylate [1,25 g, Reference Example 3(a)] in tetrahydrofuran (15 ml). The brown solution was allowed to warm to room temperature and the resulting yellow suspension was filtered. The insoluble material was washed with a little tetrahydrofuran then air dried. The yellow solid (2.3 g) was dissolved in water (75 ml) and the solution extracted three times with dichloromethane (25 ml). The combined extracts were dried over magnesium sulphate and then evaporated. The resulting yellow solid (1.53 g) was subjected to flash chromatography on silica eluting initially with a mixture of methanol and dichloromethane (5:95, v/v) to give 1-(7-methoxy-2-methoxymethyl-3H-benzimidazol-4-yl)-2-(4-pyridyl)ethanone (0.39 g) recrystallised from toluene as a yellow solid, m.p. 218-220° C. with decomposition. [Elemental analysis:—C, 66.58; H, 5.53; N, 13.76%. Calculated:—C, 66.45; H, 5.50; N, 13.5%]; then eluting with a mixture of methanol and dichloromethane (1:9, v/v) to give 1,3-bis-(4-pyridyl)-2-(7-methoxy-2-methoxymethyl-3H-benzimidazol-4-yl)-propan-2-ol (0.4 g) recrystallised from methanol as a white solid, m.p. 210° C. with decomposition. [Elemental analysis:—C, 68.40; H, 5.94; N, 13.85%. Calculated:—C, 68.30; H, 5.98; N, 14.00%].

EXAMPLE 6

7-Methoxy-2-methoxymethyl-4-[2-(4-pyridyl)ethyl]-3H-benzimidazole

A mixture of 1-(7-methoxy-2-methoxymethyl-3H-benzimidazol-4-yl)-2-(4-pyridyl)ethanone (0.92 g, Example 4), hydrazine hydrate (0.8 ml, 98%) and potassium hydroxide (1.6 g) in diethylene glycol (10 ml) was heated at 100° C. for 5 minutes. The resulting clear solution was the heated at 160° C. for 1 hour, then heated at 180° C. for 2 hours whilst removing water at intervals from an attached air condenser. The red solution was cooled to room temperature then poured into water (200 ml). The mixture was extracted three times with dichloromethane (100 ml). The combined extracts were dried over magnesium sulphate and then evaporated. The residue was subjected to flash chromatography on silica eluting with a mixture of methanol and dichloromethane (5:95, v/v). Fractions containing the required product were combined and evaporated. The resulting solid was combined with material similarly prepared from 0.47 g of 1-(7-methoxy-2-methoxymethyl-3H-benzimidazol-4-yl)-2-(4-pyridyl)ethanone and dissolved in dichloromethane (50 ml). The solution was washed with water (100 ml) then dried over magnesium sulphate and then evaporated. The residual white solid (1.03 g) was recrystallised from toluene to give the title compound (0.95 g) as a white solid, m.p. 154-156° C. [Elemental analysis:—C, 68.09; H, 6.43; N, 13.87%. Calculated:—C, 68.67; H, 6.44; N, 14.13%].

EXAMPLE 7

2-(4-carboxamidobenzyl)-N-(3,5-dichloro-4-pyridyl)-7-methoxy-3H-benzimidazole-4-carboxamide A solution of 2-(4-cyanobenzyl)-N-(3,5-dichloro-4-pyridyl)-7-methoxy-3H-benzimidazole-4-carboxamide [0.1 g, Example 1(n)] in dimethyl sulphoxide (0.3 ml) was treated with potassium carbonate (6 mg) and hydrogen peroxide (0.05 ml, 30%). The reaction mixture was stirred at ambient temperature for 12 hours then treated with water (50 ml). The resulting solid was filtered and air dried to give the title compound (77%) as a white solid, m.p. 292-293° C. [Elemental analysis:—C, 55.2; H, 3.70; N, 13.9; $H_2O$, 1.90%. Calculated for $C_{22}H_{17}Cl_2N_5O_3.0.5H_2O$:—C, 55.1; H, 3.79; N, 13.9, $H_2O$, 1.88%]. NMR {$(CD_3)_2SO$}: δ 4.00(s, 3H), 4.35(s, 2H), 5.75(s, 2H), 7.00(d, 1H), 7.45(d, 2H), 7.80(d, 2H), 7.90(d, 1H), 8.70(s, 2H), 11.90(s, 1H), 13.45(s, 1H).

EXAMPLE 8

[2-(3-Chlorophenoxy)-pyridin-3-yl]-(7-methoxy-2-methoxymethyl-1H-benzimidazol-4-yl)-methanone A solution of 3-bromo-2-(3-chlorophenoxy)pyridine (0.43 g, Reference Example 16) in dry tetrahydrofuran (6 ml), at −70° C., was treated with butyl lithium in hexane (0.64 ml, 2.5 M). The mixture was then stirred at −70° C. for 45 minutes then treated with a solution of 1-benzotriazolyl 7-methoxy-2-methoxymethyl-3H-benzimidazole-4-carboxylate [0.177 g, Reference Example 1(a)] in dry tetrahydrofuran (2 ml) and stirring was continued at −70° C. for 10 minutes. The reaction mixture was allowed to warm to room temperature, then stirred at this temperature for 2 hours, then treated with aqueous ammonium chloride solution, and then extracted with ethyl acetate (20 ml). The organic extract was dried and concentrated to give a brown syrup which was purified by flash chromatography on silica eluting initially with a mixture of diethyl ether and pentane (1:1, v/v), then with a mixture of diethyl ether and pentane (7:3, v/v) and then with diethyl ether to give the title compound (0.04 g) as white solid, m.p. 181-183° C. [Elemental analysis:—C, 62.17, H, 4.32, N, 10.15%. Calculated :—C, 62.35, H, 4.28, N, 9.91%]. NMR (CDCl_3):- δ 3.52(s, 3H), 4.13(s, 3H), 4.85(s, 2H), 6.73(d, J=8 Hz, 1H), 7.00(m, 1H), 7.12(t, J=2 Hz, 1H), 7.16(m, 1H), 7.2(dd,J=7 Hz,J=5 Hz, 1H), 7.28(t, J=8 Hz, 1H), 7.55(d, J=8 Hz, 1H), 7.85(dd,J=8 Hz,J=2 Hz, 1H), 8.83(dd,J=4 Hz,J=1 Hz, 1H).

EXAMPLE 9

(a) N-(3,5-dichloro-1-oxido-4-pyridinio)-7-methoxy-2-methoxymethyl-3H-benzimidazole-4-carboxamide A suspension of N-(3,5-dichloro-4-pyridyl)-7-methoxy-2-methoxymethyl-3H-benzimidazole-4-carboxamide [17.9 g, Example 1(a)] in dichloromethane (325 ml) was treated with a peracetic acid (140 ml, 37% in acetic acid) giving a pale yellow solution which was stirred at ambient temperature for 48 hours. The solution was concentrated under reduced pressure, at ambient temperature, to remove the volatile solvent and the remaining solution was neutralised by the slow addition of a saturated aqueous sodium hydrogen carbonate solution (500 ml). The solid which precipitated was collected by filtration then washed with water and then recrystallised from ethanol to give the title compound (12.7 g) as a white solid.

(b) By proceeding in a similar manner to Example 9(a) but using Example 1(t), there was prepared N-(3,5-dichloro-1-oxido-4-pyridinio)-2-isopropyl-7-methoxy-3H-benzimidazole-4-carboxamide recrystallised from ethanol as a white crystalline solid, m.p. 255-258° C. with decomposition. [Elemental analysis:—C, 51.14; H, 4.13; N, 13.95%. Calculated:—C, 51.60; H, 4.05; N, 14.17%].

(c) By proceeding in a similar manner to Example 9(a) but using Example 1(aa), there was prepared N-(3,5-dichloro-1-oxido-4-pyridinio)-2,7-dimethoxy-3H-benzimidazole-4-carboxamide as a cream coloured solid, m.p. decomposes above 247° C. [Elemental analysis:—C, 45.90; H, 3.06; N, 14.28%. Calculated:—C, 46.97; H, 3.13; N, 14.62%].

EXAMPLE 10

2-Cyclopropyl-N-(3,5-dichloro-1-oxido-4-pyridinio)-7-methoxy-3H-benzimidazole-4-carboxamide 2-cyclopropyl-N-(3,5-dichloro-4-pyridyl)-7-methoxy-3H-benzimidazole-4-carboxamide [0.45 g, Example 1(ab)] was treated with peracetic acid (3 ml, 32% in acetic acid) and the mixture heated at 60° C. for 2.25 hours then left at room temperature for 18 hours. The reaction mixture was diluted with diethyl ether (60 ml), then cooled and then filtered. The yellow solid was heated with ethanol (40 ml) then filtered to remove a small amount of insoluble solid. The filtrate was concentrated to about 25 ml volume and stood at ambient temperature. The resulting yellow crystals were filtered and combined with a separate batch synthesised in a similar manner from 0.40 g of 2-cyclopropyl-N-(3,5-dichloro-4-pyridyl)-7-methoxy-3H-benzimidazole-4-carboxamide. The combined material was heated with methanol (50 ml) then filtered to remove a small amount of insoluble solid. The filtrate was concentrated to about 25 ml volume and stood at ambient temperature. The resulting yellow crystals were filtered, washed with methanol and then with diethyl ether to give the title compound (0.185 g) as cream coloured crystals, m.p. 271-274° C. [Elemental analysis:—C, 51.91; H, 3.59; N, 14.24%. Calculated:—C, 52.12; H, 3.53; N, 14.26%].

EXAMPLE 11

(a) 2-Cyclopropyl-4-(3,5-dimethyl-4-pyridyl-methoxy)-7-methoxy-3H-benzimidazole A stirred solution of 2-cyclopropyl-7-(3,5-dimethyl-4-pyridylmethoxy)-4-methoxy-1(or 3)-(2-trimethylsilanyl-ethoxymethyl)-1H(or 3H)-benzimidazole (3.49 mMol, Reference Example 17) in methylated spirits (50 ml) was treated with hydrochloric acid (50 ml, 5M) and the mixture was then heated at reflux for 5 hours. The resulting solution was cooled to room temperature and then evaporated. The residue was partitioned between water (10 ml) and ethyl acetate (50 ml). The pH of the aqueous phase was adjusted to 8, with cooling, and the resulting white solid was washed with water, then with ethyl acetate, then dried at 70° C. to afford the title compound (0.47 g) as a cream coloured solid, m.p. 152-155° C. [Elemental analysis:—C, 62.60; H, 6.65; N, 11.52%. Calculated:—C, 70.57; H, 6.55; N, 12.99%].

(b) By proceeding in a similar manner to Example 11(a) but using Reference Example 18, there was prepared 4-(3,5-dimethyl-4-pyridylmethoxy)-7-methoxy-2-methoxymethyl-3H-benzimidazole as a cream coloured solid, m.p. 196-198° C. [Elemental analysis:—C, 65.74; H, 6.63; N, 12.77%. Calculated:—C, 66.04; H, 6.47; N, 12.83%].

(c) By proceeding in a similar manner to Example 11(a) but using Reference Example 36, there was prepared ethyl 5-(2-cyclopropyl-7-methoxy-benzimidazole-4-yl)pyridine-2-carboxylate as cream coloured solid, m.p. 126-128° C.

(d) By proceeding in a similar manner to Example 11(a) but using Reference Example 34 there was prepared 2-cyclopropyl-7-methoxy-4-(4-morpholinosulphonyl)-3H-benzimidazole as white solid, m.p. 294-295° C.

EXAMPLE 12

(a) 1-Benzyl-7-methoxy-2-methoxymethyl-4-(2-(4-pyridyl)ethyl)-1H-benzimidazole hydrochloride dihydrate A solution of 7-methoxy-2-methoxymethyl-4-[2-(4-pyridyl)ethyl]-3H-benzimidazole (0.35 g, Example 6) and dimethylformamide (10 ml) was treated with sodium hydride (0.06 g, 60% dispersion in mineral oil) under argon. After stirring at room temperature the mixture was treated with benzyl bromide (0.15 ml) and stirring was continued for 16 hours. The reaction mixture was evaporated and the residue was treated with hydrochloric acid solution (20 ml, 1M) then washed with three portions of ethyl acetate (20 ml). The pH of the aqueous phase was adjusted to 12 by addition of sodium hydroxide solution (1M). The resulting solid was filtered, then dried, then dissolved in isopropanol (2 ml) and then treated with a few drops of concentrated hydrochloric acid. The mixture was allowed to stand at room temperature for 16 hours and the solid formed was filtered, then washed with isopropanol and then dried at 90° C. under vacuum to give the title compound as a white solid (0.2 g), m.p. 193-196° C. (decomposed). [Elemental analysis:—C, 61.3; H, 6.1; N, 9.2%. Calculated:—C, 62.6; H, 6.3; N, 9.1%].

(b) By proceeding in a similar manner to Example 12(a) but using Example 1(be) and chloromethylcyclohexane there was prepared 1-cyclohexylmethyl-N-(3,5-dichloro-4-pyridyl)-3-methyl-1H-indole-6-carboxamide as a yellow solid, m.p. 147-151° C. [Elemental analysis: C, 62.97; H, 5.83; N, 9.52%. Calculated for $C_{22}H_{23}Cl_2N_3O.0.3H_2O$: C, 62.63; H, 5.64; N, 9.97%].

(c) By proceeding in a similar manner to Example 12(a) but using Example 1(be) and (2-chloroethyl)-cyclohexane, there was prepared 1-(2-cyclohexyl)ethyl-N-(3,5-dichloro-4-pyridyl)-3-methyl-1H-indole-6-carboxamide as a white solid, m.p. 163-165° C. [Elemental analysis: C, 63.00; H, 5.79; N, 9.71%. Calculated for $C_{23}H_{25}Cl_2N_3O.0.25H_2O$: C, 63.50; H, 5.91; N, 9.97%].

(d) By proceeding in a similar manner to Example 12(a) but using Example 1(be) and 3-cyclohexyl-chloropropane there was prepared 1-[3-(cyclohexyl)propyl]-N-(3,5-dichloro-4-pyridyl)-3-methyl-1H-indole-6-carboxamide as a white solid, m.p. 174-176° C. [Elemental analysis: C, 64.69; H, 5.98; N, 9.43%. Calculated for $C_{24}H_{27}Cl_2N_3O$: C, 64.89; H, 6.12; N, 9.46%].

(e) By proceeding in a similar manner to Example 12(a) but using Example 1(be) and 1-chloroheptane there was prepared N-(3,5-dichloro-4-pyridyl)-3-methyl-1-heptyl-1H-indole-6-carboxamide as a white solid, m.p. 151-152° C. [Elemental analysis: C, 62.94; H, 5.80; N, 9.84%. Calculated for $C_{22}H_{25}Cl_2N_3O$: C, 63.16; H, 6.02; N, 10.04%].

(i) By proceeding in a similar manner to Example 12(a) but using Example 1(be) and 2-(chloromethyl)tetrahydro-2H-pyran there was prepared N-(3,5-dichloro-4-pyridyl)-3-methyl-1-(tetrahydro-2H-pyran-2-yl)methyl-1H-indole-6-carboxamide as a white solid, m.p. 159-161° C. [Elemental analysis: C, 60.20; H, 5.30; N, 9.80%. Calculated for $C_{21}H_{21}Cl_2N_3O_2$: C, 60.30; H, 5.06; N, 10.04%].

(j) By proceeding in a similar manner to Example 12(a) but using Example 1(be) and 2-(chloromethyl)-tetrahydrofuran there was prepared N-(3,5-dichloro-4-pyridyl)-3-methyl-1-(tetrahydrofuran-2-yl)methyl-1H-indole-6-carboxamide as a yellow solid, m.p. 189-191° C. [Elemental analysis: C, 59.40; H, 4.90; N, 10.00%. Calculated for $C_{20}H_{19}Cl_2N_3O_2$: C, 59.42; H, 4.74; N, 10.39%].

(k) By proceeding in a similar manner to Example 12(a) but using Example 1(be) and 4-toluenesulphonyl chloride there was prepared N-(3,5-dichloro-4-pyridyl)-3-methyl-1-(toluene-4-sulphonyl)-1H-indole-6-carboxamide as a white solid, m.p. 186-190° C. [Elemental analysis: C, 55.48; H, 3.95; N, 8.43%. Calculated for $C_{22}H_{17}Cl_2N_3O_3S$: C, 55.70; H, 3.61; N, 8.86%].

(l) By proceeding in a similar manner to Example 12(a) but using Example 1(be) and 3-chlorotetrahydrofuran there was prepared N-(3,5-dichloro-4-pyridyl)-3-methyl-1-(tetrahydrofuran-3-yl)-1H-indole-6-carboxamide as a beige coloured solid, m.p. 184° C. [Elemental analysis: C, 58.30; H, 4.60; N, 10.30%. Calculated for $C_{19}H_{17}Cl_2N_3O_2$: C, 58.48; H, 4.39; N, 10.77%].

(m) By proceeding in a similar manner to Example 12(a) but using Example 1(be) and 3-methoxy-chlorocyclopentane there was prepared N-(3,5-dichloro-4-pyridyl)-3-methyl-1-(3-methoxy)cyclopentyl-1H-indole-6-carboxamide as a beige coloured solid, m.p. 100-120° C. with decomposition. [Elemental analysis: C, 59.90; H, 5.10; N, 9.80%. Calculated for $C_{21}H_{21}Cl_2N_3O_2$: C, 60.30; H, 5.06; N, 10.04%].

(n) By proceeding in a similar manner to Example 12(a) but using Example 1(be) and 5-chloro-2-chloromethyl-thiophene there was prepared N-(3,5-dichloro-4-pyridyl)-3-methyl-1-(5-chlorothiophen-2-yl)methyl-1H-indole-6-carboxamide as a yellow solid, m.p. >165° C. with decomposition. [Elemental analysis: C, 52.84; H, 2.98; N, 9.04%. Calculated for $C_{20}H_{14}Cl_3N_3O$: C, 53.29; H, 3.13; N, 9.32%].

(o) By proceeding in a similar manner to Example 12(a) but using Example 1(be) and 4-(chloromethyl)-3,5-dimethylisoxazole there was prepared N-(3,5-dichloro-4-pyridyl)-

3-methyl-1-(3,5-dimethylisoxazol-4-yl)methyl-1H-indole-6-carboxamide as a white solid, m.p. 243-246° C. [Elemental analysis: C, 58.62; H, 4.43; N, 12.72%. Calculated for $C_{21}H_{18}Cl_2N_4O_2$: C, 58.75; H, 4.23; N, 13.05%].

(p) By proceeding in a similar manner to Example 12(a) but using N-(3,5-dichloro-4-pyridyl)-3-methyl-1H-indole-6-carboxamide [Example 1(be)] and 4-chloromethyl-2-methyl-thiazole there was prepared N-(3,5-dichloro-4-pyridyl)-3-methyl-1-(2-methyl-thiazol-4-yl)methyl-1H-indole-6-carboxamide as a white solid, m.p. 217-219° C. [Elemental analysis: C, 55.22; H, 3.63; N, 12.74%. Calculated for $C_{20}H_{16}Cl_2N_4OS.0.25H_2O$: C, 55.10; H, 3.82; N, 12.86%].

(q) By proceeding in a similar manner to Example 12(a) but using Example 1(be) and methyl 2-chloromethylfuran-2-carboxylate there was prepared methyl 5-[6-(3,5-dichloropyridin-4-ylcarbamoyl)-3-methyl-indol-1-ylmethyl]-furan-2-carboxylate as a white solid, m.p. 217° C. [Elemental analysis: C, 57.03; H, 3.50; N, 8.88%. Calculated for $C_{22}H_{17}Cl_2N_3O_4.0.25H_2O$: C, 57.05; H, 3.81; N, 9.08%].

(r) By proceeding in a similar manner to Example 12(a) but using Example 1(be) and 3-chloromethyl-5-phenyl-[1,2,4]-oxadiazole there was prepared N-(3,5-dichloro-4-pyridyl)-3-methyl-1-(5-phenyl-[1,2,4]oxadiazol-3-yl)methyl-1H-indole-6-carboxamide as a white solid, m.p. 225-227° C. [Elemental analysis: C, 59.24; H, 3.73; N, 14.09%. Calculated for $C_{24}H_{17}Cl_2N_5O_2.0.5H_2O$: C, 59.13; H, 3.72; N, 14.38%].

(s) By proceeding in a similar manner to Example 12(a) but using Example 1(be) and 4-(2-chloroethyl)-morpholine there was prepared N-(3,5-dichloro-4-pyridyl)-3-methyl-1-(2-morpholin-4-yl)ethyl-1H-indole-6-carboxamide as a yellow solid, m.p. 172° C. [Elemental analysis: C, 57.78; H, 5.07; N, 12.76%. Calculated for $C_{21}H_{22}Cl_2N_4O_2$: C, 58.21; H, 5.12; N, 12.93%].

(t) By proceeding in a similar manner to Example 12(a) but using Example 1(be) and methyl 5-chloro-pentanoate there was prepared methyl 5-[6-(3,5-dichloro-pyridin-4-ylcarbamoyl)-3-methyl-indol-1-yl]-pentanoate as a white solid, m.p. 134° C. [Elemental analysis: C, 58.09; H, 5.05; N, 9.50%. Calculated for $C_{21}H_{21}Cl_2N_3O_3$: C, 58.07; H, 4.87; N, 9.67%].

(u) By proceeding in a similar manner to Example 12(a) but using Example 1(be) and 4-trifluoromethylbenzyl chloride there was prepared N-(3,5-dichloro-4-pyridyl)-1-(4-trifluorobenzyl)-3-methyl-1H-indole-6-carboxamide as a white solid, m.p. 221-222° C. [Elemental analysis: C, 57.63; H, 3.39; N, 8.81%. Calculated for $C_{23}H_{16}Cl_2F_3N_3O$: C, 57.76; H, 3.37; N, 8.79%].

(v) By proceeding in a similar manner to Example 12(a) but using Example 1(be) and 4-methylsulphonylbenzyl chloride there was prepared N-(3,5-dichloro-4-pyridyl)-3-methyl-1-(4-methylsulphonylbenzyl)-1H-indole-6-carboxamide as a white solid, m.p. 125-140° C. NMR(CDCl$_3$): δ 2.3(3H, s), 3.2(3H, s), 5.6(2H, s), 7.3-7.4(2H, m), 7.5(1H, s), 7.6-7.75(2H, m), 7.9(2H, m), 8.1(1H, s), 8.7(2H, s).

(w) By proceeding in a similar manner to Example 12(a) but using Example 1(be) and 4-methoxycarbonylbenzyl chloride there was prepared N-(3,5-dichloro-4-pyridyl)-1-(4-methoxycarbonylbenzyl)-3-methyl-1H-indole-6-carboxamide as a white solid, m.p. 172-174° C. [Elemental analysis: C, 61.10; H, 4.02; N, 8.81%. Calculated for $C_{24}H_{19}Cl_2N_3O_3$: C, 61.55; H, 4.09; N, 8.97%].

(x) By proceeding in a similar manner to Example 12(a) but using Example 1(be) and 3-nitrobenzyl chloride there was prepared N-(3,5-dichloro-4-pyridyl)-3-methyl-1-(3-nitrobenzyl)-1H-indole-6-carboxamide as a yellow solid, m.p. 239-240° C. [Elemental analysis: C, 57.63; H, 3.75; N, 11.80%. Calculated for $C_{22}H_{16}Cl_2N_4O_3.0.25H_2O$: C, 57.45; H, 3.62; N, 12.19%].

(y) By proceeding in a similar manner to Example 12(a) but using Example 1(be) and 2-chloromethylnaphthalene there was prepared N-(3,5-dichloro-4-pyridyl)-1-(naphthalen-2-yl)methyl-3-methyl-1H-indole-6-carboxamide as a white solid, m.p. 241-243° C. [Elemental analysis: C, 67.32; H, 4.02; N, 9.06%. Calculated for $C_{26}H_{19}Cl_2N_3O.0.25H_2O$: C, 67.15; H, 4.23; N, 9.05%].

(z) By proceeding in a similar manner to Example 12(a) but using Example 1(be) and 2-chloromethyl-4-biphenyl there was prepared N-(3,5-dichloro-4-pyridyl)-1-(biphenyl-4-yl)methyl-3-methyl-1H-indole-6-carboxamide as a white solid, m.p. 229-230° C. [Elemental analysis: C, 68.63; H, 4.63; N, 8.26%. Calculated for $C_{28}H_{21}Cl_2N_3O.0.25H_2O$: C, 68.48; H, 4.42; N, 8.57%].

(aa) By proceeding in a similar manner to Example 12(a) but using Example 1(be) and 1-benzyl-2-(chloromethyl)-imidazole there was prepared N-(3,5-dichloro-4-pyridyl)-3-methyl-1-(1-benzyl-imidazol-2-yl)methyl-1H-indole-6-carboxamide as a yellow solid, m.p. 92-94° C.

EXAMPLE 13

(a) 1-Cyclohexylmethyl-3-methyl-N-(3,5-dichloro-1-oxido-4-pyridinio)-1H-indole-6-carboxamide A solution of N-(3,5-dichloro-1-oxido-4-pyridinio)-3-methyl-1H-indole-6-carboxamide (0.25 g, Example 14) in a mixture of dimethyl sulphoxide (5 ml) and tetrahydrofuran (5 ml) was added to a suspension of sodium hydride (0.045 g) in a mixture of dimethyl sulphoxide (2 ml) and tetrahydrofuran (2 ml) at 0° C. The mixture was stirred for 15 minutes then treated with cyclohexylbromide (0.142 g) in a mixture of dimethyl sulphoxide (3 ml) and tetrahydrofuran (3 ml). This mixture was stirred at 0° C. for 10 minutes then allowed to warm to room temperature. The reaction mixture was quenched with ice-water then diluted with water and then extracted three times with dichloromethane (15 ml). The combined extracts were washed three times with water (25 ml), then with brine (15 ml), then dried over sodium sulphate and then evaporated. The residue was subjected to flash column chromatography on silica eluting with a mixture of ethyl acetate and hexane (gradient elution, 4:1 to 4:0, v/v) to give the title compound (0.19 g) as a white solid, m.p. 127° C.

(b) By proceeding in a similar manner to Example 13(a) but using 4-methoxycarbonylbenzyl bromide there was prepared 1-(4-methoxycarbonylbenzyl)-3-methyl-N-(3,5-dichloro-1-oxido-4-pyridinio)-1H-indole-6-carboxamide as a white solid, m.p 169-172° C. [Elemental analysis:—C, 57.43; H, 4.26; N, 8.15%. Calculated for $C_{24}H_{19}Cl_2N_3O_4.H_2O$:—C, 57.36; H, 4.22; N, 8.37%]. NMR {(CD$_3$)$_2$CO}: δ 2.30(s, 3H); 3.80(s, 3H); 5.60(s, 2H); 7.20-7.30(s, 2H); 7.40(s, 1H); 7.60-7.65(m, 1H); 7.75-7.80(m, 1H); 7.85-7.90(m, 2H); 8.29(s, 1H); 8.35(s, 2H); 9.50 (bs, 1H).

(c) By proceeding in a similar manner to Example 13(a) but using 4-carboxybenzyl bromide there was prepared 1-(4-carboxybenzyl)-3-methyl-N-(3,5-dichloro-1-oxido-4-pyridinio)-1H-indole-6-carboxamide as a white solid, m.p 255-257° C. with decomposition. [Elemental analysis:—C, 58.05; H, 3.84; N, 8.66%. Calculated for $C_{23}H_{17}Cl_2N_3O_4$:—C, 58.74; H, 3.64; N, 8.93%].

(d) By proceeding in a similar manner to Example 13(a) but using (5-chlorothiophen-2-yl)methyl bromide there was prepared 1-(5-chlorothiophen-2-yl)methyl-N-(3,5-dichloro-1-oxido-4-pyridinio)-3-methyl-1H-indole-6-carboxamide as a beige coloured solid, m.p 140-142° C. with decomposition. [Elemental analysis:—C, 50.95; H, 3.13; N, 8.38%. Calculated for $C_{20}H_{14}Cl_3N_3O_2S.0.4H_2O$:—C, 50.65; H, 3.152; N, 8.87%]. NMR $\{(CD_3)_2SO)\}$: δ 2.30(s, 3H); 5.50(s, 2H); 7.00(s, 2H); 7.40-7.45(m, 1H); 7.60-7.65 and 7.70-7.75(m, 2H); 8.20(s, 1H); 8.70(s, 2H); 10.30(bs, 1H).

(e) By proceeding in a similar manner to Example 13(a) but using 1-benzyl-2-(chloromethyl)imidazole there was prepared 1-(1-benzyl-imidazol-2-yl)methyl-N-(3,5-dichloro-1-oxido-4-pyridinio)-3-methyl-1H-indole-6-carboxamide as a white solid, m.p >112° C. with decomposition. NMR $\{(CD_3)_2CO)\}$: δ 2.20(s, 3H); 5.20(s, 2H); 5.40(s, 2H); 6.90-7.00(m, 3H); 7.10-7.15(m, 2H); 7.15-7.20(m, 3H); 7.50-7.55 and 7.70-7.75(m, 1H); 8.30(s, 1H); 8.40(s, 2H); 9.60(bs, 1H).

(f) By proceeding in a similar manner to Example 13(a) but using 4-(chloromethyl)-2-methylthiazole there was prepared 1-(2-methylthiazol-4-yl)methyl-N-(3,5-dichloro-1-oxido-4-pyridinio)-3-methyl-1H-indole-6-carboxamide as a yellow solid, m.p 125-127° C. with decomposition. [Elemental analysis:—C, 53.25; H, 3.65; N, 12.25%. Calculated for $C_{20}H_{16}Cl_2N_4O_2$:—C, 53.70; H, 3.61; N, 12.52%].

(g) By proceeding in a similar manner to Example 13(a) but using methyl 5-(bromomethyl)-furan-2-carboxylate there was prepared methyl 5-[6-N-(3,5-dichloro-1-oxido-4-pyridinio)carbamoyl-3-methyl-indol-1-ylmethyl]-furan-2-carboxylate as a white solid, m.p 196-198° C. [Elemental analysis:—C, 57.20; H, 4.80; N, 9.70%. Calculated for $C_{20}H_{19}Cl_2N_3O_4$:—C, 57.16; H, 4.56; N, 10.00%].

(h) By proceeding in a similar manner to Example 13(a) but using 4-(chloromethyl)-3,5-dimethylisoxazole there was prepared 1-(3,5-dimethylisoxazol-4-yl)methyl-N-(3,5-dichloro-1-oxido-4-pyridinio)-3-methyl-1H-indole-6-carboxamide as a yellow solid, m.p 145-148° C. [Elemental analysis:—C, 55.16; H, 4.02; N, 12.10%. Calculated for $C_{21}H_{18}Cl_2N_3O_3$:—C, 56.64; H, 4.07; N, 12.58%].

(i) By proceeding in a similar manner to Example 12(a) but using 4-(chloromethyl)-2-methylthiazole there was prepared 1-(2-methylthiazol-4-yl)methyl-N-(3,5-dichloro-1-oxido-4-pyridinio)-3-methyl-1H-indole-6-carboxamide as a yellow solid, m.p 125-127° C. with decomposition. [Elemental analysis:—C, 53.25; H, 3.65; N, 12.25%. Calculated for $C_{20}H_{16}Cl_2N_4O_2$:—C, 53.70; H, 3.61; N, 12.52%].

EXAMPLE 14

N-(3,5-Dichloro-1-oxido-4-pyridinio)-3-methyl-1H-indole-6-carboxamide

1-Butyloxycarbonyl-N-(3,5-dichloro-1-oxido-4-pyridinio)-3-methyl-indole-6-carboxamide (0.2 g, Example 1(bf) was heated at 170-180° C. for 10 minutes to give the title compound as a white solid which was used without further purification. NMR $\{(CD_3)_2SO\}$: δ 2.30(s), 7.30(s), 7.50-7.60(m), 8.00(s), 8.70(s), 10.30(s), 11.20(s).

EXAMPLE 15

(a) N-(3,5-Dichloro-pyridin-4-yl)-3-ethyl-1-(toluene-4-sulphonyl)-1H-indole-6-carboxamide A stirred solution of N-(3,5-dichloro-pyridin-4-yl)-3-(1-hydroxyethyl)-1-(toluene-4-sulphonyl)-1H-indole-6-carboxamide [0.06 g, Example 16(a)] in dichloromethane (2 ml), under nitrogen and at 0° C., was treated with triethylsilane (0.028 g,) and boron trifluoride dietherate (0.015 ml). The mixture was allowed to warm to room temperature and then stirred at this temperature for 3 hours. The solution was partitioned between ethyl acetate (15 ml) and saturated sodium bicarbonate solution (15 ml). The organic layer was dried over sodium sulphate then evaporated. The residue was subjected to flash column chromatography on silica eluting with a mixture of ethyl acetate and hexane (gradient elution, 1:3 to 2:1, v/v) to give the title compound (22 mg) as a white solid, m.p. 147-149° C. [Elemental analysis:—C, 56.69; H, 4.04; N, 8.15%. Calculated for $C_{23}H_{19}Cl_2N_3O_3S$:—C, 56.56; H, 3.92; N, 8.60%].

(b) By proceeding in a similar manner to Example 15(a) but using N-(3,5-dichloro-pyridin-4-yl)-3-(1-hydroxy-1-methyl-propyl)-1-(toluene-4-sulphonyl)-1H-indole-6-carboxamide, Example 16(b), there was prepared N-(3,5-dichloro-pyridin-4-yl)-3-(2-methyl-propyl)-1-(toluene-4-sulphonyl)-1H-indole-6-carboxamide as a white solid, m.p. 104-108° C. [Elemental analysis:—C, 58.84; H, 4.67; N, 7.80%. Calculated for $C_{25}H_{23}Cl_2N_3O_3S$:—C, 58.14; H, 4.49; N, 8.14%].

EXAMPLE 16

(a) N-(3,5-Dichloro-pyridin-4-yl)-3-(1-hydroxyethyl)-1-(toluene-4-sulphonyl)-1H-indole-6-carboxamide A stirred solution of N-(3,5-dichloro-pyridin-4-yl)-3-formyl-1-(toluene-4-sulphonyl)-1H-indole-6-carboxamide (0.1 g, Example 17) in tetrahydrofuran (3 ml), at 0° C., was treated with a solution of methylmagnesium bromide in diethyl ether (0.11 ml, 3M). The mixture was allowed to warm to room temperature then stirred for 2 hours. The reaction mixture was quenched with water (15 ml) and then extracted with ethyl acetate (15 ml). The organic extract was dried over sodium sulphate then evaporated. The residue was subjected to flash column chromatography on silica eluting with a mixture of ethyl acetate and hexane (2:1, v/v) to yield the title compound (68 mg) as a white solid, m.p. 206-211° C. [Elemental analysis:—C, 55.07; H, 4.00; N, 7.92%. Calculated for $C_{23}H_{19}Cl_2N_3O_4S$:—C, 54.77; H, 3.80; N, 8.33%].

(b) By proceeding in a similar manner to Example 16(a) but using isopropylmagnesium chloride there was prepared N-(3,5-dichloro-pyridin-4-yl)-3-(1-hydroxy-2-methyl-propyl)-1-(toluene-4-sulphonyl)-1H-indole-6-carboxamide.

EXAMPLE 17

N-(3,5-Dichloro-pyridin-4-yl)-3-formyl-1-(toluene-4-sulphonyl)-1H-indole-6-carboxamide A stirred solution of N-(3,5-dichloro-pyridin-4-yl)-3-formyl-1H-indole-6-carboxamide (0.518 g, Example 18) in dimethylformamide at 0° C. was treated with sodium hydride (0.136 g). The mixture was stirred for 15 minutes, then cooled to −40° C. and then treated with 4-toluenesulphonyl chloride (0.325 g). The reaction mixture was gradually allowed to warm to −20° C. over a period of 90 minutes, then quenched with water (20 ml), then extracted three times with ethyl acetate (25 ml). The combined extracts were dried over sodium sulphate then evaporated to give the title compound (800 mg), which was used without further purification as a white solid, m.p. 245° C. [Elemental analysis:—C, 53.91; H, 3.34; N, 8.30%. Calculated for $C_{22}H_{15}Cl_2N_3O_4S$:—C, 54.11; H, 3.10; N, 8.60%].

EXAMPLE 18

N-(3,5-Dichloro-pyridin-4-yl)-3-formyl-1H-indole-6-carboxamide

A stirred solution of dimethylformamide (10 ml), under nitrogen and at 0° C., was treated with phosphorus oxychloride (0.6 ml). After stirring for 30 minutes at 0° C. the mixture was treated with a solution of N-(3,5-dichloro-pyridin-4-yl)-1H-indole-6-carboxamide [1.55 g, Example 1(bg)] in dimethylformamide (5 ml). The mixture was then heated at 40° C. for 45 minutes then cooled to room temperature and then partitioned between ethyl acetate (25 ml) and saturated sodium bicarbonate (50 ml). The organic layer was washed with water (75 ml) then dried over sodium sulphate then evaporated. The residue was subjected to flash chromatography on silica eluting with a mixture of ethyl acetate and hexane (1:2, v/v) to yield the title compound (0.53 g) as a white solid. [Elemental analysis:—C, 53.83; H, 2.99; N, 12.31%. Calculated for $C_{15}H_9Cl_2N_3O_2$:—C, 53.92; H, 2.71; N, 12.57%].

EXAMPLE 19

1-Benzyl-4-[3-methyl-1-(3-phenyl-propyl)-1H-indole-6-yl]-pyrrolidine-2-one

A solution of sodium hydride (0.013 g) in tetrahydrofuran at 0° C., under argon, was treated with a solution of 4-[3-methyl-1-(3-phenyl-propyl)-1H-indole-6-yl]-pyrrolidine-2-one (0.184 g, Example 20) and benzyl bromide (0.094 g) in dry tetrahydrofuran. The mixture was allowed to warm to room temperature then treated with N,N'-dimethylpropyleneurea (0.05 g). After stirring at room temperature overnight the solution was partitioned between ethyl acetate (15 ml) and 1N hydrochloric acid (15 ml). The organic phase was dried over magnesium sulphate then evaporated. The residue was subjected to preparative layer chromatography on silica using a mixture of ethyl acetate and hexane (3:7, v/v) as eluent to yield the title compound (0.18 g) as an oil. [Elemental analysis:—C, 79.16; H, 6.98; N, 6.14%. Calculated for $C_{29}H_{30}N_2O.H_2O$:—C, 79.04; H, 7.33; N, 6.36%].

EXAMPLE 20

4-[3-Methyl-1-(3-phenyl-propyl)-1H-indole-6-yl]-pyrrolidine-2-one

A solution of methyl 3-(3-methyl-1-{3-(phenyl)propyl}-1H-indol-6-yl)-3-nitromethyl-propionate (0.296 g, Reference Example 38) in methanol (100 ml), under argon, was treated with excess Raney® nickel. The argon atmosphere was replaced by hydrogen at 1 atmosphere then the mixture was stirred at room temperature for 2 hours. The reaction mixture was filtered through celite. The filtrate was evaporated and the residual crude methyl 3-(3-methyl-1-{3-(phenyl)propyl}-1H-indol-6-yl)-3-aminomethyl-propionate was dissolved in sodium hydroxide solution (15 ml, 1N). After stirring at room temperature for 1 hour the reaction mixture was extracted three times with ethyl acetate (15 ml). The combined extracts were dried over sodium sulphate then evaporated. The residue was subjected to preparative layer chromatography on silica using a mixture of ethyl acetate and hexane (1:1, v/v) as eluent to yield the title compound (0.198 g) as an oil. NMR ($CDCl_3$): δ 2.05-2.15(m); 2.30(s); 2.55-2.60(m); 2.65-2.70(m); 2.85-2.95(m); 3.30-3.40(m); 3.60-3.70(m); 3.90-4.00(m); 4.40-4.60(m); 6.80-7.40(m). $M^+$332.1941.

EXAMPLE 21

1-(4-Methoxybenzyl)-3-methyl-6-(1-phenyl-2-pyridin-4-yl-ethyl)-1H-indole

A solution of cis- and trans-[1-(4-methoxybenzyl)-3-methyl-6-(1-phenyl-2-pyridin-4-yl-vinyl)-1H-indole (70 mg, Example 22) in a mixture of tetrahydrofuran and methanol (20 ml; 1:1, v/v) was heated at 45-50° C. under an atmosphere of hydrogen in the presence of 6% palladium on activated charcoal then stirred overnight at room temperature. The mixture was filtered through celite then evaporated. The residue was subjected to high pressure liquid chromatography using a hypersilC18 BDS column (250×20 ml, 8 micron) and eluting with methanol containing 0.1% ammonium hydroxide to yield the title compound (13 mg) as an oil. NMR ($CDCl_3$): δ 2.30(s, 3H); 3.30-3.40(m, 2H); 3.70(s, 3H); 4.30-4.40(m, 1H); 5.10(s, 2H); 6.80-7.50 (m, 13H); 8.30-8.35(m, 2H); 8.50(bs, 2H).

EXAMPLE 22 cis- and trans-[1-(4-Methoxybenzyl)-3-methyl-6-(1-phenyl-2-pyridin-4-yl-vinyl)-1H-indole A stirred solution of 6-(1-hydroxy-1-phenyl-2-pyridin-4-yl)ethyl-1-(4-methoxybenzyl)-3-methyl-1H-indole (50 mg, Example 23) in benzene (1.5 ml) at 0° C. was treated with 4-toluenesulphonic acid (42 mg). After stirring at 0° C. for 20 minutes the reaction mixture was partitioned between ethyl acetate (10 ml) and saturated sodium bicarbonate solution (10 ml). The organic layer was dried over sodium sulphate then evaporated to yield the title compound (45 mg) as a yellow solid. [Elemental analysis:—C, 82.40; H, 6.20; N, 6.30%. Calculated for $C_{30}H_{26}N_2O.0.5H_2O$:—C, 81.96; H, 6.20; N, 6.38%]. NMR($CDCl_3$): [3:1, trans:cis isomers]δ 2.30 and 2.32(s, 3H); 3.78 and 3.79(s, 3H); 5.05 and 5.07(s, 2H); 6.70-6.95, 6.95-7.05, 7.10-7.25 and 7.30-7.50 (m, 11H); 8.35 (bs, 2H).

EXAMPLE 23

6-(1-hydroxy-1-phenyl-2-pyridin-4-yl)ethyl-1-(4-methoxybenzyl)-3-methyl-1H-indole A stirred solution of 4-methylpyridine (60 mg) in tetrahydrofuran (3 ml), under nitrogen and at −78° C., was treated dropwise with a solution of n-butyllithium in hexane (0.385 ml). After 30 minutes a solution of 1-(4-methoxybenzyl)-3-methyl-1H-indol-6-yl]-1-phenylmethanone (200 mg, Example 24) in tetrahydrofuran (3 ml) was added and the mixture was stirred at −78° C. for 1 hour, then warmed to room temperature and then stirred overnight. The reaction mixture was quenched with water (15 ml) and then extracted three times with ethyl acetate (15 ml). The combined extracts were dried over sodium sulphate and then evaporated. The residue was subjected to flash column chromatography on silica eluting with a mixture of ethyl acetate and hexane (gradient elution, 1:3 to 3:1, v/v) to yield the title compound (15 mg) as a white solid. [Elemental analysis:—C, 79.5; H, 6.30; N, 6.10%. Calculated for $C_{30}H_{28}N_2O_2.0.25H_2O$:—C, 79.5; H, 6.34; N, 6.18%]. NMR ($CDCl_3$): δ 2.30(3H, s), 3.5-3.7(2H, m), 3.75(3H, s), 5.05 (2H, s), 6.75-7.55 (m), 8.15-8.20(m, 2H).

EXAMPLE 24

[1-(4-Methoxy-benzyl)-3-methyl-1H-indol-6-yl]-phenyl methanone

A stirred solution of N-methoxy-1-(4-methoxybenzyl)-3-methyl-N-methyl-1H-indole-6-carboxamide (2.215 g, Example 25) in tetrahydrofuran (55 ml) was treated with a solution of phenylmagnesium chloride in tetrahydrofuran (9.83 ml, 2M). The solution was stirred at 0° C. for 2 hours then poured into a mixture of ice and 1N hydrochloric acid (10 ml) and then partitioned between ethyl acetate (50 ml) and water (50 ml). The organic layer was dried over sodium sulphate then evaporated. The residue was subjected to flash chromatography on silica eluting with a mixture of ethyl acetate and hexane (1:2, v/v) to yield the title compound (2.05 g) as a yellow solid, m.p. 146-147° C. [Elemental analysis:—C, 80.80; H, 6.00; N, 3.80%. Calculated for $C_{24}H_{21}NO_2$:—C, 81.10; H, 5.96; N, 3.94%].

EXAMPLE 25

N-methoxy-1-(4-methoxybenzyl)-3-methyl-N-methyl-1H-indole-6-carboxamide

A stirred solution of 1-(4-methoxybenzyl)-3-methyl-1H-indole-6-carbonyl chloride [2.8 g, Reference Example 42(b)] in chloroform (90 ml) at 0° C. was treated with N,O-dimethylhydroxylamine hydrochloride (0.982 g) and pyridine (1.55 ml). The solution was stirred at room temperature for 1 hour then evaporated. The residue was partitioned between dichloromethane (100 ml) and brine (50 ml). The organic layer was dried over sodium sulphate then evaporated. The residue was subjected to flash chromatography on silica eluting with a mixture of ethyl acetate and hexane (1:2, v/v) to yield the title compound (2.8 g).

EXAMPLE 26

(a) 1-Benzyl-N-(3,5-dichloro-1-oxido-4-pyridinio)-3-methyl-1H-indazole-6-carboxamide A solution of 4-amino-3,5-dichloropyridine-N-oxide (0.501 g, prepared as described in the specification of International Patent Application Publication No. WO 92/12961) in a mixture of toluene and tetrahydrofuran (20 ml; 1:1, v/v) was treated with trimethylaluminium (2.8 ml). After stirring at ambient temperature for 1 hour the mixture was treated dropwise with a solution of 1-benzyl-3-methyl-1H-indazole carbonyl chloride (0.16 g, Reference Example 42(a) in dry tetrahydrofuran (25 ml). Stirring was continued at ambient temperature for 2 hours then the mixture was heated at 90° C. for 12 hours. The reaction mixture was cooled to room temperature then poured into water (15 ml) then extracted three times with ethyl acetate (45 ml). The combined extracts were dried over sodium sulphate then evaporated. The residue was subjected to preparative layer chromatography on silica using a mixture of ethyl acetate and hexane (2:1, v/v) as eluent to yield the title compound (0.071 g) as a white solid. [Elemental analysis:—C, 58.03; H, 3.78; N, 12.60%. Calculated for $C_{21}H_{16}Cl_2N_4O_2.0.5H_2O$:—C, 57.79; H, 3.93; N, 12.85%].

(b) By proceeding in a similar manner to Example 26(a) but using 4-amino-3,5-dichloropyridine and Reference Example 42(e) there was prepared N-(3,5-dichloro-4-pyridyl)-1-(4-methoxybenzyl)-3-methyl-1H-indazole-6-carboxamide as a white solid, m.p. 213-214° C. [Elemental analysis:—C, 59.47; H, 4.21; N, 12.24%. Calculated for $C_{22}H_{18}Cl_2N_4O_2.0.25H_2O$:—C, 59.25; H, 4.18; N, 12.57%]. NMR (CDCl$_3$): δ 2.60(s, 3H); 3.70(s, 3H); 5.50(s, 2H); 6.70-6.80 and 7.10-7.20(m, 4H); 7.60-7.65, 7.70-7.75 and 8.00-8.05(m, 3H); 8.50(bs, 2H).

EXAMPLE 27

(a) N-(3,5-Dichloro-1-oxido-4-pyridinio)-4-methoxy-2-methoxymethyl-benzoxazole-6-carboxamide A stirred solution of 4-acetylamino-3,5-dichloro-pyridine N-oxide (0.64 g) in dry dimethylformamide (40 ml), under nitrogen and at room temperature, was treated portionwise with sodium hydride (2.15 g, 60% dispersion in mineral oil). After stirring for 1.5 hours the pale yellow solution was treated with a solution of 4-methoxy-2-methoxymethyl-benzoxazole-6-carbonyl chloride [Reference Example 42(c), prepared from 0.68 g of 4-methoxy-2-methoxymethyl-benzoxazole-6-carboxylic acid] in dry dimethylformamide (15 ml) whilst maintaining the reaction temperature at about 10° C. The reaction mixture was allowed to warm to room temperature, then stood at room temperature for 18 hours, then treated with piperidine (1 ml), then stood at room temperature for 24 hours. The mixture was evaporated and the residual dark brown oil was treated with ethyl acetate, then filtered. The filtrate was treated with silica (1 g) then evaporated. The residue was subjected to flash chromatography on silica eluting initially with dichloromethane then with a mixture of dichloromethane and methanol (49:1,v/v) and then with a mixture of dichloromethane and methanol (25:1,v/v). Fractions containing the required product were combined and evaporated and the resulting white solid was washed with diethyl ether to give the title compound (0.44 g) as a white powder, m.p. 199-202° C. [Elemental analysis:—C, 48.26; H, 3.43; N, 10.83%. Calculated:—C, 48.22; H, 3.29; N, 10.55%].

(b) By proceeding in a similar manner to Example 27(a) but using 4-amino-3,5-dichloropyridine and Reference Example 42(d), there was prepared N-(3,5-dichloro-4-pyridyl)-3-isopropyl-1-methyl-1H-indole-5-carboxamide which was recrystallised form toluene as a colourless solid, m.p. 186-189° C.

REFERENCE EXAMPLE 1

(a) 1'-Benzotriazolyl 7-methoxy-2-methoxymethyl-3H-benzimidazole-4-carboxylate

A stirred solution of 7-methoxy-2-methoxymethyl-3H-benzimidazole-4-carboxylic acid [10.6 g, Reference Example 2(a)] in a mixture of dichloromethane (120 ml) and diisopropylethylamine (12.5 ml) was treated with O-benzotriazol-1-yl-N,N,N',N'-bis(tetramethylene)uronium tetrafluoroborate (15.4 g). After stirring for 2 hours the reaction mixture was evaporated. The residue was treated with toluene and concentrated under vacuum affording the title compound which was used without further purification.

(b) By proceeding in a similar manner to Reference Example 1(a) but using Reference Example 2(b), there was prepared 1'-benzotriazolyl 7-methoxy-2-phenyl-3H-benzimidazole-4-carboxylate.

(c) By proceeding in a similar manner to Reference Example 1(a) but using Reference Example 2(c), there was prepared 1'-benzotriazolyl 7-methoxy-2-phenethyl-3H-benzimidazole-4-carboxylate.

(d) By proceeding in a similar manner to Reference Example 1(a) but using Reference Example 2(d), there was prepared 1'-benzotriazolyl 2-benzyl-7-methoxy-3H-benzimidazole-4-carboxylate.

(e) By proceeding in a similar manner to Reference Example 1(a) but using Reference Example 2(e), there was prepared (RS)-1'-benzotriazolyl 7-methoxy-2-(1-phenylethyl)-3H-benzimidazole-4-carboxylate.

(f) By proceeding in a similar manner to Reference Example 1(a) but using Reference Example 2(f), there was prepared 1'-benzotriazolyl 7-methoxy-2-(4-methoxybenzyl)-3H-benzimidazole-4-carboxylate (g) By proceeding in a similar manner to Reference Example 1(a) but using Reference Example 2(g), there was prepared (RS)-1'-benzotriazolyl 2-(cyclohexyl-phenyl-methyl)-7-methoxy-3H-benzimidazole-4-carboxylate.

(h) By proceeding in a similar manner to Reference Example 1(a) but using Reference Example 2(h), there was prepared (RS)-1'-benzotriazolyl 2-(1,2-diphenylethyl)-7-methoxy-3H-benzimidazole-4-carboxylate (i) By proceeding in a similar manner to Reference Example 1(a) but using Reference Example 2(i), there was prepared (RS)-1'-benzotriazolyl 7-methoxy-2-(2-phenylpropyl)-3H-benzimidazole-4-carboxylate.

(j) By proceeding in a similar manner to Reference Example 1(a) but using Reference Example 2(j), there was prepared 1'-benzotriazolyl 7-methoxy-2-(4-methoxyphenoxymethyl)-3H-benzimidazole-4-carboxylate (k) By proceeding in a similar manner to Reference Example 1(a) but using Reference Example 2(k), there was prepared (RS)-1'-benzotriazolyl 7-methoxy-2-(1-phenylbutyl)-3H-benzimidazole-4-carboxylate.

(l) By proceeding in a similar manner to Reference Example 1(a) but using Reference Example 2(l), there was prepared 1'-benzotriazolyl 2-(4-bromobenzyl)-7-methoxy-3H-benzimidazole-4-carboxylate.

(m) By proceeding in a similar manner to Reference Example 1(a) but using Reference Example 2(m), there was prepared (RS)-1'-benzotriazolyl 7-methoxy-2-(3-methoxy-1-phenyl-propyl)-3H-benzimidazole-4-carboxylate.

(n) By proceeding in a similar manner to Reference Example 1(a) but using Reference Example 2(n), there was prepared 1'-benzotriazolyl 2-(4-cyanobenzyl)-7-methoxy-3H-benzimidazole-4-carboxylate.

(o) By proceeding in a similar manner to Reference Example 1(a) but using Reference Example 2(o), there was prepared 1'-benzotriazolyl 7-methoxy-2-(4-{3-pyridyl}benzyl)-3H-benzimidazole-4-carboxylate.

(p) By proceeding in a similar manner to Reference Example 1(a) but using Reference Example 2(p), there was prepared 1'-benzotriazolyl 7-methoxy-2-(2-methoxybenzyl)-3H-benzimidazole-4-carboxylate.

(q) By proceeding in a similar manner to Reference Example 1(a) but using Reference Example 2(q), there was prepared (RS)-1'-benzotriazolyl 7-methoxy-2-(methoxyphenyl-methyl)-3H-benzimidazole-4-carboxylate.

(r) By proceeding in a similar manner to Reference Example 1(a) but using Reference Example 2(r), there was prepared 1'-benzotriazolyl 7-methoxy-2-(2-methoxyphenoxy)methyl-3H-benzimidazole-4-carboxylate.

(s) By proceeding in a similar manner to Reference Example 1(a) but using Reference Example 2(s), there was prepared 1'-benzotriazolyl 7-methoxy-2-(3-pyridyl)-3H-benzimidazole-4-carboxylate.

(t) By proceeding in a similar manner to Reference Example 1(a) but using Reference Example 2(t), there was prepared 1'-benzotriazolyl 2-isopropyl-7-methoxy-3H-benzimidazole-4-carboxylate.

(u) By proceeding in a similar manner to Reference Example 1(a) but using Reference Example 2(u), there was prepared 1'-benzotriazolyl 7-methoxy-2-methyl-3H-benzimidazole-4-carboxylate.

(v) By proceeding in a similar manner to Reference Example 1(a) but using Reference Example 2(v), there was prepared 1'-benzotriazolyl 7-methoxy-2-phenoxymethyl-3H-benzimidazole-4-carboxylate.

(w) By proceeding in a similar manner to Reference Example 1(a) but using Reference Example 2(w), there was prepared 1'-benzotriazolyl 2-cyclopentyl-7-methoxy-3H-benzimidazole-4-carboxylate.

(x) By proceeding in a similar manner to Reference Example 1(a) but using Reference Example 2(x), there was prepared 1'-benzotriazolyl 2-benzyl-3H-benzimidazole-4-carboxylate.

(y) By proceeding in a similar manner to Reference Example 1(a) but using Reference Example 2(y), there was prepared 1'-benzotriazolyl 2-cyclopentyl-7-methoxy-1-methyl-1H-benzimidazole-4-carboxylate.

(z) By proceeding in a similar manner to Reference Example 1(a) but using Reference Example 2(z), there was prepared 1'-benzotriazolyl 2-cyclopentyl-7-methoxy-3-methyl-3H-benzimidazole-4-carboxylate.

(aa) By proceeding in a similar manner to Reference Example 1(a) but using Reference Example 2(aa), there was prepared 1'-benzotriazolyl 2,7-dimethoxy-3H-benzimidazole-4-carboxylate.

(ab) By proceeding in a similar manner to Reference Example 1(a) but using Reference Example 2(ab), there was prepared 1'-benzotriazolyl 2-cyclopropyl-7-methoxy-3H-benzimidazole-4-carboxylate.

(ac) By proceeding in a similar manner to Reference Example 1(a) but using Reference Example 28(a), there was prepared 1'-benzotriazolyl 1-cyclohexylmethyl-3-methyl-1H-indole-6-carboxylate.

(ad) By proceeding in a similar manner to Reference Example 1(a) but using Reference Example 31(b), there was prepared 1'-benzotriazolyl 1-cyclohexyl-3-methyl-1H-indole-6-carboxylate.

(ae) By proceeding in a similar manner to Reference Example 1(a) but using Reference Example 28(c), there was prepared 1'-benzotriazolyl 1-(2-cyclohexyl)ethyl-3-methyl-1H-indole-6-carboxylate.

(af) By proceeding in a similar manner to Reference Example 1(a) but using Reference Example 28(d), there was prepared 1'-benzotriazolyl 1-(3-cyclohexyl)propyl-3-methyl-1H-indole-6-carboxylate.

(ag) By proceeding in a similar manner to Reference Example 1(a) but using Reference Example 28(e), there was prepared 1'-benzotriazolyl 1-heptyl-3-methyl-1H-indole-6-carboxylate.

(ah) By proceeding in a similar manner to Reference Example 1(a) but using Reference Example 31(d), there was prepared 1'-benzotriazolyl 1-cycloheptylmethyl-3-methyl-1H-indole-6-carboxylate.

(ai) By proceeding in a similar manner to Reference Example 1(a) but using Reference Example 31(a), there was prepared 1'-benzotriazolyl 1-(6,6-dimethyl-bicyclo[3.1.1.]hept-3-ylmethyl)-3-methyl-1H-indole-6-carboxylate.

(aj) By proceeding in a similar manner to Reference Example 1(a) but using Reference Example 28(f), there was prepared 1'-benzotriazolyl 1-(3-phenyl)butyl-3-methyl-1H-indole-6-carboxylate.

(ak) By proceeding in a similar manner to Reference Example 1(a) but using Reference Example 28(g), there was prepared 1'-benzotriazolyl 1-(4-trifluoromethylbenzyl)-3-methyl-1H-indole-6-carboxylate.

(al) By proceeding in a similar manner to Reference Example 1(a) but using Reference Example 28(h), there was prepared 1'-benzotriazolyl 1-(4-methylsulphonylbenzyl)-3-methyl-1H-indole-6-carboxylate.

(am) By proceeding in a similar manner to Reference Example 1(a) but using Reference Example 28(i), there was prepared 1'-benzotriazolyl 1-(1,3-benzodioxol-5-yl)methyl-3-methyl-1H-indole-6-carboxylate.

(an) By proceeding in a similar manner to Reference Example 1(a) but using Reference Example 28(j), there was prepared 1'-benzotriazolyl 3-methyl-1-(naphthalen-2-yl)methyl-1H-indole-6-carboxylate.

(ao) By proceeding in a similar manner to Reference Example 1(a) but using Reference Example 28(k), there was prepared 1'-benzotriazolyl 3-methyl-1-(tetrahydro-2H-pyran-2-yl)methyl-1H-indole-6-carboxylate.

(ap) By proceeding in a similar manner to Reference Example 1(a) but using Reference Example 28(l), there was prepared 1'-benzotriazolyl 3-methyl-1-(tetrahydrofurfuryl)methyl-1H-indole-6-carboxylate.

(aq) By proceeding in a similar manner to Reference, Example 1(a) but using Reference Example 28(m), there was prepared 1'-benzotriazolyl 3-methyl-1-(4-toluenesulphonyl)-1H-indole-6-carboxylate.

(ar) By proceeding in a similar manner to Reference Example 1(a) but using Reference Example 28(n), there was prepared 1'-benzotriazolyl 3-methyl-1-(tetrahydrofuran-3-yl)-1H-indole-6-carboxylate.

(as) By proceeding in a similar manner to Reference Example 1(a) but using Reference example 26(a), there was prepared 1'-benzotriazolyl-8-methoxy-2-n-propylquinoline-5-carboxylate.

(at) By proceeding in a similar manner to Reference Example 1(a) but using Reference Example 28(b), there was prepared 1'-benzotriazolyl 3-methyl-1H-indole-6-carboxylate.

(au) By proceeding in a similar manner to Reference Example 1(a) but using Reference Example 32, there was prepared 1'-benzotriazolyl 1-butyloxycarbonyl-3-methyl-indole-6-carboxylate.

(av) By proceeding in a similar manner to Reference Example 1(a) but using Reference Example 37, there was prepared 1'-benzotriazolyl 1-benzyl-3-methyl-1H-indoline-6-carboxylate.

(aw) By proceeding in a similar manner to Reference Example 1(a) but using 1H-indole-6-carboxylic acid, there was prepared 1'-benzotriazolyl 1H-indole-6-carboxylate.

(ax) By proceeding in a similar manner to Reference Example 1(a) but using Reference Example 2(ac), there was prepared 1'-benzotriazolyl 7-methoxy-2-n-propyl-3H-benzimidazole-4-carboxylate.

REFERENCE EXAMPLE 2 a) 7-Methoxy-2-methoxymethyl-3H-benzimidazole-4-carboxylic acid

A solution of methyl 7-methoxy-2-methoxymethyl-3H-benzimidazole-4-carboxylate [12.12 g, Reference Example 3(a)] in methanol (100 ml) was treated with 2M sodium hydroxide (48 ml). The resulting mixture was heated to 50° C. then stirred at this temperature for 6 hours. The reaction mixture was concentrated to half its original volume then treated with 1M hydrochloric acid (98 ml). The solution was cooled in an icebath and the resulting solid filtered then dried under high vacuum overnight to give the title compound (11.0 g) as a solid. M$^+$236. This material was used without further purification.

(b) By proceeding in a similar manner to Reference Example 2(a) but using Reference Example 3(b), there was prepared 7-methoxy-2-phenyl-3H-benzimidazole-4-carboxylic acid as a white solid. M$^+$268.

(c) By proceeding in a similar manner to Reference Example 2(a) but using Reference Example 3(c), there was prepared 7-methoxy-2-phenethyl-3H-benzimidazole-4-carboxylic acid as a white solid. NMR $\{(CD_3)_2SO\}$: δ 3.10(m, 2H), 3.25(m, 2H), 4.05(s, 3H), 6.90(d, J=8 Hz, 1H), 7.25(m, 5H), 7.83(d, J=8 Hz, 1H).

(d) By proceeding in a similar manner to Reference Example 2(a) but using Reference Example 3(d), there was prepared 2-benzyl-7-methoxy-3H-benzimidazole-4-carboxylic acid as a solid. NMR $\{(CD_3)_2SO\}$: δ 4.00(s, 3H), 4.28(s, 2H), 6.92(d, J=8 Hz, 1H), 7.30(m, 5H), 7.78(d, J=8 Hz, 1H).

(e) By proceeding in a similar manner to Reference Example 2(a) but using Reference Example 3(e), there was prepared (RS)-7-methoxy-2-(1-phenylethyl)-3H-benzimidazole-4-carboxylic acid. M$^+$296.

(f) By proceeding in a similar manner to Reference Example 2(a) but using Reference Example 3(f), there was prepared 7-methoxy-2-(4-methoxybenzyl)-3H-benzimidazole-4-carboxylic acid. M$^+$312.

(g) By proceeding in a similar manner to Reference Example 2(a) but using Reference Example 3(g), there was prepared (RS)-2-(cyclohexyl-phenyl-methyl)-7-methoxy-3H-benzimidazole-4-carboxylic acid as a tan coloured solid.

(h) By proceeding in a similar manner to Reference Example 2(a) but using Reference Example 3(h), there was prepared (RS)-2-(1,2-diphenylethyl)-7-methoxy-3H-benzimidazole-4-carboxylic acid. M$^+$372.

(i) By proceeding in a similar manner to Reference Example 2(a) but using Reference Example 3(i), there was prepared (RS)-7-methoxy-2-(2-phenylpropyl)-3H-benzimidazole-4-carboxylic acid. NMR $\{(CD_3)_2SO\}$: δ 1.20(d, 3H), 3.50(m, 3H), 3.95(s, 3H), 7.15(m, 1H), 7.15-7.20(m, 1H), 7.23-7.36(m, 4H), 7.69(d, 1H), 12.10(bs, 1H).

(j) By proceeding in a similar manner to Reference Example 2(a) but using Reference Example 3(j), there was prepared 7-methoxy-2-(4-methoxyphenoxymethyl)-3H-benzimidazole-4-carboxylic acid. M$^+$328.

(k) By proceeding in a similar manner to Reference Example 2(a) but using Reference Example 3(k), there was prepared (RS)-7-methoxy-2-(1-phenylbutyl)-3H-benzimidazole-4-carboxylic acid. M$^+$324.

(l) By proceeding in a similar manner to Reference Example 2(a) but using Reference Example 3(l), there was prepared 2-(4-bromobenzyl)-7-methoxy-3H-benzimidazole-4-carboxylic acid. NMR $\{(CD_3)_2SO\}$: δ 3.90(s, 3H), 4.30(s, 2H), 6.80(d, 1H), 7.20(d, 2H), 7.40(d, 2H), 7.75(d, 1H).

(m) By proceeding in a similar manner to Reference Example 2(a) but using Reference Example 3(m), there was prepared (RS)-7-methoxy-2-(3-methoxy-1-phenyl-propyl)-3H-benzimidazole-4-carboxylic acid. M$^+$340.

(n) By proceeding in a similar manner to Reference Example 2(a) but using Reference Example 14, there was prepared 2-(4-cyanobenzyl)-7-methoxy-3H-benzimidazole-4-carboxylic acid. NMR {(CD$_3$)$_2$SO}: δ 4.00(s, 3H), 4.35(s, 2H), 6.80(d, 1H), 7.35(d, 2H), 7.50(d, 2H), 7.75(d, 1H).

(o) By proceeding in a similar manner to Reference Example 2(a) but Reference Example 15, there was prepared 7-methoxy-2-(4-{3-pyridyl}benzyl)-3H-benzimidazole-4-carboxylic acid. NMR {(CD$_3$)$_2$SO}: δ 3.95(s, 3H), 4.30(s, 2H), 6.75(d, 1H), 7.45(d, 3H), 7.70(d, 3H), 8.05(dd, 1H), 8.55(d, 1H), 8.85(d, 1H).

(p) By proceeding in a similar manner to Reference Example 2(a) but using Reference Example 3(n)], there was prepared 7-methoxy-2-(2-methoxybenzyl)-3H-benzimidazole-4-carboxylic acid. M$^+$312.

(q) By proceeding in a similar manner to Reference Example 2(a) but using Reference Example 3(o) or Reference Example 12, there was prepared (RS)-7-methoxy-2-(methoxy-phenyl-methyl)-3H-benzimidazole-4-carboxylic acid. M$^+$312.

(r) By proceeding in a similar manner to Reference Example 2(a) but using Reference Example 3(p), there was prepared 7-methoxy-2-(2-methoxyphenoxy)methyl-3H-benzimidazole-4-carboxylic acid.

(s) By proceeding in a similar manner to Reference Example 2(a) but using Reference Example 13, there was prepared 7-methoxy-2-(3-pyridyl)-3H-benzimidazole-4-carboxylic acid.

(t) By proceeding in a similar manner to Reference Example 2(a) but using Reference Example 3(q), there was prepared 2-isopropyl-7-methoxy-3H-benzimidazole-4-carboxylic acid as a solid. NMR {(CD$_3$)$_2$SO}: δ 1.36(d, J=6 Hz, 6H), 3.50(m, 1H), 4.05(s, 3H), 6.95(d, J=8 Hz, 1H), 7.85(d, J=8 Hz, 1H).

(u) By proceeding in a similar manner to Reference Example 2(a) but using Reference Example 3(r), there was prepared 7-methoxy-2-methyl-3H-benzimidazole-4-carboxylic acid as a white solid. M$^+$206.

(v) By proceeding in a similar manner to Reference Example 2(a) but using Reference Example 3(s), there was prepared 7-methoxy-2-phenoxymethyl-3H-benzimidazole-4-carboxylic acid as a solid. M$^+$298.

(w) By proceeding in a similar manner to Reference Example 2(a) but using Reference Example 3(t), there was prepared 2-cyclopentyl-7-methoxy-3H-benzimidazole-4-carboxylic acid as a solid. NMR {(CD$_3$)$_2$SO}: δ 1.68(m, 2H), 1.82(m, 2H), 1.94(m, 2H), 2.09(m, 2H), 3.56(m, 1H), 4.04(s, 3H), 7.00(d, J=8 Hz, 1H), 7.86(d, J=8 Hz, 1H).

(x) By proceeding in a similar manner to Reference Example 2(a) but using Reference Example 3(u), there was prepared 2-benzyl-3H-benzimidazole-4-carboxylic acid. M$^+$252.

(y) By proceeding in a similar manner to Reference Example 2(a) but using Reference Example 5, there was prepared 2-cyclopentyl-7-methoxy-1-methyl-1H-benzimidazole-4-carboxylic acid. M$^+$274.

(z) By proceeding in a similar manner to Reference Example 2(a) but using Reference Example 6, there was prepared 2-cyclopentyl-7-methoxy-3-methyl-3H-benzimidazole-4-carboxylic acid.

(aa) By proceeding in a similar manner to Reference Example 2(a) but using Reference Example 7, there was prepared 2,7-dimethoxy-3H-benzimidazole-4-carboxylic acid. M$^+$222.

(ab) By proceeding in a similar manner to Reference Example 2(a) but using Reference Example 3(v), there was prepared 2-cyclopropyl-7-methoxy-3H-benzimidazole-4-carboxylic acid. [Elemental analysis:—C, 62.06; H, 5.21; N, 12.05%. Calculated:—C, 62.07; H, 5.17; N, 12.07%].

(ac) By proceeding in a similar manner to Reference Example 2(a) but using Reference Example 3(x), there was prepared 7-methoxy-2-n-propyl-3H-benzimidazole-4-carboxylic acid.

REFERENCE EXAMPLE 3

(a) Methyl 7-methoxy-2-methoxymethyl-3H-benzimidazole-4-carboxylate

A solution of methyl 3-(1-imino-2-methoxy-ethylamino)-4-methoxybenzoate [15.7 g, Reference Example 4(a)] in methanol (150 ml) was treated with 1M hydrochloric acid (62.6 ml) then with sodium hypochlorite solution (32.3 ml, 13%). Further aliquots of sodium hypochlorite solution were added until all the starting material was consumed. The solution containing methyl 3-(1-chloroimino-2-methoxy-ethylamino)-4-methoxybenzoate was treated with a saturated solution of sodium carbonate (8.62 g) in water. The mixture was then refluxed for 1 hour, then cooled to room temperature, then diluted with water and then extracted with chloroform. The chloroform extract was washed with brine, dried over magnesium sulphate and then evaporated. The residue was subjected to flash chromatography on silica eluting with a mixture of ethyl acetate and hexane (1:1, v/v) then with a mixture of ethyl acetate and hexane (6:1, v/v) to give the title compound (13.0 g) as a solid. M$^+$250. NMR (CDCl$_3$): δ 3.48(s, 3H), 3.98(s, 3H), 4.10(s, 3H), 4.78(s, 2H), 6.70(d, J=8 Hz, 1H), 7.87(d, J=8 Hz, 1H).

(b) By proceeding in a similar manner to Reference Example 3(a) but using Reference Example 4(b), there was prepared methyl 7-methoxy-2-phenyl-3H-benzimidazole-4-carboxylate as a solid. NMR (CDCl$_3$): δ 4.00(s, 3H), 4.11(s, 3H), 6.74(d, J=8 Hz, 1H), 7.5(m, 3H), 7.88(d, J=8 Hz, 1H), 8.12(m, 2H), 10.69(bs, 1H).

(c) By proceeding in a similar manner to Reference Example 3(a) but using Reference Example 4(c), there was prepared methyl 7-methoxy-2-phenethyl-3H-benzimidazole-4-carboxylate as a white solid. NMR (CDCl$_3$): δ 3.20 (m, 4H), 3.90(s, 3H), 4.08(s, 3H), 6.70(d, J=8 Hz, 1H), 7.25(m, 5H), 7.83(d, J=8 Hz, 1H), 9.95(bs, 1H).

(d) By proceeding in a similar manner to Reference Example 3(a) but using Reference Example 4(d), there was prepared methyl 2-benzyl-7-methoxy-3H-benzimidazole-4-carboxylate. NMR (CDCl$_3$): δ 3.90(s, 3H), 4.10(s, 3H), 4.35(s, 2H), 6.70(d, J=8 Hz, 1H), 7.30(m, 5H), 7.80(d, J=8 Hz, 1H), 9.97(bs, 1H).

(e) By proceeding in a similar manner to Reference Example 3(a) but using Reference Example 4(e), there was prepared (RS)-methyl 7-methoxy-2-(1-phenylethyl)-3H-benzimidazole-4-carboxylate. NMR (CDCl$_3$): δ 1.88(d, J=7.5 Hz, 3H), 3.90(s, 3H), 4.10(s, 3H), 4.44(q, J=7.5 Hz, 1H), 6.70(d, J=8 Hz, 1H), 7.30(m, 5H), 7.82(d, J=8 Hz, 1H).

(f) By proceeding in a similar manner to Reference Example 3(a) but using Reference Example 4(f), there was prepared methyl 7-methoxy-2-(4-methoxybenzyl)-3H-benzimidazole-4-carboxylate. NMR (CDCl$_3$): δ 3.80(s, 3H), 3.90(s, 3H), 4.08(s, 3H), 4.27(s, 2H), 6.69(d, J=8 Hz, 1H), 6.88(m, 2H), 7.25(m, 2H), 7.90(d, J=8 Hz, 1H), 9.90(bs, 1H).

(g) By proceeding in a similar manner to Reference Example 3(a) but using Reference Example 4(g), there was prepared (RS)-methyl 2-(cyclohexyl-phenyl-methyl)-7-methoxy-3H-benzimidazole-4-carboxylate. NMR (CDCl$_3$): δ 0.80-1.40(m, 5H), 1.6(m, 5H), 2.4(m, 1H), 3.86(d, 1H), 3.90(s, 3H), 4.07(s, 3H), 6.65(d, J=8 Hz, 1H), 7.20(m, 1H), 7.3(m, 2H), 7.45(m, 2H), 7.78(d, J=8 Hz, 1H), 10.1(bs, 1H).

(h) By proceeding in a similar manner to Reference Example 3(a) but using Reference Example 4(h), there was prepared (RS)-methyl 2-(1,2-diphenylethyl)-7-methoxy-3H-benzimidazole-4-carboxylate as a solid. NMR (CDCl$_3$): δ 3.40(dd, J=15 and 8.5 Hz, 3H), 3.87(s, 3H), 3.94(dd, J=15 and 7 Hz, 1H), 4.10(s, 3H), 4.43(dd, J=8.5 and 7 Hz, 1H), 6.70(d, J=8 Hz, 1H), 7.00-7.30 (m, 10H), 7.33(d, J=8 Hz, 1H), 9.93(bs, 1H).

(i) By proceeding in a similar manner to Reference Example 3(a) but using Reference Example 4(i), there was prepared (RS)-methyl 7-methoxy-2-(2-phenylpropyl)-3H-benzimidazole-4-carboxylate. NMR (CDCl$_3$): δ 1.38(d, 3H), 3.22(d, 2H), 3.36-3.49(m, 1H), 3.90(s, 3H), 4.08(s, 3H), 6.70(d, 1H), 7.22-7.39(m, 5H), 7.81(d, 1H), 9.65(bs, 1H).

(j) By proceeding in a similar manner to Reference Example 3(a) but using Reference Example (j), there was prepared methyl 7-methoxy-2-(4-methoxyphenoxymethyl)-3H-benzimidazole-4-carboxylate. NMR (CDCl$_3$): δ 3.79(s, 3H), 3.94(s, 3H), 4.10(s, 3H), 5.32(s, 2H), 6.71(d, J=8 Hz, 1H), 6.84(m, 2H), 6.97(m, 2H), 7.90(d, J=8 Hz, 1H).

(k) By proceeding in a similar manner to Reference Example 3(a) but using Reference Example 4(k), there was prepared (RS)-methyl 7-methoxy-2-(1-phenylbutyl)-3H-benzimidazole-4-carboxylate. NMR (CDCl$_3$): δ 0.93(t, J=7.5 Hz, 3H), 1.3(m, 2H), 2.06(m, 1H), 2.46(m, 1H), 3.90(bs, 3H), 4.10(s, 3H), 4.23(dd, J=9 and 7 Hz, 1H), 6.69(d, J=8 Hz, 1H), 7.30(m, 5H), 7.79(d, J=8 Hz, 1H), 9.90(bs, 1H).

(l) By proceeding in a similar manner to Reference Example 3(a) but using Reference Example 4(l), there was prepared methyl 2-(4-bromobenzyl)-7-methoxy-3H-benzimidazole-4-carboxylate as a solid. NMR (CDCl$_3$): δ 3.90(s, 3H), 4.06(s, 3H), 4.25(s, 2H), 6.70(d, J=8 Hz, 1H), 7.19(d, J=8 Hz, 1H), 7.45(d, J=8 Hz, 2H), 7.83(d, J=8 Hz, 1H), 10.04(bs, 1H).

(m) By proceeding in a similar manner to Reference Example 3(a) but using Reference Example 4(m), there was prepared (RS)-methyl 7-methoxy-2-(3-methoxy-1-phenylpropyl)-3H-benzimidazole-4-carboxylate. NMR (CDCl$_3$): δ 2.39(m, 1H), 2.73(m, 1H), 3.31(s, 3H), 3.39(s, 2H), 3.91(s, 3H), 4.10(s, 3H), 4.50(t, J=8 Hz, 1H), 6.70(d, J=8 Hz, 1H), 7.30(m, 5H), 7.84(d, J=8 Hz, 1H).

(n) By proceeding in a similar manner to Reference Example 3(a) but using Reference Example 4(n), there was prepared methyl 7-methoxy-2-(2-methoxybenzyl)-3H-benzimidazole-4-carboxylate. NMR (CDCl$_3$): δ 3.92(s, 3H), 4.02(s, 3H), 4.03(s, 3H), 4.79(s, 2H), 6.62(d, J=9 Hz, 1H), 6.92(m, 2H), 7.24(m, 1H), 7.30(m, 1H), 7.78(d, J=9 Hz, 1H), 10.58(bs, 1H).

(o) By proceeding in a similar manner to Reference Example 3(a) but using Reference Example 4(o), there was prepared (RS)-methyl 7-methoxy-2-(methoxy-phenyl-methyl)-3H-benzimidazole-4-carboxylate.

(p) By proceeding in a similar manner to Reference Example 3(a) but using Reference Example 4(p), there was prepared methyl 7-methoxy-2-(2-methoxyphenoxy)methyl-3H-benzimidazole-4-carboxylate. NMR (CDCl$_3$): δ 3.95 (s, 3H), 3.96(s, 3H), 4.07(s, 3H), 5.47(s, 2H), 6.71(d, J=8 Hz, 1H), 6.82-7.05(m, 3H), 7.10(m, 1H), 7.90(d, J=8 Hz, 1H).

(q) By proceeding in a similar manner to Reference Example 3(a) but using Reference Example 4(q), there was prepared methyl 2-isopropyl-7-methoxy-3H-benzimidazole-4-carboxylate as a tan coloured solid.

(r) By proceeding in a similar manner to Reference Example 3(a) but using Reference Example 4(r), there was prepared methyl 7-methoxy-2-methyl-3H-benzimidazole-4-carboxylate. NMR (CDCl$_3$): δ 2.65(s, 3H), 3.96(s, 3H), 4.07(s, 3H), 6.68(d, J=8 Hz, 1H), 7.80(d, J=8 Hz, 1H).

(s) By proceeding in a similar manner to Reference Example 3(a) but using Reference Example 4(s), there was prepared methyl 7-methoxy-2-phenoxymethyl-3H-benzimidazole-4-carboxylate. NMR (CDCl$_3$): δ 3.95(s, 3H), 4.10(s, 3H), 5.40(s, 2H), 6.73(d, J=8 Hz, 1H), 7.05(m, 3H), 7.73(m, 2H), 7.90(d, J=8 Hz, 1H).

(t) By proceeding in a similar manner to Reference Example 3(a) but using Reference Example 4(t), there was prepared methyl 2-cyclopentyl-7-methoxy-3H-benzimidazole-4-carboxylate, as a solid. NMR (CDCl$_3$): δ 1.73(m, 2H), 1.85(m, 2H), 2.00(m, 2H), 2,16(m, 2H), 3.31(m, 1H), 3.98(s, 3H), 4.08(s, 3H), 6.70(d, J=8 Hz, 1H), 7.80(d, J=8 Hz, 1H), 10.10(bs, 1H).

(u) By proceeding in a similar manner to Reference Example 3(a) but using Reference Example 4(u), there was prepared methyl 2-benzyl-3H-benzimidazole-4-carboxylate. NMR (CDCl$_3$): δ 3.90(s, 3H), 4.33(s, 2H), 7.20-7.40(m, 5H), 7.82(d, J=7.6 Hz, 1H), 7.93(d, J=7.6 Hz, 1H), 10.02(bs, 1H).

(v) By proceeding in a similar manner to Reference Example 3(a) but using Reference Example 4(v), there was prepared methyl 2-cyclopropyl-7-methoxy-3H-benzimidazole-4-carboxylate, m.p. 124-126° C. [Elemental analysis:—C, 53.89; H, 5.11; N, 9.62%. Calculated:—C, 55.21; H, 5.35; N, 9.90%].

(w) By proceeding in a similar manner to Reference Example 3(a) but using Reference Example 4(w) and isolating the intermediate 1-bromo-3-(cyclopropyl-chloroimino-methylamino)-4-methoxybenzene then treating with potassium carbonate there was prepared 4-bromo-2-cyclopropyl-7-methoxy-3H-benzimidazole as a pale brown solid, m.p. 185° C.

(x) By proceeding in a similar manner to Reference Example 3(a) but using Reference Example 4(x), there was prepared methyl 7-methoxy-2-n-propyl-3H-benzimidazole-4-carboxylate.

REFERENCE EXAMPLE 4

(a) Methyl 3-(1-imino-2-methoxy-ethylamino)-4-methoxybenzoate

Method A: 4-Toluenesulphonic acid monohydrate (17.8 g) was heated under vacuum at 100° C. for 4 hours then allowed to cool to room temperature and then treated with methoxy-acetonitrile (7.4 g) and methyl 3-amino-4-methoxybenzoate (17.5 g). The resulting mixture was heated to 180° C. and then stirred at this temperature for 4 hours. The reaction mixture was allowed to cool to room temperature then diluted with chloroform and then washed sequentially with 1M sodium hydroxide solution, saturated sodium bicarbonate and brine. The organic phase was dried over magnesium sulphate then evaporated. The residue was subjected to flash chromatography on silica eluting initially with a mixture of hexane and ethyl acetate (4:1, v/v) then with a mixture of hexane and ethyl acetate (1:1, v/v) and finally with a mixture of ethyl acetate and triethylamine (50:1, v/v) to give the title compound (15.79 g) as a solid. M$^+$252. NMR (CDCl$_3$): δ 3.48(bs, 3H), 3.90(bs, 6H), 4.20(bs, 2H), 4.95 (bs, 1H), 6.92(d, J=8 Hz, 1H), 7.60(bs, 1H), 7.77(d, J=8 Hz, 1H).

Method B: A solution of methyl 2-methoxyacetimidate (36.5 g, prepared by treating the corresponding hydrochloride [prepared according to the procedure of C. G. Bakker et. al., Rec. Trav. Chim. Pays-Bas, 1981, 100, page 13] with aqueous sodium hydroxide) and methyl 3-amino-4-methoxybenzoate (64.1 g) in butan-2-one (256 ml) was heated at reflux with stirring under a nitrogen atmosphere for 3.5 hours then a further quantity of methyl 2-methoxyacetimidate (36.5 g) was added. After heating at reflux for a further 4 hours the reaction mixture was left at ambient temperature for 18 hours and then concentrated under reduced pressure. The residual brown oil was treated with cyclohexane (100 ml) and then evaporated. The residual oil was dissolved in a mixture of cyclohexane and ethyl acetate (150 ml, 7:3, v/v) and heated to 50° C. Some seed crystals of methyl 3-(1-imino-2-methoxy-ethylamino)-4-methoxybenzoate were added and then mixture was allowed to cool to ambient temperature with stirring. The resulting solid was collected by filtration, then washed with a small amount of a mixture of cyclohexane and ethyl acetate (7:3, v/v), and then dried to give the title compound (62.72 g).

(b) By proceeding in a similar manner to Reference Example 4(a), method A, but using benzonitrile, there was prepared methyl 3-(imino-phenyl-methylamino)-4-methoxybenzoate as a tan coloured solid. NMR (CDCl$_3$): δ 3.85(s, 3H), 3.86(s, 3H), 6.94(bd,J=8.8 Hz, 1H), 7.45(m, 3H), 7.65(s, 1H), 7.75(m, 2H), 7.90(bs, 1H)]

(c) By proceeding in a similar manner to Reference Example 4(a), method A, but using hydrocinnamonitrile, there was prepared methyl 3-(1-imino-3-phenyl-propylamino)-4-methoxybenzoate as a tan coloured solid. NMR (CDCl$_3$) δ 2.65(bt, 2H), 3.10(bt, 2H), 3.90(s, 6H), 4.34(bs, 1H), 6.90(d, J=8 Hz, 1H), 7.30(m, 5H), 7.52(bs, 1H), 7.74(dd, J=8 and 1 Hz, 1H)]

(d) By proceeding in a similar manner to Reference Example 4(a), method A, but using phenylacetonitrile, there was prepared methyl 3-(1-imino-2-phenyl-ethylamino)-4-methoxybenzoate as a solid. M$^+$298.

(e) By proceeding in a similar manner to Reference Example 4(a), method A, but using α-methylbenzyl cyanide, there was prepared (RS)-methyl 3-(1-imino-2-phenyl-propylamino)-4-methoxybenzoate. M$^+$312.

(f) By proceeding in a similar manner to Reference Example 4(a), method A, but using 4-methoxyphenylacetonitrile, there was prepared methyl 3-(1-imino-2-{4-methoxyphenyl}-ethylamino)-4-methoxybenzoate. M$^+$328.

(g) By proceeding in a similar manner to Reference Example 4(a), method A, but using α-cyclohexylbenzyl cyanide, there was prepared (RS)-methyl 3-(2-cyclohexyl-1-imino-2-phenyl-ethylamino)-4-methoxybenzoate as an orange solid. M$^+$H 381.

(h) By proceeding in a similar manner to Reference Example 4(a), method A, but using 2,3-diphenylpropionitrile, there was prepared (RS)-methyl 3-(2,3-diphenyl-1-imino-propylamino)-4-methoxybenzoate as a solid.

(i) By proceeding in a similar manner to Reference Example 4(a), method A, but using 3-phenylbutyronitrile, there was prepared (RS)-methyl 3-(1-imino-3-phenyl-butylamino)-4-methoxybenzoate. NMR (CDCl$_3$): δ 1.43(d, 3H), 2.60(d, 2H), 3.26-3.39(m, 1H), 3.85(s, 3H), 3.87(s, 3H), 4.20(bs, 2H), 6.89(d, 1H), 7.25-7.35(m, 5H), 7.42(bs, 1H), 7.75(dd, 1H).

(j) By proceeding in a similar manner to Reference Example 4(a), method A, but using 4-methoxyphenoxy-acetonitrile, there was prepared methyl 3-(1-imino-2-{4-methoxyphenoxy}-ethylamino)-4-methoxybenzoate. NMR (CDCl$_3$): δ3.79 (s, 3H), 3.88(s, 3H), 3.99(s, 3H), 4.74(bs, 2H), 5.00(bs, 1H), 6.80-7.00(m, 5H), 7.60(bs, 1H), 7.78(dd, J=8 and 1 Hz, 1H).

(k) By proceeding in a similar manner to Reference Example 4(a), method A, but using α-propylphenylacetonitrile, there was prepared (RS)-methyl 3-(1-imino-2-phenyl-pentylamino)-4-methoxybenzoate. M$^+$H 341.

(l) By proceeding in a similar manner to Reference Example 4(a), method A, but using 4-bromophenylacetonitrile, there was prepared methyl 3-(2-{4-bromophenyl}-1-imino-ethylamino)-4-methoxybenzoate as a tan coloured solid. M$^+$H 378. NMR (CDCl$_3$): δ 3.70(s, 2H), 3.90(d, 6H), 4.35(s, 1H), 6.90(d, 1H), 7.30(d, 2H), 7.50(m, 3H), 7.75(d, 1H).

(m) By proceeding in a similar manner to Reference Example 4(a), method A, but using 4-methoxy-2-phenylbutyronitrile, there was prepared (RS)-methyl 3-(1-imino-4-methoxy-2-phenyl-butylamino)-4-methoxybenzoate. NMR (CDCl$_3$): δ 2.10(m, 1H), 2.54(m, 1H), 3.35(bs, 3H), 3.40(m, 1H), 3.60(m, 1H), 3.74(m, 1H), 3.85(bs, 6H), 4.25(bs, 2H), 6.90(bd,J=8 Hz, 1H), 7.30(m, 1H), 7.38(m, 2H), 7.50(m, 2H), 7.75(m, 1H).

(n) By proceeding in a similar manner to Reference Example 4(a), method A, but using 2-methoxyphenyl-acetonitrile, there was prepared methyl 3-(1-imino-2-{2-methoxyphenyl}-ethylamino)-4-methoxybenzoate.

(o) By proceeding in a similar manner to Reference Example 4(a), method A, but using methoxy-phenylacetonitrile, there was prepared methyl 3-(1-imino-2-methoxy-2-phenyl-ethylamino)-4-methoxybenzoate.

(p) By proceeding in a similar manner to Reference Example 4(a), method A, but using (2-methoxyphenoxy) acetonitrile, there was prepared methyl 3-(1-imino-2-{2-methoxyphenoxy}-ethylamino)-4-methoxybenzoate. M$^+$344.

(q) By proceeding in a similar manner to Reference Example 4(a), method A, but using iso-butyronitrile, there was prepared methyl 3-(1-imino-2-methyl-propylamino)-4-methoxybenzoate. NMR (CDCl$_3$): δ 1.29(d, J=6 Hz, 6H), 2.60(m, 1H), 3.88(bs, 6H), 4.33(bs, 1H), 6.89(d, J=8 Hz, 1H), 7.50(bs, 1H), 7.72(dd, J=8 Hz, 1H).

(r) By proceeding in a similar manner to Reference Example 4(a), method A, but using acetonitrile, there was prepared methyl 3-(1-imino-ethylamino)-4-methoxybenzoate. M$^+$222.

(s) By proceeding in a similar manner to Reference Example 4(a), method A, but using phenoxy-acetonitrile, there was prepared methyl 3-(1-imino-2-phenoxy-ethylamino)-4-methoxybenzoate. M$^+$314.

(t) By proceeding in a similar manner to Reference Example 4(a), method A, but using cyclopentanecarbonitrile, there was prepared methyl 3-(cyclopentyl-imino-methylamino)-4-methoxybenzoate as a solid. NMR (CDCl$_3$): δ 1.54-2.10(m, 8H), 2.75(m, 1H), 3.86(bs, 6H), 4.30(bs, 1H), 6.88(bd,J=8 Hz, 1H), 7.53(bs, 1H), 7.73(d, J=8 Hz, 1H).

(u) By proceeding in a similar manner to Reference Example 4(a), method A, but using phenylacetonitrile and methyl 3-aminobenzoate, there was prepared methyl 3-(2-phenyl-1-imino-ethylamino)benzoate as a tan coloured solid. M$^+$312.

(v) By proceeding in a similar manner to Reference Example 4(a), method A, but using cyclopropyl cyanide and methyl 3-amino-4-methoxybenzoate, there was prepared methyl 3-(cyclopropyl-imino-methylamino)benzoate as a colourless solid.

(w) By proceeding in a similar manner to Reference Example 4(a), method A, but using cyclopropyl cyanide and 5-bromo-2-methoxyaniline (Reference Example 50), there was prepared 1-bromo-3-(cyclopropyl-imino-methylamino)-4-methoxybenzene.

(x) By proceeding in a similar manner to Reference Example 4(a), method A, but using propyl cyanide there was prepared methyl 3-(propyl-imino-methylamino)-4-methoxybenzoate.

(y) By proceeding in a similar manner to Reference Example 4(a), method A, but using 3-amino-4-methoxysalicylate (Reference Example 8(b)), there was prepared methyl 4-methoxy-2-methoxymethyl-benzoxazole-7-carboxylate as a white solid, m.p. 104-106° C.

REFERENCE EXAMPLES 5(a) AND 6(a)

Methyl 2-cyclopentyl-7-methoxy-1-methyl-1H-benzimidazole-4-carboxylate and methyl 2-cyclopentyl-7-methoxy-3-methyl-3H-benzimidazole-4-carboxylate A suspension of sodium hydride (0.55 g, 60% dispersion in mineral oil) in dimethylformamide (1 ml), cooled to 0° C., was treated with a solution of methyl 2-cyclopentyl-7-methoxy-3H-benzimidazole-4-carboxylate [3.61 g, Reference Example 3(t)] in dimethylformamide (34 ml). The resulting mixture was stirred for 40 minutes then treated with iodomethane (0.82 ml). The reaction mixture was allowed to stand at 4° C. for 2 days then diluted with diethyl ether, then washed with brine, then dried over magnesium sulphate and then evaporated. The residue was subjected to flash chromatography on silica to give methyl 2-cyclopentyl-7-methoxy-1-methyl-1H-benzimidazole-4-carboxylate (3.18 g), [NMR (CDCl$_3$): δ 1.70 (m, 2H), 1.90(m, 2H), 2,16(m, 4H), 3.25(m, 1H), 3.95(s, 6H), 4.00(s, 3H), 6.64(d, J=8 Hz, 1H), 7.89(d, J=8 Hz, 1H)]; and methyl 2-(cyclopentyl)-7-methoxy-3-methyl-3H-benzimidazole-4-carboxylate (0.37 g), [M$^+$288, NMR (CDCl$_3$): δ 1.70(m, 2H), 1.90(m, 2H), 2.14(m, 4H), 3.25(m, 1H), 3.92(s, 6H), 4.02(s, 3H), 6.64(d, J=8 Hz, 1H), 7.75(d, J=8 Hz, 1H)].

(5b) By proceeding in a similar manner but using methyl 3-isopropyl-1H-indole-5-carboxylate (Reference Example 52) with tetrahydrofuran as the solvent, there was prepared methyl 3-isopropyl-1-methyl-1H-indole-5-carboxylate as an orange-brown coloured solid.

REFERENCE EXAMPLE 7

Methyl 2,7-dimethoxy-3H-benzimidazole-4-carboxylate

A mixture of methyl 2,3-diamino-4-methoxybenzoate [0.5 g, Reference Example 8(a)] acetic acid (0.15 ml) and tetramethoxymethane (0.53 ml) was stirred at 80° C. for 40 minutes. After cooling to room temperature the reaction mixture was diluted with a mixture of methanol (3.6 ml), 1N sodium hydroxide (2.55 ml) and water (8 ml). The resulting precipitate was filtered and then passed through a short filtration silica gel column to give the title compound (0.49 g) as a tan coloured solid. M$^+$236. NMR (CDCl$_3$): δ 3.93(s, 3H), 4.05(s, 3H), 4.23(s, 3H), 6.69(d, J=8 Hz, 1H), 7.74(d, J=8 Hz, 1H), 9.48(bs, 1H)]

REFERENCE EXAMPLE 8

(a) Methyl 2,3-diamino-4-methoxybenzoate

A solution of methyl 2-amino-4-methoxy-3-nitrobenzoate (1.84 g, Reference Example 9) in ethanol (100 ml) was treated with 10% palladium on carbon (0.2 g). The resulting suspension was stirred under 3 atmospheres of hydrogen for 3 hours. The catalyst was then removed by filtration and the filtrate evaporated to give the title compound (1.6 g) as a black solid which was used without further purification. M$^+$196.

(b) By proceeding in a similar manner to Reference Example 8(a) but using methyl 2-hydroxy-4-methoxy-3-nitrobenzoate (Reference Example 51) and ethyl acetate as the solvent, there was prepared methyl 3-amino-2-hydroxy-4-methoxybenzoate as a white solid, m.p. 72-74° C.

REFERENCE EXAMPLE 9

Methyl 2-amino-4-methoxy-3-nitrobenzoate

A solution of methyl 2-carboxy-4-methoxy-3-nitrobenzoate (3.43 g, Reference Example 10) was dissolved in toluene (20 ml) was treated with thionyl chloride (1.5 ml) then with dimethylformamide (0.015 ml). The resulting solution was stirred at reflux for 1 hour then cooled to room temperature and then evaporated. The residue was dissolved in acetone (20 ml) and added to a solution of sodium azide (1.3 g) in water (20 ml) cooled in an ice bath. The mixture was stirred for 1 hour then diluted with water. The resulting precipitate was collected by filtration. This solid was dissolved in a mixture of t-butanol and water (20 ml, 9:1) and gradually warmed to reflux and held at this temperature for 1 hour. The solution was cooled to room temperature and then evaporated. The residue was subjected to flash chromatography on silica to give the title compound (1.8 g). M$^+$H 227. NMR ((CD$_3$)$_2$SO): δ 3.82 (s, 3H), 3.90(s, 3H), 6.53(d, J=8 Hz, 1H), 7.1(bs, 2H), 7.96(d, J=8 Hz, 1H).

REFERENCE EXAMPLE 10

Methyl 2-carboxy-4-methoxy-3-nitrobenzoate

A solution of 3-nitro-4-methoxyphthallic acid (25.1 g, Reference Example 11) in methanol (160 ml), cooled to 0° C., was saturated with hydrogen chloride gas then allowed to stand at 4° C. for 2 days. The reaction mixture was then diluted with water and then extracted with ether. The ether extract was washed with saturated sodium bicarbonate solution. The bicarbonate washings were acidified and then extracted with ether. These ether extracts were dried over magnesium sulphate and then evaporated. The residue was recrystallised from a mixture of chloroform and methanol to give the title compound (3.42 g). M$^+$255. NMR {(CD$_3$)$_2$SO} δ 3.85(s, 3H), 4.00(s, 3H), 7.55(d, J=8.5 Hz, 1H), 8.07(d, J=8.5 Hz, 1H).

A further quantity of the title compound (3.54 g) was obtained after subjecting the mother liquors from the recrystallisation to flash chromatography on silica.

REFERENCE EXAMPLE 11

3-Nitro-4-methoxyphthallic acid

4-Methoxyphthallic acid (21.5 g) was treated dropwise with fuming nitric acid (75 ml). The resulting mixture was heated to 60° C. and stirred for 15 minutes whereupon the reaction mixture became homogenous. This solution was then cooled to room temperature and then diluted with water. The mixture was extracted with diethyl ether. The combined extracts were washed with brine then dried over magnesium sulphate and then evaporated to give the title compound (25.1 g) as a tan coloured solid. M$^+$241.

REFERENCE EXAMPLE 12

Methyl 7-methoxy-2-(α-methoxybenzyl)-3H-benzimidazole-4-carboxylate

A solution of (α-methoxy-phenylacetic acid (0.596 g) in chloroform (10 ml) was treated with dimethylformamide (10 g) then with thionyl chloride (0.52 ml). The reaction mixture was stirred at ambient temperature for 2 hours then evaporated. The residue was dissolved in chloroform (4 ml) and the solution added to a stirred solution of methyl 2,3-diamino-4-methoxybenzoate [0.352 g, Reference Example 8(a)] in a mixture of chloroform (6 ml) and triethylamine (1 ml). After stirring for 1 hour the mixture was treated with ether and then with water. The organic phase was washed with sodium bicarbonate solution, then with brine, then dried over magnesium sulphate and then evaporated. The residue was dissolved in acetic acid (8 ml) and the solution heated at 80° C. for 1.5 hours. The solution was cooled to ambient temperature then diluted with ether. The mixture was washed with water, then with sodium bicarbonate solution, then with brine and then dried over magnesium sulphate. The ethereal solution was evaporated and the residue subjected to flash chromatography on silica eluting with a mixture of ethyl acetate and hexane (1:1, v/v) to give the tide compound (0.36 g). NMR (CDCl$_3$): δ 3.50(s, 3H), 3.96(s, 3H), 4.05(s, 3H), 5.17(s, 1H), 6.70(d, J=8 Hz, 1H), 7.24-7.40(m, 3H), 7.46(m, 2H), 7.85(d, J=8 Hz, 1H)].

REFERENCE EXAMPLE 13

Methyl 7-methoxy-2-(3-pyridyl)-3H-benzimidazole-4-carboxylate

A solution of methyl 2,3-diamino-4-methoxybenzoate [0.73 g, Reference Example 8(a)] and triethylamine (0.94 g) in dry dichloromethane (20 ml), at 0° C., was treated with nicotinyl chloride (0.53 g). The reaction mixture was stirred at ambient temperature for 2 hours and then evaporated. The residue was dissolved in acetic acid (8 ml) and the solution heated at 80° C. for 2 hours. After cooling to room temperature the reaction mixture was treated with water. The insoluble material was subjected to flash chromatography on silica to give the title compound (0.46 g). NMR (CDCl$_3$): δ 4.00(s, 3H), 4.15(s, 3H), 6.70(d, 1H), 7.40(m, 1H), 7.90(d, 1H), 8.45(m, 1H), 8.75(d, 1H), 9.30(d, 1H), 10.80(s, 1H)].

REFERENCE EXAMPLE 14

Methyl 2-(4-cyanobenzyl)-7-methoxy-3H-benzimidazole-4-carboxylate

A solution of methyl 2-(4-bromobenzyl)-7-methoxy-3H-benzimidazole-4-carboxylate [1.4 g, Reference Example 3(1)] in dry dimethylformamide was treated with tetrakis (triphenylphosphine) palladium (0) (0.266 g) and zinc cyanide (0.275 g). The reaction mixture was heated at 100° C. for 12 hours then cooled to room temperature. The mixture was diluted with ethyl acetate and then washed with ammonium hydroxide (2N), then with water and then with brine. The organic solution was dried over magnesium sulphate then evaporated. The residue was subjected to flash chromatography on silica to give the title compound (0.88 g). NMR (CDCl$_3$): δ 3.85(s, 3H), 4.00(s, 3H), 4.40(s, 2H), 6.70(d, 1H), 7.40(d, 2H), 7.65(d, 2H), 7.85(d, 1H).

REFERENCE EXAMPLE 15

Methyl 7-methoxy-2-(4-{pyrid-3-yl}benzyl)-3H-benzimidazole-4-carboxylate

A solution of methyl 2-(4-bromobenzyl)-7-methoxy-3H-benzimidazole-4-carboxylate [0.268 g, Reference Example 3(l)] in toluene (8 ml) was treated with tetrakis(triphenylphosphine) palladium (0) (0.266 g), aqueous sodium carbonate solution (0.5 ml, 2M) and diethyl (3-pyridyl) borane (0.085 g). The mixture was heated at reflux for 12 hours then cooled to room temperature. Aqueous work-up and subjected to flash chromatography on silica to give the title compound (0.128 g). NMR {(CD$_3$)$_2$SO}: δ 3.90(s, 3H), 4.10(s, 3H), 4.40(s, 2H), 6.70(d, 1H), 7.45(d, 3H), 7.60(d, 3H), 7.90 (dd, 1H), 8.60(d, 1H), 8.85(d, 1H), 10.10(s, 1H).

REFERENCE EXAMPLE 16

3-Bromo-2-(3-chlorophenoxy)pyridine

A solution of 3-chlorophenol (5.34 g) in tetrahydrofuran (50 ml) was added dropwise to a suspension of sodium hydride (1.66 g, 60% dispersion in mineral oil) in tetrahydrofuran (50 ml). The solvent was evaporated and the residue was treated with 3-bromo-2-chloropyridine (6.15 g) and the mixture heated at 180° C. for 6 hours. The reaction mixture was cooled to 100° C., then poured into water. The mixture was extracted with dichloromethane. The combined organic extracts were washed with 1N sodium hydroxide, then with brine, then dried over magnesium sulphate and then evaporated. The residual brown solid was subjected to flash column chromatography eluting with a mixture of ethyl acetate and pentane (2:98, v/v) to give the title compound as white solid, m.p. 88-90° C. NMR (CDCl$_3$): δ 6.94(dd, J=7 Hz and 4 Hz, 1H), 7.07(m, 1H), 7.19(t, J=2 Hz, 1H), 7.22(m, 1H), 7.35(t, J=8 Hz, 1H), 7.95(dd, J=6 Hz and 1 Hz, 1H), 8.09(dd, J=4 Hz and 1 Hz, 1H).

REFERENCE EXAMPLE 17

2-Cyclopropyl-7-(3,5-dimethyl-4-pyridylmethoxy)-4-methoxy-1(or 3)-(2-trimethylsilanyl-ethoxymethyl)-1H(or 3H)-benzimidazole A stirred solution of 2-cyclopropyl-7-methoxy-1(or 3)-(2-trimethylsilanyl-ethoxymethyl)-1H(or 3H)-benzimidazol-4-ol [0.69 g, Reference Example 19(a)], triphenylphosphine (0.12 g) and (3,5-dimethyl-4-pyridyl)methanol (0.31 g, Reference Example 23) in tetrahydrofuran (15 ml) was treated with diisopropyl azodicarboxylate (0.48 g). After stirring at room temperature for 4 hours the resulting homogeneous solution was allowed to stand for a further 12 hours then evaporated. The residue was subjected to column chromatography on neutral alumina eluting with a mixture of ethyl acetate and pentane (1:1, v/v) to give a mixture of the title compound and triphenylphosphine oxide which was used without further purification.

REFERENCE EXAMPLE 18

By proceeding in a similar manner to Reference Example 17, but using 7-methoxy-2-methoxymethyl-1(3)-(2-trimethylsilanyl-ethoxymethyl)-1H(3H)-benzimidazol-4-ol [mixture of isomers, Reference Example 19(b)], there was prepared a mixture of 7-(3,5-dimethyl-4-pyridylmethoxy)-4-methoxy-2-methoxymethyl-1(3)-(2-trimethylsilanyl-ethoxymethyl)-1H(3H)-benzimidazole and triphenylphosphine oxide which was used without further purification.

REFERENCE EXAMPLE 19

(a) 2-Cyclopropyl-7-methoxy-1(or 3)-(2-trimethylsilanyl-ethoxymethyl)-1H(or 3H)-benzimidazol-4-ol, isomer A A cooled solution of 2-cyclopropyl-7-methoxy-1(or 3)-(2-trimethylsilanyl-ethoxymethyl)-1H(or 3H)-benzimidazole-4-carbaldehyde [2.00 g, isomer A, Reference Example 20(a)] in dichloromethane (40 ml) was treated with m-chloroperbenzoic acid (3.66 g). The mixture was allowed to warm to room temperature then allowed to stand at room temperature for a further 12 hours. The reaction mixture was diluted with dichloromethane (40 ml), then washed twice with a saturated aqueous solution of sodium metabisulphite (100 ml), then washed twice with a saturated aqueous solution of sodium hydrogen carbonate (100 ml), then washed with brine (100 ml), then dried over magnesium sulphate and then evaporated to yield the title compound as a colourless oil.

(b) By proceeding in a similar manner to Reference Example 19(a), but using Reference Example 20(b), there was prepared 7-methoxy-2-methoxymethyl-1(or 3)-(2-trimethylsilanyl-ethoxymethyl)-1H(or 3H)-benzimidazol-4-ol.

REFERENCE EXAMPLE 20

(a) 2-Cyclopropyl-7-methoxy-1(or 3)-(2-trimethylsilanyl-ethoxymethyl)-1H(or 3H)-benzimidazole-4-carbaldehyde, isomer A A stirred solution of 2-cyclopropyl-7-methoxy-3H-benzimidazole-4-carbaldehyde [7.23 g, Reference Example 21(a)] in dry dimethylformamide (115 ml), at room temperature and under nitrogen, was treated portionwise with sodium hydride (1.60 g, 60% dispersion in mineral oil,). After stirring for a further 40 minutes the orange-brown suspension was treated dropwise with 2-(trimethylsilyl) ethoxymethyl chloride (7.15 ml), over 30 minutes. The resulting yellow-orange suspension was allowed to stand at room temperature for 12 hours then treated carefully with a little water. The mixture was evaporated to yield a yellow oil which was dissolved in ethyl acetate (400 ml). The solution was washed twice with water (100 ml), then dried over magnesium sulphate and then evaporated to yield a yellow oil (10.5 g) which was subjected to flash chromatography on silica, eluting with a mixture of dichloromethane and methanol (99:1, v/v) to give 2-cyclopropyl-7-methoxy-1(3)-(2-trimethylsilanyl-ethoxymethyl)-1H(3H)-benzimidazole-4-carbaldehyde (mixture of isomers), as a yellow oil (7.00 g). The mixture of isomers was further subjected to flash chromatography on silica, eluting with a mixture of dichloromethane and methanol (99:1, v/v) to give 2-cyclopropyl-7-methoxy-1(or 3)-(2-trimethylsilanyl-ethoxymethyl)-1H (or 3H)-benzimidazole-4-carbaldehyde (isomer A).

(b) By proceeding in a similar manner to Reference Example 20(a), but using Reference Example 21(b), there was prepared 7-methoxy-2-methoxymethyl-1 (3)-(2-trimethylsilanyl-ethoxymethyl)-1H(3H)-benzimidazole-4-carbaldehyde, (mixture of isomers), as a pale yellow oil.

(c) By proceeding in a similar manner to Reference Example 20(a), but Reference Example 3(w) there was prepared 4-bromo-2-cyclopropyl-7-methoxy-1(3)-(2-trimethylsilanyl-ethoxymethyl)-1H(3H)-benzimidazole, (mixture of isomers), as a yellow oil. The mixture of isomers was subjected to flash chromatography on silica, eluting with a mixture of dichloromethane and methanol (99:1, v/v) to give 4-bromo-2-cyclopropyl-7-methoxy-1(or 3)-(2-trimethylsilanyl-ethoxymethyl)-1H(or 3H)-benzimidazole, (isomer A).

REFERENCE EXAMPLE 21

(a) 2-Cyclopropyl-7-methoxy-3H-benzimidazole-4-carbaldehyde

A stirred suspension of 2-cyclopropyl-7-methoxy-3H-benzimidazole-4-methanol [7.73 g, Reference Example 22(a)] in a mixture of toluene (250 ml) and dichloromethane (150 ml), at room temperature and under nitrogen, was treated portionwise with activated manganese dioxide (11 g). The resulting suspension was stirred under nitrogen at 85° C. for 3 hours. The suspension was allowed to cool slightly and was then filtered through hyflosupercel washing the filter pad six times with hot ethyl acetate (50 ml). The combined filtrate and washings were dried over magnesium sulphate and then evaporated to yield the title compound as a cream coloured powder (7.26 g).

(b) By proceeding in a similar manner to Reference Example 22(a), but using Reference Example 22(b), there was prepared 7-methoxy-2-methoxymethyl-3H-benzimidazole-4-carbaldehyde as a pale yellow solid.

REFERENCE EXAMPLE 22

(a) 2-Cyclopropyl-7-methoxy-3H-benzimidazole-4-methanol

A stirred solution of methyl 2-cyclopropyl-7-methoxy-3H-benzimidazole-4-carboxylate [15.5 g, Reference Example 3(v)], in dry tetrahydrofuran (220 ml), at −78° C. and under nitrogen, was treated dropwise over 3 hours with a solution of diisobutylaluminium hydride in dichloromethane (270 ml, 1.0M). The reaction mixture was allowed to warm to room temperature over 30 minutes, then cooled to −78° C., then treated dropwise with water (27 ml), then allowed to warm to room temperature. The reaction mixture was diluted with ice-water (500 ml) and the pH of the mixture was adjusted to above 12 by the addition of aqueous sodium hydroxide (750 ml, 1M). The resulting white suspension was filtered to yield a clear filtrate which was extracted seven times with ethyl acetate (500 ml). The combined extracts were dried over magnesium sulphate and then evaporated to yield the title compound as a cream coloured powder (10.13 g).

b) By proceeding in a similar manner to Reference Example 22(a), but using Reference Example 3(a), there was prepared 7-methoxy-2-methoxymethyl-3H-benzimidazole-4-methanol as a cream coloured solid.

c) By proceeding in a similar manner to Reference Example 22(a), but using Reference Example 41 there was prepared 3-methyl-1-{3-(phenyl)propyl}-1H-indole-6-methanol.

REFERENCE EXAMPLE 23

(3,5-Dimethyl-4-pyridyl)methanol

A stirred solution of 3,5-dimethyl-pyridyl-4-carbaldehyde (2.3 g, Reference Example 24) in methylated spirit (50 ml), at room temperature and under nitrogen, was treated with powdered sodium borohydride (1.28 g). After stirring for 6 hours the resulting homogeneous solution was allowed to stand at room temperature for a further 12 hours then treated with water (10 ml). The reaction mixture was evaporated, then azeotroped with toluene. The residue was extracted three times with hot dichloromethane (100 ml). The combined extracts were evaporated to afford a white solid which was subjected to flash chromatography on silica, eluting with a mixture of ethyl acetate and pentane (1:1, v/v) to afford the title compound (1.2 g) as a white solid, m.p. 93-95° C.

REFERENCE EXAMPLE 24

3,5-Dimethyl-pyridine-4-carbaldehyde

A stirred solution of 4-bromo-3,5-dimethylpyridine (3.72 g, Reference Example 25) in diethyl ether (50 ml), at −78° C. and under nitrogen, was treated dropwise with n-butyl lithium (0.025 ml, 1.6M). After stirring at −78° C. for 1 hour the resulting homogeneous solution was treated with dry dimethylformamide (6 ml) whilst maintaining the temperature below −65° C. The reaction mixture was allowed to warm to room temperature over 1 hour, then treated with a saturated aqueous solution of ammonium chloride (10 ml), and then extracted twice with ethyl acetate (100 ml). The combined extracts were evaporated to yield an orange oil which was subjected to flash chromatography on silica, eluting with a mixture of ethyl acetate and pentane (1:4, v/v) to afford the title compound (2.3 g) as a semi-solid.

REFERENCE EXAMPLE 25

4-Bromo-3,5-dimethylpyridine

By proceeding in a similar manner to the procedure contained in J. Chem. Soc., 1956, page 771 but using 4-nitro-3,5-dimethylpyridine-N-oxide (23.06 g), phosphorous tribromide (111.47 g) in toluene (50 ml) there was prepared the title compound (8 g) as a yellow oil.

REFERENCE EXAMPLE 26

(a) 8-Methoxy-2-n-propylquinoline-5-carboxylic acid

A mixture of methyl 8-methoxy-2-n-propylquinoline-5-carboxylate (1.0 g, Reference Example 27), potassium carbonate (0.8 g), methanol (30 ml), and water (2 ml) was refluxed for 5 hours. The solution was concentrated, then diluted with water and then washed with diethyl ether. The pH of the aqueous phase was adjusted to 6 by addition of hydrochloric acid (6M). The resulting cream precipitate was washed with water and then dried at 60° C. to give the title compound (0.43 g) as a cream coloured solid, m.p. 214-217° C. [Elemental analysis:—C,67.00; H,6.32; N,5.53%. Calculated for $C_{14}H_{15}NO_3.0.25H_2O$:—C,67.30; H,6.06; N,5.61%].

b) By proceeding in a similar manner to Reference Example 26(a), but using Reference Example 4(y), there was prepared 4-methoxy-2-methoxymethyl-benzoxazole-7-carboxylic acid as a cream coloured solid.

c) By proceeding in a similar manner to Reference Example 26(a), but using Reference Example 5(b), there was prepared 3-isopropyl-1-methyl-1H-indole-5-carboxylic acid as a cream coloured solid.

REFERENCE EXAMPLE 27

Methyl-8-methoxy-2-n-propylquinoline-5-carboxylate

Methyl-3-amino-4-methoxybenzoate (100 g) was treated with concentrated hydrochloric acid (14 ml) and n-butanol (10 ml), under nitrogen, with stirring. The stirred mixture was treated with p-chloranil (13.65 g) and then heated at reflux whilst a mixture of trans-2-hexanal (8 ml) and n-butanol (5 ml) was added dropwise over 2 hours using a syringe pump. After heating at reflux for a further 30 minutes the mixture was treated with a solution of anhydrous zinc chloride (7.52 g) in tetrahydrofuran (60 ml), then allowed to cool slowly to room temperature and then cooled to 0° C. for 18 hours. The reaction mixture was evaporated, then diluted with hydrochloric acid (1M) and then washed with diethyl ether. The pH of the solution was adjusted to 6 and the resulting emulsion was treated with ammonium hydroxide and the solution extracted with diethyl ether. The combined dark green extracts were dried over magnesium sulphate then evaporated. The resulting dark green oil was subjected to flash chromatography on silica eluting with a mixture of ethyl acetate and pentane (3:7, v/v) to give the title compound (1.5 g) as an orange oil. NMR(CDCl$_3$): δ 9.36(d, J=8.9 Hz, 1H), 8.26(d, J=8.4 Hz, 1H), 7.47(d, J=8.9 Hz, 1H), 7.03(d, J=8.4 Hz, 1H), 4.14(s, 3H), 3.97(s, 3H), 3.02(m, 2H), 1.86(m, 2H), 1.03(t, J=7.3 Hz, 3H).

REFERENCE EXAMPLE 28

(a) 1-Cyclohexylmethyl-3-methyl-1H-indole-6-carboxylic acid

A mixture of methyl 1-cyclohexylmethyl-3-methyl-1H-indole-6-carboxylate [9.0 g, Reference Example 29(a)] and lithium hydroxide (8.0 g) in aqueous methanol (300 ml, 1:2, v/v) was heated at 70° C. for 4 hours. The reaction mixture was cooled to room temperature, then acidified by addition of dilute hydrochloric acid and then extracted three times with ethyl acetate (150 ml). The combined extracts were dried over sodium sulphate then evaporated to give the title compound as a white solid (7.3 g). M$^+$271.

(b) By proceeding in a similar manner to Reference Example 28(a) but using Reference Example 30, there was prepared 3-methyl-1H-indole-6-carboxylic acid as a white solid. NMR (CD$_3$OD): δ 2.10(s), 7.10(s), 7.30-7.40(m), 7.50-7.60(m), 8.00(s).

(c) By proceeding in a similar manner to Reference Example 28(a) but using Reference Example 29(b), there was prepared 1-(2-cyclohexyl)ethyl-3-methyl-1H-indole-6-carboxylic acid as a white solid.

(d) By proceeding in a similar manner to Reference Example 28(a) but using Reference Example 29(c), there was prepared 1-(3-cyclohexyl)propyl-3-methyl-1H-indole-6-carboxylic acid as a white solid. NMR (CDCl$_3$): δ 0.80-0.90, 1.00-1.30, 1.60-1.70 and 1.79-1.80(m, 15H); 2.30(s, 3H); 4.00-4.10(m, 2H); 7.00(s, 1H); 7.50-7.60(m, 1H); 7.80-7.90(m, 1H); 8.20(s, 1H).

(e) By proceeding in a similar manner to Reference Example 28(a) but using Reference Example 29(d), there was prepared 1-heptyl-3-methyl-1H-indole-6-carboxylic acid.

(f) By proceeding in a similar manner to Reference Example 28(a) but using Reference Example 29(e), there was prepared 1-(3-phenyl)butyl-3-methyl-1H-indole-6-carboxylic acid as a white solid. NMR (CDCl$_3$): δ 1.60-1.70(m, 2H); 1.80-1,90(m, 2H); 2.30(s, 3H); 2.60-2.70(m, 2H); 4.10-4.20(m, 2H); 7.00(s, 1H); 7.10-7.30(m, 5H); 7.50-7.60 (m, 1H); 7.80-7.90(m, 1H); 8.20(s, 1H).

(g) By proceeding in a similar manner to Reference Example 28(a) but using Reference Example 29(f), there was prepared 1-(4-trifluoromethylbenzyl)-3-methyl-1H-indole-6-carboxylic acid as a white solid. NMR {(CD$_3$)$_2$SO}: δ 2.30(s), 5.50(s), 7.20-7.30(m), 7.30-7.40(m), 7.60-7.70 (m), 7.90(s).

(h) By proceeding in a similar manner to Reference Example 28(a) but using Reference Example 29(g), there was prepared 1-(4-methylsulphonylbenzyl)-3-methyl-1H-indole-6-carboxylic acid as a white solid.

(i) By proceeding in a similar manner to Reference Example 28(a) but using Reference Example 29(h), there was prepared 1-(1.3-benzodioxol-5-yl)methyl-3-methyl-1H-indole-6-carboxylic acid.

(j) By proceeding in a similar manner to Reference Example 28(a) but using Reference Example 29(i), there was prepared 1-(naphthalen-2-yl)methyl-3-methyl-1H-indole-6-carboxylic acid as a white solid. NMR {(CD$_3$)$_2$SO}: δ 2.30(s), 5.60(s), 7.30-8.10(m).

(k) By proceeding in a similar manner to Reference Example 28(a) but using Reference Example 29(j), there was prepared 1-(tetrahydro-2H-pyran-2-yl)methyl-3-methyl-1H-indole-6-carboxylic acid.

(l) By proceeding in a similar manner to Reference Example 28(a) but using Reference Example 29(k), there was prepared 3-methyl-1-(tetrahydrofurfuryl)-1H-indole-6-carboxylic acid, as a white solid, m.p. 217-219° C. [Elemental analysis: C,69.3; H,6.6; N,5.2%. Calculated for C$_{15}$H$_7$NO$_3$: C,69.48; H,6.61; N,5.40%].

(m) By proceeding in a similar manner to Reference Example 28(a) but using Reference Example 29(l), there was prepared 3-methyl-1-(4-toluenesulphonyl)-1H-indole-6-carboxylic acid. NMR (CD$_3$OD): δ 2.1(s, 3H), 2.3(s, 3H), 4.8(s, 2H), 7.1-7.2(m, 2H), 7.4-7.5(m, 2H), 7.6-7.7(m, 2H), 7.75-7.80(m, 1H), 8.5(s, 1H).

(n) By proceeding in a similar manner to Reference Example 28(a) but using Reference Example 29(m), there was prepared 3-methyl-1-(tetrahydrofuran-3-yl)-1H-indole-6-carboxylic acid as a white solid, m.p. 211-213° C. [Elemental analysis: C,68.00; H,6.20; N,5.60%. Calculated for C$_{14}$H$_{15}$NO$_3$: C,68.56; H,6.16; N,5.71%].

(o) By proceeding in a similar manner to Reference Example 28(a) but using Reference Example 43(a), there was prepared 1-benzyl-3-methyl-indazole-6-carboxylic acid.

(p) By proceeding in a similar manner to Reference Example 28(a) but using Reference Example 29(o), there was prepared 1-(4-methoxybenzyl)-3-methyl-1H-indole-6-carboxylic acid as a white solid. NMR (CD$_3$OD): δ 2.2(s, 3H), 3.6(s, 3H), 5.2(s, 2H), 6.6-6.7(m, 2H), 6.95-7.0(m, 2H), 7.1(s, 1H), 7.4-7.45, 7.55-7.60(m, 2H), 8.0(s, 1H).

(o) By proceeding in a similar manner to Reference Example 28(a) but using Reference Example 43(b), there was prepared 1-(4-methoxybenzyl)-3-methyl-indazole-6-carboxylic acid.

REFERENCE EXAMPLE 29

(a) Methyl 1-cyclohexylmethyl-3-methyl-1H-indole-6-carboxylate

A mixture of methyl 3-methyl-1H-indole-6-carboxylate (10 g, Reference Example 30), cyclohexylmethylbromide (19 g), potassium hydroxide (12 g) and sodium iodide (0.1 g) in acetone (200 ml) was stirred at room temperature for 6 hours. The reaction mixture was evaporated. The residue was partitioned between ethyl acetate (250 ml) and water (250 ml). The aqueous layer was extracted three times with ethyl acetate (250 ml). The total combined organic phases were dried over sodium sulphate then evaporated. The residue was subjected to flash column chromatography on silica eluting with a mixture of ethyl acetate and hexane (gradient elution, 0:10 to 1:9, v/v)to yield the title compound (9.5 g). NMR (CDCl$_3$): δ 0.90-1.10(m), 1.10-1.40(m), 1.60-1.90(m), 2.30(s), 3.90-4.00(m), 3.90(s), 7.00(s), 7.50-7.60 (m), 7.70-7.80(m), 8.00(s). MH$^+$ 271.

(b) By proceeding in a similar manner to Reference Example 29(a) but using (2-cyclohexyl)ethyl bromide there was prepared methyl 1-(2-cyclohexyl)ethyl-3-methyl-1H-indole-6-carboxylate. NMR (CDCl$_3$): δ 0.80-1.00(m), 1.10-1.30(m), 1.60-1.80(m), 2.30(s), 3.90(s), 4.10-4.20(t), 7.00(s), 7.60(d), 7.80(d), 8.10(s).

(c) By proceeding in a similar manner to Reference Example 29(a) but using (3-cyclohexyl)propyl bromide there was prepared methyl 1-(3-cyclohexyl)propyl-3-methyl-1H-indole-6-carboxylate.

(d) By proceeding in a similar manner to Reference Example 29(a) but using heptyl bromide there was prepared methyl 1-heptyl-3-methyl-1H-indole-6-carboxylate.

(e) By proceeding in a similar manner to Reference Example 29(a) but using (3-phenyl)butyl bromide there was prepared methyl 1-(3-phenyl)butyl-3-methyl-1H-indole-6-carboxylate.

(f) By proceeding in a similar manner to Reference Example 29(a) but using 4-trifluoromethylbenzyl bromide there was prepared methyl 1-(4-trifluoromethylbenzyl)-3-methyl-1H-indole-6-carboxylate as a white solid. NMR (CDCl$_3$): δ 2.30(s); 3.90(s); 5.40(s); 7.00(s); 7.10-7.20(m); 7.50-7.60(m); 7.80-7.90(m); 8.00(s).

(g) By proceeding in a similar manner to Reference Example 29(a) but using 4-methylsulphonylbenzyl bromide there was prepared methyl 1-(4-methylsulphonylbenzyl)-3-methyl-1H-indole-6-carboxylate as a white solid. NMR (CDCl$_3$): δ 2.40(s); 3.00(s); 3.90(s); 5.40(s); 7.00(s); 7.20-7.30(m); 7.50-7.70(m); 7.80-7.90(m); 8.00(s).

(h) By proceeding in a similar manner to Reference Example 29(a) but using piperonyl chloride there was prepared methyl 1-(1,3-benzodioxol-5-yl)methyl-3-methyl-1H-indole-6-carboxylate.

(i) By proceeding in a similar manner to Reference Example 29(a) but using (naphthalen-2-yl)methyl chloride there was prepared methyl 1-(naphthalen-2-yl)methyl-3-methyl-1H-indole-6-carboxylate.

(j) By proceeding in a similar manner to Reference Example 29(a) but using (tetrahydro-2H-pyran-2-yl)methyl chloride there was prepared methyl 1-(tetrahydro-2H-pyran-2-yl)methyl-3-methyl-1H-indole-6-carboxylate.

(k) By proceeding in a similar manner to Reference Example 29(a) but using tetrahydrofurfuryl chloride there was prepared methyl 3-methyl-1-(tetrahydrofurfuryl)-1H-indole-6-carboxylate.

(l) By proceeding in a similar manner to Reference Example 29(a) but using toluene-4-sulphonyl chloride there was prepared methyl 3-methyl-1-(toluene-4-sulphonyl)-1H-indole-6-carboxylate. NMR (CDCl$_3$): δ 2.2(s, 3H), 2.3(s, 3H), 4.0(s, 3H), 7.15-7.2(m,2H), 7.4-7.5(m, 2H), 7.7-7.8(m, 2H), 7.9-8.0(m, 1H), 8.7(s, 1H).

(m) By proceeding in a similar manner to Reference Example 29(a) but using tetrahydrofuran-3-yl chloride there was prepared methyl 3-methyl-1-(tetrahydrofuran-3-yl)-1H-indole-6-carboxylate.

(n) By proceeding in a similar manner to Reference Example 29(a) but using benzyl bromide there was prepared methyl 1-benzyl-3-methyl-1H-indole-6-carboxylate as a white solid. NMR (CDCl$_3$): δ 2.30(s), 3.80(s), 5.20(s), 7.00(s), 7.00-7.10(m), 7.10-7.20(m), 7.50-7.60(m), 7.70-7.80(m), 8.00(s).

(o) By proceeding in a similar manner to Reference Example 29(a) but using 4-methoxybenzyl bromide there was prepared methyl 1-(4-methoxybenzyl)-3-methyl-1H-indole-6-carboxylate as a white solid, m.p. 116-118° C. [Elemental analysis: C,73.48; H,6.27; N,4.36%. Calculated for C$_{19}$H$_{19}$NO$_3$: C,73.77; H,6.19; N,4.53%].

REFERENCE EXAMPLE 30

Methyl 3-methyl-1H-indole-6-carboxylate

A mixture of methyl 3-formyl-1H-indole-6-carboxylate (12.0 g), p-toluenesulphonic acid (2.0 g) and p-toluenesulphonylhydrazide (13.0 g) in a mixture of dimethylformamide (100 ml) and sulpholane (50 ml) was heated at 100° C. for 15 minutes and then cooled to room temperature. The mixture was treated with sodium cyanoborohydride (15.0 g, 5 g portions after 10 minute intervals), then heated at 100° C. for 2 hours. After cooling to ambient temperature the reaction mixture was treated with ice water (500 ml) giving a white precipitate. Water (1000 ml) was added and the mixture stirred for 30 minutes then filtered. The off-white solid was washed with warm water then azeotroped with toluene to yield the title compound (10.2 g) as a white solid.

REFERENCE EXAMPLE 31

(a) 1-(6,6-Dimethyl-bicyclo[3.1.1.]hept-3-ylmethyl)-3-methyl-1H-indole-6-carboxylic acid A mixture of 3-methyl-indole-6-carboxylic acid [1.8 g, Reference Example 28(b)], (1S,2S,5S)-(−)-myrtanol tosylate and potassium hydroxide (3.17 g) in dimethyl sulphoxide (35 ml) was stirred at room temperature for 18 hours. The reaction mixture was partitioned twice between ethyl acetate (25 ml) and dilute hydrochloric acid (25 ml, 1N). The combined organic layers were dried over sodium sulphate then evaporated. The residue was subjected to flash chromatography on silica to give the title compound (2.45 g) as a white solid. M$^+$325.

(b) By proceeding in a similar manner to Reference Example 31(a) but using cyclohexanol tosylate there was prepared 1-cyclohexyl-3-methyl-1H-indole-6-carboxylic acid as a white solid.

(c) By proceeding in a similar manner to Reference Example 31(a) but using cyclopentanol tosylate there was prepared 1-cyclopentyl-3-methyl-1H-indole-6-carboxylic acid as a white solid. NMR {(CD$_3$)$_2$CO}: δ 0.80-0.90(m), 1.20-1.30(m), 1.70-1.90(m), 2.10-2.30(m), 2.30(s), 4.90-5.00(m), 7.30(s), 7.50(d), 7.70(d), 8.20(s).

(d) By proceeding in a similar manner to Reference Example 31(a) but using cycloheptyl methanol tosylate there was prepared 1-cycloheptylmethyl-3-methyl-1H-indole-6-carboxylic acid as a white solid. NMR {(CD$_3$)$_2$CO}: δ 1.10-1.80(m), 2.30(s), 3.30-3.40(m), 4.00-4.10(m), 7.30(s), 7.50-7.60(m), 7.70-7.80(m), 8.10(s).

REFERENCE EXAMPLE 32

1-Butyloxycarbonyl-3-methyl-indole-6-carboxylic acid

A stirred solution of 3-methyl-indole-6-carboxylic acid [2.0 g, Reference Example 28(b)]) in dichloromethane (100 ml) was treated with di-tert-butyl dicarbonate (5.4 g), triethylamine (3.5 ml) and 4-dimethylaminopyridine (0.1 g). After stirring at room temperature for 4 hours the reaction mixture was evaporated. The residue was partitioned three times between dichloromethane (100 ml) and water (100 ml). The combined organic layers were washed with ice-cold dilute hydrochloric acid (200 ml, 0.1N), then with brine (150 ml), then dried over sodium sulphate and then evaporated. The residue was subjected to flash chromatography to yield the title compound (2.5 g) as a white solid. NMR {(CD$_3$)$_2$SO}: δ 2.30(s), 7.50-7.60(m), 7.80-7.90(s), 8.70(s).

REFERENCE EXAMPLE 33

2-Cyclopropyl-7-methoxy-1(or 3)-(2-trimethylsilanyl-ethoxymethyl)-1H(or 3H)-benzimidazole-4-yl tributyl tin A solution of 4-bromo-2-cyclopropyl-7-methoxy-1(or 3)-(2-trimethylsilanyl-ethoxymethyl)-1H(or 3H)-benzimidazole [3.6 g, Reference Example 20(c)] in dry tetrahydrofuran at −70° C. was treated with a solution of butyl lithium in hexane (6.8 ml, 1.6M). After stirring for 1 hour the mixture was treated with tributyltin chloride (3.07 ml) whilst maintaining the temperature below −70° C., and the reaction mixture was stirred for 1 hour, then allowed to warm to room temperature and then left overnight at room temperature. The reaction mixture was quenched with water and then extracted twice with diethyl ether (100 ml). The combined extracts were dried over magnesium sulphate then evaporated. The residual yellow oil was subjected to flash column chromatography on silica eluting with a mixture of ether and pentane (1:1, v/v) to give the title compound as colourless thick oil (3.83 g).

REFERENCE EXAMPLE 34

2-Cyclopropyl-7-methoxy-1(or 3)-(2-trimethylsilanyl-ethoxymethyl)-4-(4-morpholinosulphonyl)-1H(or 3H)-benzimidazole A solution of 2-cyclopropyl-7-methoxy-1(or 3)-(2-trimethylsilanyl-ethoxymethyl)-1H(or 3H)-benzimidazol-4-yl-sulphonyl chloride (0.67 g, Reference example 35) in dichloromethane (16 ml) was treated with pyridine (0.56 ml) and morpholine (0.15 ml). After stirring at room temperature for 1 hour then standing overnight at room temperature the reaction mixture was evaporated. The residue was azeotroped with toluene to give the title compound which was used without further purification.

REFERENCE EXAMPLE 35

2-Cyclopropyl-7-methoxy-1(or 3)-(2-trimethylsilanyl-ethoxymethyl)-1H(or 3H)-benzimidazole-4-yl-sulphonyl chloride A solution of 4-bromo-2-cyclopropyl-7-methoxy-1(or 3)-(2-trimethylsilanyl-ethoxymethyl)-1H(or 3H)-benzimidazole (5.96 g, Reference Example 20(c)]) in dry tetrahydrofuran (80 ml) at −70° C. was treated dropwise with a solution of butyllithium in hexane (11 ml, 1.6 M) whilst maintaining the reaction temperature below −60° C. After stirring at this temperature for 1 hour the solution was then transferred under nitrogen via a cannula to a cooled solution of excess sulphur dioxide in tetrahydrofuran (80 ml) below −60° C. and stirred for a further 30 minutes at −60° C. The reaction mixture was then allowed to warm to room temperature over 1 hour and then evaporated to dryness under reduced pressure. The residue was triturated with ether to give lithium 2-cyclopropyl-7-methoxy-1(or 3)-(2-trimethylsilanyl-ethoxymethyl)-4-1H(or 3H)-benzimidazolyl sulphinate as cream solid (4.82 g). A mixture of this solid and dichloromethane (80 ml), cooled to 0° C. was treated dropwise with a solution of sulphuryl chloride (2 ml) in dichloromethane (20 ml). After allowing to warm to room temperature the reaction mixture was evaporated and the residue was azeotroped with toluene and then triturated with toluene. The mixture was filtered, the solid was washed with ether. The combined filtrate plus washings were evaporated to give the title compound as yellow gum (2.2 g).

REFERENCE EXAMPLE 36

5-[2-Cyclopropyl-7-methoxy-1(or 3)-(2-trimethylsilanyl-ethoxymethyl)-1H(or 3H)-benzimidazole-4-yl] pyridine-2-carboxamide A solution of 2-cyclopropyl-7-methoxy-1(or 3)-(2-trimethylsilanyl-ethoxymethyl)-1H(or 3H)-benzimidazole-4-yl tributyl tin (1 g, Reference Example 33) in dimethylformamide (10 ml) was treated with a mixture of 5-bromo-pyridine-2-carboxamide (0.275 g), bis(dibenzylidene)acetone palladium(0) (39.45 mg) and triphenylphosphine (36 mg) in dimethylformamide (1 ml). The mixture was heated at 120° C. under an atmosphere of $N_2$ for 5 hours then diluted with methanol and then filtered through a pad of hyflosupercel. The filtrate was evaporated and the residue was subjected to flash column chromatography on silica eluting with a mixture of ethyl acetate and pentane (2:8 to 1:0, v/v) to give the title compound as cream solid (0.4 g).

REFERENCE EXAMPLE 37

Methyl 1-benzyl-3-methyl-1H-indoline-6-carboxylate

A solution of methyl 1-benzyl-3-methyl-1H-indole-6-carboxylate [0.8 g, Reference Example 29(n)] in trifluoroacetic acid at 0° C. was treated with a solution of borane-tetrahydrofuran complex in tetrahydrofuran (9 ml, 1M). The solution was kept at 0° C. for 24 hours, then quenched with methanol, then evaporated. The residual solid was dried under high vacuum and used without purification.

REFERENCE EXAMPLE 38

Methyl 3-{3-methyl-1-1-3-(phenyl)propyl}-H-indol-6-yl)-3-nitromethyl-propionate

A stirred solution of methyl 3-(3-methyl-1-{3-(phenyl) propyl}-1H-indol-6-yl)-propenoate (0.263 g, Reference Example 39) in nitromethane (5 ml) was treated with tetramethylguanidine (0.091 g). The mixture was heated to 65° C. for 2 hours then treated with a further aliquot of tetramethylguanidine (0.091 g). After heating at 65° C. for a further hour the reaction mixture was cooled to room temperature then poured into hydrochloric acid (20 ml, 1N) then extracted three times with ethyl acetate (25 ml). The combined extracts were dried over magnesium sulphate then evaporated. The residue was subjected to preparative layer chromatography on silica using a mixture of ethyl acetate and hexane (1:2, v/v) as eluent to yield the title compound (0.296 g).

REFERENCE EXAMPLE 39

Methyl 3-(3-methyl-1-{3-(phenyl)propyl}-1H-indol-6-yl)-propenoate

A stirred 3-methyl-1-{3-(phenyl)propyl}-1H-indole-6-carboxaldehyde (0.283 g, Reference Example 40) in dry toluene (20 ml), under argon, was treated with carbomethoxymethylene triphenylphosphorane (0.409 g). The mixture was heated at 80° C. for 4 hours then cooled to room temperature and then poured into water (20 ml). The organic phase was separated and the aqueous phase was extracted three times with ethyl acetate (30 ml). The combined organic phases were dried over magnesium sulphate then evaporated. The residue was subjected to flash chromatography on silica eluting with a mixture of diethyl ether and hexane (10:1, v/v) to yield the title compound (0.263 g).

REFERENCE EXAMPLE 40

3-methyl-1-{3-(phenyl)propyl}-1H-indole-6-carboxaldehyde

Dimethylsulphoxide (0.311 g) was added to a stirring solution of oxalyl chloride in dichloromethane (1 ml, 2M) in dichloromethane (25 ml) at −60° C. under argon and the mixture was stirred for 2 minutes. A solution of 3-methyl-1-{3-(phenyl)propyl}-1H-indole-6-methanol [0.501 g, Reference Example 22(c)] in dichloromethane (10 ml) was then added dropwise and the mixture stirred for 15 minutes at −60° C. Triethylamine (0.956 g) was then added and the solution warmed to room temperature and stirred for 1 hour. The mixture was poured into water (20 ml) and then extracted three times with dichloromethane (25 ml). The combined extracts were washed with brine (30 ml), then dried over sodium sulphate and then evaporated. The residue was subjected to flash chromatography on silica eluting with a mixture of ethyl acetate and hexane (1:1, v/v) to yield the title compound (0.283 g).

REFERENCE EXAMPLE 41

Methyl 3-methyl-1-{3-(phenyl)propyl}-1H-indole-6-carboxylate

A stirred solution of methyl 3-methyl-1H-indole-6-carboxylate (0.5 g, Reference Example 30) in acetone (35 ml) was treated with 1-bromo-3-phenylpropane (0.577 g) and sodium hydroxide (0.116 g). The mixture was stirred at room temperature for 12 hours then poured into water (35 ml) and then extracted three times with ethyl acetate (50 ml). The combined extracts were washed with dilute hydrochloric acid (50 ml, 1N) then with saturated sodium bicarbonate solution (50 ml), then dried over magnesium sulphate and then evaporated. The residue was subjected to flash column chromatography on silica eluting with a mixture of ethyl acetate and hexane (50:1, v/v) to yield the title compound (0.58 g).

REFERENCE EXAMPLE 42

(a) 1-Benzyl-3-methyl-1H-indazole carbonyl chloride

A solution of 1-benzyl-3-methyl-indazole-6-carboxylic acid [0.15 g, Reference Example 28(o)] in dichloromethane (20 ml) was treated with dimethylformamide (2 drops) then with oxalyl chloride (1.69 ml). After stirring for 2 hours the reaction mixture was evaporated and the residue was dried under high vacuum to give the title compound (0.16 g) which was used without further purification.

(b) By proceeding in a similar manner to Reference Example 42(a) but using Reference Example 28(p) there was prepared 1-(4-methoxybenzyl)-3-methyl-1H-indole-6-carbonyl chloride.

(c) By proceeding in a similar manner to Reference Example 42(a) but using Reference Example 26(b) there was prepared 4-methoxy-2-methoxymethyl-benzoxazole-6-carbonyl chloride as a pale orange-brown coloured solid.

(d) By proceeding in a similar manner to Reference Example 42(a) but using Reference Example 26(c) there was prepared 3-isopropyl-1-methyl-1H-indole-5-carbonyl chloride.

(e) By proceeding in a similar manner to Reference Example 42(a) but using Reference Example 28(q) there was prepared 1-(4-methoxybenzyl)-3-methyl-1H-indazole-6-carbonyl chloride.

REFERENCE EXAMPLE 43

(a) Methyl 1-benzyl-3-methyl-1H-indazole-6-carboxylate

A solution of methyl 3-methyl-indazole-6-carboxylate (0.2 g, Reference Example 44) in acetone (15 ml) was treated with benzyl bromide (0.898 g) then with potassium carbonate (0.290 g) and a catalytic amount of 18-crown-6. The mixture was stirred for 12 hours at room temperature then poured into water (30 ml) and then extracted three times with ethyl acetate (30 ml). The combined extracts were dried over sodium sulphate then evaporated. The residue was subjected to flash chromatography on silica eluting with a mixture of ethyl acetate and hexane (7:1, v/v) to yield the title compound (0. 161 g) and methyl 2-benzyl-3-methyl-indazole-6-carboxylate (0.069 g).

(b) By proceeding in a similar manner to Reference Example 43(a) but using 4-methoxybenzyl bromide there was prepared methyl 1-(4-methoxybenzyl)-3-methyl-indazole-6-carboxylate.

REFERENCE EXAMPLE 44

Methyl 3-methyl-1H-indazole-6-carboxylate

A solution of 3-methyl-indazole-6-carboxylic acid (1.57 g, Reference Example 45) in methanol (75 ml) was treated with hydrogen chloride gas for 10 minutes. The reaction mixture was stirred for 12 hours at room temperature then evaporated. The residue was partitioned between ethyl acetate (50 ml) and saturated sodium bicarbonate solution (50 ml). The combined extracts were dried over sodium sulphate then evaporated. The residue was washed with hexane to give the title compound (1.56 g) which was used without further purification.

REFERENCE EXAMPLE 45

3-methyl-1H-indazole-6-carboxylic acid

A solution of methyl 1-triflyl-3-methyl-indazole-6-carboxylate(0.668 g, Reference Example 46) in a mixture of methanol and water (3:1, 80 ml) was treated with potassium carbonate (1.15 g). The mixture was heated at reflux for 5 hours then cooled to room temperature then poured into 1N hydrochloric acid (50 ml). The mixture was extracted three times with ethyl acetate (50 ml). The combined extracts were dried over sodium sulphate then evaporated. The residue was washed with a mixture of hexane and ether to give the title compound (0.360 g).

REFERENCE EXAMPLE 46

Methyl 1-triflyl-3-methyl-1H-indazole-6-carboxylate

The 6-triflyloxy-1-triflyl-3-methyl-indazole (1.0 g, Reference Example 47) was dissolved in dimethylformamide under argon and the solution was flushed with carbon monoxide for 5 minutes. The solution was treated with palladium acetate (0.11 g), diphenylphosphine ferrocene (0.272 g), triethylamine (0.491 g) and methanol (1.56 g) then stirred at room temperature for 12 hours under an atmosphere of carbon monoxide. The reaction mixture was poured into water (150 ml) and the aqueous layer was extracted three times with ethyl acetate (35 ml). The combined extracts were dried over sodium sulphate then evaporated. The residue was subjected to flash chromatography on silica eluting with a mixture of ethyl acetate and hexane (1:7, v/v) to yield the title compound.

REFERENCE EXAMPLE 47

6-triflyloxy-1-triflyl-3-methyl-1H-indazole

A solution of 6-hydroxy-3-methyl-1H-indazole (0.45 g, Reference Example 48) in tetrahydrofuran (30 ml) under argon was treated with sodium hydride (0.198 g). After the initial effervescence had subsided the solution was warmed to 50° C. for 1 hour. The reaction mixture was cooled to room temperature and N-phenyltrifluoromethane sulphonimide (2.48 g) was added. The mixture was stirred for 2 hours then poured into water (50 ml) then extracted three times with ethyl acetate (50 ml). The combined extracts were dried over sodium sulphate then evaporated. The residue was subjected to flash chromatography on silica eluting with a mixture of ethyl acetate and hexane (1:7, v/v) to yield the title compound (1.10 g).

REFERENCE EXAMPLE 48

6-hydroxy-3-methyl-1H-indazole

A solution of 6-methoxy-3-methyl-1H-indazole(2.0 g, Reference Example 49) in dichloromethane (75 ml) was cooled to 0° C. then treated with a solution of boron tribromide in dichloromethane (54 ml, 1M). The mixture was allowed to warm to room temperature and then stirred for 12 hours. The solution was poured into an ice-saturated sodium bicarbonate mixture and the aqueous layer was extracted three times with ethyl acetate (50 ml). The combined extracts were dried over sodium sulphate then evaporated. The residue was subjected to flash chromatography on silica eluting with a mixture of ethyl acetate and hexane (2:1, v/v) to yield the title compound (1.7 g).

REFERENCE EXAMPLE 49

6-methoxy-3-methyl-1H-indazole 2-fluoro-4-methoxyacetophenone (5.0 g) was treated with hydrazine (75 ml) under argon and the mixture was heated to reflux for 12 hours. After cooling to room temperature, the reaction mixture was poured into water (200 ml) then extracted three times with ethyl acetate (50 ml). The combined extracts were dried over sodium sulphate then evaporated. The residue was subjected to flash chromatography on silica eluting with a mixture of ethyl acetate and hexane (1:3, v/v) to yield the title compound (4.05 g).

REFERENCE EXAMPLE 50

5-bromo-2-methoxyaniline

A stirred mixture of 4-bromo-2-nitroanisole (98.56 g) and iron powder (113.7 g) in ethanol (1.51) was heated to reflux and treated dropwise with hydrochloric acid (350 ml, 0.5N) over 1 hour. After refluxing for a further 3 hours the reaction mixture was cooled to room temperature then filtered through hyflosupercel. The filtrate was evaporated and the residue was treated with saturated sodium bicarbonate solution (21) then filtered. The solid was washed with water then recrystallised from cyclohexane to give the title compound (61.98 g) as a pale brown solid, m.p. 93-93° C.

REFERENCE EXAMPLE 51

Methyl 2-hydroxy-4-methoxy-3-nitrobenzoate

A solution of methyl 4-methoxysalicylate (50 g) in glacial acetic acid (700 ml) was treated dropwise with concentrated nitric acid (50 ml) over 15 minutes. After stirring for 2 hours, then standing at room temperature for 18 hours, the mixture was treated with a further aliquot of concentrated nitric acid (10 ml) then stirred for 6 hours. The reaction mixture was diluted with ice then poured into water (1000 ml), then filtered. The solid was dried then subjected to flash chromatography on silica eluting with a mixture of toluene and dichloromethane (2:1, v/v) to give the title compound as a white solid, m.p. 185-187° C.

REFERENCE EXAMPLE 52

Methyl 3-isopropyl-1H-indole-5-carboxylate

A solution of methyl 3-iodo-4-(3-methyl-but-2-enylamino)-benzoate (2.0 g, Reference Example 53) in triethylamine (1.6 ml) and acetonitrile (35 ml) was treated with palladium acetate (0.05 g). The mixture was sealed in a bomb and heated at 110° C. for 18 hours. After cooling the reaction mixture was filtered and the filtrate was evaporated. The residue was subjected to flash chromatography on silica eluting with a mixture of ethyl acetate and petroleum ether (1:4, v/v) to give the title compound (1.0 g).

REFERENCE EXAMPLE 53

Methyl 3-iodo-4-(3-methyl-but-2-enylamino)-benzoate

A solution of diisopropylamine (2.8 ml) in tetrahydrofuran (25 ml), under nitrogen, cooled to −10° C. was treated with butyl lithium in hexane (12.4 ml, 1.6M). The solution was added slowly via a syringe to a cooled to solution of methyl 4-amino-3-iodobenzoate (5 g, prepared according to the procedure of M. L. Hill, Tetrahedron, 1990, 46, page 4587) in tetrahydrofuran (100 ml), under nitrogen and at −78° C. The mixture was allowed to warm to 0° C. and after stirring for a further 10 minutes the mixture was cooled to −78° C. and then treated with 4-bromo-2-methyl-2-butene (2.49 ml). The reaction mixture was allowed to warm to room temperature over 1.5 hours then poured into saturated brine (100 ml). The organic layer was separated and the aqueous phase was extracted with ethyl acetate (100 ml). the combined organic phases were evaporated and the residue was subjected to flash chromatography on silica eluting with a mixture of ethyl acetate and petroleum ether (1:9, v/v) to give the title compound (5 g).

In Vitro and In Vivo Test Procedures 1. (a) Inhibitory Effects of Compounds on PDE IV Activity 1.1 Preparation of PDE from Guinea Pig Macrophages.

The method is described by Turner et al., Br. J. Pharmacol, 1993, 108, pages 876-883. Briefly, cells are harvested from the peritoneal cavity of horse-serum treated (0.5 ml i.p.) Dunkin Hartley guinea pigs (250-400 g) and the macrophages purified by discontinuous (55%, 65%, 70% v/v) gradient (Percoll) centrifugation. Washed macrophages are plated out in cell culture flasks and allowed to adhere. The cells are washed with Hank's balanced salt solution, scraped from the flasks and centrifuged (1000 g). The supernatant is removed and the pellets stored at −80° C. until use. The pellet is homogenised in 20 mM tris(hydroxymethyl)aminomethane HCl, pH7.5, 2 mM magnesium chloride, 1 mM dithiothreitol, 5 mM ethylenediaminetetraacetic acid, 0.25 mM sucrose, 20 mM p-tosyl-L-lycine chloromethyl ketone, 10 mg/ml leupeptin and 2000 U/ml aprotinin.

1.2 Measurement of PDE Activity.

PDE activity is determined in macrophage homogenates by the two-step radioisotopic method of Thompson et al., Adv. Cyclic Nucl. Res., 1979, 10, pages 69-92. The reaction mixture contains 20 mM tris(hydroxymethyl)-aminomethane HCl (pH8.0), 10 mM magnesium chloride, 4 mM 2-mercaptoethanol, 0.2 mM ethylenebis(oxyethylenenitrilo)-tetraacetic acid and 0.05 mg of bovine serum albumin/mL. The concentration of substrate is 1 μM. The $IC_{50}$ values (i.e. concentrations which produce 50% inhibition of substrate hydrolysis) for the compounds examined are determined from concentration-response curves in which concentrations range from 0.03 nM to 10 μM.

1.3 Results.

Compounds within the scope of the invention exhibit $IC_{50}$ values against guinea pig macrophage cyclic AMP-specific phosphodiesterase (PDE IV) of between $10^{-10}$M to about $10^{-5}$M, preferably from about $10^{-10}$M up to about $10^{-6}$M. The compounds of the invention are from about 10,000-fold to about 50-fold more selective for cyclic AMP phosphodiesterase IV than cyclic nucleotide phosphodiesterase types I, II, III or V.

(b) Inhibitory Effects of Compounds on PDE V Activity 1.4 Preparation of PDE from Human Platelets.

The method is described by R. E. Weishaar et al., Biochem. Pharmacol., 1986, 35 pages 787-800.

1.5 Measurement of PDE Activity.

PDE activity is determined by the radioisotopic method of Thompson et al., Adv. Cyclic Nucl. Res., 1979, 10, pages 69-92. Following incubation for 30 minutes at 30° C., [$^3$H]-guanosine 5'-monophosphate is separated from the substrate, guanosine [$^3$H]-guanosine 3':5'-cyclic monophosphate, by elution on cation-exchange columns, and radioactivity is determined using a liquid scintillation counter (LS 1701, Beckman) using a liquid scintillation cocktail (Flow Scint III, Packard). The concentration of substrate is 1 µM. The $IC_{50}$ values for the compounds examined are determined from concentration-response curves in which concentrations range from $10^{-9}$M to $10^{-5}$M.

2. In vivo Bronchodilator Actions of Compounds 2.1 Measurement of Bronchodilatation.

Bronchorelaxant activity is measured in in vivo tests in the anaesthetized guinea-pig or rat according to the method described by Underwood et al., Pulm. Pharmacol., 1992, 5, pages 203-212, in which the effects on bronchospasm induced by histamine (or other spasmogens such as methacholine or leukotriene D4) is determined. Compounds are administered orally 1 hour prior to administration of spasmogen.

3. In Vivo Actions of Compounds on Antigen (Ovalbamin)-induced Eosinophilia in Guinea-Pigs 3.1 Treatment of Animals and Measurement of Eosinophil Numbers.

Male Dunkin-Hartley guinea-pigs weighing 200-250 g are sensitized using 10 µg ovalbumin in 1 mL of a 100 mg/mL suspension of aluminium hydroxide, i.p.

28 days after sensitization guinea-pigs are dosed orally. 23 Hours later this procedure is repeated and 60 minutes later the guinea-pigs are challenged with nebulised saline or ovalbumin (1% in saline) for 15 seconds. 24 Hours after challenge the guinea-pigs are killed and the lungs are lavaged with warm saline. Total and differential cell counts are made.

4. Inhibitory Effects of Compounds Against Antigen-induced Eosinophilia in the Rat In Vivo 4.1. Treatment of Rats and Measurement of Eosinophil Numbers.

Male Brown Norway rats weighing 150-250 g are sensitized on days 0, 12 and 21 with ovalbumin (100 µg, i.p.). Rats are challenged on any one day between days 27-32. 24 hours and 1 hour before antigen challenge the test compound is orally dosed. Rats are challenged by exposure for 30 minutes to nebulized saline or ovalbumin (1% in saline). 24 hours after challenge, rats are killed and the airways are lavaged with RPMI and 10% foetal calf serum. Total and differential cell counts are made.

5. In Vitro Inhibitory Effects on TNF-alpha Release by Human Monocytes

The effects of compounds on TNF-alpha production by human peripheral blood monocytes (PBMs) are examined as follows.

5.1. Preparation of Blood Monocytes.

Blood is drawn from normal donors into sodium citrate (3.8%) as an anticoagulant. Mononuclear cells are fractionated by centrifugation through a histopaque gradient system (Accuspin, Sigma, U.K.). The monouclear cell fraction comprising 90% mononuclear cells (contaminating cells being neutrophils), is suspended in Hanks balanced salt solution (HBSS), (Life Technologies Ltd U.K.) containing 1% v/v Human serum albumin (HSA) (Sigma U.K.). The cells are washed, counted and resuspended at $10^6$ cells/ml in RPMI 1640 tissue culture medium containing 1% v/v foetal calf serum (FCS), 50 U/ml penicillin, 50 mg/ml streptomycin (Life Technologies Ltd), then plated out in 96 well plates at $2 \times 10^6$ cells/well.

5.2. TNF-alpha Release.

Following 2 hours incubation (37° C., 5% $CO_2$) medium and non adherent cells are removed leaving pure adherent monocytes. RPMI (200 µl) medium is replaced with that containing compounds for evaluation, or vehicle. Control treatments and compounds for test are assayed in quadruplicate wells. Compounds are tested within the concentration range $10^{-10}$-$10^{-5}$ M, and allowed to incubate with the cells for 1 hour. LPS (*E. coli* 055:B5 Sigma, U.K.) is added in RPMI to give a final concentration of 10 ng/ml and the incubation is continued for a further 18 hours.

5.3. TNF-alpha Measurement.

Cell supernatants are removed and assayed for TNF-alpha by sandwich ELISA as follows.

ELISA plates (Costar, U.K.) are coated overnight at 4° C. with 2.5 µg/ml polyclonal goat anti-human TNF-alpha antibody (R&D Systems, U.K.) in pH 9.9 bicarbonate buffer. Polyclonal rabbit anti-human TNF-alpha antibody (Endogen, U.S.A.) is used as the second antibody (2.5 µg/ml) and polyclonal goat anti-rabbit IgG-horseradish peroxidase (Calbiochem, U.K.) is used as the detection antibody (1:8000 dilution).

Colour development following addition of the substrate tetramethybenzidine (TMB) solution (Sigma, U.K.) is measured by absorbance at 450 nm using a Titertek plate reader (ICN, U.K.).

TNF-alpha levels are calculated by interpolation from a standard curve using recombinant human TNF-alpha (R&D Systems) (0.125-16 ng/ml). Data are fitted by linear regression using GraphPad PRIZM v 2.01 software. Basal TNF-alpha levels are less than 100 pg/ml whilst LPS stimulation of monocytes increases TNF-alpha levels to 5-10 ng/ml.

5.4. Results.

Compounds within the scope of the invention produce 50% inhibition of LPS induced TNF-alpha release from human monocytes at concentrations within the range of about $10^{-9}$M-$10^{-6}$M, preferably about $10^{-9}$M-$10^{-7}$M.

6. Inhibitory Effects of Compounds on Antigen-Induced Bronchoconstriction in the Conscious Guinea-pig 6.1 Sensitisation of Guinea-pigs and Measurement of Antigen-induced Bronchoconstriction.

Male Dunkin-Hartley guinea-pigs (550-700 g) are sensitized as above. Specific airways resistance (SRaw) is measured in conscious animals by whole body plethysmography using a variation of the method of Pennock et. al. J. Appl. Physiol., 1979, 46, 399). Test compounds or vehicle are administered orally 24 hours and 1 hour before antigen challenge. 30 Minutes before challenge the animals are injected with mepyramine (30 mg/kg i.p.) to prevent anaphyl-actic collapse and placed into the plethysmography chambers where SRaw is determined at 1 minute intervals. Resting SRaw is then determined. Animals are challenged with an aerosol of ovalbumin and SRaw is determined every 5 minutes for 15 minutes.

7. Inhibitory Effects of Compounds Against Antigen-induced Bronchoconstriction in the Anaesthetized Rat In vivo 7.1. Treatment of Rats and Measurement of Antigen-induced Bronchoconstriction.

Male Brown Norway rats weighing 150-250 g are sensitized on days 0, 12 and 21 with ovalbumin (100 µg, i.p.).

Rats are challenged on any one day between days 27-32. 24 hours and 1 hour before antigen challenge the test compounds are orally dosed. Rats are anaesthetized to allow recording of lung function (airway resistance and lung compliance) using respiratory mechanics software. Rats are challenged with ovalbumin i.v. and the peak changes in airway resistance and lung compliance are determined.

7.2 Results.

Compounds within the scope of the invention inhibit antigen-induced bronchoconstriction by up to 89% at doses of 10 mg/kg.

8. Inhibitory Effects of Compounds on Serum TNF-alpha Levels in LPS-challenged Mice 8.1 Treatment of Animals and Measurement of Murine TNF-alpha.

Female Balb/c mice (age 6-8 weeks, weight 20-22 g) are orally dosed with the test compound. After a minimum of 30 minutes they are challenged i.p. with 30 µg of LPS per mouse. After 90 minutes the animals are killed by carbon dioxide asphyxiation and bled by cardiac puncture. Blood is allowed to clot at 4° C., centrifuged (385 g for 5 minutes) and serum taken for TNF-alpha analysis. TNF-alpha levels are measured using a commercially available murine TNF-alpha ELISA kit, purchased from Genzyme (Cat. no. 1509.00), as recommended by the manufacturer. Values for TNF-alpha are calculated from a recombinant murine TNF-alpha standard curve.

9. Systemic Bioavailability in Female Balb/c Mouse

Intravenous Administration:

Following surgery to expose the jugular vein for dosing, a solution of test compound in dimethylsulphoxide is added at a dose of 1 mg/kg body weight.

Oral Administration:

A suspension of test compound in 1.5% aqueous carboxymethylcellulose is introduced into the stomach by gavage at a dose of 1 mg/kg body weight. Following either i.v. or oral dosing, blood is obtained by cardiac puncture following carbon dioxide asphyxiation and is obtained at a single time post-dose for each animal. Three animals are sacrificed at each time point. Blood samples are obtained at the following times after dosing by both the i.v. and oral routes; 5 minutes (i.v. only), 0.25, 0.5, 1, 2, 3, 4, 5.5, 7 and 24 hours. Corresponding plasma is obtained by centrifugation of each blood sample. The drug content in the plasma samples is then determined using conventional methods.

9.1 Metabolism (i) Preparation of Mouse Liver Homogenate.

Fresh mouse liver is homogenised in sucrose-phosphate buffer. Following centrifugation the resulting supernatant (liver homogenate) is used fresh or frozen in liquid nitrogen for one minute and stored at −30° C. to −40° C. prior to use.

(ii) Incubation of Compounds with Mouse Liver Homogenate.

To 0.5 ml of mouse liver homogenate is added 0.5 ml taken from a vortexed mixture of 8 mg NADPH added to a mixture of aqueous magnesium chloride (1 ml, 0.15M) nicotinamide (1 ml, 0.5M) and pH 7.4 tris buffer (8.5 ml, 0.1M). The compound is added at a concentration of 1 µg/ml in 10 µl of solvent. Incubates are maintained at 37° C. Samples are taken at 0 minutes, 5 minutes, 10 minutes, 20 minutes and 30 minutes and the incubation stopped by the addition of 100 µl acetonitrile. The drug content in the incubation samples is determined using conventional methods.

10. Streptococcal Cell Wall-induced Arthritis in Rats 10.1 Preparation of S. pyogenes Purified Cell Wall Purified S. pyogenes cell wall is prepared from the cell pellet of a log-phase culture of S. pyogenes, group A, strain D-58. The whole bacteria are homogenized by grinding with glass beads and the crude cell wall collected by centrifugation and subsequently washed with 2% sodium dodecyl sulphate in phosphate buffered saline followed by phosphate buffered saline to remove contaminating proteins and nucleic acids. The cell wall is further purified by sonication and differential centrifugation to obtain a purified preparation which pelleted at 100,000 g. This material is suspended in sterile phosphate buffered saline and the quantity of cell wall determined by measuring the rhamnose content of the preparation (purified cell wall contains 28% rhamnose by weight). The material is filtered through a 0.22 µM filter and stored at 4° C. until used for arthritis induction.

10.2 Arthritis Induction and Measurement of Joint Diameters.

Female Lewis rats weighing 140-160 g are injected intra-articularly into the left or right tibio-tarsal joint of one hind leg on day 0 with purified S. pyogenes cell wall extract (10 mg in 10 ml sterile saline). On day 20, rats received an intravenous injection of purified cell wall (100 µg in 100 µl sterile saline) via the lateral vein of the tail. Joint diameters are measured with calipers across the lateral and medial malleoli of the previously intra-articularly injected joint immediately prior to the i.v. injection and then daily through day 24. The net joint diameter is determined by subtracting the value for the contralateral joint. Body weights are also measured daily. Compounds or vehicle are administered by oral gavage on days 20-23. Typically, 8-10 animals are used per group. For each dose, the total daily dose is divided into two equal aliquots which are given at approximately 9 a.m. and 3 p.m.

The invention claimed is:

1. A compound of the general formula (I):

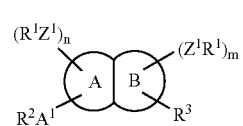

(I)

wherein

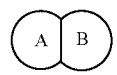

represents a bicyclic ring system, of 9 ring members, in which the ring

is an azaheterocycle, selected from imidazolyl, pyrrolyl, pirrolinyl and pyrazolyl, and the ring

represents a benzene ring;

$R^1$ represents hydrogen or a straight- or branched-chain alkyl group of 1 to about 4 carbon atoms, optionally substituted by hydroxy or one or more halogen atoms;

$R^2$ represents heterocycloalkyl;

$R^3$ represents —C(=O)NHR$^6$, —C(=O)CH$_2$R$^6$, or —OCH$_2$R$^6$;

$R^4$ and $R^5$, which may be the same or different, each represent a hydrogen atom, or an alkyl, aryl, arylalkyl, cycloalkyl, heteroaryl, or heteroarylalkyl group;

$R^6$ is optionally substituted pyridyl or isoxazolyl;

$A^1$ represents a direct bond, or a straight or branched $C_{1-6}$alkylene chain optionally substituted by hydroxyl, alkoxy, oxo, cycloalkyl, aryl or heteroaryl, or $A^1$ represents a straight or branched $C_{2-6}$alkenylene or $C_{2-6}$alkynylene chain;

$Z^1$ represents a direct bond, an oxygen or sulphur atom or NH;

n and m each represent zero or 1, provided that n is 1 when m is zero and n is zero when m is 1;

and N-oxides thereof, and pharmaceutically acceptable salts of the compounds of formula (I) and N-oxides thereof.

2. The compound according to claim 1 in which $R^1$ represents $C_{1-4}$alkyl optionally substituted by one or more halogen atoms.

3. The compound according to claim 1 in which $Z^1$ represents a direct bond or an oxygen atom.

4. The compound according to claim 1 in which $A^1$ represents a direct bond or a straight- or branched-chain alkylene linkage containing from 1 to 6 carbon atoms and optionally substituted by alkoxy.

5. The compound according to claim 1 in which $R^3$ represents —C(=O)NHR$^6$, —C(=O)CH$_2$R$^6$ or —OCH$_2$R$^6$ wherein $R^6$ is an optionally substituted azaheteroaryl group.

6. The compound according to claim 5 in which $R^6$ is pyridyl or isoxazolyl substituted on both positions adjacent to the position of attachment of $R^6$ to the rest of the molecule.

7. The compound according to claim 5 in which $R^6$ is pyridyl or isoxazolyl substituted by two methyl or halogen moieties on both positions adjacent to the position of attachment of $R^6$ to the rest of the molecule.

8. The compound according to claim 5 in which $R^6$ is 3,5-dimethylpyrid-4-yl, 3,5-dihalopyrid-4-yl or an N-oxide of such groups.

9. The compound according to claim 5 in which $R^6$ is 3,5-dimethylisoxazol-4-yl.

10. A compound of formula (Ib)

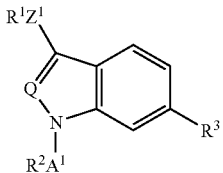

(Ib)

wherein $R^1$, $R^2$, $R^3$, $A^1$ and $Z^1$ are as defined in claim 1, and Q represents a CH linkage or a nitrogen atom, and N-oxides thereof, and pharmaceutically acceptable salts of the compounds of formula (Ib) and N-oxides thereof.

11. The compound according to claim 10 in which $R^1$ is hydrogen or methyl, $R^2$ is heterocycloalkyl, $R^3$ is —C(=O)—NHR$^6$, —C(=O)—CH$_2$R$^6$ or —O—CH$_2$R$^6$, where $R^6$ is a dimethyl- or dihalo-azaheteroaryl. $A^1$ is a direct bond or a methylene linkage, $Z^1$ is a direct bond, and Q is a CH linkage or a nitrogen atom, and N-oxides thereof, and pharmaceutically acceptable salts of the compounds of formula (Ib) herein and N-oxides thereof.

12. A compound of formula (Ie)

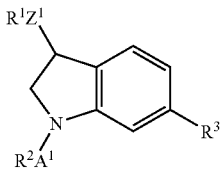

(Ie)

wherein $R^1$, $R^2$, $R^3$, $A^1$ and $Z^1$ are as defined in claim 1, and N-oxides thereof, and pharmaceutically acceptable salts of the compounds of formula (Ie) and N-oxides thereof.

13. The compound according to claim 12 in which $R^1$ is hydrogen or methyl, $R^2$ is heterocycloalkyl, $R^3$ is —C(=O)—NHR$^6$, —C(=O)—CH$_2$R$^6$ or —O—CH$_2$R$^6$, where $R^6$ is a dimethyl- or dihalo-azaheteroaryl, $A^1$ is a direct bond or a methylene linkage and $Z^1$ is a direct bond, and N-oxides thereof, and pharmaceutically acceptable salts of the compounds of formula (Ie) herein and N-oxides thereof.

14. A pharmaceutical composition comprising an effective amount of a compound according to claim 1 or pharmaceutically acceptable salts thereof in association with a pharmaceutically acceptable carrier or excipient.

15. A compound according to claim 1 selected from the group consisting of:
N(3,5-dichloro-4-pyridyl)-3-methyl-1-(tetrahydro-2H-pyran-2-yl)methyl-1H-indole-6-carboxamide;
N(3,5-dichloro-4-pyridyl)-3-methyl-1-(tetrahydro-furan-3-yl)-1H-indole-6-carboxamide; and the corresponding pyridine N-oxides, and pharmaceutically acceptable salts thereof.

* * * * *

UNITED STATES PATENT AND TRADEMARK OFFICE
CERTIFICATE OF CORRECTION

PATENT NO. : 7,329,675 B2  
APPLICATION NO. : 10/933077  
DATED : February 12, 2008  
INVENTOR(S) : Cox et al.

Page 1 of 1

It is certified that error appears in the above-identified patent and that said Letters Patent is hereby corrected as shown below:

Column 132, lines 51-58, cancel the text beginning with "15. A compound" to and ending "salts thereof.", and insert the following claim:

15.     A compound according to claim 1 selected from the group consisting of:
N (3,5-dichloro-4-pyridyl)-3-methyl-1-(tetrahydro-2H-pyran-2-yl)methyl-1H-indole-6-carboxamide;
N (3,5-dichloro-4-pyridyl)-3-methyl-1-(tetrahydrofuran-2-yl)methyl-1H-indole-6-carboxamide;
N (3,5-dichloro-4-pyridyl)-3-methyl-1-(tetrahydro-furan-3-yl)-1H-indole-6-carboxamide; and the corresponding pyridine N-oxides, and pharmaceutically acceptable salts thereof.

Signed and Sealed this

Tenth Day of June, 2008

JON W. DUDAS  
*Director of the United States Patent and Trademark Office*